US011103122B2

(12) United States Patent
Border

(10) Patent No.: US 11,103,122 B2
(45) Date of Patent: Aug. 31, 2021

(54) CONTENT PRESENTATION IN HEAD WORN COMPUTING

(71) Applicant: Mentor Acquisition One, LLC, Plantation, FL (US)

(72) Inventor: John N. Border, Eaton, NH (US)

(73) Assignee: Mentor Acquisition One, LLC, Plantation, FL (US)

( * ) Notice: Subject to any disclaimer, the term of this patent is extended or adjusted under 35 U.S.C. 154(b) by 276 days.

(21) Appl. No.: 14/337,371

(22) Filed: Jul. 22, 2014

(65) Prior Publication Data

US 2016/0015470 A1    Jan. 21, 2016

Related U.S. Application Data

(63) Continuation-in-part of application No. 14/331,481, filed on Jul. 15, 2014, now abandoned.

(51) Int. Cl.
*A61B 1/00* (2006.01)
*A61B 17/00* (2006.01)
(Continued)

(52) U.S. Cl.
CPC ............... *A61B 1/00* (2013.01); *A61B 3/113* (2013.01); *A61B 5/1103* (2013.01); *A61B 5/1114* (2013.01); *A61B 5/1122* (2013.01); *A61B 5/1128* (2013.01); *A61B 5/6803* (2013.01); *A61B 17/00* (2013.01); *A61B 34/20* (2016.02); *A61B 90/39* (2016.02); *A61B 90/50* (2016.02); *G02B 27/017* (2013.01); *G06K 9/00597* (2013.01); *G06T 19/006* (2013.01); *A61B 3/112* (2013.01); *A61B 3/12* (2013.01); *A61B 3/1216* (2013.01); *A61B 5/0077* (2013.01);
(Continued)

(58) Field of Classification Search
CPC .......................... G06T 7/0024; G02B 27/017; G02B 27/0172; G02B 27/0176; G02B 2027/0178; G02B 2027/0156; G02B 27/01; G02B 27/0101; G02B 27/0132; G02B 27/0149; G02B 27/0187; G02B 2027/011; G02B 27/0118; G02B 5/30; G09G 3/003; H04N 13/0497; H04N 13/0285; H04N 13/044; H04N 13/0059
See application file for complete search history.

(56) References Cited

U.S. PATENT DOCUMENTS 1,897,833 A   2/1933   Benway
2,064,604 A   12/1936  Hempel
(Continued)

FOREIGN PATENT DOCUMENTS

EP   368898 A1   5/1990
EP   177867 A1   6/1997
(Continued)

OTHER PUBLICATIONS

US 8,743,465 B2, 06/2014, Totani et al. (withdrawn)
(Continued)

*Primary Examiner* — Phuc N Doan
(74) *Attorney, Agent, or Firm* — Morrison & Foerster LLP

(57) ABSTRACT

Aspects of the present invention relate to providing assistance to medical professionals during the performance of medical procedures through the use of technologies facilitated through a head-worn computer.

20 Claims, 105 Drawing Sheets

(51) Int. Cl.

| | | |
|---|---|---|
| *A61B 3/113* | (2006.01) | |
| *A61B 5/06* | (2006.01) | |
| *A61B 5/11* | (2006.01) | |
| *A61B 90/00* | (2016.01) | |
| *A61B 90/50* | (2016.01) | |
| *G02B 27/01* | (2006.01) | |
| *G06T 19/00* | (2011.01) | |
| *A61B 5/00* | (2006.01) | |
| *A61B 34/20* | (2016.01) | |
| *G06K 9/00* | (2006.01) | |
| *A61B 5/1455* | (2006.01) | |
| *A61B 5/145* | (2006.01) | |
| *A61B 5/01* | (2006.01) | |
| *A61B 3/11* | (2006.01) | |
| *A61B 3/12* | (2006.01) | |
| *A61B 34/10* | (2016.01) | |
| *G06K 9/22* | (2006.01) | |

(52) U.S. Cl.
CPC .............. *A61B 5/015* (2013.01); *A61B 5/066* (2013.01); *A61B 5/067* (2013.01); *A61B 5/14532* (2013.01); *A61B 5/14551* (2013.01); *A61B 5/742* (2013.01); *A61B 2017/00216* (2013.01); *A61B 2034/107* (2016.02); *A61B 2090/363* (2016.02); *A61B 2090/365* (2016.02); *A61B 2090/373* (2016.02); *A61B 2090/374* (2016.02); *A61B 2090/3762* (2016.02); *A61B 2090/3945* (2016.02); *A61B 2090/3979* (2016.02); *A61B 2090/502* (2016.02); *G02B 2027/0198* (2013.01); *G06K 9/222* (2013.01); *G06T 2210/41* (2013.01)

(56) References Cited

U.S. PATENT DOCUMENTS

| | | |
|---|---|---|
| 3,305,294 A | 2/1967 | Alvarez |
| 3,531,190 A | 9/1970 | Leblanc |
| 3,671,111 A | 6/1972 | Okner |
| 4,034,401 A | 7/1977 | Mann et al. |
| 4,145,125 A | 3/1979 | Chika |
| 4,668,155 A | 5/1987 | Kaufmann et al. |
| 4,788,535 A | 11/1988 | Chikara et al. |
| 4,811,739 A | 3/1989 | Silver et al. |
| 4,852,988 A | 8/1989 | Velez et al. |
| 4,928,301 A | 5/1990 | Smoot et al. |
| D327,674 S | 7/1992 | Kuo |
| 5,151,722 A | 9/1992 | Massof et al. |
| 5,257,094 A | 10/1993 | LaRussa et al. |
| D352,930 S | 11/1994 | Tsuji |
| 5,483,307 A | 1/1996 | Anderson |
| D375,748 S | 11/1996 | Hartman |
| D376,790 S | 12/1996 | Goulet et al. |
| 5,596,451 A | 1/1997 | Handschy et al. |
| 5,621,424 A | 4/1997 | Shimada et al. |
| 5,699,057 A | 12/1997 | Ikeda et al. |
| 5,699,194 A | 12/1997 | Takahashi |
| 5,717,422 A | 2/1998 | Fergason et al. |
| D392,959 S | 3/1998 | Edwards |
| 5,729,242 A | 3/1998 | Margerum et al. |
| 5,767,841 A | 6/1998 | Hartman |
| 5,788,195 A | 8/1998 | Rice |
| 5,808,589 A | 9/1998 | Fergason |
| 5,808,800 A | 9/1998 | Handschy et al. |
| 5,808,802 A | 9/1998 | Hur |
| D410,638 S | 6/1999 | Sheehan et al. |
| 5,914,818 A | 6/1999 | Tejada et al. |
| 5,949,583 A | 9/1999 | Rallison et al. |
| 5,991,084 A | 11/1999 | Hildebrand et al. |
| 6,028,608 A | 2/2000 | Jenkins |
| 6,034,653 A | 3/2000 | Robertson et al. |
| 6,046,712 A | 4/2000 | Beller et al. |
| 6,147,805 A | 11/2000 | Fergason |
| 6,160,552 A | 12/2000 | Wilsher et al. |
| 6,160,666 A | 12/2000 | Rallinson et al. |
| 6,195,136 B1 | 2/2001 | Handschy et al. |
| 6,204,974 B1 | 3/2001 | Spitzer |
| 6,222,677 B1 | 4/2001 | Budd |
| 6,297,749 B1 | 10/2001 | Smith et al. |
| D451,892 S | 12/2001 | Carrere |
| 6,347,764 B1 | 2/2002 | Brandon et al. |
| 6,359,723 B1 | 3/2002 | Handschy et al. |
| 6,369,952 B1 | 4/2002 | Rallison et al. |
| 6,379,009 B1 | 4/2002 | Fergason |
| 6,384,982 B1 | 5/2002 | Spitzer |
| 6,392,656 B1 | 5/2002 | Someya et al. |
| D460,071 S | 7/2002 | Sheehan et al. |
| 6,433,760 B1 | 8/2002 | Vaissie et al. |
| 6,456,438 B1 | 9/2002 | Lee et al. |
| 6,461,000 B1 | 10/2002 | Magarill |
| 6,478,429 B1 | 11/2002 | Aritake et al. |
| 6,480,174 B1 | 11/2002 | Kaufmann et al. |
| 6,491,389 B2 | 12/2002 | Yaguchi et al. |
| D470,144 S | 2/2003 | Li |
| 6,535,182 B2 | 3/2003 | Stanton |
| D473,871 S | 4/2003 | Santos |
| 6,563,626 B1 | 5/2003 | Iwasaki et al. |
| D478,052 S | 8/2003 | Thomas, Jr. |
| 6,612,840 B1 * | 9/2003 | Turner .................. G02B 27/01 434/29 |
| 6,642,945 B1 | 11/2003 | Sharpe et al. |
| 6,747,611 B1 | 6/2004 | Budd et al. |
| 6,771,294 B1 | 8/2004 | Pulli et al. |
| 6,795,041 B2 | 9/2004 | Ogawa et al. |
| 6,847,336 B1 | 1/2005 | Lemelson et al. |
| 6,906,836 B2 | 6/2005 | Parker et al. |
| D512,027 S | 11/2005 | Sarasjoki et al. |
| D513,233 S | 12/2005 | Stauffer |
| 6,987,787 B1 | 1/2006 | Mick |
| D514,525 S | 2/2006 | Stauffer |
| 7,003,308 B1 | 2/2006 | Fuoss et al. |
| 7,016,116 B2 | 3/2006 | Dolgoff et al. |
| 7,030,925 B1 | 4/2006 | Tsunekawa et al. |
| D521,493 S | 5/2006 | Wai |
| 7,088,234 B2 | 8/2006 | Naito et al. |
| D529,467 S | 10/2006 | Rose et al. |
| D541,226 S | 4/2007 | Wakisaka et al. |
| 7,199,934 B2 | 4/2007 | Yamasaki |
| 7,206,134 B2 | 4/2007 | Weissman et al. |
| D559,793 S | 1/2008 | Fan |
| D571,816 S | 6/2008 | Corcoran et al. |
| 7,380,936 B2 | 6/2008 | Howell et al. |
| 7,401,918 B2 | 7/2008 | Howell et al. |
| 7,414,791 B2 | 8/2008 | Urakawa et al. |
| 7,417,617 B2 | 8/2008 | Eichenlaub |
| 7,457,040 B2 | 11/2008 | Amitai |
| 7,481,531 B2 | 1/2009 | Howell et al. |
| 7,500,747 B2 | 3/2009 | Howell et al. |
| 7,522,344 B1 | 4/2009 | Curatu et al. |
| 7,542,210 B2 | 6/2009 | Chirieleison et al. |
| 7,543,943 B1 | 6/2009 | Hubby et al. |
| 7,646,540 B2 | 1/2010 | Dolgoff et al. |
| 7,677,723 B2 | 3/2010 | Howell et al. |
| 7,690,799 B2 | 4/2010 | Nestorovic et al. |
| 7,728,799 B2 | 6/2010 | Kerr et al. |
| 7,733,571 B1 | 6/2010 | Li |
| 7,771,046 B2 | 8/2010 | Howell et al. |
| 7,777,690 B2 | 8/2010 | Winsor et al. |
| 7,777,723 B2 | 8/2010 | Namiki et al. |
| 7,777,960 B2 | 8/2010 | Freeman |
| 7,792,552 B2 | 9/2010 | Thomas et al. |
| 7,806,525 B2 | 10/2010 | Howell et al. |
| 7,812,842 B2 | 10/2010 | Gordon et al. |
| 7,813,743 B1 | 10/2010 | Loeb et al. |
| 7,830,370 B2 | 11/2010 | Yamazaki et al. |
| 7,850,301 B2 | 12/2010 | DiChiara et al. |
| 7,855,743 B2 | 12/2010 | Sako et al. |
| D631,881 S | 2/2011 | Quinn et al. |
| D631,882 S | 2/2011 | Odgers |
| 7,928,926 B2 | 4/2011 | Yamamoto et al. |
| 8,004,765 B2 | 8/2011 | Amitai |

(56) References Cited

U.S. PATENT DOCUMENTS

| | | |
|---|---|---|
| 8,018,579 B1 | 9/2011 | Krah et al. |
| 8,079,713 B2 | 12/2011 | Ashkenazi et al. |
| 8,092,007 B2 | 1/2012 | DiChiara et al. |
| 8,166,421 B2 | 4/2012 | Magal et al. |
| 8,212,859 B2 | 7/2012 | Tang et al. |
| 8,228,315 B1 | 7/2012 | Starner et al. |
| 8,235,529 B1 | 8/2012 | Raffle et al. |
| 8,246,170 B2 | 8/2012 | Yamamoto et al. |
| D669,066 S | 10/2012 | Olsson et al. |
| 8,337,013 B2 | 12/2012 | Howell et al. |
| 8,376,548 B2 | 2/2013 | Schultz |
| 8,378,924 B2 | 2/2013 | Jacobsen et al. |
| 8,384,999 B1 | 2/2013 | Crosby et al. |
| D680,112 S | 4/2013 | Monahan |
| D680,152 S | 4/2013 | Olsson et al. |
| 8,427,396 B1 | 4/2013 | Kim |
| 8,430,507 B2 | 4/2013 | Howell et al. |
| 8,434,863 B2 | 5/2013 | Howell et al. |
| D685,019 S | 6/2013 | Li |
| 8,467,133 B2 | 6/2013 | Miller et al. |
| 8,472,120 B2 | 6/2013 | Border et al. |
| 8,473,241 B2 | 6/2013 | Foxlin |
| 8,477,425 B2 | 7/2013 | Border et al. |
| 8,482,859 B2 | 7/2013 | Border et al. |
| 8,487,838 B2 | 7/2013 | Kipman et al. |
| 8,488,246 B2 | 7/2013 | Border et al. |
| 8,489,326 B1 | 7/2013 | Na et al. |
| 8,494,215 B2 | 7/2013 | Kimchi et al. |
| 8,505,430 B2 | 8/2013 | Andryukov et al. |
| D689,862 S | 9/2013 | Liu |
| 8,531,394 B2 | 9/2013 | Maltz et al. |
| D690,684 S | 10/2013 | Lee et al. |
| 8,553,910 B1 | 10/2013 | Dong et al. |
| 8,564,883 B2 | 10/2013 | Totani et al. |
| 8,570,273 B1 | 10/2013 | Smith |
| 8,570,656 B1 * | 10/2013 | Weissman ............ G02B 27/283 359/631 |
| 8,576,276 B2 | 11/2013 | Bar-Zeev et al. |
| 8,576,491 B2 | 11/2013 | Takagi et al. |
| 8,587,869 B2 | 11/2013 | Totani et al. |
| 8,593,795 B1 | 11/2013 | Chi et al. |
| 8,594,467 B2 | 11/2013 | Lu et al. |
| D696,668 S | 12/2013 | Chen et al. |
| 8,611,015 B2 | 12/2013 | Wheeler et al. |
| 8,662,686 B2 | 3/2014 | Takagi et al. |
| 8,670,183 B2 | 3/2014 | Clavin et al. |
| 8,678,581 B2 | 3/2014 | Blum et al. |
| 8,698,157 B2 | 4/2014 | Hanamura |
| 8,711,487 B2 | 4/2014 | Takeda et al. |
| 8,730,129 B2 | 5/2014 | Solomon et al. |
| 8,743,052 B1 | 6/2014 | Keller et al. |
| 8,745,058 B1 | 6/2014 | Garcia-Barrio |
| 8,750,541 B1 | 6/2014 | Dong et al. |
| 8,752,963 B2 | 6/2014 | McCulloch et al. |
| 8,760,765 B2 | 6/2014 | Gupta et al. |
| 8,767,306 B1 | 7/2014 | Miao et al. |
| 8,770,742 B2 | 7/2014 | Howell et al. |
| 8,786,675 B2 | 7/2014 | Deering et al. |
| 8,786,686 B1 | 7/2014 | Amirparviz |
| 8,787,006 B2 | 7/2014 | Golko et al. |
| 8,803,867 B2 | 8/2014 | Oikawa |
| 8,814,691 B2 | 8/2014 | Osterhout et al. |
| 8,823,071 B2 | 9/2014 | Oyamada |
| 8,824,779 B1 | 9/2014 | Smyth |
| 8,832,557 B2 | 9/2014 | Tang et al. |
| 8,836,768 B1 | 9/2014 | Zuccarino et al. |
| 8,837,880 B2 | 9/2014 | Takeda et al. |
| 8,854,433 B1 | 10/2014 | Rafii |
| 8,854,735 B2 | 10/2014 | Totani et al. |
| 8,866,702 B1 | 10/2014 | Mirov et al. |
| 8,866,849 B1 | 10/2014 | Chun et al. |
| 8,867,139 B2 | 10/2014 | Gupta |
| D716,808 S | 11/2014 | Yeom et al. |
| D716,813 S | 11/2014 | Deng |
| 8,878,749 B1 | 11/2014 | Wu et al. |
| D719,568 S | 12/2014 | Heinrich et al. |
| D719,569 S | 12/2014 | Heinrich et al. |
| D719,570 S | 12/2014 | Heinrich et al. |
| 8,922,530 B2 | 12/2014 | Pance |
| 8,947,323 B1 | 2/2015 | Geiss et al. |
| 8,948,935 B1 | 2/2015 | Peeters et al. |
| 8,955,973 B2 | 2/2015 | Raffle et al. |
| 8,964,298 B2 | 2/2015 | Haddick et al. |
| D724,083 S | 3/2015 | Olsson et al. |
| 8,970,495 B1 | 3/2015 | Weaver et al. |
| 8,971,023 B2 | 3/2015 | Olsson et al. |
| 8,982,014 B2 | 3/2015 | Evans et al. |
| 8,982,471 B1 | 3/2015 | Starner et al. |
| D727,317 S | 4/2015 | Olsson et al. |
| 9,020,832 B2 | 4/2015 | Fisher et al. |
| D728,573 S | 5/2015 | Deng |
| 9,024,842 B1 | 5/2015 | Wheeler et al. |
| 9,031,273 B2 | 5/2015 | Dong et al. |
| 9,033,502 B2 | 5/2015 | Schmidt et al. |
| D732,025 S | 6/2015 | Heinrich et al. |
| 9,046,686 B2 | 6/2015 | Saito |
| 9,046,999 B1 | 6/2015 | King et al. |
| 9,063,563 B1 | 6/2015 | Gray et al. |
| D733,709 S | 7/2015 | Kawai |
| 9,076,368 B2 | 7/2015 | Evans et al. |
| 9,094,677 B1 * | 7/2015 | Mendis ............... H04N 13/332 |
| 9,096,920 B1 | 8/2015 | Gomez |
| 9,107,622 B2 | 8/2015 | Nistico et al. |
| 9,116,337 B1 | 8/2015 | Miao |
| D738,373 S | 9/2015 | Davies et al. |
| 9,122,054 B2 | 9/2015 | Osterhout et al. |
| 9,128,281 B2 | 9/2015 | Osterhout et al. |
| 9,129,157 B2 | 9/2015 | Chao et al. |
| 9,129,295 B2 | 9/2015 | Border et al. |
| 9,143,693 B1 | 9/2015 | Zhou et al. |
| 9,158,115 B1 | 10/2015 | Worley et al. |
| 9,158,116 B1 | 10/2015 | Osterhout et al. |
| D743,963 S | 11/2015 | Osterhout |
| 9,176,582 B1 | 11/2015 | Johnson et al. |
| D745,007 S | 12/2015 | Cazalet et al. |
| 9,202,233 B1 | 12/2015 | Siegel et al. |
| 9,225,934 B2 | 12/2015 | Cho |
| 9,229,233 B2 | 1/2016 | Osterhout et al. |
| 9,229,234 B2 | 1/2016 | Osterhout |
| 9,235,051 B2 | 1/2016 | Salter et al. |
| 9,269,193 B2 | 2/2016 | Saito |
| D751,551 S | 3/2016 | Ho et al. |
| D751,552 S | 3/2016 | Osterhout |
| 9,286,728 B2 | 3/2016 | Osterhout et al. |
| 9,298,001 B2 | 3/2016 | Border et al. |
| 9,298,002 B2 | 3/2016 | Border et al. |
| 9,298,007 B2 | 3/2016 | Border |
| 9,299,194 B2 | 3/2016 | Border et al. |
| D753,114 S | 4/2016 | Osterhout |
| 9,310,610 B2 | 4/2016 | Border |
| 9,316,833 B2 | 4/2016 | Border et al. |
| D756,363 S | 5/2016 | Mathis |
| D757,006 S | 5/2016 | Cazalet et al. |
| 9,329,387 B2 | 5/2016 | Border et al. |
| 9,354,445 B1 | 5/2016 | Weaver et al. |
| 9,366,867 B2 | 6/2016 | Border et al. |
| 9,366,868 B2 | 6/2016 | Border et al. |
| 9,377,625 B2 | 6/2016 | Border et al. |
| 9,400,390 B2 | 7/2016 | Osterhout et al. |
| 9,401,540 B2 | 7/2016 | Osterhout et al. |
| 9,423,612 B2 | 8/2016 | Border et al. |
| 9,423,842 B2 | 8/2016 | Osterhout et al. |
| 9,436,006 B2 | 9/2016 | Border |
| 9,448,409 B2 | 9/2016 | Border et al. |
| 9,494,800 B2 | 11/2016 | Border et al. |
| 2001/0019240 A1 | 9/2001 | Takahashi et al. |
| 2001/0050817 A1 | 12/2001 | Travers et al. |
| 2002/0005108 A1 | 1/2002 | Ludwig et al. |
| 2002/0021498 A1 | 2/2002 | Ohtaka et al. |
| 2002/0082498 A1 * | 6/2002 | Wendt ................ G06F 19/00 600/411 |
| 2002/0085843 A1 | 7/2002 | Mann |
| 2002/0109903 A1 | 8/2002 | Kaeriyama et al. |
| 2002/0148655 A1 | 10/2002 | Cho et al. |

(56) References Cited

U.S. PATENT DOCUMENTS

| | | |
|---|---|---|
| 2002/0149545 A1 | 10/2002 | Hanayama et al. |
| 2002/0183101 A1 | 12/2002 | Oh et al. |
| 2002/0191297 A1 | 12/2002 | Gleckman et al. |
| 2003/0030597 A1 | 2/2003 | Geist |
| 2003/0030912 A1 | 2/2003 | Gleckman et al. |
| 2003/0151834 A1 | 8/2003 | Penn et al. |
| 2003/0209953 A1 | 11/2003 | Park et al. |
| 2003/0227470 A1 | 12/2003 | Genc et al. |
| 2003/0234823 A1 | 12/2003 | Sato et al. |
| 2004/0008158 A1 | 1/2004 | Chi et al. |
| 2004/0024287 A1 | 2/2004 | Patton et al. |
| 2004/0027312 A1 | 2/2004 | Owada et al. |
| 2004/0030448 A1 | 2/2004 | Solomon |
| 2004/0032392 A1 | 2/2004 | Chi et al. |
| 2004/0066363 A1 | 4/2004 | Yamano et al. |
| 2004/0066547 A1 | 4/2004 | Parker et al. |
| 2004/0080541 A1 | 4/2004 | Saiga et al. |
| 2004/0130522 A1 | 7/2004 | Lin et al. |
| 2004/0132509 A1 | 7/2004 | Glezerman |
| 2004/0150631 A1 | 8/2004 | Fleck et al. |
| 2004/0194880 A1 | 10/2004 | Jiang et al. |
| 2004/0227994 A1 | 11/2004 | Ma et al. |
| 2005/0010091 A1 | 1/2005 | Woods et al. |
| 2005/0010563 A1 | 1/2005 | Gross et al. |
| 2005/0041289 A1 | 2/2005 | Berman et al. |
| 2005/0091338 A1 | 4/2005 | De La |
| 2005/0122319 A1 | 6/2005 | Sakurai et al. |
| 2005/0154505 A1 | 7/2005 | Nakamura et al. |
| 2005/0156915 A1 | 7/2005 | Fisher et al. |
| 2005/0157949 A1 | 7/2005 | Aiso et al. |
| 2005/0212980 A1 | 9/2005 | Miyazaki et al. |
| 2006/0047386 A1 | 3/2006 | Kanevsky et al. |
| 2006/0050146 A1 | 3/2006 | Richardson |
| 2006/0061542 A1 | 3/2006 | Stokic et al. |
| 2006/0092131 A1 | 5/2006 | Kuroki et al. |
| 2006/0098293 A1 | 5/2006 | Garoutte et al. |
| 2006/0119794 A1 | 6/2006 | Hillis et al. |
| 2006/0132457 A1 | 6/2006 | Rimas-Ribikauskas et al. |
| 2006/0132924 A1 | 6/2006 | Mimran et al. |
| 2006/0152686 A1 | 7/2006 | Yeralan et al. |
| 2006/0170652 A1 | 8/2006 | Bannai et al. |
| 2006/0173351 A1* | 8/2006 | Marcotte ............... A61B 5/0059 600/473 |
| 2006/0178827 A1 | 8/2006 | Aoyama et al. |
| 2006/0215111 A1 | 9/2006 | Mihashi et al. |
| 2006/0224238 A1 | 10/2006 | Azar et al. |
| 2006/0238550 A1 | 10/2006 | Page et al. |
| 2006/0239629 A1 | 10/2006 | Qi et al. |
| 2006/0250322 A1 | 11/2006 | Hall et al. |
| 2006/0250696 A1 | 11/2006 | McGuire |
| 2006/0285315 A1 | 12/2006 | Tufenkjian et al. |
| 2006/0288233 A1 | 12/2006 | Kozlay et al. |
| 2007/0003168 A1 | 1/2007 | Oliver et al. |
| 2007/0004451 A1 | 1/2007 | C. Anderson et al. |
| 2007/0024750 A1 | 2/2007 | Wing Chung et al. |
| 2007/0024763 A1 | 2/2007 | Chung et al. |
| 2007/0024764 A1 | 2/2007 | Chung et al. |
| 2007/0024820 A1 | 2/2007 | Chung et al. |
| 2007/0024823 A1 | 2/2007 | Chung et al. |
| 2007/0025273 A1 | 2/2007 | Chung et al. |
| 2007/0030243 A1 | 2/2007 | Ishii et al. |
| 2007/0030456 A1 | 2/2007 | Duncan et al. |
| 2007/0035563 A1 | 2/2007 | Biocca et al. |
| 2007/0038960 A1 | 2/2007 | Rekimoto et al. |
| 2007/0058868 A1 | 3/2007 | Seino et al. |
| 2007/0069976 A1 | 3/2007 | Willins et al. |
| 2007/0070859 A1 | 3/2007 | Hirayama |
| 2007/0074043 A1* | 3/2007 | Lacey ................... G06F 19/323 713/186 |
| 2007/0100637 A1 | 5/2007 | McCune et al. |
| 2007/0109284 A1 | 5/2007 | Yamazaki et al. |
| 2007/0120806 A1 | 5/2007 | Schmidt et al. |
| 2007/0120836 A1 | 5/2007 | Yamaguchi |
| 2007/0132662 A1 | 6/2007 | Morita et al. |
| 2007/0178950 A1 | 8/2007 | Lewis et al. |
| 2007/0233376 A1 | 10/2007 | Gershony et al. |
| 2007/0263174 A1 | 11/2007 | Shyu et al. |
| 2007/0273611 A1 | 11/2007 | Torch |
| 2007/0282682 A1 | 12/2007 | Dietz et al. |
| 2007/0296684 A1 | 12/2007 | Thomas et al. |
| 2008/0005702 A1 | 1/2008 | Skourup et al. |
| 2008/0066973 A1 | 3/2008 | Furuki et al. |
| 2008/0121441 A1 | 5/2008 | Sheets et al. |
| 2008/0122736 A1 | 5/2008 | Ronzani et al. |
| 2008/0143954 A1 | 6/2008 | Abreu et al. |
| 2008/0186255 A1 | 8/2008 | Cohen et al. |
| 2008/0191965 A1 | 8/2008 | Pandozy et al. |
| 2008/0219025 A1 | 9/2008 | Spitzer et al. |
| 2008/0266645 A1 | 10/2008 | Dharmatilleke et al. |
| 2008/0291277 A1 | 11/2008 | Jacobsen et al. |
| 2008/0298639 A1 | 12/2008 | Tsunekawa et al. |
| 2009/0013204 A1 | 1/2009 | Kobayashi et al. |
| 2009/0015735 A1 | 1/2009 | Simmonds et al. |
| 2009/0040296 A1 | 2/2009 | Moscato et al. |
| 2009/0093702 A1* | 4/2009 | Vollmer ................. A61B 5/064 600/407 |
| 2009/0108837 A1 | 4/2009 | Johansson et al. |
| 2009/0110241 A1 | 4/2009 | Takemoto et al. |
| 2009/0147331 A1 | 6/2009 | Ashkenazi et al. |
| 2009/0183929 A1 | 7/2009 | Zhang et al. |
| 2009/0209884 A1* | 8/2009 | Van Vorhis ................... 600/595 |
| 2009/0251441 A1 | 10/2009 | Edgecomb et al. |
| 2009/0279180 A1 | 11/2009 | Amitai et al. |
| 2010/0001572 A1 | 1/2010 | Masunaga et al. |
| 2010/0007852 A1 | 1/2010 | Bietry et al. |
| 2010/0046075 A1 | 2/2010 | Powell et al. |
| 2010/0056274 A1 | 3/2010 | Uusitalo et al. |
| 2010/0060713 A1 | 3/2010 | Snyder et al. |
| 2010/0073376 A1 | 3/2010 | Schmale |
| 2010/0079508 A1 | 4/2010 | Hodge et al. |
| 2010/0079733 A1 | 4/2010 | Lu et al. |
| 2010/0082368 A1 | 4/2010 | Gecelter et al. |
| 2010/0085325 A1 | 4/2010 | King-Smith et al. |
| 2010/0094161 A1 | 4/2010 | Kiderman et al. |
| 2010/0097580 A1 | 4/2010 | Yamamoto et al. |
| 2010/0103075 A1 | 4/2010 | Kalaboukis et al. |
| 2010/0113062 A1 | 5/2010 | Lee et al. |
| 2010/0130140 A1 | 5/2010 | Waku et al. |
| 2010/0149073 A1 | 6/2010 | Chaum et al. |
| 2010/0178101 A1 | 7/2010 | Day et al. |
| 2010/0194682 A1 | 8/2010 | Orr et al. |
| 2010/0240988 A1 | 9/2010 | Varga et al. |
| 2010/0241450 A1 | 9/2010 | Gierhart et al. |
| 2010/0253594 A1 | 10/2010 | Szczerba et al. |
| 2010/0254017 A1 | 10/2010 | Martins et al. |
| 2010/0280904 A1 | 11/2010 | Ahuja |
| 2010/0283774 A1 | 11/2010 | Bovet et al. |
| 2010/0290127 A1 | 11/2010 | Kessler et al. |
| 2010/0309426 A1 | 12/2010 | Howell et al. |
| 2010/0329301 A1 | 12/2010 | Pang et al. |
| 2011/0006982 A1 | 1/2011 | Rhee et al. |
| 2011/0007081 A1 | 1/2011 | Gordon |
| 2011/0012874 A1 | 1/2011 | Kurozuka et al. |
| 2011/0089325 A1 | 4/2011 | Ottney |
| 2011/0090343 A1 | 4/2011 | Alt et al. |
| 2011/0096100 A1 | 4/2011 | Sprague et al. |
| 2011/0102234 A1 | 5/2011 | Adams et al. |
| 2011/0130958 A1 | 6/2011 | Stahl et al. |
| 2011/0131495 A1 | 6/2011 | Bull et al. |
| 2011/0157236 A1 | 6/2011 | Inoue et al. |
| 2011/0159931 A1 | 6/2011 | Boss et al. |
| 2011/0164047 A1 | 7/2011 | Pance et al. |
| 2011/0164163 A1 | 7/2011 | Bilbrey et al. |
| 2011/0164221 A1 | 7/2011 | Tilleman et al. |
| 2011/0176106 A1 | 7/2011 | Lewkowski et al. |
| 2011/0196610 A1 | 8/2011 | Waldman et al. |
| 2011/0199171 A1 | 8/2011 | Prest et al. |
| 2011/0201213 A1 | 8/2011 | Dabov et al. |
| 2011/0202823 A1 | 8/2011 | Berger et al. |
| 2011/0205209 A1 | 8/2011 | Kurokawa et al. |
| 2011/0213664 A1 | 9/2011 | Osterhout et al. |
| 2011/0221672 A1 | 9/2011 | Osterhout et al. |
| 2011/0221896 A1 | 9/2011 | Haddick et al. |
| 2011/0227820 A1 | 9/2011 | Haddick et al. |

(56) References Cited

U.S. PATENT DOCUMENTS

| | | |
|---|---|---|
| 2011/0228997 A1 | 9/2011 | Sharp et al. |
| 2011/0234631 A1 | 9/2011 | Kim et al. |
| 2011/0248963 A1 | 10/2011 | Lawrence et al. |
| 2011/0285638 A1 | 11/2011 | Harris et al. |
| 2011/0285764 A1 | 11/2011 | Kimura et al. |
| 2012/0026088 A1 | 2/2012 | Goran et al. |
| 2012/0032874 A1 | 2/2012 | Mukawa |
| 2012/0035934 A1 | 2/2012 | Cunningham et al. |
| 2012/0050140 A1 | 3/2012 | Border et al. |
| 2012/0050493 A1 | 3/2012 | Ernst et al. |
| 2012/0056093 A1 | 3/2012 | Poteet et al. |
| 2012/0062444 A1 | 3/2012 | Cok et al. |
| 2012/0062594 A1 | 3/2012 | Campbell et al. |
| 2012/0062850 A1 | 3/2012 | Travis |
| 2012/0062998 A1 | 3/2012 | Schultz et al. |
| 2012/0068913 A1 | 3/2012 | Bar-Zeev et al. |
| 2012/0069413 A1 | 3/2012 | Schultz et al. |
| 2012/0075168 A1 | 3/2012 | Osterhout et al. |
| 2012/0078628 A1 | 3/2012 | Ghulman et al. |
| 2012/0081800 A1 | 4/2012 | Cheng et al. |
| 2012/0092328 A1 | 4/2012 | Flaks et al. |
| 2012/0092329 A1 | 4/2012 | Koo et al. |
| 2012/0096095 A1 | 4/2012 | Bhargava et al. |
| 2012/0113514 A1 | 5/2012 | Rodman |
| 2012/0119978 A1 | 5/2012 | Bietry et al. |
| 2012/0120103 A1 | 5/2012 | Border et al. |
| 2012/0120498 A1 | 5/2012 | Harrison et al. |
| 2012/0127062 A1 | 5/2012 | Bar-Zeev et al. |
| 2012/0127284 A1 | 5/2012 | Bar-Zeev et al. |
| 2012/0133885 A1 | 5/2012 | Howell et al. |
| 2012/0154920 A1 | 6/2012 | Harrison et al. |
| 2012/0162270 A1 | 6/2012 | Fleck et al. |
| 2012/0163013 A1 | 6/2012 | Buelow, II et al. |
| 2012/0169608 A1 | 7/2012 | Forutanpour et al. |
| 2012/0176682 A1 | 7/2012 | DeJong et al. |
| 2012/0184252 A1 | 7/2012 | Hirsch et al. |
| 2012/0188245 A1 | 7/2012 | Hyatt et al. |
| 2012/0194550 A1 | 8/2012 | Osterhout et al. |
| 2012/0194553 A1 | 8/2012 | Osterhout et al. |
| 2012/0194784 A1 | 8/2012 | Shih et al. |
| 2012/0200935 A1 | 8/2012 | Miyao et al. |
| 2012/0206817 A1 | 8/2012 | Totani et al. |
| 2012/0212398 A1 | 8/2012 | Border et al. |
| 2012/0212484 A1 | 8/2012 | Haddick et al. |
| 2012/0212499 A1 | 8/2012 | Haddick et al. |
| 2012/0212593 A1 | 8/2012 | Na'aman et al. |
| 2012/0218301 A1 | 8/2012 | Miller |
| 2012/0223885 A1 | 9/2012 | Perez |
| 2012/0224060 A1 | 9/2012 | Gurevich et al. |
| 2012/0229367 A1 | 9/2012 | Magyari et al. |
| 2012/0233000 A1 | 9/2012 | Fisher et al. |
| 2012/0235885 A1 | 9/2012 | Miller et al. |
| 2012/0237085 A1 | 9/2012 | Meier et al. |
| 2012/0242251 A1 | 9/2012 | Kwisthout et al. |
| 2012/0242697 A1 | 9/2012 | Border et al. |
| 2012/0242698 A1 | 9/2012 | Haddick et al. |
| 2012/0249741 A1 | 10/2012 | Maciocci et al. |
| 2012/0249797 A1 | 10/2012 | Haddick et al. |
| 2012/0250152 A1 | 10/2012 | Larson et al. |
| 2012/0264510 A1 | 10/2012 | Wigdor et al. |
| 2012/0287398 A1 | 11/2012 | Baker et al. |
| 2012/0293548 A1 | 11/2012 | Perez et al. |
| 2012/0294478 A1 | 11/2012 | Publicover et al. |
| 2012/0306850 A1 | 12/2012 | Balan et al. |
| 2012/0307198 A1 | 12/2012 | Ifergan |
| 2012/0326948 A1 | 12/2012 | Crocco et al. |
| 2012/0327040 A1 | 12/2012 | Simon et al. |
| 2012/0327116 A1 | 12/2012 | Liu et al. |
| 2013/0009366 A1 | 1/2013 | Hannegan et al. |
| 2013/0009907 A1 | 1/2013 | Rosenberg et al. |
| 2013/0044042 A1 | 2/2013 | Olsson et al. |
| 2013/0063695 A1 | 3/2013 | Hsieh |
| 2013/0069924 A1 | 3/2013 | Robinson et al. |
| 2013/0069985 A1 | 3/2013 | Wong et al. |
| 2013/0070344 A1 | 3/2013 | Takeda et al. |
| 2013/0077049 A1 | 3/2013 | Bohn et al. |
| 2013/0083009 A1 | 4/2013 | Geisner et al. |
| 2013/0083055 A1 | 4/2013 | Piemonte et al. |
| 2013/0088413 A1 | 4/2013 | Raffle et al. |
| 2013/0100259 A1 | 4/2013 | Ramaswamy |
| 2013/0106674 A1 | 5/2013 | Wheeler et al. |
| 2013/0120224 A1 | 5/2013 | Cajigas et al. |
| 2013/0120841 A1 | 5/2013 | Shpunt et al. |
| 2013/0127906 A1 | 5/2013 | Sugita et al. |
| 2013/0127980 A1 | 5/2013 | Haddick |
| 2013/0135198 A1 | 5/2013 | Hodge et al. |
| 2013/0141434 A1 | 6/2013 | Sugden et al. |
| 2013/0154913 A1 | 6/2013 | Genc et al. |
| 2013/0162632 A1 | 6/2013 | Varga et al. |
| 2013/0169530 A1 | 7/2013 | Bhaskar et al. |
| 2013/0176533 A1 | 7/2013 | Raffle et al. |
| 2013/0185052 A1 | 7/2013 | Boyd et al. |
| 2013/0194389 A1 | 8/2013 | Vaught et al. |
| 2013/0196757 A1 | 8/2013 | Latta et al. |
| 2013/0201080 A1 | 8/2013 | Evans et al. |
| 2013/0201081 A1 | 8/2013 | Evans et al. |
| 2013/0207887 A1 | 8/2013 | Raffle et al. |
| 2013/0207970 A1 | 8/2013 | Shpunt et al. |
| 2013/0214909 A1 | 8/2013 | Meijers et al. |
| 2013/0215149 A1 | 8/2013 | Hayashi et al. |
| 2013/0215499 A1* | 8/2013 | Wang .................... G02B 5/284 359/359 |
| 2013/0222919 A1 | 8/2013 | Komatsu et al. |
| 2013/0230215 A1 | 9/2013 | Gurman et al. |
| 2013/0234914 A1 | 9/2013 | Fujimaki et al. |
| 2013/0235191 A1 | 9/2013 | Miao et al. |
| 2013/0235331 A1 | 9/2013 | Heinrich et al. |
| 2013/0241805 A1 | 9/2013 | Gomez et al. |
| 2013/0241948 A1 | 9/2013 | Kimura |
| 2013/0242405 A1 | 9/2013 | Gupta et al. |
| 2013/0248691 A1 | 9/2013 | Mirov et al. |
| 2013/0249778 A1 | 9/2013 | Morimoto et al. |
| 2013/0249787 A1 | 9/2013 | Morimoto |
| 2013/0250207 A1 | 9/2013 | Bohn et al. |
| 2013/0250430 A1 | 9/2013 | Robbins et al. |
| 2013/0250503 A1 | 9/2013 | Olsson et al. |
| 2013/0257622 A1 | 10/2013 | Davalos et al. |
| 2013/0257709 A1 | 10/2013 | Raffle et al. |
| 2013/0258111 A1 | 10/2013 | Frank et al. |
| 2013/0265212 A1 | 10/2013 | Kato et al. |
| 2013/0265227 A1 | 10/2013 | Julian et al. |
| 2013/0278631 A1 | 10/2013 | Border et al. |
| 2013/0293530 A1 | 11/2013 | Perez et al. |
| 2013/0293580 A1 | 11/2013 | Spivack et al. |
| 2013/0300637 A1 | 11/2013 | Smits et al. |
| 2013/0300652 A1 | 11/2013 | Raffle et al. |
| 2013/0321265 A1 | 12/2013 | Bychkov et al. |
| 2013/0321271 A1 | 12/2013 | Bychkov et al. |
| 2013/0321641 A1 | 12/2013 | McManus et al. |
| 2013/0321932 A1 | 12/2013 | Hsu et al. |
| 2013/0335301 A1 | 12/2013 | Wong et al. |
| 2013/0335435 A1 | 12/2013 | Ambrus et al. |
| 2013/0335461 A1 | 12/2013 | Rekimoto et al. |
| 2013/0336528 A1 | 12/2013 | Itani et al. |
| 2013/0336629 A1 | 12/2013 | Mulholland et al. |
| 2013/0342564 A1 | 12/2013 | Kinnebrew et al. |
| 2013/0342571 A1 | 12/2013 | Kinnebrew et al. |
| 2013/0342981 A1 | 12/2013 | Cox et al. |
| 2013/0346245 A1 | 12/2013 | Desore et al. |
| 2014/0028704 A1 | 1/2014 | Wu et al. |
| 2014/0043682 A1 | 2/2014 | Hussey et al. |
| 2014/0062854 A1 | 3/2014 | Cho |
| 2014/0063054 A1 | 3/2014 | Osterhout et al. |
| 2014/0063055 A1 | 3/2014 | Osterhout et al. |
| 2014/0063473 A1 | 3/2014 | Pasolini |
| 2014/0078043 A1 | 3/2014 | Kim et al. |
| 2014/0078282 A1 | 3/2014 | Aoki et al. |
| 2014/0091984 A1 | 4/2014 | Ashbrook et al. |
| 2014/0101608 A1 | 4/2014 | Ryskamp et al. |
| 2014/0104142 A1 | 4/2014 | Bickerstaff et al. |
| 2014/0104692 A1 | 4/2014 | Bickerstaff et al. |
| 2014/0125668 A1 | 5/2014 | Steed et al. |
| 2014/0125785 A1 | 5/2014 | Na et al. |
| 2014/0129328 A1 | 5/2014 | Mathew |

(56) References Cited

U.S. PATENT DOCUMENTS

| | | |
|---|---|---|
| 2014/0139655 A1 | 5/2014 | Mimar |
| 2014/0146394 A1 | 5/2014 | Tout et al. |
| 2014/0147829 A1 | 5/2014 | Jerauld |
| 2014/0152530 A1 | 6/2014 | Venkatesha et al. |
| 2014/0152558 A1 | 6/2014 | Salter et al. |
| 2014/0152676 A1 | 6/2014 | Rohn et al. |
| 2014/0153173 A1 | 6/2014 | Pombo et al. |
| 2014/0159995 A1 | 6/2014 | Adams et al. |
| 2014/0160055 A1 | 6/2014 | Margolis et al. |
| 2014/0160137 A1 | 6/2014 | Martin et al. |
| 2014/0160157 A1 | 6/2014 | Poulos et al. |
| 2014/0160170 A1 | 6/2014 | Lyons |
| 2014/0168056 A1 | 6/2014 | Swaminathan et al. |
| 2014/0168266 A1 | 6/2014 | Kimura et al. |
| 2014/0168716 A1 | 6/2014 | King et al. |
| 2014/0168735 A1 | 6/2014 | Yuan et al. |
| 2014/0176591 A1 | 6/2014 | Klein et al. |
| 2014/0176603 A1 | 6/2014 | Kumar et al. |
| 2014/0177023 A1 | 6/2014 | Gao et al. |
| 2014/0183269 A1 | 7/2014 | Glaser et al. |
| 2014/0204759 A1 | 7/2014 | Orlik et al. |
| 2014/0213280 A1 | 7/2014 | Sandel et al. |
| 2014/0222929 A1 | 8/2014 | Grossman et al. |
| 2014/0225814 A1 | 8/2014 | English et al. |
| 2014/0225916 A1* | 8/2014 | Theimer ............... G06T 19/006 345/633 |
| 2014/0232651 A1 | 8/2014 | Kress et al. |
| 2014/0240313 A1 | 8/2014 | Varga |
| 2014/0247286 A1 | 9/2014 | Chi et al. |
| 2014/0253588 A1 | 9/2014 | Mandela et al. |
| 2014/0253605 A1 | 9/2014 | Border et al. |
| 2014/0267010 A1 | 9/2014 | Pasquero et al. |
| 2014/0275760 A1* | 9/2014 | Lee ................... A61B 1/00045 600/102 |
| 2014/0285631 A1 | 9/2014 | Janky et al. |
| 2014/0306866 A1 | 10/2014 | Miller et al. |
| 2014/0310075 A1 | 10/2014 | Ricci et al. |
| 2014/0320389 A1 | 10/2014 | Scavezze et al. |
| 2014/0320971 A1 | 10/2014 | Gupta et al. |
| 2014/0341441 A1 | 11/2014 | Slaby et al. |
| 2014/0351896 A1* | 11/2014 | Koo ........................ G06F 21/62 726/4 |
| 2014/0361957 A1 | 12/2014 | Hua et al. |
| 2014/0361976 A1 | 12/2014 | Mao et al. |
| 2014/0362110 A1 | 12/2014 | Stafford |
| 2014/0362195 A1 | 12/2014 | Ng-thow-hing et al. |
| 2014/0363797 A1 | 12/2014 | Hu et al. |
| 2014/0372957 A1 | 12/2014 | Kipman et al. |
| 2014/0375542 A1 | 12/2014 | Bohn et al. |
| 2014/0375545 A1 | 12/2014 | Finocchio et al. |
| 2014/0375680 A1 | 12/2014 | Ackerman et al. |
| 2014/0375683 A1 | 12/2014 | Massey et al. |
| 2015/0002371 A1 | 1/2015 | Herrod et al. |
| 2015/0022542 A1 | 1/2015 | Baba |
| 2015/0029088 A1 | 1/2015 | Kim et al. |
| 2015/0035744 A1 | 2/2015 | Robbins et al. |
| 2015/0042544 A1 | 2/2015 | Sugihara et al. |
| 2015/0097719 A1 | 4/2015 | Balachandreswaran et al. |
| 2015/0134143 A1 | 5/2015 | Willenborg |
| 2015/0143297 A1 | 5/2015 | Wheeler et al. |
| 2015/0145839 A1 | 5/2015 | Hack et al. |
| 2015/0146004 A1 | 5/2015 | Kritt et al. |
| 2015/0147000 A1 | 5/2015 | Salvador et al. |
| 2015/0161913 A1 | 6/2015 | Dominguez et al. |
| 2015/0169953 A1 | 6/2015 | Border |
| 2015/0175068 A1 | 6/2015 | Szostak et al. |
| 2015/0178932 A1 | 6/2015 | Wyatt et al. |
| 2015/0181383 A1 | 6/2015 | Schulz et al. |
| 2015/0186636 A1 | 7/2015 | Tharappel et al. |
| 2015/0198807 A1 | 7/2015 | Hirai |
| 2015/0201834 A1 | 7/2015 | Border et al. |
| 2015/0201835 A1 | 7/2015 | Border et al. |
| 2015/0201836 A1 | 7/2015 | Border et al. |
| 2015/0202962 A1 | 7/2015 | Habashima et al. |
| 2015/0205035 A1 | 7/2015 | Border et al. |
| 2015/0205100 A1 | 7/2015 | Border |
| 2015/0205101 A1 | 7/2015 | Border |
| 2015/0205102 A1 | 7/2015 | Border |
| 2015/0205103 A1 | 7/2015 | Border |
| 2015/0205104 A1 | 7/2015 | Border |
| 2015/0205105 A1 | 7/2015 | Border |
| 2015/0205107 A1 | 7/2015 | Border |
| 2015/0205108 A1 | 7/2015 | Border et al. |
| 2015/0205111 A1 | 7/2015 | Border et al. |
| 2015/0205112 A1 | 7/2015 | Border |
| 2015/0205113 A1 | 7/2015 | Border et al. |
| 2015/0205114 A1 | 7/2015 | Border et al. |
| 2015/0205115 A1 | 7/2015 | Border et al. |
| 2015/0205116 A1 | 7/2015 | Border et al. |
| 2015/0205117 A1 | 7/2015 | Border et al. |
| 2015/0205118 A1 | 7/2015 | Border et al. |
| 2015/0205119 A1 | 7/2015 | Osterhout et al. |
| 2015/0205120 A1 | 7/2015 | Border et al. |
| 2015/0205121 A1 | 7/2015 | Border et al. |
| 2015/0205122 A1 | 7/2015 | Border et al. |
| 2015/0205123 A1 | 7/2015 | Border |
| 2015/0205124 A1 | 7/2015 | Border |
| 2015/0205125 A1 | 7/2015 | Border et al. |
| 2015/0205126 A1 | 7/2015 | Schowengerdt |
| 2015/0205127 A1 | 7/2015 | Border et al. |
| 2015/0205128 A1 | 7/2015 | Border |
| 2015/0205129 A1 | 7/2015 | Border et al. |
| 2015/0205130 A1 | 7/2015 | Border |
| 2015/0205131 A1 | 7/2015 | Border et al. |
| 2015/0205132 A1 | 7/2015 | Osterhout et al. |
| 2015/0205135 A1 | 7/2015 | Border et al. |
| 2015/0205346 A1 | 7/2015 | Border |
| 2015/0205347 A1 | 7/2015 | Border |
| 2015/0205348 A1 | 7/2015 | Nortrup et al. |
| 2015/0205349 A1 | 7/2015 | Nortrup et al. |
| 2015/0205351 A1 | 7/2015 | Osterhout et al. |
| 2015/0205373 A1 | 7/2015 | Osterhout et al. |
| 2015/0205378 A1 | 7/2015 | Osterhout |
| 2015/0205384 A1 | 7/2015 | Osterhout et al. |
| 2015/0205385 A1 | 7/2015 | Osterhout et al. |
| 2015/0205387 A1 | 7/2015 | Osterhout et al. |
| 2015/0205388 A1 | 7/2015 | Osterhout |
| 2015/0205401 A1 | 7/2015 | Osterhout |
| 2015/0205402 A1 | 7/2015 | Osterhout |
| 2015/0205494 A1 | 7/2015 | Scott et al. |
| 2015/0205566 A1 | 7/2015 | Osterhout |
| 2015/0206008 A1 | 7/2015 | Border et al. |
| 2015/0206173 A1 | 7/2015 | Nortrup et al. |
| 2015/0212324 A1 | 7/2015 | Osterhout |
| 2015/0212327 A1 | 7/2015 | Osterhout et al. |
| 2015/0213584 A1 | 7/2015 | Ishikawa et al. |
| 2015/0213650 A1 | 7/2015 | Barzuza et al. |
| 2015/0213754 A1 | 7/2015 | Amjad |
| 2015/0226966 A1 | 8/2015 | Osterhout |
| 2015/0226967 A1 | 8/2015 | Osterhout et al. |
| 2015/0228099 A1 | 8/2015 | Osterhout |
| 2015/0228119 A1 | 8/2015 | Osterhout et al. |
| 2015/0228120 A1 | 8/2015 | Osterhout et al. |
| 2015/0229019 A1 | 8/2015 | Osterhout |
| 2015/0234508 A1 | 8/2015 | Cho et al. |
| 2015/0235422 A1 | 8/2015 | Lohse et al. |
| 2015/0235429 A1 | 8/2015 | Miller et al. |
| 2015/0235622 A1 | 8/2015 | Border et al. |
| 2015/0241963 A1 | 8/2015 | Nortrup et al. |
| 2015/0241964 A1 | 8/2015 | Nortrup et al. |
| 2015/0241965 A1 | 8/2015 | Nortrup et al. |
| 2015/0241966 A1 | 8/2015 | Nortrup et al. |
| 2015/0243039 A1 | 8/2015 | Holz |
| 2015/0245131 A1 | 8/2015 | Facteau et al. |
| 2015/0253573 A1 | 9/2015 | Sako et al. |
| 2015/0257735 A1* | 9/2015 | Ball ..................... A61B 8/5261 600/440 |
| 2015/0260887 A1 | 9/2015 | Salisbury et al. |
| 2015/0260986 A1 | 9/2015 | Nortrup |
| 2015/0261015 A1 | 9/2015 | Ha et al. |
| 2015/0277113 A1 | 10/2015 | Border et al. |
| 2015/0277116 A1 | 10/2015 | Richards et al. |
| 2015/0277118 A1 | 10/2015 | Border et al. |
| 2015/0277120 A1 | 10/2015 | Border |

(56) References Cited

U.S. PATENT DOCUMENTS

| | | |
|---|---|---|
| 2015/0277122 A1 | 10/2015 | Border |
| 2015/0277549 A1 | 10/2015 | Border |
| 2015/0277559 A1 | 10/2015 | Vescovi |
| 2015/0279010 A1 | 10/2015 | Cianfrone et al. |
| 2015/0279104 A1 | 10/2015 | Border et al. |
| 2015/0279107 A1 | 10/2015 | Border et al. |
| 2015/0279108 A1 | 10/2015 | Border |
| 2015/0287048 A1 | 10/2015 | Nortrup et al. |
| 2015/0293587 A1 | 10/2015 | Wilairat et al. |
| 2015/0294156 A1 | 10/2015 | Border et al. |
| 2015/0294627 A1 | 10/2015 | Yoo et al. |
| 2015/0301593 A1 | 10/2015 | Border et al. |
| 2015/0302646 A1 | 10/2015 | Osterhout et al. |
| 2015/0302647 A1 | 10/2015 | Osterhout et al. |
| 2015/0304368 A1 | 10/2015 | Vaccari et al. |
| 2015/0309313 A1 | 10/2015 | Border et al. |
| 2015/0309314 A1 | 10/2015 | Border et al. |
| 2015/0309317 A1 | 10/2015 | Osterhout et al. |
| 2015/0309534 A1 | 10/2015 | Osterhout |
| 2015/0309562 A1 | 10/2015 | Shams et al. |
| 2015/0309995 A1 | 10/2015 | Osterhout |
| 2015/0316766 A1 | 11/2015 | Weaver et al. |
| 2015/0316769 A1 | 11/2015 | Border et al. |
| 2015/0316770 A1 | 11/2015 | Border et al. |
| 2015/0316771 A1 | 11/2015 | Border et al. |
| 2015/0316772 A1 | 11/2015 | Border et al. |
| 2015/0331241 A1 | 11/2015 | Haddick et al. |
| 2015/0332032 A1 | 11/2015 | Alameh et al. |
| 2015/0338661 A1 | 11/2015 | Osterhout et al. |
| 2015/0346496 A1 | 12/2015 | Haddick et al. |
| 2015/0346511 A1 | 12/2015 | Osterhout et al. |
| 2015/0347823 A1 | 12/2015 | Monnerat et al. |
| 2015/0355466 A1 | 12/2015 | Border |
| 2015/0355468 A1 | 12/2015 | Osterhout et al. |
| 2015/0356772 A1 | 12/2015 | Osterhout et al. |
| 2015/0356775 A1 | 12/2015 | Osterhout et al. |
| 2015/0356776 A1 | 12/2015 | Osterhout et al. |
| 2015/0356777 A1 | 12/2015 | Osterhout et al. |
| 2015/0356778 A1 | 12/2015 | Osterhout et al. |
| 2015/0356779 A1 | 12/2015 | Osterhout et al. |
| 2015/0363975 A1 | 12/2015 | Osterhout et al. |
| 2015/0363979 A1* | 12/2015 | Takano .......... A61B 6/461 345/633 |
| 2015/0382305 A1 | 12/2015 | Drincic |
| 2016/0005003 A1 | 1/2016 | Norris et al. |
| 2016/0011417 A1 | 1/2016 | Border et al. |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0018644 A1 | 1/2016 | Border et al. |
| 2016/0018645 A1 | 1/2016 | Haddick et al. |
| 2016/0018646 A1 | 1/2016 | Osterhout et al. |
| 2016/0018647 A1 | 1/2016 | Osterhout et al. |
| 2016/0018648 A1 | 1/2016 | Osterhout et al. |
| 2016/0018649 A1 | 1/2016 | Osterhout et al. |
| 2016/0018650 A1 | 1/2016 | Haddick et al. |
| 2016/0018651 A1 | 1/2016 | Haddick et al. |
| 2016/0018652 A1 | 1/2016 | Haddick et al. |
| 2016/0018653 A1 | 1/2016 | Haddick et al. |
| 2016/0018654 A1 | 1/2016 | Haddick et al. |
| 2016/0019715 A1 | 1/2016 | Haddick et al. |
| 2016/0019719 A1 | 1/2016 | Osterhout et al. |
| 2016/0021304 A1 | 1/2016 | Osterhout |
| 2016/0025974 A1 | 1/2016 | Osterhout et al. |
| 2016/0025977 A1 | 1/2016 | Osterhout |
| 2016/0025979 A1 | 1/2016 | Border et al. |
| 2016/0025980 A1 | 1/2016 | Osterhout et al. |
| 2016/0026239 A1 | 1/2016 | Border et al. |
| 2016/0027211 A1 | 1/2016 | Osterhout et al. |
| 2016/0027414 A1 | 1/2016 | Osterhout et al. |
| 2016/0035139 A1 | 2/2016 | Fuchs et al. |
| 2016/0045810 A1 | 2/2016 | Minkovitch |
| 2016/0048018 A1 | 2/2016 | De Matos |
| 2016/0048019 A1 | 2/2016 | Haddick et al. |
| 2016/0048021 A1 | 2/2016 | Border |
| 2016/0048023 A1 | 2/2016 | Haddick et al. |
| 2016/0048160 A1 | 2/2016 | Haddick et al. |
| 2016/0049008 A1 | 2/2016 | Haddick et al. |
| 2016/0054566 A1 | 2/2016 | Osterhout et al. |
| 2016/0055675 A1 | 2/2016 | Kasahara et al. |
| 2016/0062118 A1 | 3/2016 | Osterhout |
| 2016/0062121 A1 | 3/2016 | Border et al. |
| 2016/0062122 A1 | 3/2016 | Border |
| 2016/0077342 A1 | 3/2016 | Osterhout et al. |
| 2016/0085071 A1 | 3/2016 | Border |
| 2016/0085072 A1 | 3/2016 | Haddick et al. |
| 2016/0085278 A1 | 3/2016 | Osterhout et al. |
| 2016/0091718 A1 | 3/2016 | Border et al. |
| 2016/0091719 A1 | 3/2016 | Border |
| 2016/0109709 A1 | 4/2016 | Osterhout |
| 2016/0109711 A1 | 4/2016 | Border |
| 2016/0109713 A1 | 4/2016 | Osterhout |
| 2016/0116738 A1 | 4/2016 | Osterhout et al. |
| 2016/0116745 A1 | 4/2016 | Osterhout et al. |
| 2016/0116979 A1 | 4/2016 | Border |
| 2016/0131904 A1 | 5/2016 | Border et al. |
| 2016/0131911 A1 | 5/2016 | Border et al. |
| 2016/0131912 A1 | 5/2016 | Border et al. |
| 2016/0132082 A1 | 5/2016 | Border et al. |
| 2016/0133201 A1 | 5/2016 | Border et al. |
| 2016/0137312 A1 | 5/2016 | Osterhout |
| 2016/0147063 A1 | 5/2016 | Border et al. |
| 2016/0147064 A1 | 5/2016 | Border et al. |
| 2016/0147065 A1 | 5/2016 | Border et al. |
| 2016/0147070 A1 | 5/2016 | Border et al. |
| 2016/0154242 A1 | 6/2016 | Border |
| 2016/0154244 A1 | 6/2016 | Border et al. |
| 2016/0161743 A1 | 6/2016 | Osterhout et al. |
| 2016/0161747 A1 | 6/2016 | Osterhout |
| 2016/0170207 A1 | 6/2016 | Haddick et al. |
| 2016/0170208 A1 | 6/2016 | Border et al. |
| 2016/0170209 A1 | 6/2016 | Border et al. |
| 2016/0170699 A1 | 6/2016 | Border et al. |
| 2016/0171769 A1 | 6/2016 | Haddick et al. |
| 2016/0187651 A1 | 6/2016 | Border et al. |
| 2016/0187658 A1 | 6/2016 | Osterhout et al. |
| 2016/0202946 A1 | 7/2016 | Osterhout et al. |
| 2016/0207457 A1 | 7/2016 | Border et al. |
| 2016/0216516 A1 | 7/2016 | Border |
| 2016/0216517 A1 | 7/2016 | Border |
| 2016/0225192 A1* | 8/2016 | Jones .............. G06F 3/012 |
| 2016/0231571 A1 | 8/2016 | Border et al. |
| 2016/0239985 A1 | 8/2016 | Haddick et al. |
| 2016/0240008 A1 | 8/2016 | Haddick et al. |
| 2016/0246055 A1 | 8/2016 | Border et al. |
| 2016/0252731 A1 | 9/2016 | Border et al. |
| 2016/0259166 A1 | 9/2016 | Border et al. |
| 2016/0274361 A1 | 9/2016 | Border et al. |
| 2016/0274365 A1 | 9/2016 | Bailey et al. |
| 2016/0282626 A1 | 9/2016 | Border et al. |
| 2016/0286177 A1 | 9/2016 | Border et al. |
| 2016/0286203 A1 | 9/2016 | Border et al. |
| 2016/0286210 A1 | 9/2016 | Border et al. |
| 2016/0302870 A1* | 10/2016 | Wilkinson ........ A61B 17/1764 |
| 2016/0306173 A1 | 10/2016 | Tsukahara et al. |
| 2016/0329634 A1 | 11/2016 | Osterhout et al. |
| 2016/0357019 A1 | 12/2016 | Border et al. |
| 2017/0318235 A1* | 11/2017 | Schneider ........ G02B 27/2228 |
| 2018/0130548 A1 | 5/2018 | Fisher |
| 2018/0185665 A1 | 7/2018 | Osterhout et al. |

FOREIGN PATENT DOCUMENTS

| | | |
|---|---|---|
| EP | 777867 A1 | 6/1997 |
| EP | 1326121 A2 | 7/2003 |
| EP | 2207164 A2 | 7/2010 |
| EP | 2486450 A1 | 8/2012 |
| EP | 2490130 A1 | 8/2012 |
| EP | 2502410 A1 | 9/2012 |
| EP | 2674834 A2 | 12/2013 |
| GB | 2491984 A | 12/2012 |
| JP | 07110735 A | 4/1995 |
| JP | 2000102036 A | 4/2000 |
| JP | 2005138755 A | 6/2005 |

(56) References Cited

FOREIGN PATENT DOCUMENTS

| | | |
|---|---|---|
| JP | 2009171505 A | 7/2009 |
| JP | 5017989 B2 | 9/2012 |
| JP | 2012212990 A | 11/2012 |
| KR | 1020110101944 A | 9/2011 |
| WO | 2011143655 A1 | 11/2011 |
| WO | 2012040030 A2 | 3/2012 |
| WO | 2012058175 A1 | 5/2012 |
| WO | 2012064546 A1 | 5/2012 |
| WO | 2012082807 A2 | 6/2012 |
| WO | 2012118573 A1 | 9/2012 |
| WO | 2012118575 A2 | 9/2012 |
| WO | 2013043288 A2 | 3/2013 |
| WO | 2013049248 A2 | 4/2013 |
| WO | 2013050650 A1 | 4/2013 |
| WO | 2013103825 A1 | 7/2013 |
| WO | 2013110846 A1 | 8/2013 |
| WO | 2013170073 A1 | 11/2013 |
| WO | 2013176079 A1 | 11/2013 |
| WO | 2015/109145 A1 | 7/2015 |
| WO | 2015109145 A9 | 7/2015 |
| WO | 2015164276 A1 | 10/2015 |
| WO | 2015175681 A1 | 11/2015 |
| WO | 2015179877 A2 | 11/2015 |
| WO | 2015179877 A3 | 11/2015 |
| WO | 2015195444 A1 | 12/2015 |
| WO | 2016/044035 | 3/2016 |
| WO | 2016073734 A1 | 5/2016 |
| WO | 2016133886 A1 | 8/2016 |

OTHER PUBLICATIONS

US 8,792,178 B2, 07/2014, Totani et al. (withdrawn)
US 9,195,056 B2, 11/2015, Border et al. (withdrawn)
Meeks, Optically Guided Patient Positioning Techniques, Semin Radiat Oncol, 2005, p. 15:192-201.*
Wikipedia, Motion capture, URL: https://en.wikipedia.org/w/index.php?title=Motion_capture&oldid=562563895 (Year: 2013).*
Sigal, Lecture 3 (Marker-based) Motion Capture, URL: http://www.cs.cmu.edu/~yaser/Lecture-3-MarkerBasedMocap.pdf Feb. 2012, p. 114 (Year: 2012).*
"Audio Spotlight", by Holosonics, http://www.holosonics.com, accessed Jul. 3, 2014, 3 pages.
"Genius Ring Mice", http://www.geniusnet.com/Genius/wSite/productCompare/compare.jsp, Dec. 23, 2014, 1 page.
"Help Requested! Comments and input needed for new coaxial UAS-DIY Drones", http://diydrones.com/profiles/blogs/help-requested-comments-and-input-needed-for-new-coaxial-uas, Mar. 05, 2015, pp. 1-3.
"How Ascent AeroSystems is looking to add to your outdoor adventure", http://droneblog.com/2015/03/23/how-ascent-aerosystems-is-looking-to-add-to-your-outdoor-adventure/#!prettyPhoto, Mar. 23, 2015, 1-10.
"Lightberry", https://web.archive.org/web/20131201194408/http:1/lightberry.eu/, Dec. 1, 2013, 11 Pages.
"Meet Nod, the Bluetooth Ring That Wants to Replace Your Mouse", http://www.pcmag.com/article2/0,2817,2457238,00.asp, Apr. 29, 2014, 6 pages.
"Sound from Ultrasound", Wikipedia entry, http://en.m.wikipedia.org/wiki/Sound_from_ultrasound, accessed Jul. 3, 2014, 13 pages.
Allison, Robert S. et al., ""Tolerance of Temporal Delay in Virtual Environments"", VR '01 Proceedings of the Virtual Reality 2001 Conference (VR'01), Centre for Vision Research and Departments of Computer Science and Psychology, Mar. 2001, 2-8.
Bezryadin, Sergey et al., "Brightness Calculation in Digital Image Processing", Technologies for Digital Fulfillment 2007, Las Vegas, NV, 2007, pp. 1-6.
Fathi, Alircza et al., "Social interactions: A first-person perspective.", Computer Vision and Pattern Recognition (CVPR), IEEE Conference on. IEEE, 2012., 2012, 8 Pages.

Huang, Jin-Bin, "Image Completion Using Planar Structure Guidelines", ACM Transactions on Graphics, vol. 33, No. 4, Article 129, Jul. 2014, pp. 1-10.
Janin, Adam L. et al., "Calibration of Head-Mounted Displays for Augmented Reality Applications", Research and Technology Boeing Computer Services MS 7L-48 P.O. Box 24346 Seattle, WA 98124-0346 Virtual Reality Annual International Symposium, 1993., 1993 IEEE,, 1993, 10 Pages.
Lang, Manuel et al., "Nonlinear Disparity Mapping for Stereoscopic 3D", Jul. 2010, pp. 1-10.
Logbar Inc., "Ring: Shortcut Everything", https://www.kickstarter.com/projects/1761670738/ring-shortcut-everything, Jun. 2012, 1 page.
Losev, Oleg et al., "Light-emitting diode", Nov. 2016, https://en.wikipedia.org/wiki/Lightemitting_diode, pp. 1-25.
Mastandrea, Nick , "Mycestro, The Next Generation 3D Mouse", https://www.kickstarter.com/projects/mycestro/mycestrotm-the-next-generation-3d-mouse, Dec. 2014, 22 pages.
Pamplona, Vitor R. et al., "Photorealistic Models for Pupil Light Reflex and Iridal Pattern Deformation", ACM Transactions on Graphics, vol. 28, No. 4, Article 106, Publication date: Aug. 2009, pp. 1-12.
PCT/US2015/011697, "International Application Serial No. PCT/US2015/011697, International Search Report and Written Opinion dated Apr. 13, 2015", Osterhout Group, Inc., 14 pages.
PCT/US2015/011697, "International Application Serial No. PCT/US2015/011697, International Preliminary Report on Patentability and Written Opinion dated Jul. 28, 2016", Osterhout Group, Inc., 10 pages.
PCT/US2015/026704, "International Application Serial No. PCT/US2015/026704, International Preliminary Report on Patentability and Written Opinion dated Nov. 3, 2016", Osterhout Group, Inc., 10 Pages.
PCT/US2015/026704, "International Search Report and Written Opinion", Osterhout Group, Inc., 15 pages.
PCT/US2015/033379, "International Application serial No. PCT/US2015/033379, International Preliminary Report on Patentability and Written Opinion dated Dec. 1, 2016", Osterhout Group, Inc., 8 Pages.
PCT/US2015/035192, "International Application Serial No. PCT/US2015/035192, International Search Report and Written Opinion dated Sep. 3, 2015", Osterhout Group, Inc., 11 pages.
PCT/US2015/059264, "International Application Serial No. PCT/US2015/059264, International Search Report and Written Opinion dated Feb. 19, 2016", Osterhout Group, Inc., 11 Pages.
PCT/US2016/018040, "International Application Serial No. PCT/US2016/018040, International Search Report and Written Opinion dated Jul. 6, 2016", Osterhout Group, Inc., 10 pages.
PCT/US2016/038008, "Application Serial No. PCT/US2016/038008, International Search Report and Written Opinion dated Oct. 27, 2016", Osterhout Group, Inc., 8 pages.
PCT/US2016/042440, "Application Serial No. PCT/US2016/042440, The International Search Report and Written Opinion dated Oct. 13, 2016", Osterhout Group, Inc., 7 pages.
PCTUS2015033379, "International Application Serial No. PCT/US2015/033379, International Search Report and Written Opinion dated Nov. 30, 2015", Osterhout Group, Inc., 12 Pages.
Plainis, Sotiris et al., "The Physiologic Mechanism of Accommodation", Cataract & Refractive Surgery Today Europe, Apr. 2014, pp. 23-29.
Walton, Zach , "Wear This Smartphone Controller on Your Finger", http://www.webpronews.com/wear-this-smartphone-controller-on-your-finger-2012-06, 5 pages.
Ye, Hui et al., "High Quality Voice Morphing", Cambridge University Engineering Department Trumpington Street, Cambridge, England, CB2 1PZ, 2004, pp. I-9-I-11.
Losev, et al., "Light-emitting diode", pp. 1-25.
Schedwill, "Bidirectional OLED Microdisplay", Fraunhofer Research Institution for Organics, Materials and Electronic Device Comedd, Apr. 11, 2014, 2 pages.
Vogel, et al., "Data glasses controlled by eye movements", Information and communication, Fraunhofer-Gesellschaft, Sep. 22, 2013, 2 pages.

(56) References Cited

OTHER PUBLICATIONS

"Thermal Imaging Camera for Scanning Elevated Body Temperatures", Nov. 2016, pp. 1-2.
Huang, et al., "The Application of Infrared Thermography in Evaluation of Patients at High Risk for Lower Extremity Peripheral Arterial Disease", Journal of Vascular Surgery, 2011, pp. 1074-1080.
Final Office Action dated Jan. 13, 2017, for U.S. Appl. No. 14/331,481, filed Jul. 15, 2014, 14 pages.
Non-Final Office Action dated Aug. 10, 2017, for U.S. Appl. No. 14/331,481, filed Jul. 15, 2014, 12 pages.
Non-Final Office Action dated Jun. 2, 2016, for U.S. Appl. No. 14/331,481, filed Jul. 15, 2014, 14 pages.

* cited by examiner

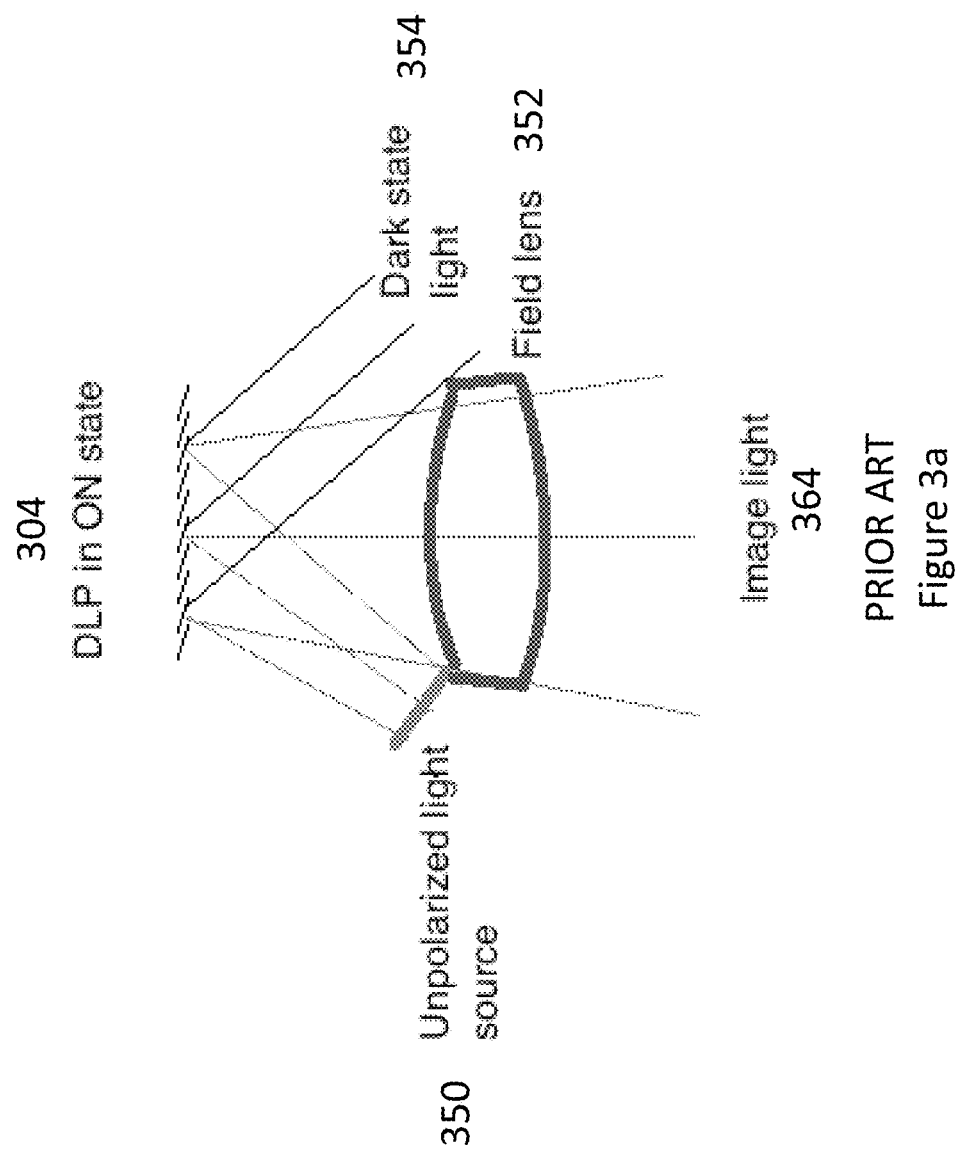

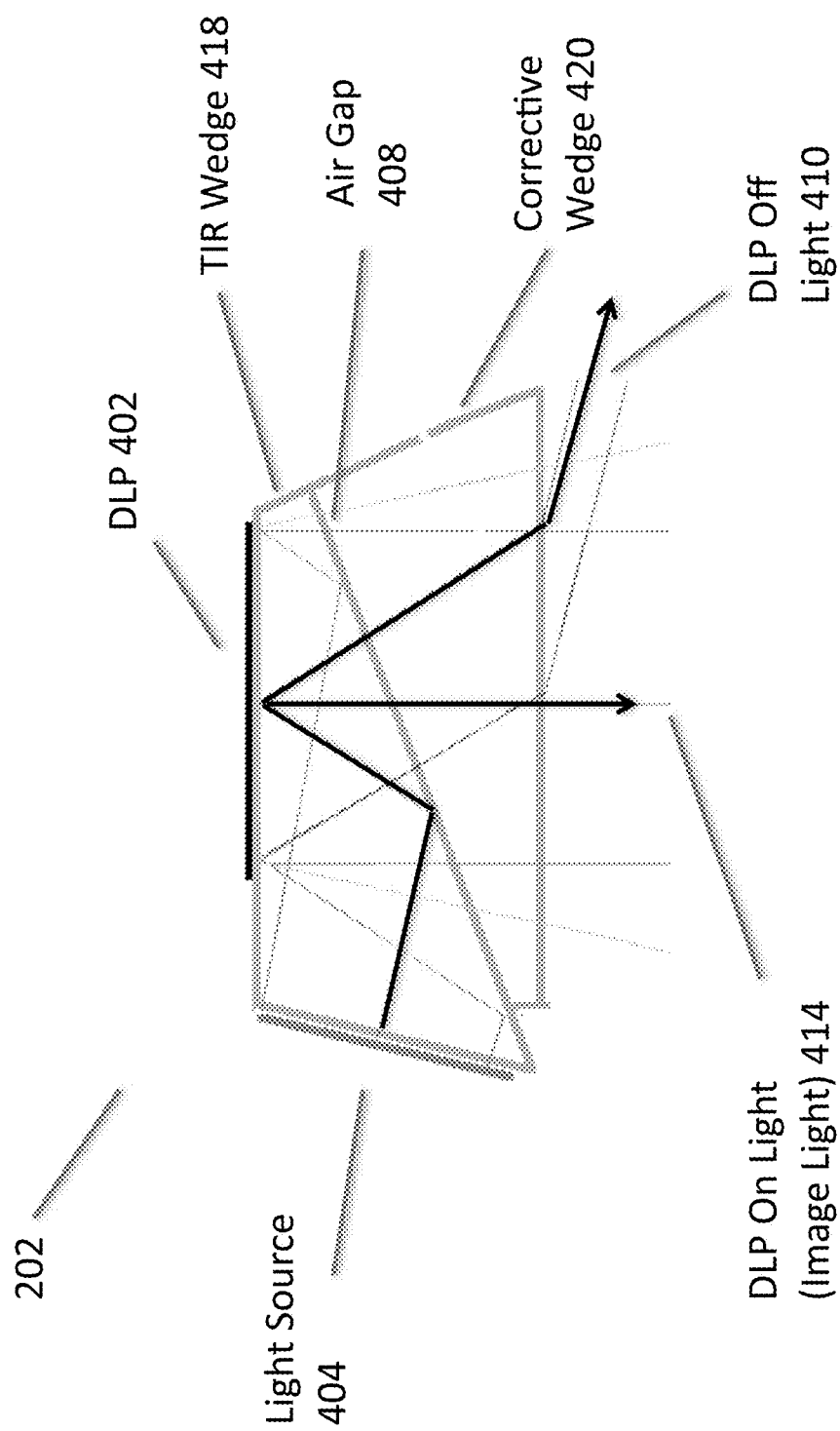

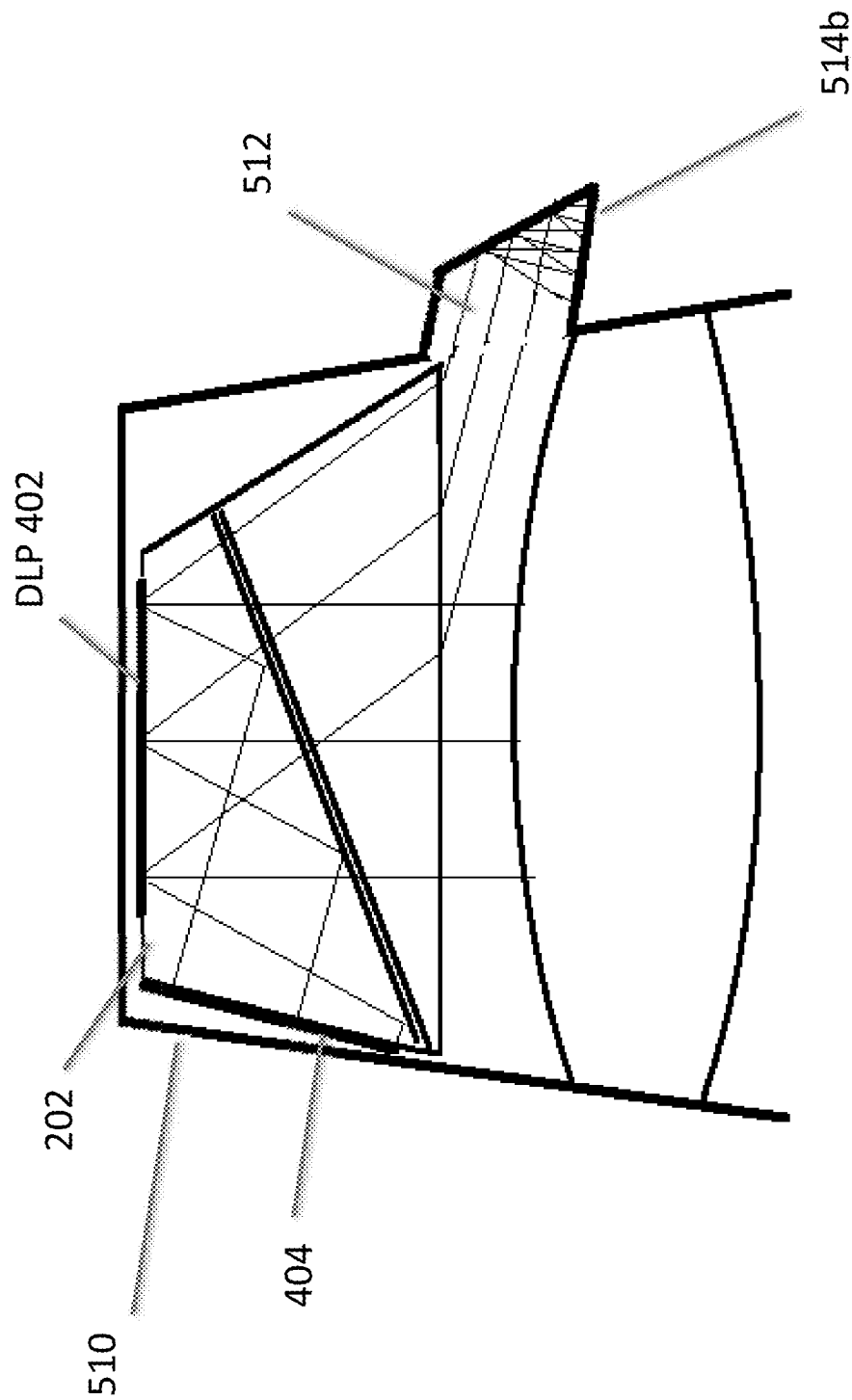

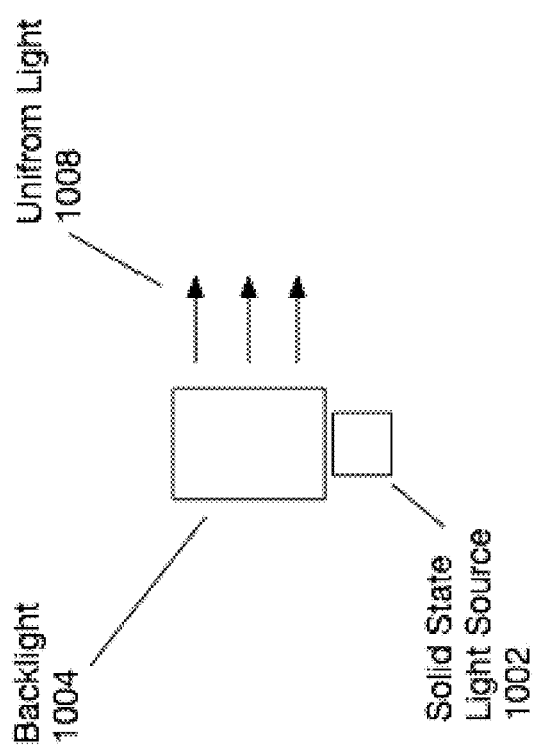

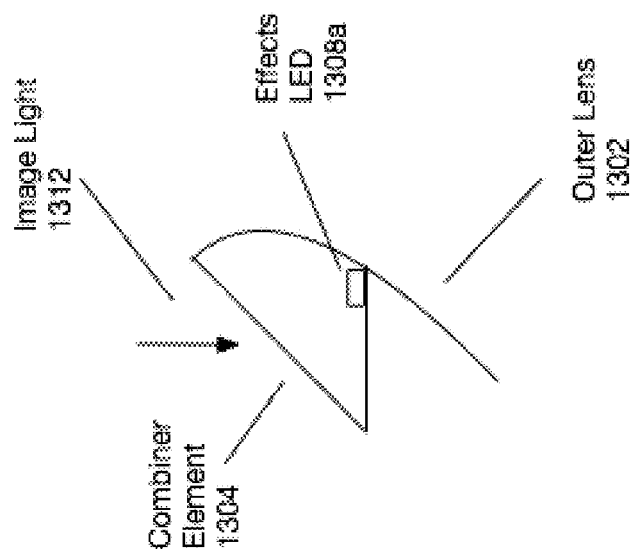

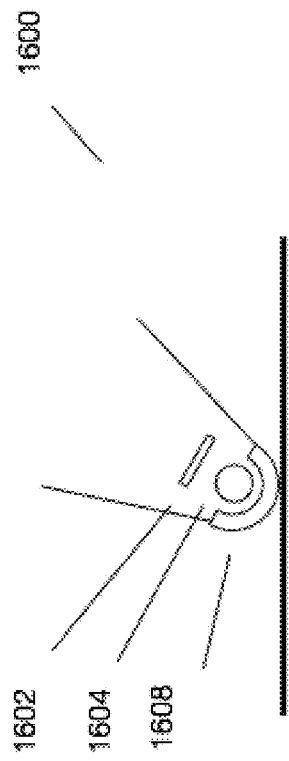
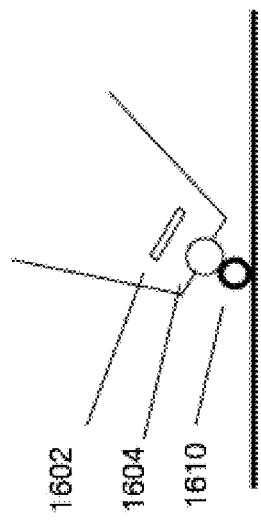
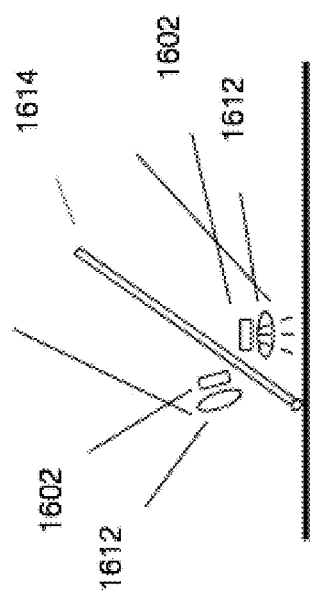

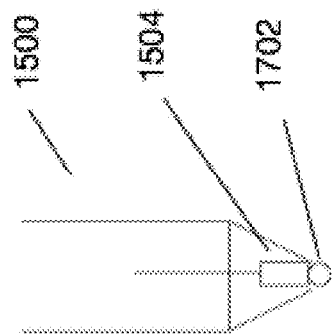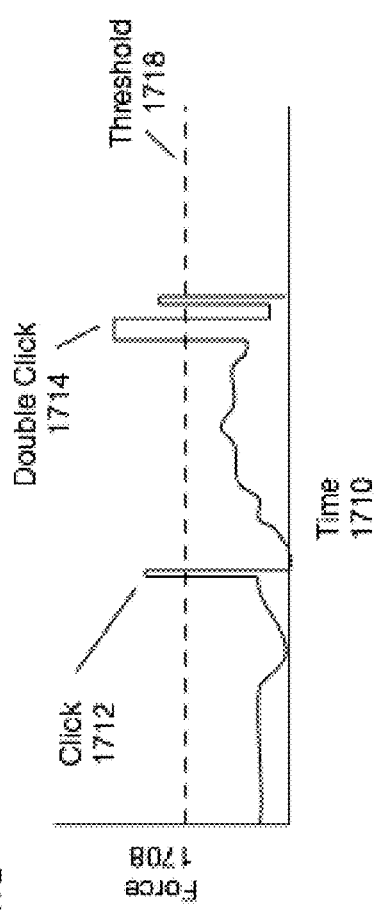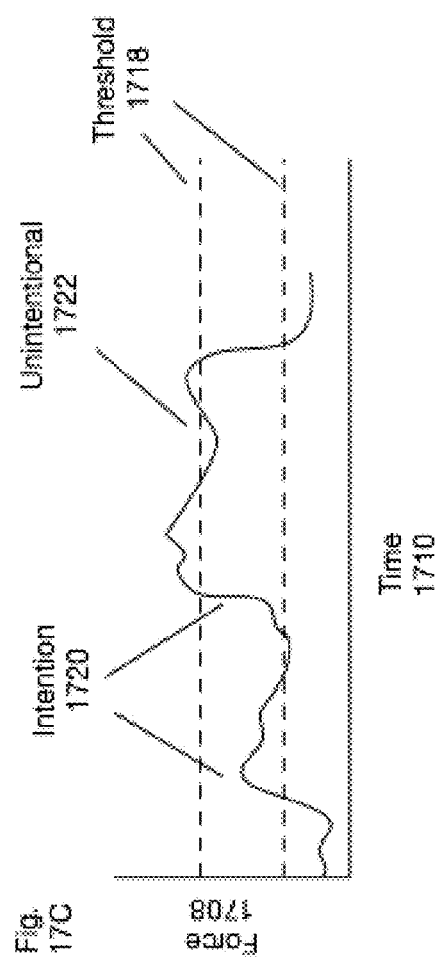

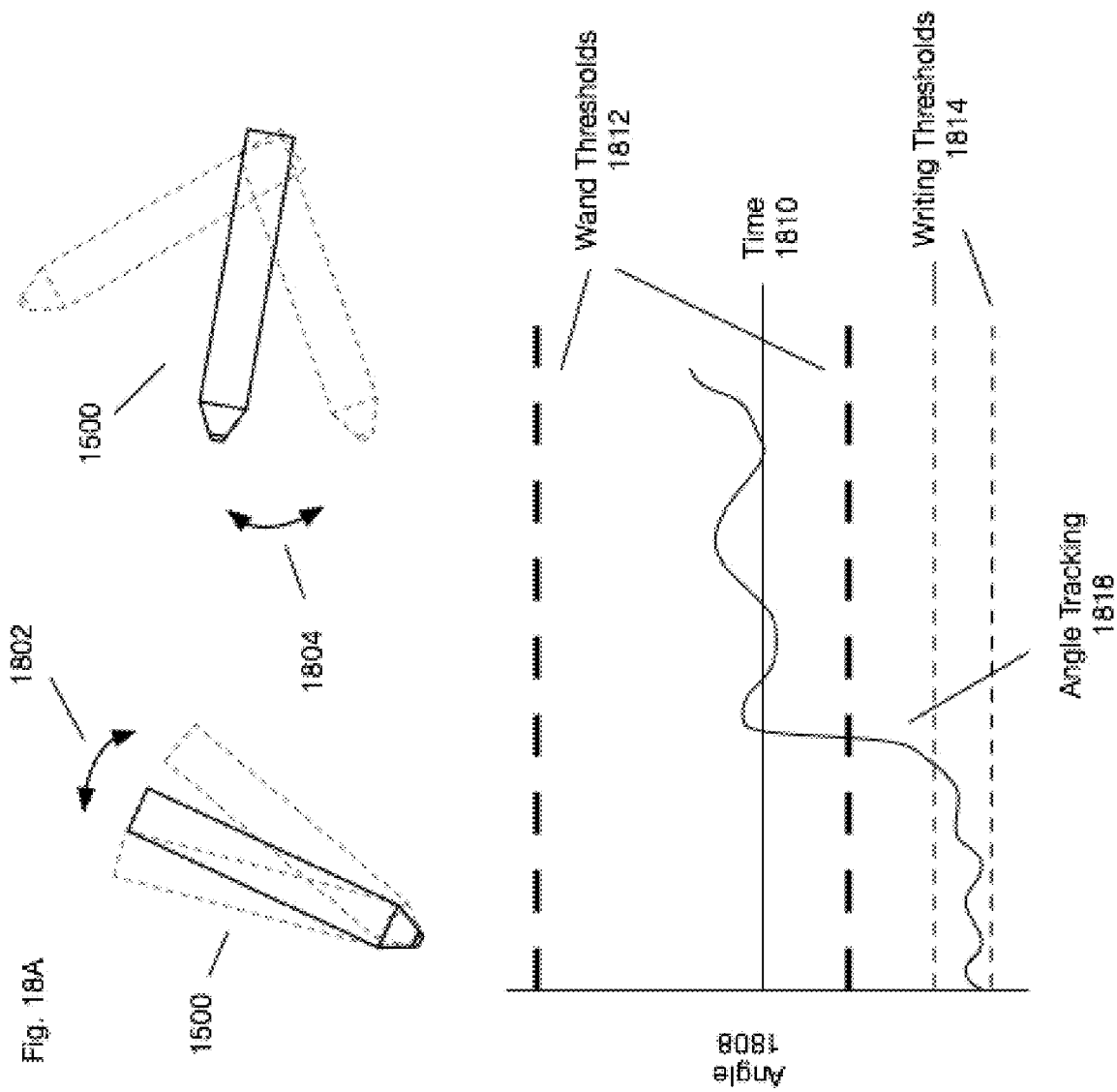

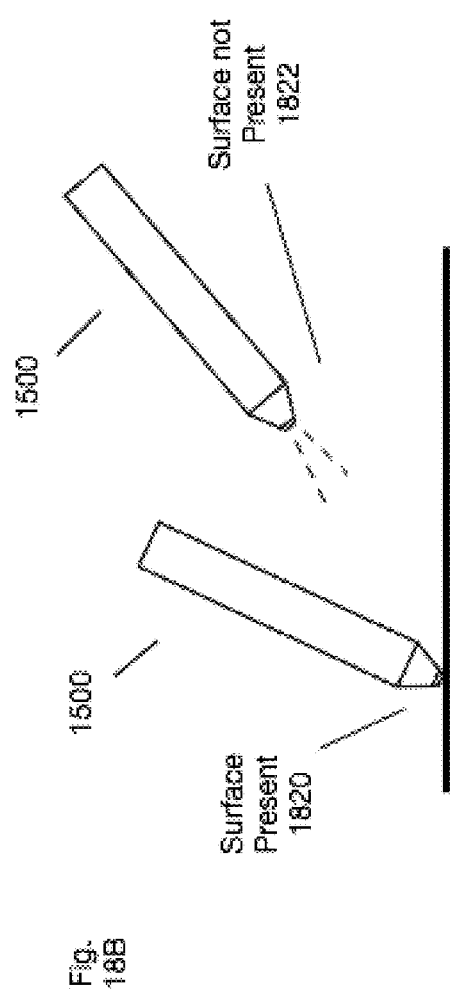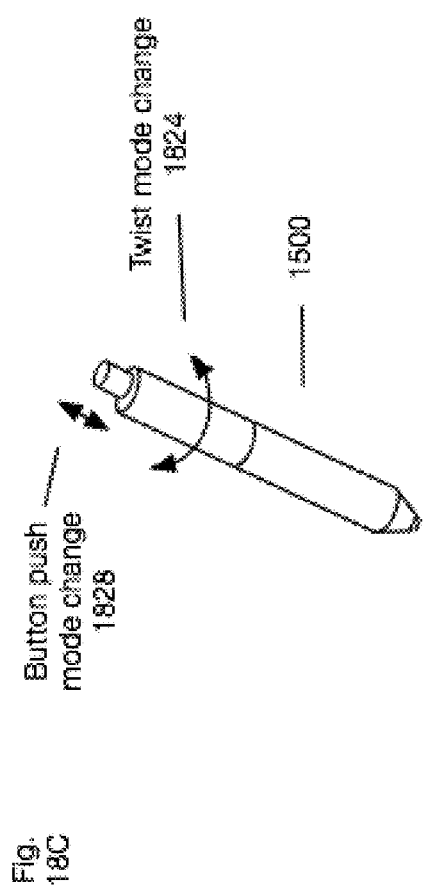
Fig. 18B
Fig. 18C

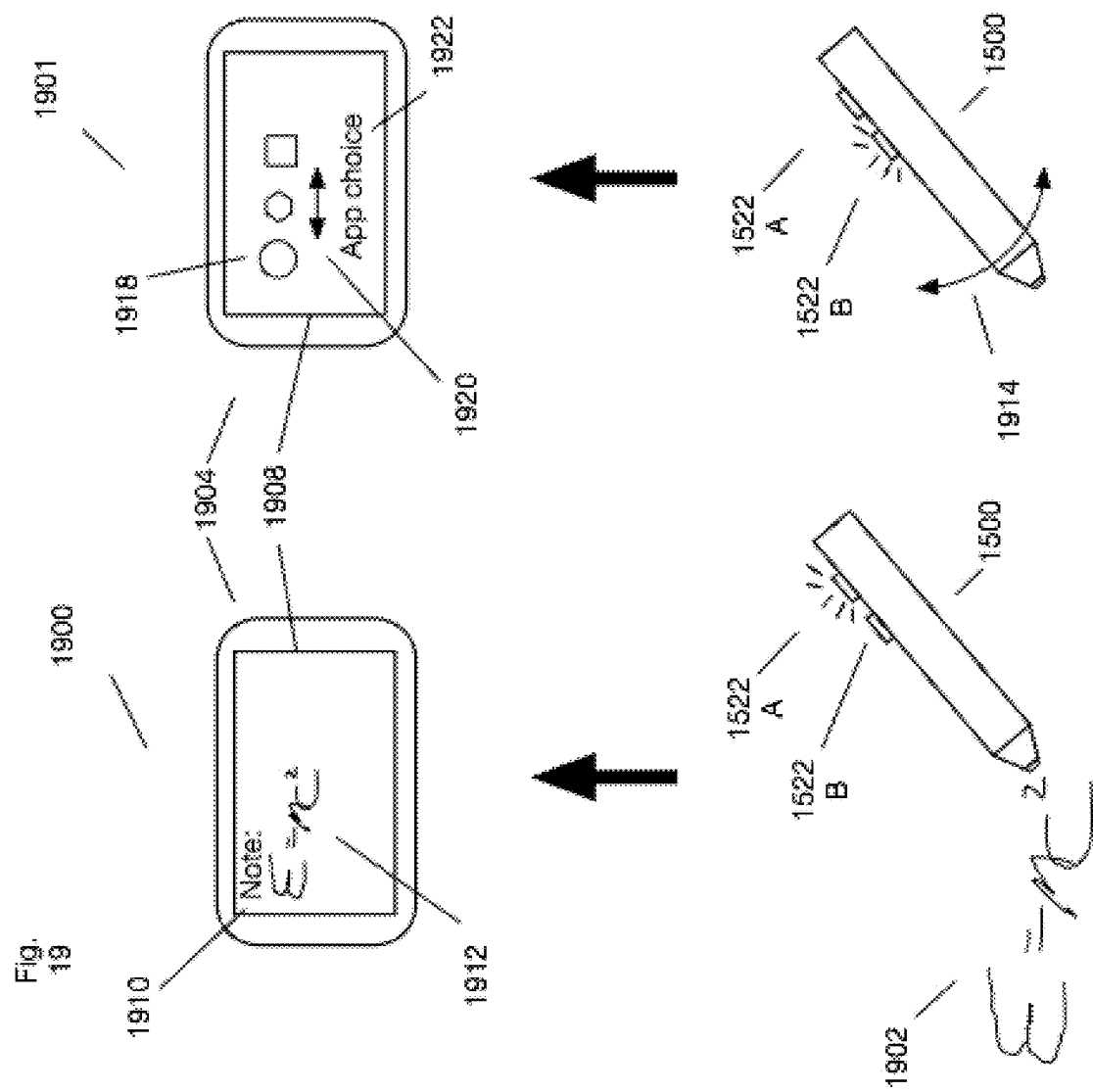

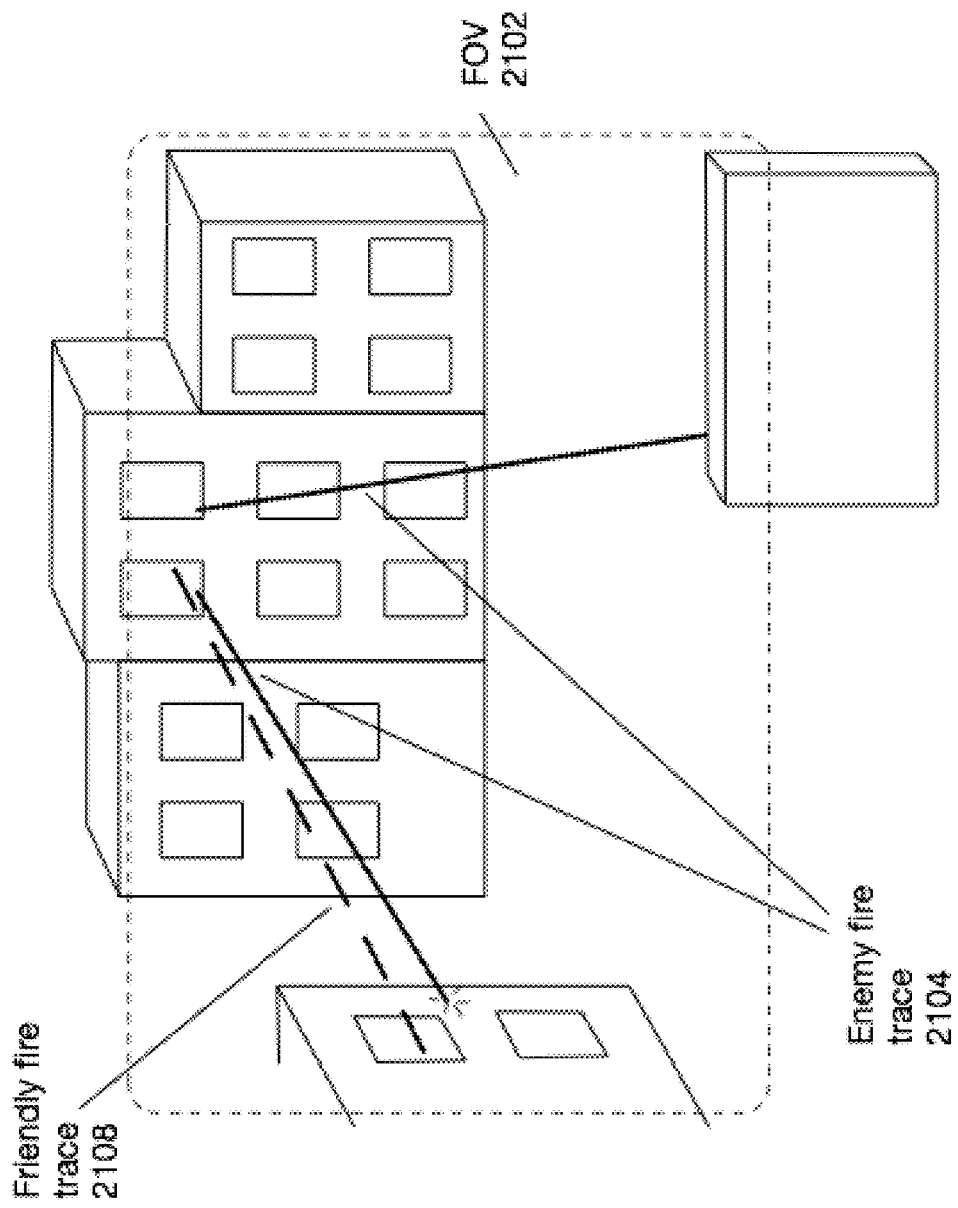

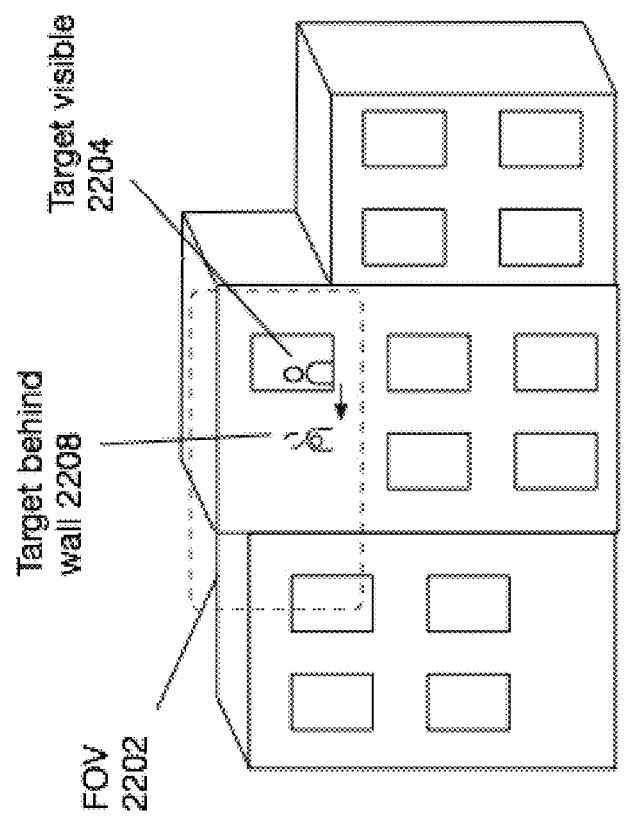

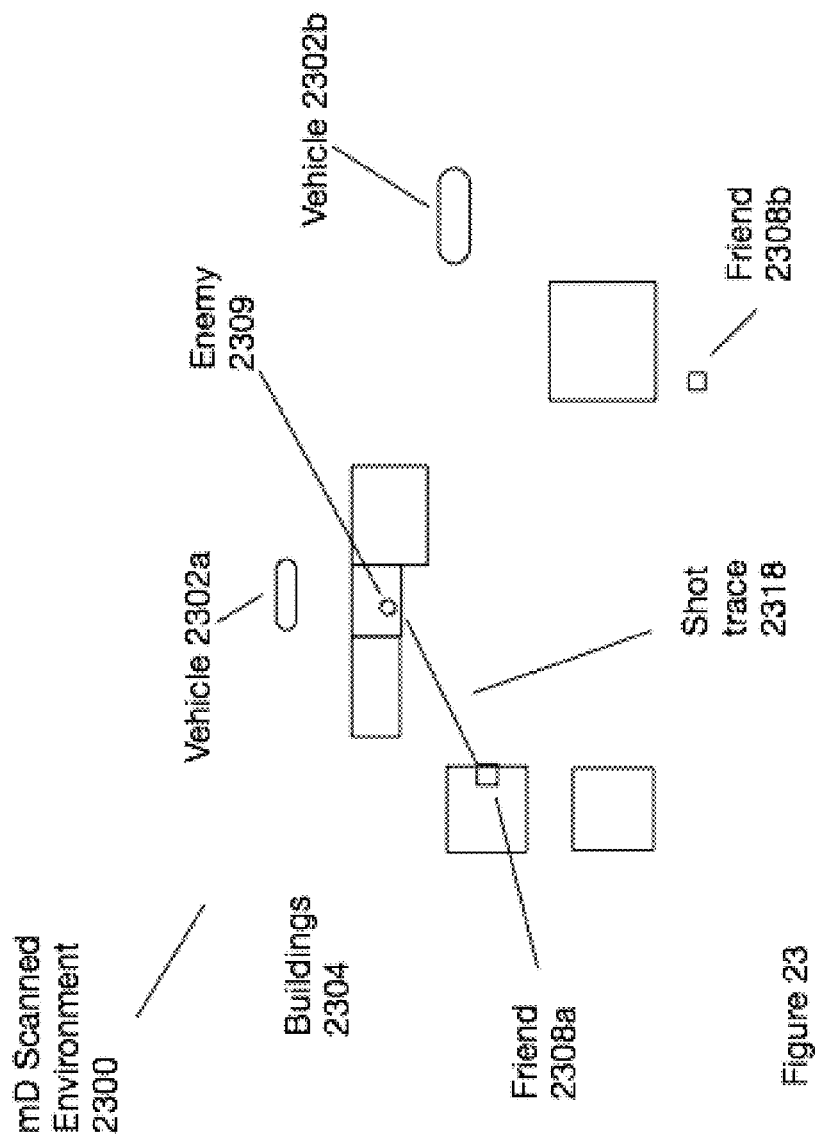

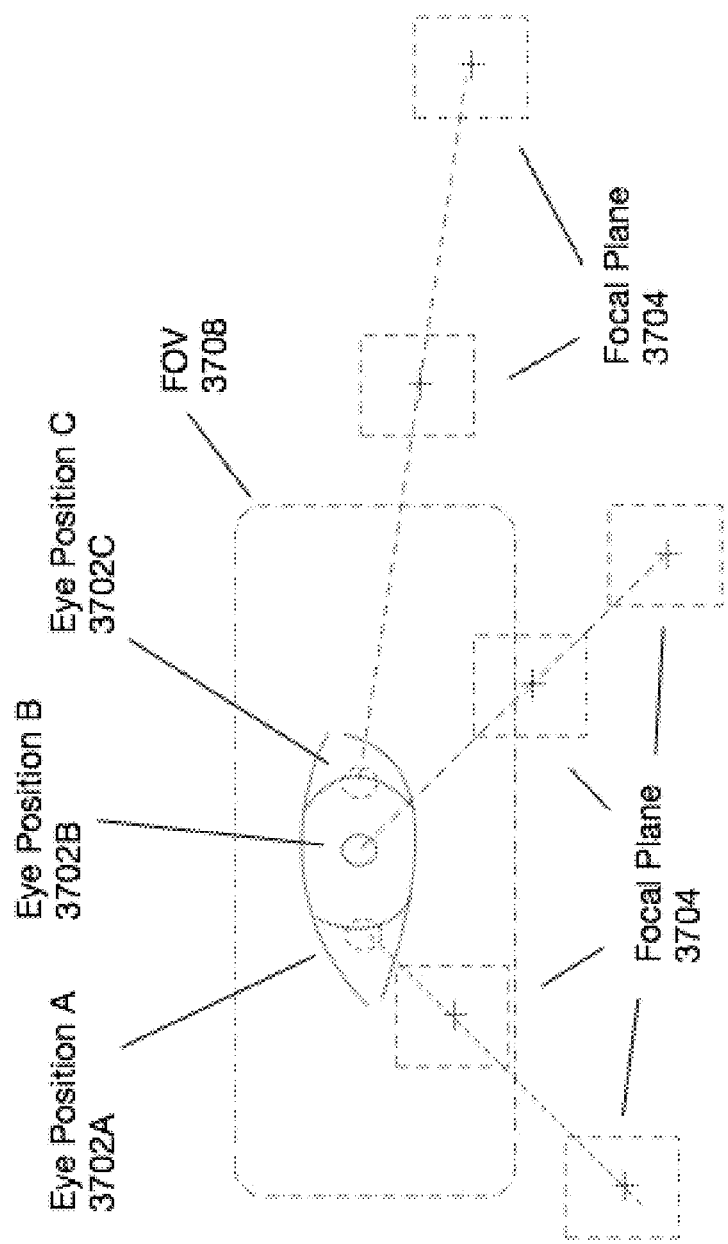

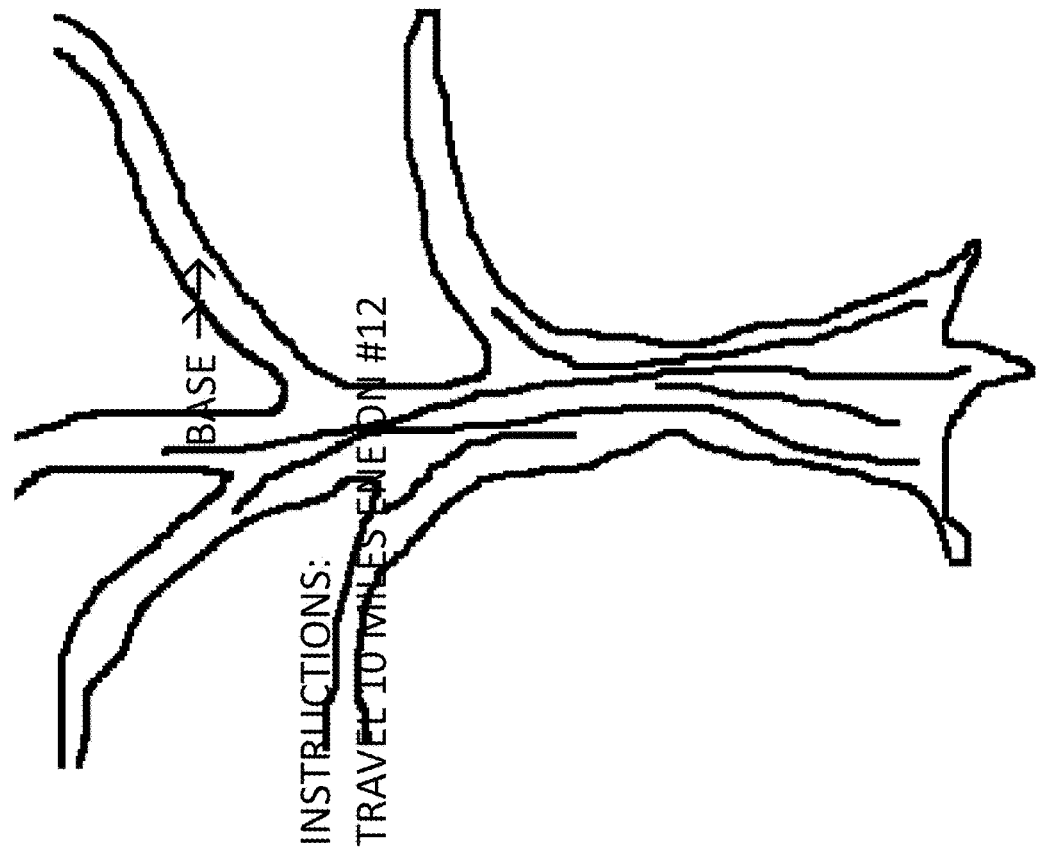
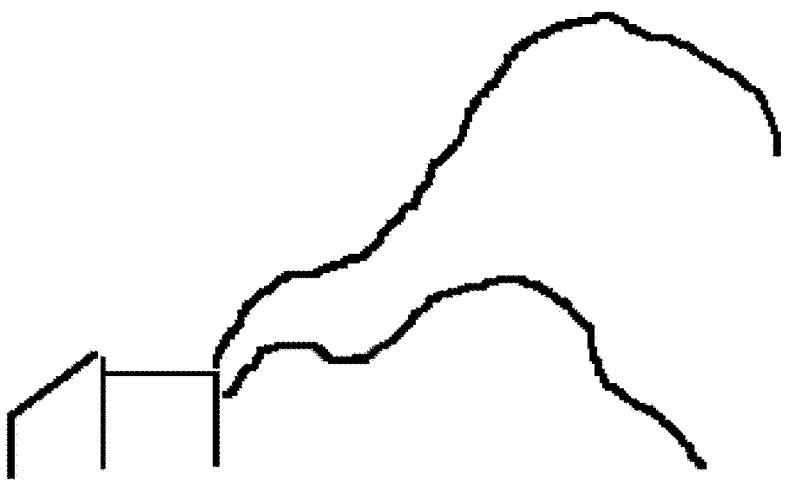
Figure 47

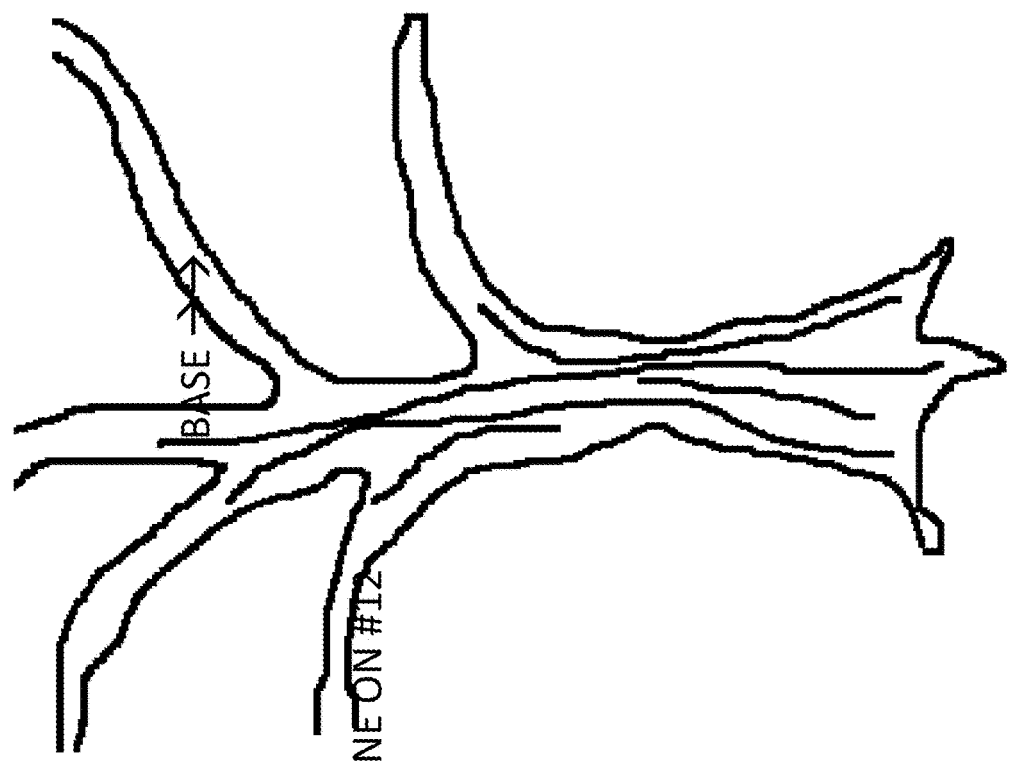
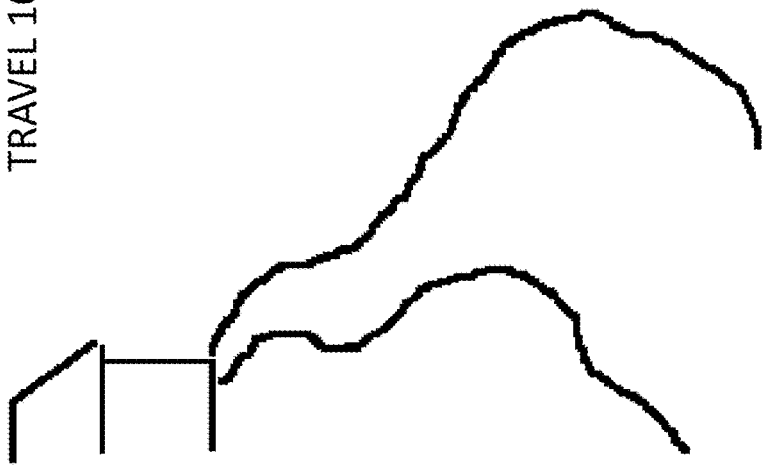
Figure 48

CONTENT PRESENTATION IN HEAD WORN COMPUTING

RELATED APPLICATIONS

This application is a continuation-in-part and claims the priority of the following patent application: U.S. patent application Ser. No. 14/331,481, entitled CONTENT PRESENTATION IN HEAD WORN COMPUTING, filed Jul. 15, 2014.

The above application is incorporated herein by reference in its entirety.

BACKGROUND

Field of the Invention

This invention relates to head worn computing. More particularly, this invention relates to technologies used in connection with medical procedures with the assistance of head worn computing.

Description of Related Art

Wearable computing systems have been developed and are beginning to be commercialized. Many problems persist in the wearable computing field that need to be resolved to make them meet the demands of the market.

SUMMARY

Aspects of the present invention relate to methods and systems for the assistance of medical professionals in medical procedures through the use of a head-worn computer.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE DRAWINGS

Embodiments are described with reference to the following Figures. The same numbers may be used throughout to reference like features and components that are shown in the Figures:

FIG. 3a illustrates a large prior art optical arrangement.

FIG. 4 illustrates an upper optical module in accordance with the principles of the present invention.

FIG. 5c illustrates an upper optical module and dark light trap according to the principles of the present invention.

FIG. 10 illustrates a light source in accordance with the principles of the present invention.

FIGS. 13a to 13c illustrate peripheral lighting systems in accordance with the principles of the present invention.

FIGS. 16a to 16c illustrate distance control systems in accordance with the principles of the present invention.

FIGS. 17a to 17c illustrate force interpretation systems in accordance with the principles of the present invention.

FIGS. 18a to 18c illustrate user interface mode selection systems in accordance with the principles of the present invention.

FIG. 19 illustrates interaction systems in accordance with the principles of the present invention.

FIG. 21 illustrates mD trace representations presented in accordance with the principles of the present invention.

FIG. 22 illustrates mD trace representations presented in accordance with the principles of the present invention.

FIG. 23 illustrates an mD scanned environment in accordance with the principles of the present invention.

FIG. 37 illustrates eye imaging along various virtual target lines and various focal planes in accordance with the principles of the present invention.

FIG. 47 illustrates content position dependent on sensor feedback in accordance with the principles of the present invention.

FIG. 48 illustrates content position dependent on sensor feedback in accordance with the principles of the present invention.

FIG. 66 illustrates a location based presentation technology in accordance with the principles of the present invention.

While the invention has been described in connection with certain preferred embodiments, other embodiments would be understood by one of ordinary skill in the art and are encompassed herein.

DETAILED DESCRIPTION OF THE PREFERRED EMBODIMENT(S)

Aspects of the present invention relate to head-worn computing ("HWC") systems. HWC involves, in some instances, a system that mimics the appearance of head-worn glasses or sunglasses. The glasses may be a fully developed computing platform, such as including computer displays presented in each of the lenses of the glasses to the eyes of the user. In embodiments, the lenses and displays may be configured to allow a person wearing the glasses to see the environment through the lenses while also seeing, simultaneously, digital imagery, which forms an overlaid image that is perceived by the person as a digitally augmented image of the environment, or augmented reality ("AR").

HWC involves more than just placing a computing system on a person's head. The system may need to be designed as a lightweight, compact and fully functional computer display, such as wherein the computer display includes a high resolution digital display that provides a high level of emersion comprised of the displayed digital content and the see-through view of the environmental surroundings. User interfaces and control systems suited to the HWC device may be required that are unlike those used for a more conventional computer such as a laptop. For the HWC and associated systems to be most effective, the glasses may be equipped with sensors to determine environmental conditions, geographic location, relative positioning to other points of interest, objects identified by imaging and movement by the user or other users in a connected group, and the like. The HWC may then change the mode of operation to match the conditions, location, positioning, movements, and the like, in a method generally referred to as a contextually aware HWC. The glasses also may need to be connected, wirelessly or otherwise, to other systems either locally or through a network. Controlling the glasses may be achieved through the use of an external device, automatically through contextually gathered information, through user gestures captured by the glasses sensors, and the like. Each technique may be further refined depending on the software application being used in the glasses. The glasses may further be used to control or coordinate with external devices that are associated with the glasses.

Figure 1:
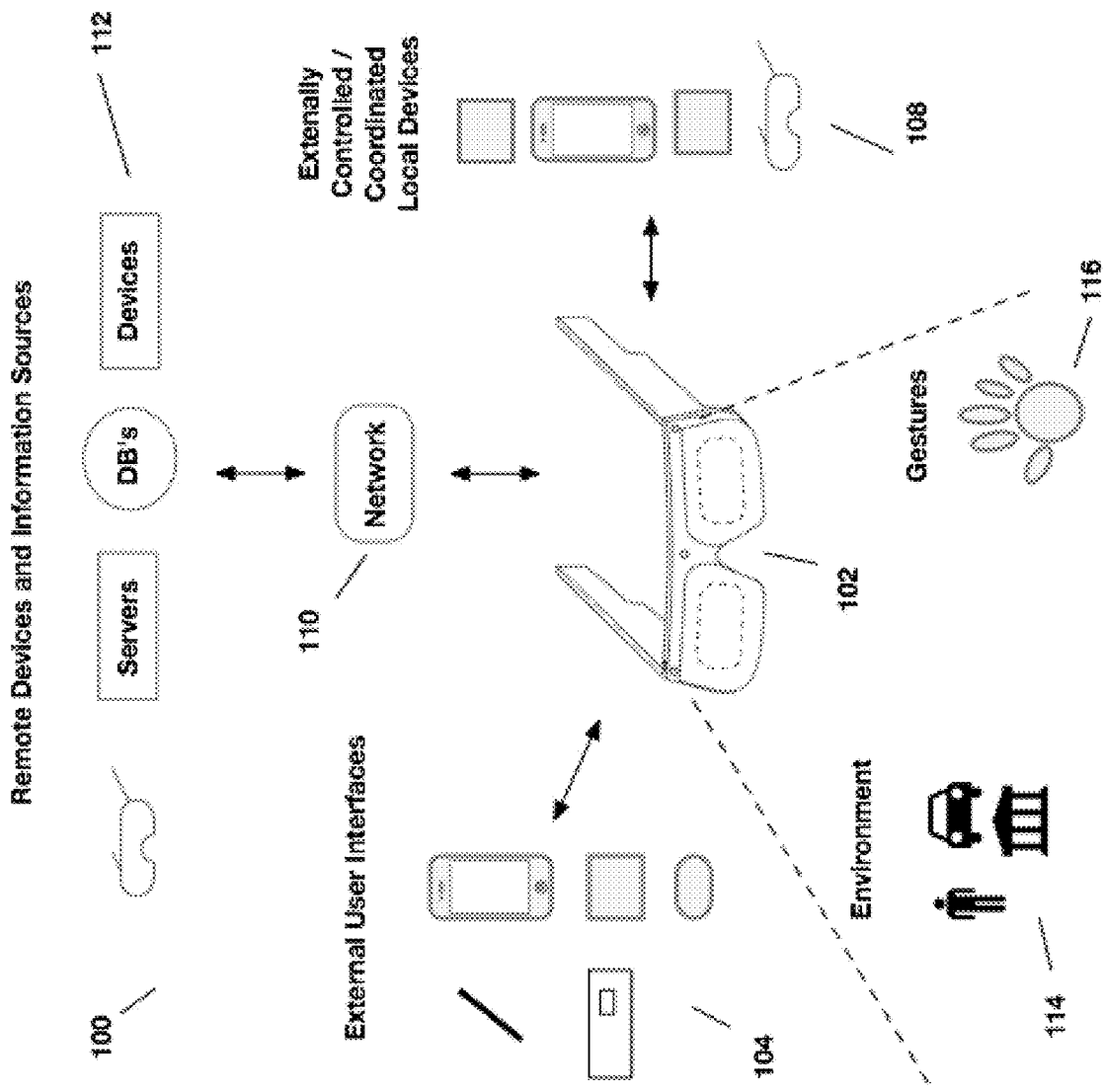
FIG. 1 illustrates a head worn computing system in accordance with the principles of the present invention.

Referring to FIG. 1, an overview of the HWC system 100 is presented. As shown, the HWC system 100 comprises a HWC 102, which in this instance is configured as glasses to be worn on the head with sensors such that the HWC 102 is aware of the objects and conditions in the environment 114. In this instance, the HWC 102 also receives and interprets control inputs such as gestures and movements 116. The HWC 102 may communicate with external user interfaces 104. The external user interfaces 104 may provide a physical user interface to take control instructions from a user of the HWC 102 and the external user interfaces 104 and the HWC 102 may communicate bi-directionally to affect the user's command and provide feedback to the external device 108. The HWC 102 may also communicate bi-directionally with externally controlled or coordinated local devices 108. For example, an external user interface 104 may be used in connection with the HWC 102 to control an externally controlled or coordinated local device 108. The externally controlled or coordinated local device 108 may provide feedback to the HWC 102 and a customized GUI may be presented in the HWC 102 based on the type of device or specifically identified device 108. The HWC 102 may also interact with remote devices and information sources 112 through a network connection 110. Again, the external user interface 104 may be used in connection with the HWC 102 to control or otherwise interact with any of the remote devices 108 and information sources 112 in a similar way as when the external user interfaces 104 are used to control or otherwise interact with the externally controlled or coordinated local devices 108. Similarly, HWC 102 may interpret gestures 116 (e.g captured from forward, downward, upward, rearward facing sensors such as camera(s), range finders, IR sensors, etc.) or environmental conditions sensed in the environment 114 to control either local or remote devices 108 or 112.

We will now describe each of the main elements depicted on FIG. 1 in more detail; however, these descriptions are intended to provide general guidance and should not be construed as limiting. Additional description of each element may also be further described herein.

The HWC 102 is a computing platform intended to be worn on a person's head. The HWC 102 may take many different forms to fit many different functional requirements. In some situations, the HWC 102 will be designed in the form of conventional glasses. The glasses may or may not have active computer graphics displays. In situations where the HWC 102 has integrated computer displays the displays may be configured as see-through displays such that the digital imagery can be overlaid with respect to the user's view of the environment 114. There are a number of see-through optical designs that may be used, including ones that have a reflective display (e.g. LCoS, DLP), emissive displays (e.g. OLED, LED), hologram, TIR waveguides, and the like. In embodiments, lighting systems used in connection with the display optics may be solid state lighting systems, such as LED, OLED, quantum dot, quantum dot LED, etc. In addition, the optical configuration may be monocular or binocular. It may also include vision corrective optical components. In embodiments, the optics may be packaged as contact lenses. In other embodiments, the HWC 102 may be in the form of a helmet with a see-through shield, sunglasses, safety glasses, goggles, a mask, fire helmet with see-through shield, police helmet with see through shield, military helmet with see-through shield, utility form customized to a certain work task (e.g. inventory control, logistics, repair, maintenance, etc.), and the like.

The HWC 102 may also have a number of integrated computing facilities, such as an integrated processor, integrated power management, communication structures (e.g. cell net, WiFi, Bluetooth, local area connections, mesh connections, remote connections (e.g. client server, etc.)), and the like. The HWC 102 may also have a number of positional awareness sensors, such as GPS, electronic compass, altimeter, tilt sensor, IMU, and the like. It may also have other sensors such as a camera, rangefinder, hyperspectral camera, Geiger counter, microphone, spectral illumination detector, temperature sensor, chemical sensor, biologic sensor, moisture sensor, ultrasonic sensor, and the like.

The HWC 102 may also have integrated control technologies. The integrated control technologies may be contextual based control, passive control, active control, user control, and the like. For example, the HWC 102 may have an integrated sensor (e.g. camera) that captures user hand or body gestures 116 such that the integrated processing system can interpret the gestures and generate control commands for the HWC 102. In another example, the HWC 102 may have sensors that detect movement (e.g. a nod, head shake, and the like) including accelerometers, gyros and other inertial measurements, where the integrated processor may interpret the movement and generate a control command in response. The HWC 102 may also automatically control itself based on measured or perceived environmental conditions. For example, if it is bright in the environment the HWC 102 may increase the brightness or contrast of the displayed image. In embodiments, the integrated control technologies may be mounted on the HWC 102 such that a user can interact with it directly. For example, the HWC 102 may have a button(s), touch capacitive interface, and the like.

As described herein, the HWC 102 may be in communication with external user interfaces 104. The external user interfaces may come in many different forms. For example, a cell phone screen may be adapted to take user input for control of an aspect of the HWC 102. The external user interface may be a dedicated UI, such as a keyboard, touch surface, button(s), joy stick, and the like. In embodiments, the external controller may be integrated into another device such as a ring, watch, bike, car, and the like. In each case, the external user interface 104 may include sensors (e.g. IMU, accelerometers, compass, altimeter, and the like) to provide additional input for controlling the HWD 104.

As described herein, the HWC 102 may control or coordinate with other local devices 108. The external devices 108 may be an audio device, visual device, vehicle, cell phone, computer, and the like. For instance, the local external device 108 may be another HWC 102, where information may then be exchanged between the separate HWCs 108.

Similar to the way the HWC 102 may control or coordinate with local devices 106, the HWC 102 may control or coordinate with remote devices 112, such as the HWC 102 communicating with the remote devices 112 through a network 110. Again, the form of the remote device 112 may have many forms. Included in these forms is another HWC 102. For example, each HWC 102 may communicate its GPS position such that all the HWCs 102 know where all of HWC 102 are located.

Figure 2:
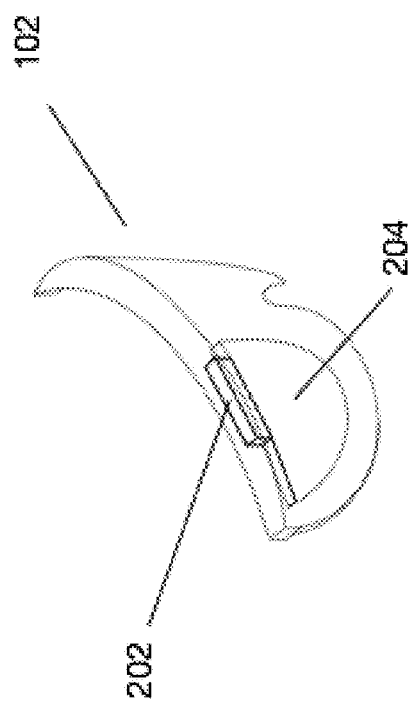
FIG. 2 illustrates a head worn computing system with optical system in accordance with the principles of the present invention.

FIG. 2 illustrates a HWC 102 with an optical system that includes an upper optical module 202 and a lower optical module 204. While the upper and lower optical modules 202 and 204 will generally be described as separate modules, it should be understood that this is illustrative only and the present invention includes other physical configurations, such as that when the two modules are combined into a single module or where the elements making up the two modules are configured into more than two modules. In embodiments, the upper module 202 includes a computer controlled display (e.g. LCoS, DLP, OLED, etc.) and image light delivery optics. In embodiments, the lower module includes eye delivery optics that are configured to receive the upper module's image light and deliver the image light to the eye of a wearer of the HWC. In FIG. 2, it should be noted that while the upper and lower optical modules 202 and 204 are illustrated in one side of the HWC such that image light can be delivered to one eye of the wearer, that it is envisioned by the present invention that embodiments will contain two image light delivery systems, one for each eye.

Figure 3B:
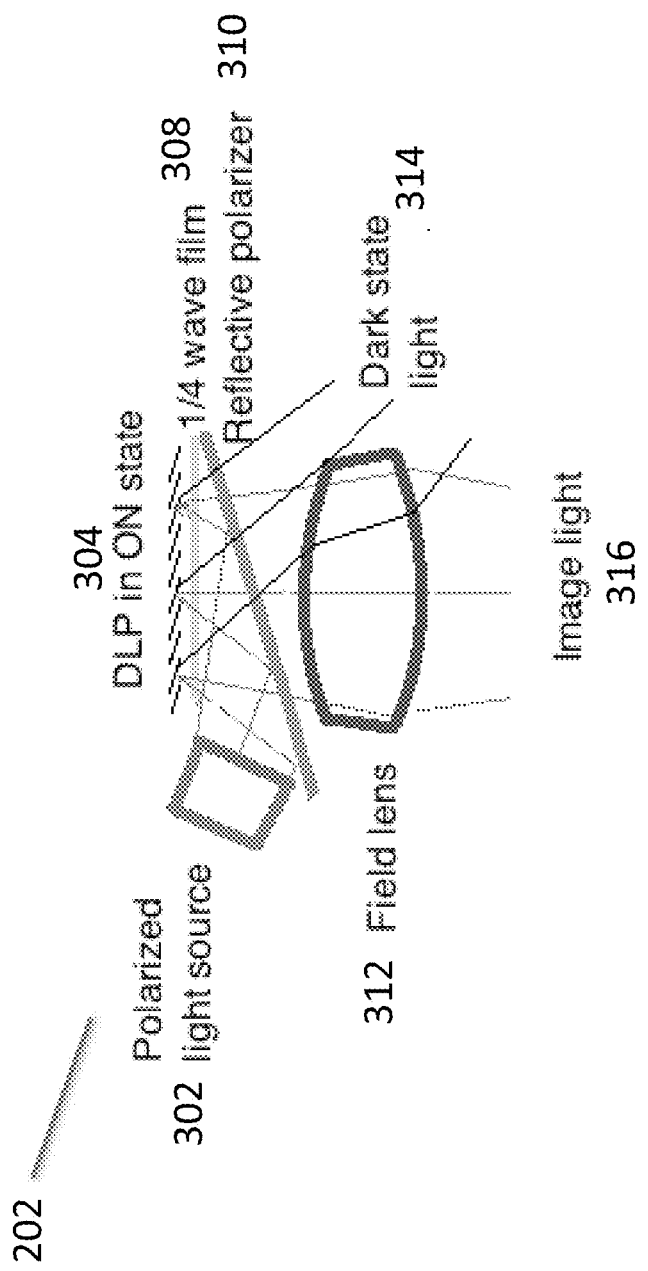
FIG. 3b illustrates an upper optical module in accordance with the principles of the present invention.

FIG. 3b illustrates an upper optical module 202 in accordance with the principles of the present invention. In this embodiment, the upper optical module 202 includes a DLP (also known as DMD or digital micromirror device) computer operated display 304 which includes pixels comprised of rotatable mirrors (such as, for example, the DLP3000 available from Texas Instruments), polarized light source 302, ¼ wave retarder film 308, reflective polarizer 310 and a field lens 312. The polarized light source 302 provides substantially uniform polarized light that is generally directed towards the reflective polarizer 310. The reflective polarizer reflects light of one polarization state (e.g. S polarized light) and transmits light of the other polarization state (e.g. P polarized light). The polarized light source 302 and the reflective polarizer 310 are oriented so that the polarized light from the polarized light source 302 is reflected generally towards the DLP 304. The light then passes through the ¼ wave film 308 once before illuminating the pixels of the DLP 304 and then again after being reflected by the pixels of the DLP 304. In passing through the ¼ wave film 308 twice, the light is converted from one polarization state to the other polarization state (e.g. the light is converted from S to P polarized light). The light then passes through the reflective polarizer 310. In the event that the DLP pixel(s) are in the "on" state (i.e. the mirrors are positioned to reflect light towards the field lens 312, the "on" pixels reflect the light generally along the optical axis and into the field lens 312. This light that is reflected by "on" pixels and which is directed generally along the optical axis of the field lens 312 will be referred to as image light 316. The image light 316 then passes through the field lens to be used by a lower optical module 204.

The light that is provided by the polarized light source 302, which is subsequently reflected by the reflective polarizer 310 before it reflects from the DLP 304, will generally be referred to as illumination light. The light that is reflected by the "off" pixels of the DLP 304 is reflected at a different angle than the light reflected by the 'on" pixels, so that the light from the "off" pixels is generally directed away from the optical axis of the field lens 312 and toward the side of the upper optical module 202 as shown in FIG. 3. The light that is reflected by the "off" pixels of the DLP 304 will be referred to as dark state light 314.

The DLP 304 operates as a computer controlled display and is generally thought of as a MEMs device. The DLP pixels are comprised of small mirrors that can be directed. The mirrors generally flip from one angle to another angle. The two angles are generally referred to as states. When light is used to illuminate the DLP the mirrors will reflect the light in a direction depending on the state. In embodiments herein, we generally refer to the two states as "on" and "off," which is intended to depict the condition of a display pixel. "On" pixels will be seen by a viewer of the display as emitting light because the light is directed along the optical axis and into the field lens and the associated remainder of the display system. "Off" pixels will be seen by a viewer of the display as not emitting light because the light from these pixels is directed to the side of the optical housing and into a light trap or light dump where the light is absorbed. The pattern of "on" and "off" pixels produces image light that is perceived by a viewer of the display as a computer generated image. Full color images can be presented to a user by sequentially providing illumination light with complimentary colors such as red, green and blue. Where the sequence is presented in a recurring cycle that is faster than the user can perceive as separate images and as a result the user perceives a full color image comprised of the sum of the sequential images. Bright pixels in the image are provided by pixels that remain in the "on" state for the entire time of the cycle, while dimmer pixels in the image are provided by pixels that switch between the "on" state and "off" state within the time of the cycle, or frame time when in a video sequence of images.

FIG. 3a shows an illustration of a system for a DLP 304 in which the unpolarized light source 350 is pointed directly at the DLP 304. In this case, the angle required for the illumination light is such that the field lens 352 must be positioned substantially distant from the DLP 304 to avoid the illumination light from being clipped by the field lens 352. The large distance between the field lens 352 and the DLP 304 along with the straight path of the dark state light 354, means that the light trap for the dark state light 354 is also located at a substantial distance from the DLP. For these reasons, this configuration is larger in size compared to the upper optics module 202 of the preferred embodiments.

The configuration illustrated in FIG. 3b can be lightweight and compact such that it fits into a small portion of a HWC. For example, the upper modules 202 illustrated herein can be physically adapted to mount in an upper frame of a HWC such that the image light can be directed into a lower optical module 204 for presentation of digital content to a wearer's eye. The package of components that combine to generate the image light (i.e. the polarized light source 302, DLP 304, reflective polarizer 310 and ¼ wave film 308) is very light and is compact. The height of the system, excluding the field lens, may be less than 8 mm. The width (i.e. from front to back) may be less than 8 mm. The weight may be less than 2 grams. The compactness of this upper optical module 202 allows for a compact mechanical design of the HWC and the light weight nature of these embodiments help make the HWC lightweight to provide for a HWC that is comfortable for a wearer of the HWC.

The configuration illustrated in FIG. 3b can produce sharp contrast, high brightness and deep blacks, especially when compared to LCD or LCoS displays used in HWC. The "on" and "off" states of the DLP provide for a strong differentiator in the light reflection path representing an "on" pixel and an "off" pixel. As will be discussed in more detail below, the dark state light from the "off" pixel reflections can be managed to reduce stray light in the display system to produce images with high contrast.

FIG. 4 illustrates another embodiment of an upper optical module 202 in accordance with the principles of the present invention. This embodiment includes a light source 404, but in this case, the light source can provide unpolarized illumination light. The illumination light from the light source 404 is directed into a TIR wedge 418 such that the illumination light is incident on an internal surface of the TIR wedge 418 (shown as the angled lower surface of the TRI wedge 418 in FIG. 4) at an angle that is beyond the critical angle as defined by Eqn 1.

$$\text{Critical angle} = \arcsin(1/n) \quad \text{Eqn 1}$$

Where the critical angle is the angle beyond which the illumination light is reflected from the internal surface when the internal surface comprises an interface from a solid with a higher refractive index (n) to air with a refractive index of 1 (e.g. for an interface of acrylic, with a refractive index of n=1.5, to air, the critical angle is 41.8 degrees; for an interface of polycarbonate, with a refractive index of n=1.59, to air the critical angle is 38.9 degrees). Consequently, the TIR wedge 418 is associated with a thin air gap 408 along the internal surface to create an interface between a solid with a higher refractive index and air. By choosing the angle of the light source 404 relative to the DLP 402 in correspondence to the angle of the internal surface of the TIR wedge 418, illumination light is turned toward the DLP 402 at an angle suitable for providing image light 414 as reflected from "on" pixels. Wherein, the illumination light is provided to the DLP 402 at approximately twice the angle of the pixel mirrors in the DLP 402 that are in the "on" state, such that after reflecting from the pixel mirrors, the image light 414 is directed generally along the optical axis of the field lens. Depending on the state of the DLP pixels, the illumination light from "on" pixels may be reflected as image light 414 which is directed towards a field lens and a lower optical module 204, while illumination light reflected from "off" pixels (generally referred to herein as "dark" state light, "off" pixel light or "off" state light) 410 is directed in a separate direction, which may be trapped and not used for the image that is ultimately presented to the wearer's eye.

The light trap for the dark state light 410 may be located along the optical axis defined by the direction of the dark state light 410 and in the side of the housing, with the function of absorbing the dark state light. To this end, the light trap may be comprised of an area outside of the cone of image light 414 from the "on" pixels. The light trap is typically made up of materials that absorb light including coatings of black paints or other light absorbing materials to prevent light scattering from the dark state light degrading the image perceived by the user. In addition, the light trap may be recessed into the wall of the housing or include masks or guards to block scattered light and prevent the light trap from being viewed adjacent to the displayed image.

The embodiment of FIG. 4 also includes a corrective wedge 420 to correct the effect of refraction of the image light 414 as it exits the TIR wedge 418. By including the corrective wedge 420 and providing a thin air gap 408 (e.g. 25 micron), the image light from the "on" pixels can be maintained generally in a direction along the optical axis of the field lens (i.e. the same direction as that defined by the image light 414) so it passes into the field lens and the lower optical module 204. As shown in FIG. 4, the image light 414 from the "on" pixels exits the corrective wedge 420 generally perpendicular to the surface of the corrective wedge 420 while the dark state light exits at an oblique angle. As a result, the direction of the image light 414 from the "on" pixels is largely unaffected by refraction as it exits from the surface of the corrective wedge 420. In contrast, the dark state light 410 is substantially changed in direction by refraction when the dark state light 410 exits the corrective wedge 420.

Figure 4A:
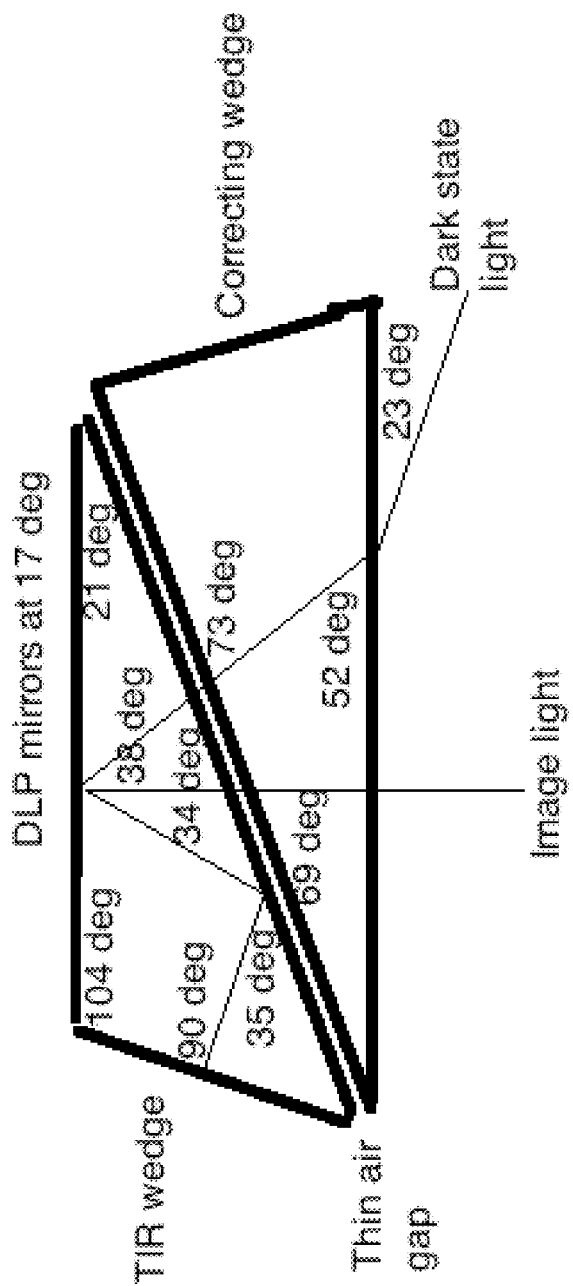
FIG. 4a illustrates an upper optical module in accordance with the principles of the present invention.

The embodiment illustrated in FIG. 4 has the similar advantages of those discussed in connection with the embodiment of FIG. 3b. The dimensions and weight of the upper module 202 depicted in FIG. 4 may be approximately 8×8 mm with a weight of less than 3 grams. A difference in overall performance between the configuration illustrated in FIG. 3b and the configuration illustrated in FIG. 4 is that the embodiment of FIG. 4 doesn't require the use of polarized light as supplied by the light source 404. This can be an advantage in some situations as will be discussed in more detail below (e.g. increased see-through transparency of the HWC optics from the user's perspective). Polarized light may be used in connection with the embodiment depicted in FIG. 4, in embodiments. An additional advantage of the embodiment of FIG. 4 compared to the embodiment shown in FIG. 3b is that the dark state light (shown as DLP off light 410) is directed at a steeper angle away from the optical axis of the image light 414 due to the added refraction encountered when the dark state light 410 exits the corrective wedge 420. This steeper angle of the dark state light 410 allows for the light trap to be positioned closer to the DLP 402 so that the overall size of the upper module 202 can be reduced. The light trap can also be made larger since the light trap doesn't interfere with the field lens, thereby the efficiency of the light trap can be increased and as a result, stray light can be reduced and the contrast of the image perceived by the user can be increased. FIG. 4a illustrates the embodiment described in connection with FIG. 4 with an example set of corresponding angles at the various surfaces with the reflected angles of a ray of light passing through the upper optical module 202. In this example, the DLP mirrors are provided at 17 degrees to the surface of the DLP device. The angles of the TIR wedge are selected in correspondence to one another to provide TIR reflected illumination light at the correct angle for the DLP mirrors while allowing the image light and dark state light to pass through the thin air gap, various combinations of angles are possible to achieve this.

Figure 4B:
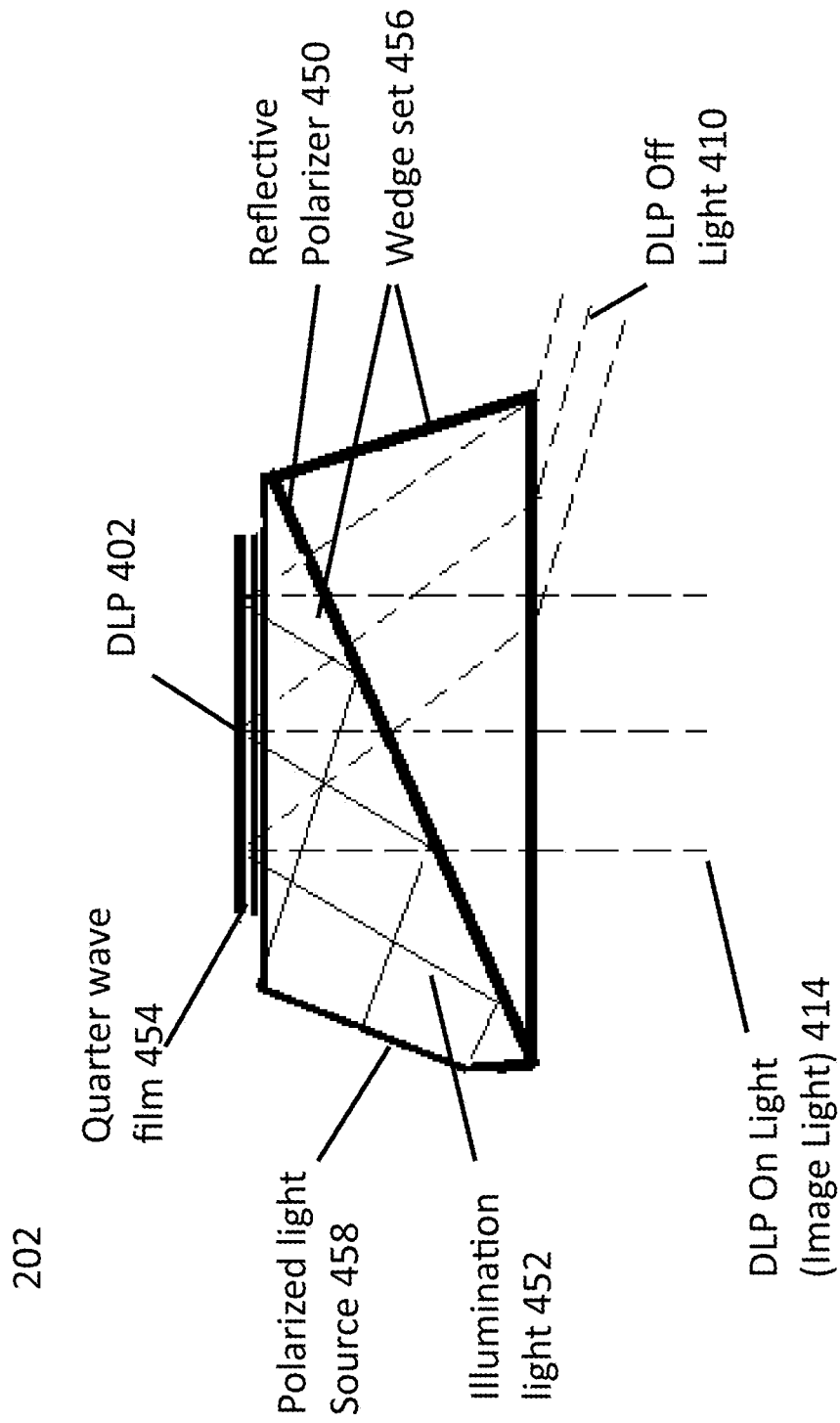
FIG. 4b illustrates an upper optical module in accordance with the principles of the present invention.
Figure 5:
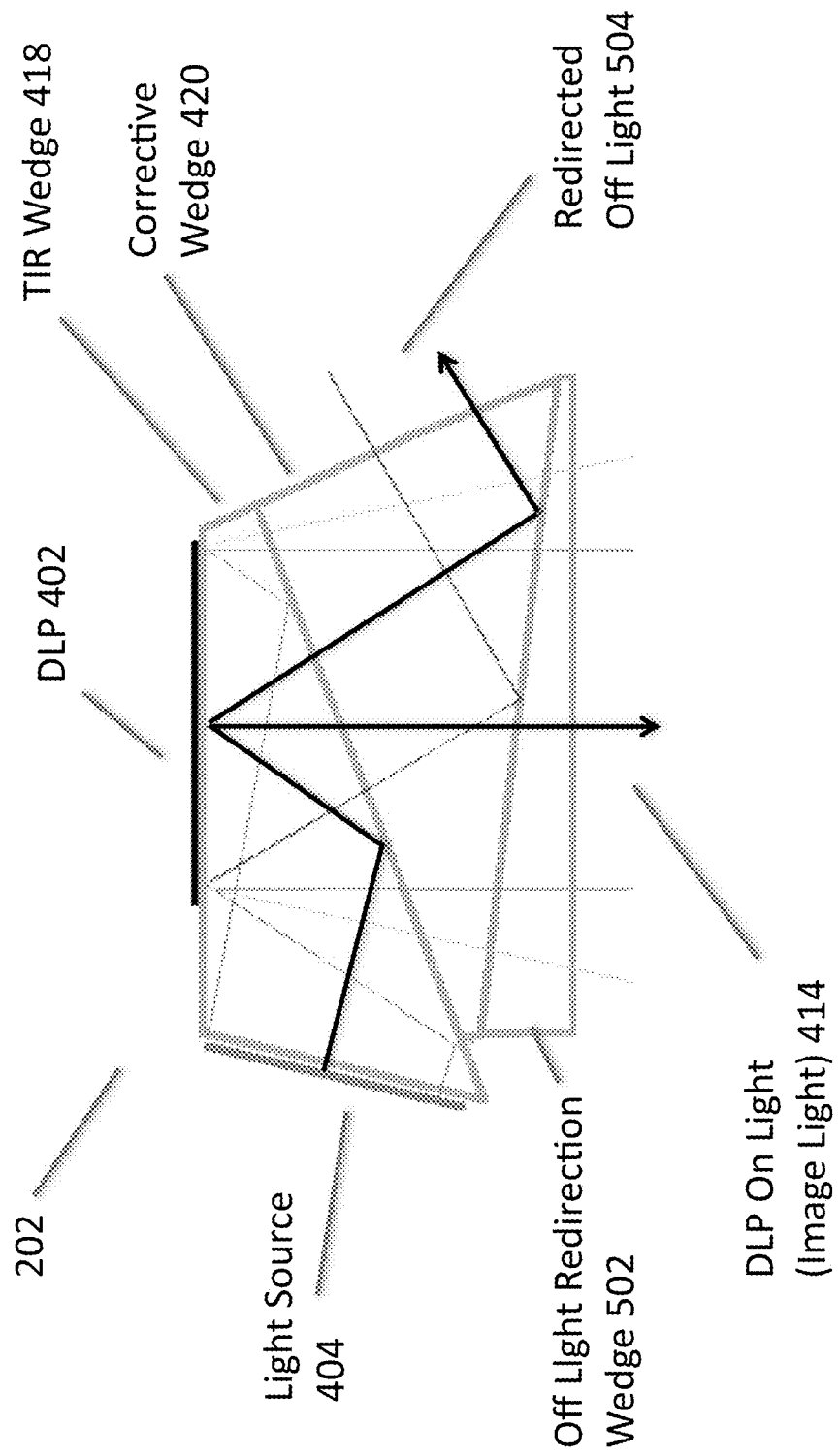
FIG. 5 illustrates an upper optical module in accordance with the principles of the present invention.
Figure 5A:
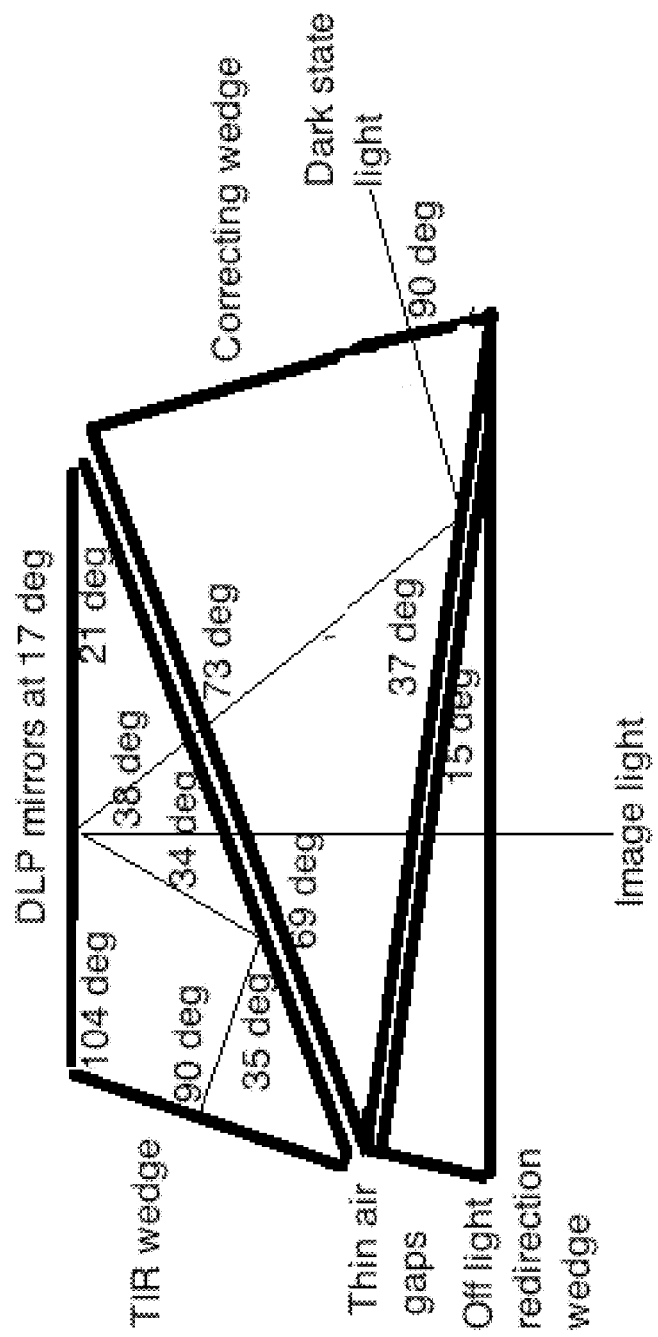
FIG. 5a illustrates an upper optical module in accordance with the principles of the present invention.

FIG. 5 illustrates yet another embodiment of an upper optical module 202 in accordance with the principles of the present invention. As with the embodiment shown in FIG. 4, the embodiment shown in FIG. 5 does not require the use of polarized light. Polarized light may be used in connection with this embodiment, but it is not required. The optical module 202 depicted in FIG. 5 is similar to that presented in connection with FIG. 4; however, the embodiment of FIG. 5 includes an off light redirection wedge 502. As can be seen from the illustration, the off light redirection wedge 502 allows the image light 414 to continue generally along the optical axis toward the field lens and into the lower optical module 204 (as illustrated). However, the off light 504 is redirected substantially toward the side of the corrective wedge 420 where it passes into the light trap. This configuration may allow further height compactness in the HWC because the light trap (not illustrated) that is intended to absorb the off light 504 can be positioned laterally adjacent the upper optical module 202 as opposed to below it. In the embodiment depicted in FIG. 5 there is a thin air gap between the TIR wedge 418 and the corrective wedge 420 (similar to the embodiment of FIG. 4). There is also a thin air gap between the corrective wedge 420 and the off light redirection wedge 502. There may be HWC mechanical configurations that warrant the positioning of a light trap for the dark state light elsewhere and the illustration depicted in FIG. 5 should be considered illustrative of the concept that the off light can be redirected to create compactness of the overall HWC. FIG. 5a illustrates an example of the embodiment described in connection with FIG. 5 with the addition of more details on the relative angles at the various surfaces and a light ray trace for image light and a light ray trace for dark light are shown as it passes through the upper optical module 202. Again, various combinations of angles are possible.

FIG. 4b shows an illustration of a further embodiment in which a solid transparent matched set of wedges 456 is provided with a reflective polarizer 450 at the interface between the wedges. Wherein the interface between the wedges in the wedge set 456 is provided at an angle so that illumination light 452 from the polarized light source 458 is reflected at the proper angle (e.g. 34 degrees for a 17 degree DLP mirror) for the DLP mirror "on" state so that the reflected image light 414 is provided along the optical axis of the field lens. The general geometry of the wedges in the wedge set 456 is similar to that shown in FIGS. 4 and 4a. A quarter wave film 454 is provided on the DLP 402 surface so that the illumination light 452 is one polarization state (e.g. S polarization state) while in passing through the quarter wave film 454, reflecting from the DLP mirror and passing back through the quarter wave film 454, the image light 414 is converted to the other polarization state (e.g. P polarization state). The reflective polarizer is oriented such that the illumination light 452 with it's polarization state is reflected and the image light 414 with it's other polarization state is transmitted. Since the dark state light from the "off" pixels 410 also passes through the quarter wave film 454 twice, it is also the other polarization state (e.g. P polarization state) so that it is transmitted by the reflective polarizer 450.

The angles of the faces of the wedge set 450 correspond to the needed angles to provide illumination light 452 at the angle needed by the DLP mirrors when in the "on" state so that the reflected image light 414 is reflected from the DLP along the optical axis of the field lens. The wedge set 456 provides an interior interface where a reflective polarizer film can be located to redirect the illumination light 452 toward the mirrors of the DLP 402. The wedge set also provides a matched wedge on the opposite side of the reflective polarizer 450 so that the image light 414 from the "on" pixels exits the wedge set 450 substantially perpendicular to the exit surface, while the dark state light from the 'off' pixels 410 exits at an oblique angle to the exit surface. As a result, the image light 414 is substantially unrefracted upon exiting the wedge set 456, while the dark state light from the "off" pixels 410 is substantially refracted upon exiting the wedge set 456 as shown in FIG. 4b.

By providing a solid transparent matched wedge set, the flatness of the interface is reduced, because variations in the flatness have a negligible effect as long as they are within the cone angle of the illuminating light 452. Which can be f #2.2 with a 26 degree cone angle. In a preferred embodiment, the reflective polarizer is bonded between the matched internal surfaces of the wedge set 456 using an optical adhesive so that Fresnel reflections at the interfaces on either side of the reflective polarizer 450 are reduced. The optical adhesive can be matched in refractive index to the material of the wedge set 456 and the pieces of the wedge set 456 can be all made from the same material such as BK7 glass or cast acrylic. Wherein the wedge material can be selected to have low birefringence as well to reduce non-uniformities in brightness. The wedge set 456 and the quarter wave film 454 can also be bonded to the DLP 402 to further reduce Fresnel reflections at the DLP interface losses. In addition, since the image light 414 is substantially normal to the exit surface of the wedge set 456, the flatness of the surface is not critical to maintain the wavefront of the image light 414 so that high image quality can be obtained in the displayed image without requiring very tightly toleranced flatness on the exit surface.

A yet further embodiment of the invention that is not illustrated, combines the embodiments illustrated in FIG. 4b and FIG. 5. In this embodiment, the wedge set 456 is comprised of three wedges with the general geometry of the wedges in the wedge set corresponding to that shown in FIGS. 5 and 5a. A reflective polarizer is bonded between the first and second wedges similar to that shown in FIG. 4b, however, a third wedge is provided similar to the embodiment of FIG. 5. Wherein there is an angled thin air gap between the second and third wedges so that the dark state light is reflected by TIR toward the side of the second wedge where it is absorbed in a light trap. This embodiment, like the embodiment shown in FIG. 4b, uses a polarized light source as has been previously described. The difference in this embodiment is that the image light is transmitted through the reflective polarizer and is transmitted through the angled thin air gap so that it exits normal to the exit surface of the third wedge.

Figure 5B:
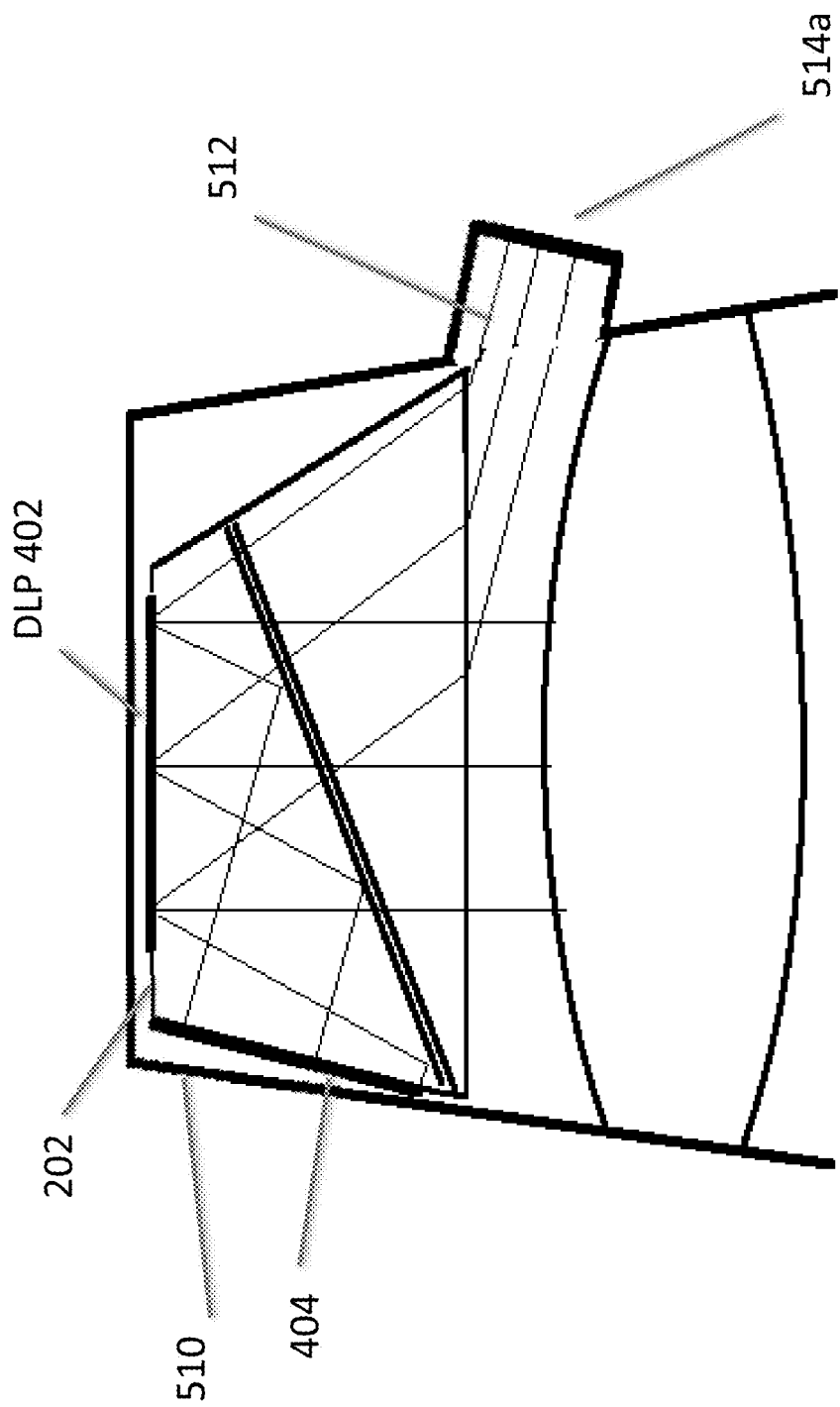
FIG. 5b illustrates an upper optical module and dark light trap according to the principles of the present invention.

FIG. 5b illustrates an upper optical module 202 with a dark light trap 514a. As described in connection with FIGS. 4 and 4a, image light can be generated from a DLP when using a TIR and corrective lens configuration. The upper module may be mounted in a HWC housing 510 and the housing 510 may include a dark light trap 514a. The dark light trap 514a is generally positioned/constructed/formed in a position that is optically aligned with the dark light optical axis 512. As illustrated, the dark light trap may have depth such that the trap internally reflects dark light in an attempt to further absorb the light and prevent the dark light from combining with the image light that passes through the field lens. The dark light trap may be of a shape and depth such that it absorbs the dark light. In addition, the dark light trap 514b, in embodiments, may be made of light absorbing materials or coated with light absorbing materials. In embodiments, the recessed light trap 514a may include baffles to block a view of the dark state light. This may be combined with black surfaces and textured or fiberous surfaces to help absorb the light. The baffles can be part of the light trap, associated with the housing, or field lens, etc.

Figure 5D:
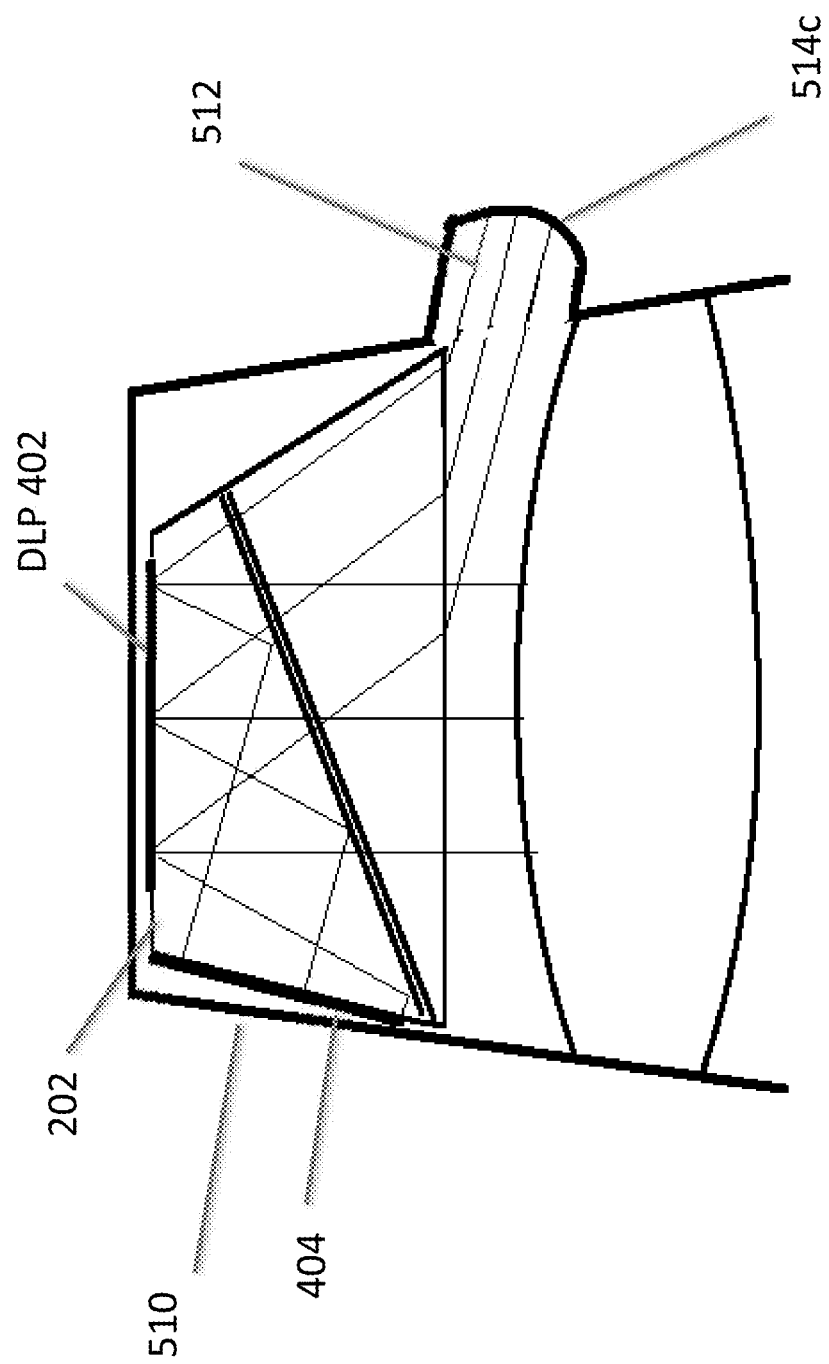
FIG. 5d illustrates an upper optical module and dark light trap according to the principles of the present invention.

FIG. 5c illustrates another embodiment with a light trap 514b. As can be seen in the illustration, the shape of the trap is configured to enhance internal reflections within the light trap 514b to increase the absorption of the dark light 512. FIG. 5d illustrates another embodiment with a light trap 514c. As can be seen in the illustration, the shape of the trap 514c is configured to enhance internal reflections to increase the absorption of the dark light 512.

Figure 5E:
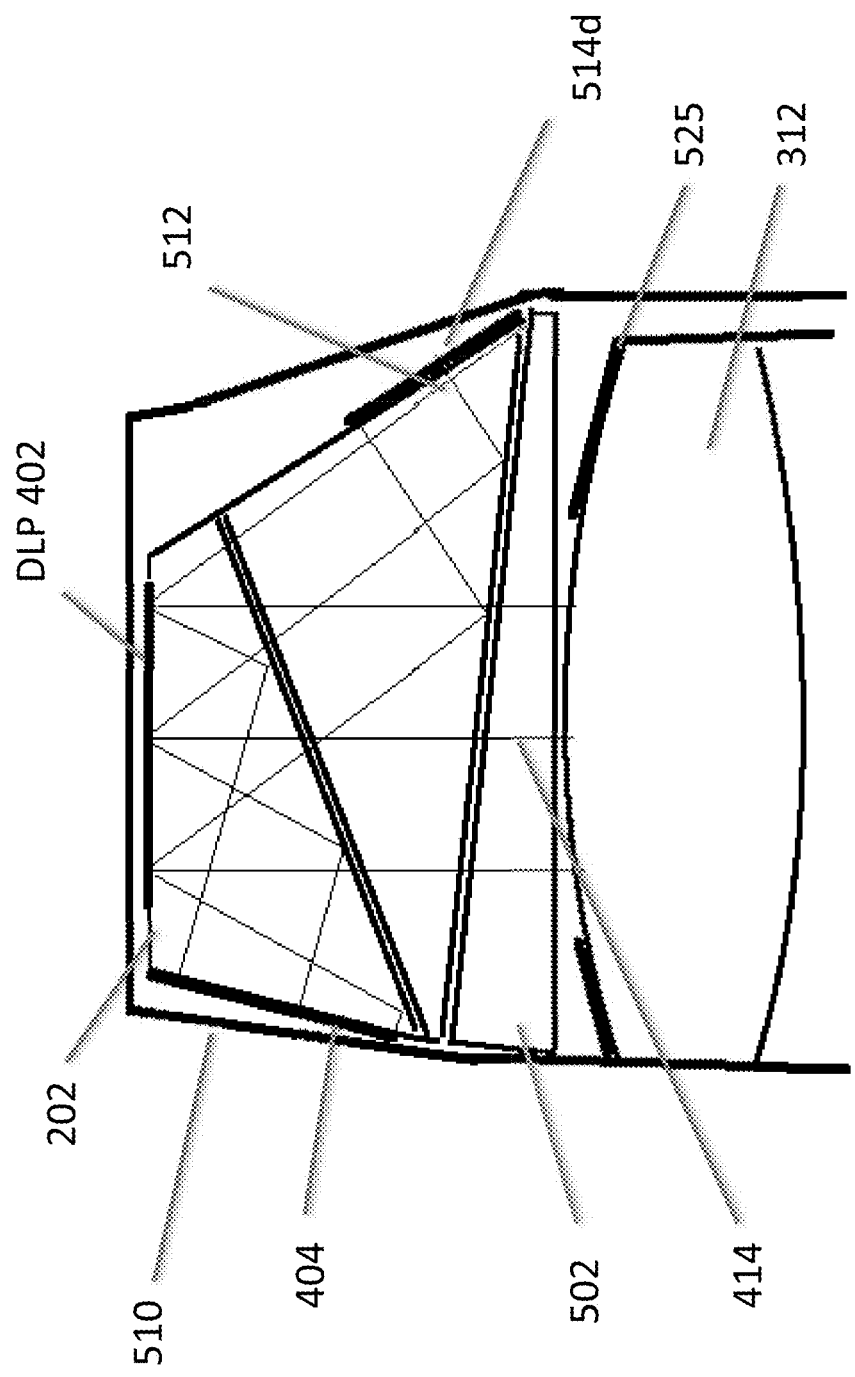
FIG. 5e illustrates an upper optical module and dark light trap according to the principles of the present invention.

FIG. 5e illustrates another embodiment of an upper optical module 202 with a dark light trap 514d. This embodiment of upper module 202 includes an off light reflection wedge 502, as illustrated and described in connection with the embodiment of FIGS. 5 and 5a. As can be seen in FIG. 5e, the light trap 514d is positioned along the optical path of the dark light 512. The dark light trap 514d may be configured as described in other embodiments herein. The embodiment of the light trap 514d illustrated in FIG. 5e includes a black area on the side wall of the wedge, wherein the side wall is located substantially away from the optical axis of the image light 414. In addition, baffles 5252 may be added to one or more edges of the field lens 312 to block the view of the light trap 514d adjacent to the displayed image seen by the user.

Figure 6:
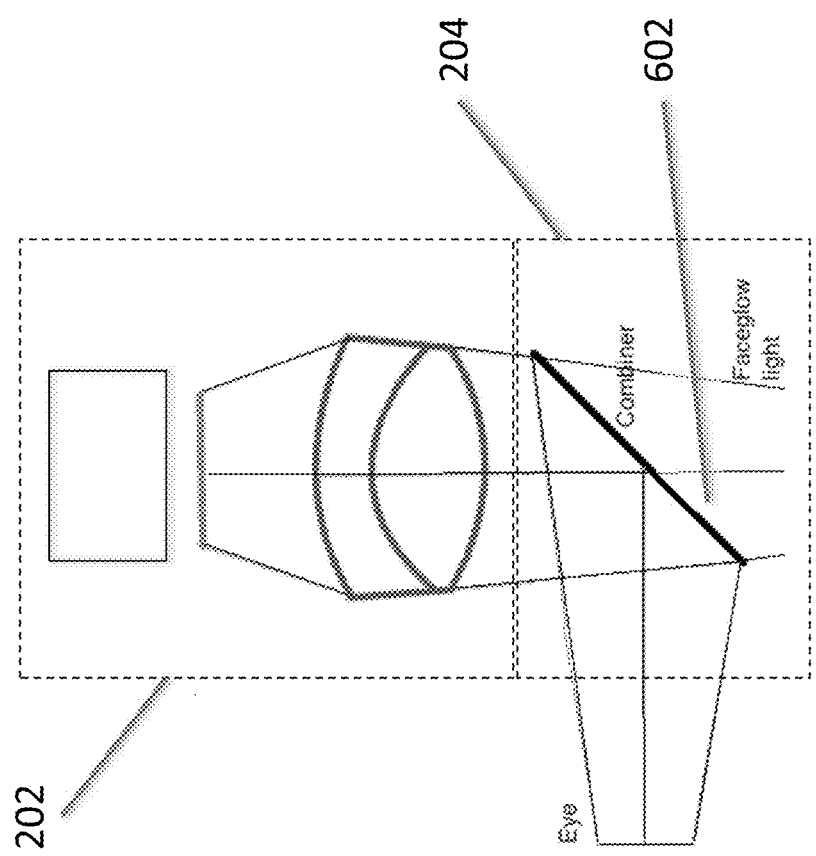
FIG. 6 illustrates upper and lower optical modules in accordance with the principles of the present invention.

FIG. 6 illustrates a combination of an upper optical module 202 with a lower optical module 204. In this embodiment, the image light projected from the upper optical module 202 may or may not be polarized. The image light is reflected off a flat combiner element 602 such that it is directed towards the user's eye. Wherein, the combiner element 602 is a partial mirror that reflects image light while transmitting a substantial portion of light from the environment so the user can look through the combiner element and see the environment surrounding the HWC.

The combiner 602 may include a holographic pattern, to form a holographic mirror. If a monochrome image is desired, there may be a single wavelength reflection design for the holographic pattern on the surface of the combiner 602. If the intention is to have multiple colors reflected from the surface of the combiner 602, a multiple wavelength holographic mirror may be included on the combiner surface. For example, in a three-color embodiment, where red, green and blue pixels are generated in the image light, the holographic mirror may be reflective to wavelengths substantially matching the wavelengths of the red, green and blue light provided by the light source. This configuration can be used as a wavelength specific mirror where predetermined wavelengths of light from the image light are reflected to the user's eye. This configuration may also be made such that substantially all other wavelengths in the visible pass through the combiner element 602 so the user has a substantially clear view of the surroundings when looking through the combiner element 602. The transparency between the user's eye and the surrounding may be approximately 80% when using a combiner that is a holographic mirror. Wherein holographic mirrors can be made using lasers to produce interference patterns in the holographic material of the combiner where the wavelengths of the lasers correspond to the wavelengths of light that are subsequently reflected by the holographic mirror.

In another embodiment, the combiner element 602 may include a notch mirror comprised of a multilayer coated substrate wherein the coating is designed to substantially reflect the wavelengths of light provided by the light source and substantially transmit the remaining wavelengths in the visible spectrum. For example, in the case where red, green and blue light is provided by the light source to enable full color images to be provided to the user, the notch mirror is a tristimulus notch mirror wherein the multilayer coating is designed to reflect narrow bands of red, green and blue light that are matched to the what is provided by the light source and the remaining visible wavelengths are transmitted through the coating to enable a view of the environment through the combiner. In another example where monochrome images are provided to the user, the notch mirror is designed to reflect a single narrow band of light that is matched to the wavelength range of the light provided by the light source while transmitting the remaining visible wavelengths to enable a see-thru view of the environment. The combiner 602 with the notch mirror would operate, from the user's perspective, in a manner similar to the combiner that includes a holographic pattern on the combiner element 602. The combiner, with the tristimulus notch mirror, would reflect the "on" pixels to the eye because of the match between the reflective wavelengths of the notch mirror and the color of the image light, and the wearer would be able to see with high clarity the surroundings. The transparency between the user's eye and the surrounding may be approximately 80% when using the tristimulus notch mirror. In addition, the image provided by the upper optical module 202 with the notch mirror combiner can provide higher contrast images than the holographic mirror combiner due to less scattering of the imaging light by the combiner.

Light can escape through the combiner 602 and may produce face glow as the light is generally directed downward onto the cheek of the user. When using a holographic mirror combiner or a tristimulus notch mirror combiner, the escaping light can be trapped to avoid face glow. In embodiments, if the image light is polarized before the combiner, a linear polarizer can be laminated, or otherwise associated, to the combiner, with the transmission axis of the polarizer oriented relative to the polarized image light so that any escaping image light is absorbed by the polarizer. In embodiments, the image light would be polarized to provide S polarized light to the combiner for better reflection. As a result, the linear polarizer on the combiner would be oriented to absorb S polarized light and pass P polarized light. This provides the preferred orientation of polarized sunglasses as well.

If the image light is unpolarized, a microlouvered film such as a privacy filter can be used to absorb the escaping image light while providing the user with a see-thru view of the environment. In this case, the absorbance or transmittance of the microlouvered film is dependent on the angle of the light. Where steep angle light is absorbed and light at less of an angle is transmitted. For this reason, in an embodiment, the combiner with the microlouver film is angled at greater than 45 degrees to the optical axis of the image light (e.g. the combiner can be oriented at 50 degrees so the image light from the file lens is incident on the combiner at an oblique angle.

Figure 7:
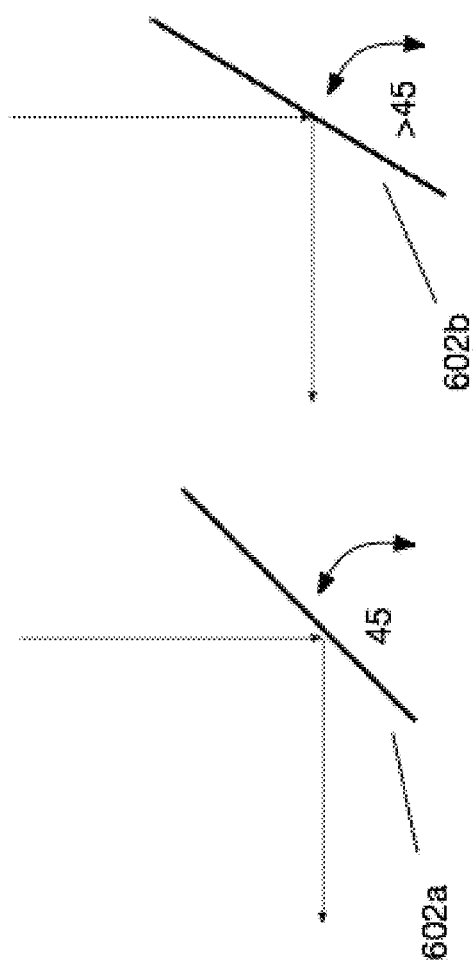
FIG. 7 illustrates angles of combiner elements in accordance with the principles of the present invention.

FIG. 7 illustrates an embodiment of a combiner element 602 at various angles when the combiner element 602 includes a holographic mirror. Normally, a mirrored surface reflects light at an angle equal to the angle that the light is incident to the mirrored surface. Typically, this necessitates that the combiner element be at 45 degrees, 602a, if the light is presented vertically to the combiner so the light can be reflected horizontally towards the wearer's eye. In embodiments, the incident light can be presented at angles other than vertical to enable the mirror surface to be oriented at other than 45 degrees, but in all cases wherein a mirrored surface is employed (including the tristimulus notch mirror described previously), the incident angle equals the reflected angle. As a result, increasing the angle of the combiner 602a requires that the incident image light be presented to the combiner 602a at a different angle which positions the upper optical module 202 to the left of the combiner as shown in FIG. 7. In contrast, a holographic mirror combiner, included in embodiments, can be made such that light is reflected at a different angle from the angle that the light is incident onto the holographic mirrored surface. This allows freedom to select the angle of the combiner element 602b independent of the angle of the incident image light and the angle of the light reflected into the wearer's eye. In embodiments, the angle of the combiner element 602b is greater than 45 degrees (shown in FIG. 7) as this allows a more laterally compact HWC design. The increased angle of the combiner element 602b decreases the front to back width of the lower optical module 204 and may allow for a thinner HWC display (i.e. the furthest element from the wearer's eye can be closer to the wearer's face).

Figure 8:
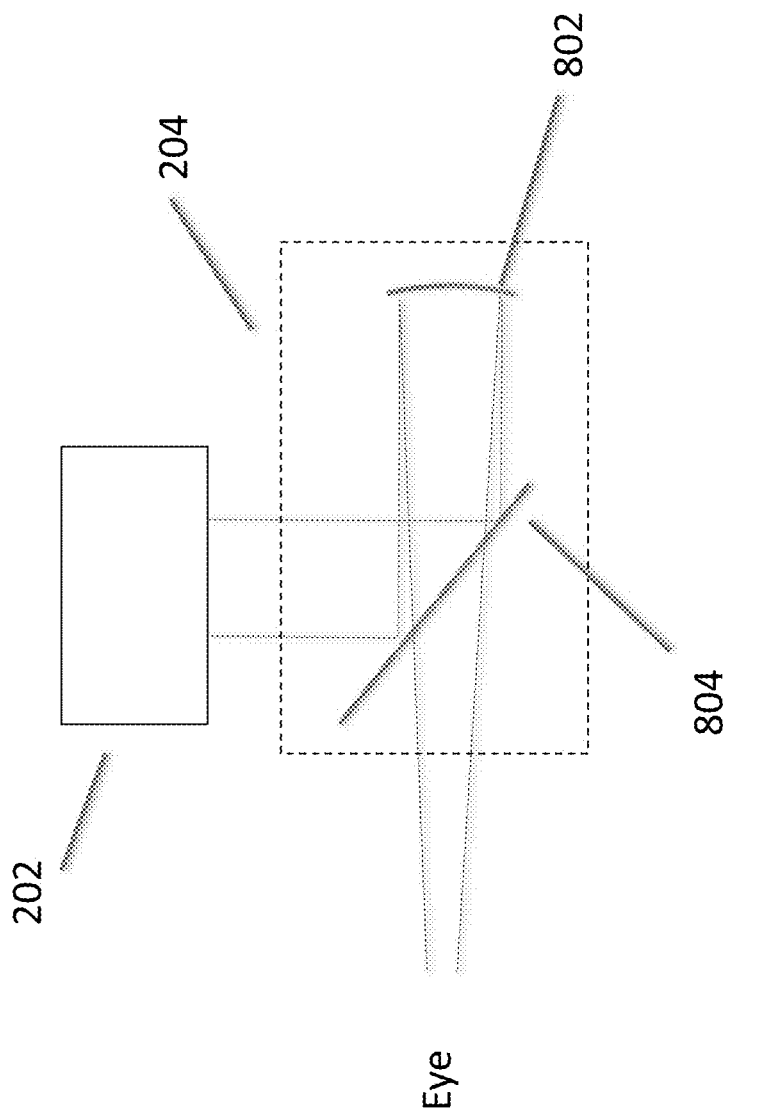
FIG. 8 illustrates upper and lower optical modules in accordance with the principles of the present invention.

FIG. 8 illustrates another embodiment of a lower optical module 204. In this embodiment, polarized image light provided by the upper optical module 202, is directed into the lower optical module 204. The image light reflects off a polarized mirror 804 and is directed to a focusing partially reflective mirror 802, which is adapted to reflect the polarized light. An optical element such as a ¼ wave film located between the polarized mirror 804 and the partially reflective mirror 802, is used to change the polarization state of the image light such that the light reflected by the partially reflective mirror 802 is transmitted by the polarized mirror 804 to present image light to the eye of the wearer. The user can also see through the polarized mirror 804 and the partially reflective mirror 802 to see the surrounding environment. As a result, the user perceives a combined image comprised of the displayed image light overlaid onto the see-thru view of the environment.

While many of the embodiments of the present invention have been referred to as upper and lower modules containing certain optical components, it should be understood that the image light and dark light production and management functions described in connection with the upper module may be arranged to direct light in other directions (e.g. upward, sideward, etc.). In embodiments, it may be preferred to mount the upper module 202 above the wearer's eye, in which case the image light would be directed downward. In other embodiments it may be preferred to produce light from the side of the wearer's eye, or from below the wearer's eye. In addition, the lower optical module is generally configured to deliver the image light to the wearer's eye and allow the wearer to see through the lower optical module, which may be accomplished through a variety of optical components.

Figure 8A:
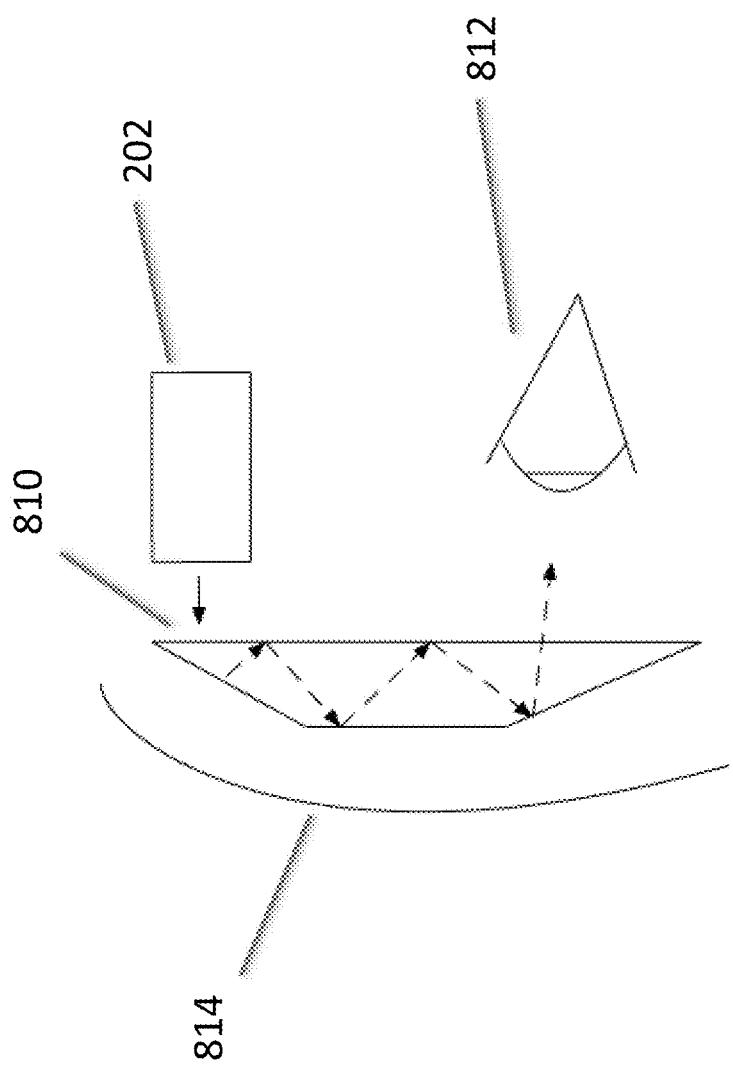
FIG. 8a illustrates upper and lower optical modules in accordance with the principles of the present invention.

FIG. 8a illustrates an embodiment of the present invention where the upper optical module 202 is arranged to direct image light into a TIR waveguide 810. In this embodiment, the upper optical module 202 is positioned above the wearer's eye 812 and the light is directed horizontally into the TIR waveguide 810. The TIR waveguide is designed to internally reflect the image light in a series of downward TIR reflections until it reaches the portion in front of the wearer's eye, where the light passes out of the TIR waveguide 812 into the wearer's eye. In this embodiment, an outer shield 814 is positioned in front of the TIR waveguide 810.

Figure 8B:
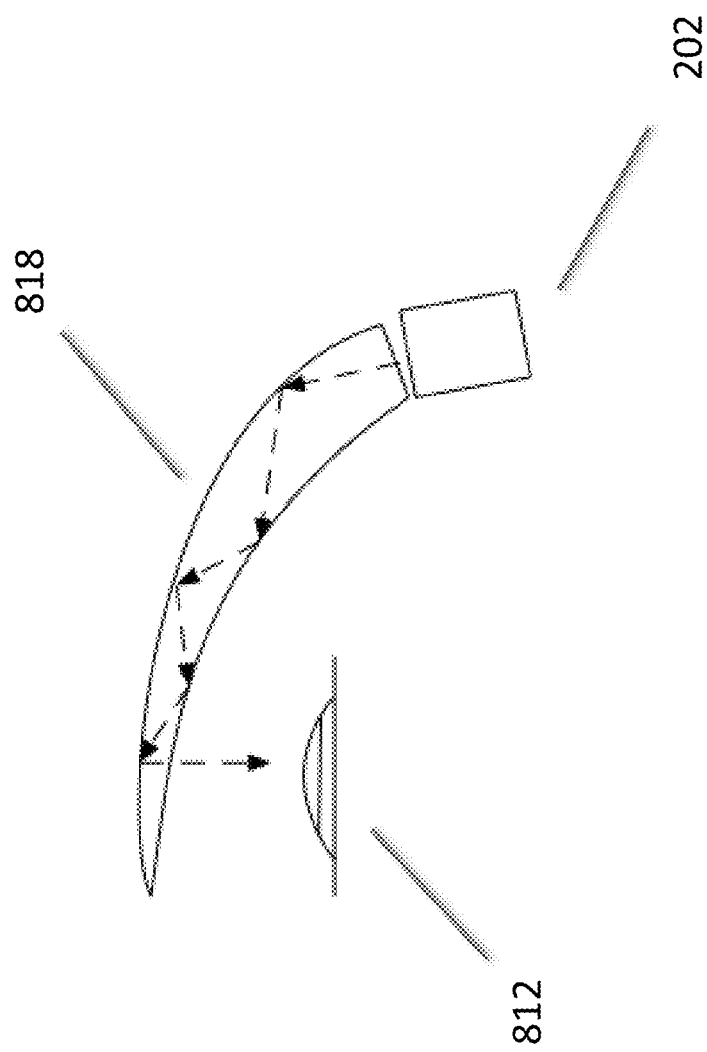
FIG. 8b illustrates upper and lower optical modules in accordance with the principles of the present invention.

FIG. 8b illustrates an embodiment of the present invention where the upper optical module 202 is arranged to direct image light into a TIR waveguide 818. In this embodiment, the upper optical module 202 is arranged on the side of the TIR waveguide 818. For example, the upper optical module may be positioned in the arm or near the arm of the HWC when configured as a pair of head worn glasses. The TIR waveguide 818 is designed to internally reflect the image light in a series of TIR reflections until it reaches the portion in front of the wearer's eye, where the light passes out of the TIR waveguide 812 into the wearer's eye.

Figure 8C:
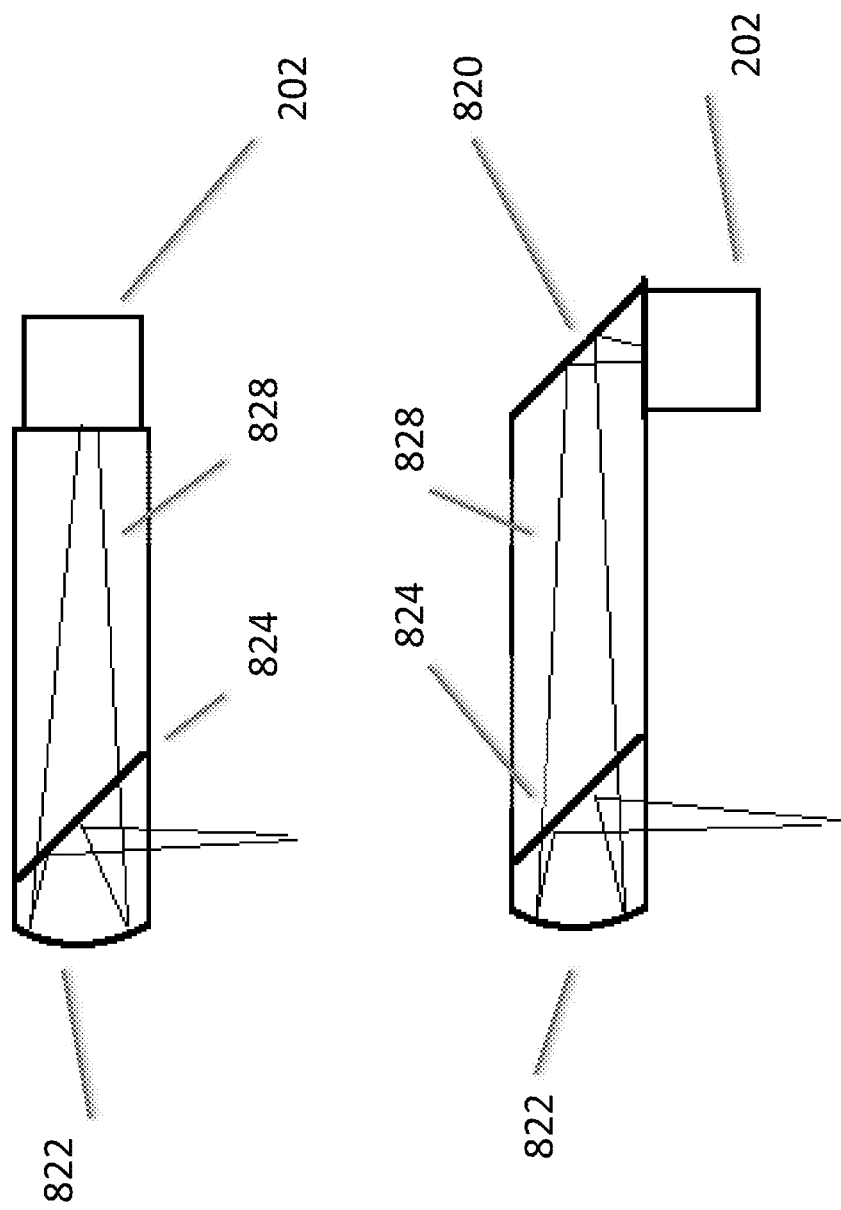
FIG. 8c illustrates upper and lower optical modules in accordance with the principles of the present invention.

FIG. 8c illustrates yet further embodiments of the present invention where an upper optical module 202 is directing polarized image light into an optical guide 828 where the image light passes through a polarized reflector 824, changes polarization state upon reflection of the optical element 822 which includes a ¼ wave film for example and then is reflected by the polarized reflector 824 towards the wearer's eye, due to the change in polarization of the image light. The upper optical module 202 may be positioned to direct light to a mirror 820, to position the upper optical module 202 laterally, in other embodiments, the upper optical module 202 may direct the image light directly towards the polarized reflector 824. It should be understood that the present invention comprises other optical arrangements intended to direct image light into the wearer's eye.

Figure 9:
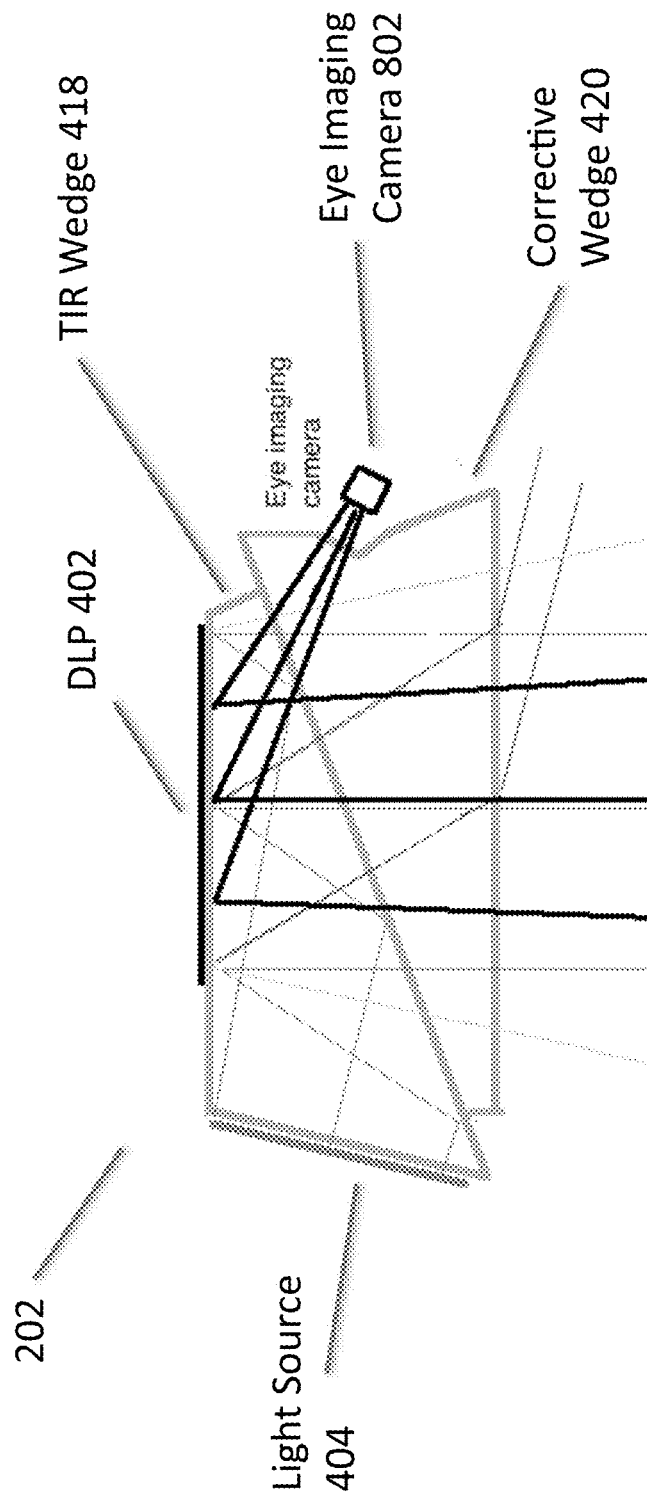
FIG. 9 illustrates an eye imaging system in accordance with the principles of the present invention.

Another aspect of the present invention relates to eye imaging. In embodiments, a camera is used in connection with an upper optical module 202 such that the wearer's eye can be imaged using pixels in the "off" state on the DLP. FIG. 9 illustrates a system where the eye imaging camera 802 is mounted and angled such that the field of view of the eye imaging camera 802 is redirected toward the wearer's eye by the mirror pixels of the DLP 402 that are in the "off" state. In this way, the eye imaging camera 802 can be used to image the wearer's eye along the same optical axis as the displayed image that is presented to the wearer. Wherein, image light that is presented to the wearer's eye illuminates the wearer's eye so that the eye can be imaged by the eye imaging camera 802. In the process, the light reflected by the eye passes back though the optical train of the lower optical module 204 and a portion of the upper optical module to where the light is reflected by the "off" pixels of the DLP 402 toward the eye imaging camera 802.

In embodiments, the eye imaging camera may image the wearer's eye at a moment in time where there are enough "off" pixels to achieve the required eye image resolution. In another embodiment, the eye imaging camera collects eye image information from "off" pixels over time and forms a time lapsed image. In another embodiment, a modified image is presented to the user wherein enough "off" state pixels are included that the camera can obtain the desired resolution and brightness for imaging the wearer's eye and the eye image capture is synchronized with the presentation of the modified image.

The eye imaging system may be used for security systems. The HWC may not allow access to the HWC or other system if the eye is not recognized (e.g. through eye characteristics including retina or iris characteristics, etc.). The HWC may be used to provide constant security access in some embodiments. For example, the eye security confirmation may be a continuous, near-continuous, real-time, quasi real-time, periodic, etc. process so the wearer is effectively constantly being verified as known. In embodiments, the HWC may be worn and eye security tracked for access to other computer systems.

The eye imaging system may be used for control of the HWC. For example, a blink, wink, or particular eye movement may be used as a control mechanism for a software application operating on the HWC or associated device.

The eye imaging system may be used in a process that determines how or when the HWC 102 delivers digitally displayed content to the wearer. For example, the eye imaging system may determine that the user is looking in a direction and then HWC may change the resolution in an area of the display or provide some content that is associated with something in the environment that the user may be looking at. Alternatively, the eye imaging system may identify different user's and change the displayed content or enabled features provided to the user. User's may be identified from a database of users eye characteristics either located on the HWC 102 or remotely located on the network 110 or on a server 112. In addition, the HWC may identify a primary user or a group of primary users from eye characteristics wherein the primary user(s) are provided with an enhanced set of features and all other user's are provided with a different set of features. Thus in this use case, the HWC 102 uses identified eye characteristics to either enable features or not and eye characteristics need only be analyzed in comparison to a relatively small database of individual eye characteristics.

FIG. 10 illustrates a light source that may be used in association with the upper optics module 202 (e.g. polarized light source if the light from the solid state light source is polarized such as polarized light source 302 and 458), and light source 404. In embodiments, to provide a uniform surface of light 1008 to be directed into the upper optical module 202 and towards the DLP of the upper optical module, either directly or indirectly, the solid state light source 1002 may be projected into a backlighting optical system 1004. The solid state light source 1002 may be one or more LEDs, laser diodes, OLEDs. In embodiments, the backlighting optical system 1004 includes an extended section with a length/distance ratio of greater than 3, wherein the light undergoes multiple reflections from the sidewalls to mix of homogenize the light as supplied by the solid state light source 1002. The backlighting optical system 1004 can also include structures on the surface opposite (on the left side as shown in FIG. 10) to where the uniform light 1008 exits the backlight 1004 to change the direction of the light toward the DLP 302 and the reflective polarizer 310 or the DLP 402 and the TIR wedge 418. The backlighting optical system 1004 may also include structures to collimate the uniform light 1008 to provide light to the DLP with a smaller angular distribution or narrower cone angle. Diffusers or polarizers can be used on the entrance or exit surface of the backlighting optical system. Diffusers can be used to spread or uniformize the exiting light from the backlight to improve the uniformity or increase the angular spread of the uniform light 1008. Elliptical diffusers that diffuse the light more in some directions and less in others can be used to improve the uniformity or spread of the uniform light 1008 in directions orthogonal to the optical axis of the uniform light 1008. Linear polarizers can be used to convert unpolarized light as supplied by the solid state light source 1002 to polarized light so the uniform light 1008 is polarized with a desired polarization state. A reflective polarizer can be used on the exit surface of the backlight 1004 to polarize the uniform light 1008 to the desired polarization state, while reflecting the other polarization state back into the backlight where it is recycled by multiple reflections within the backlight 1004 and at the solid state light source 1002. Therefore by including a reflective polarizer at the exit surface of the backlight 1004, the efficiency of the polarized light source is improved.

Figure 10A:
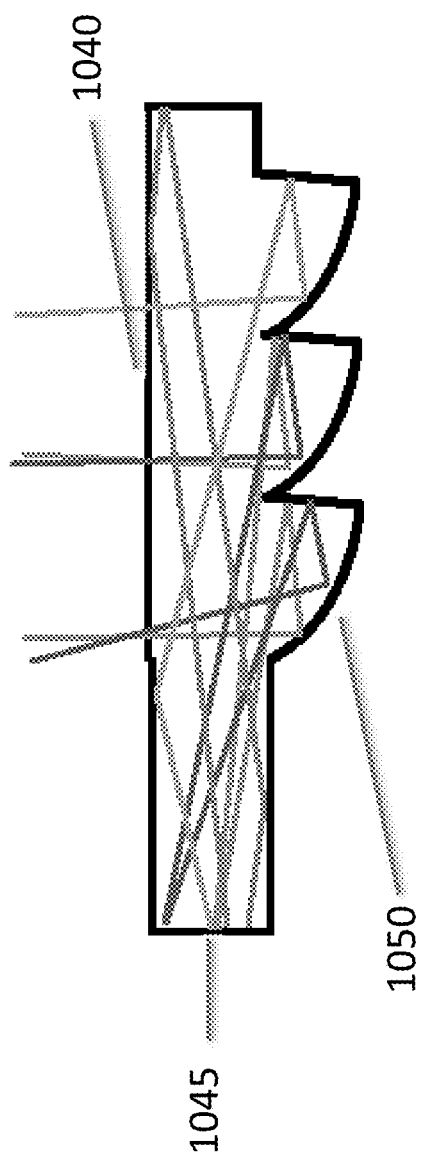
FIG. 10a illustrates a back lighting system in accordance with the principles of the present invention.
Figure 10B:
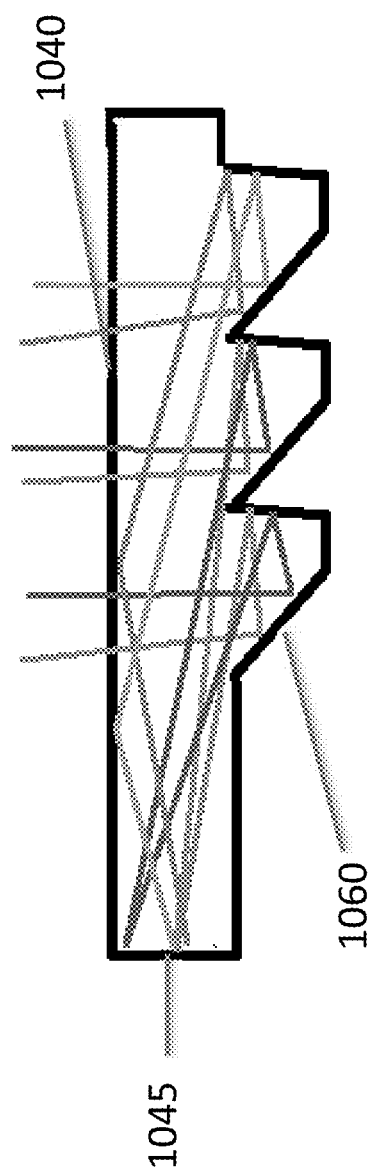
FIG. 10b illustrates a back lighting system in accordance with the principles of the present invention.

FIGS. 10*a* and 10*b* show illustrations of structures in backlight optical systems 1004 that can be used to change the direction of the light provided to the entrance face 1045 by the light source and then collimates the light in a direction lateral to the optical axis of the exiting uniform light 1008. Structure 1060 includes an angled sawtooth pattern in a transparent waveguide wherein the left edge of each sawtooth clips the steep angle rays of light thereby limiting the angle of the light being redirected. The steep surface at the right (as shown) of each sawtooth then redirects the light so that it reflects off the left angled surface of each sawtooth and is directed toward the exit surface 1040. The sawtooth surfaces shown on the lower surface in FIGS. 10*a* and 10*b*, can be smooth and coated (e.g. with an aluminum coating or a dielectric mirror coating) to provide a high level of reflectivity without scattering. Structure 1050 includes a curved face on the left side (as shown) to focus the rays after they pass through the exit surface 1040, thereby providing a mechanism for collimating the uniform light 1008. In a further embodiment, a diffuser can be provided between the solid state light source 1002 and the entrance face 1045 to homogenize the light provided by the solid state light source 1002. In yet a further embodiment, a polarizer can be used between the diffuser and the entrance face 1045 of the backlight 1004 to provide a polarized light source. Because the sawtooth pattern provides smooth reflective surfaces, the polarization state of the light can be preserved from the entrance face 1045 to the exit face 1040. In this embodiment, the light entering the backlight from the solid state light source 1002 passes through the polarizer so that it is polarized with the desired polarization state. If the polarizer is an absorptive linear polarizer, the light of the desired polarization state is transmitted while the light of the other polarization state is absorbed. If the polarizer is a reflective polarizer, the light of the desired polarization state is transmitted into the backlight 1004 while the light of the other polarization state is reflected back into the solid state light source 1002 where it can be recycled as previously described, to increase the efficiency of the polarized light source.

Figure 11A:
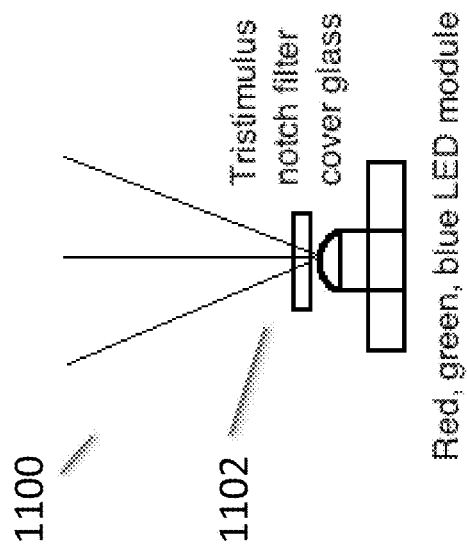
FIGS. 11a to 11d illustrate light source and filters in accordance with the principles of the present invention.
Figure 11B:
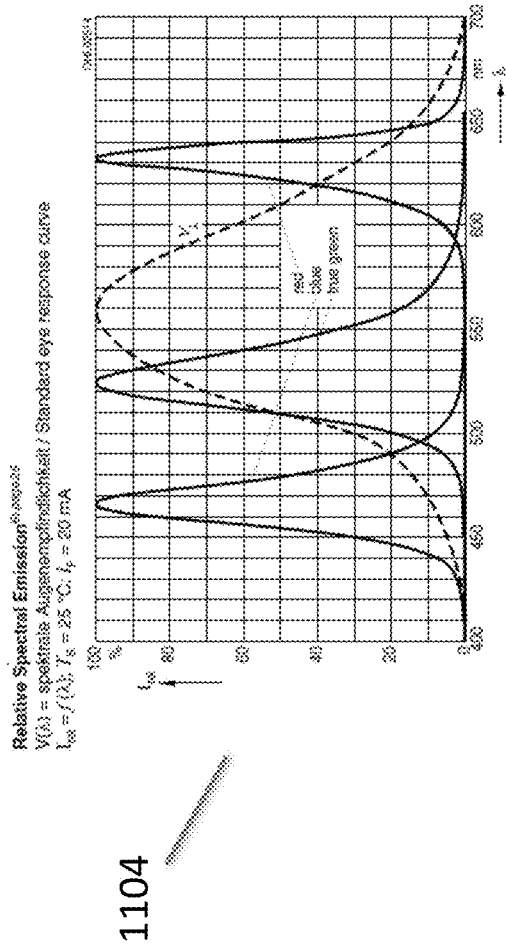
Figure 11C:
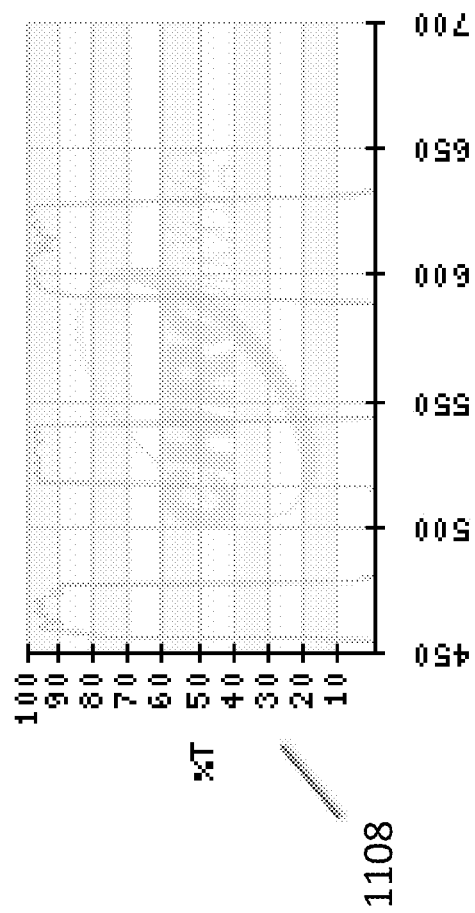
Figure 11D:
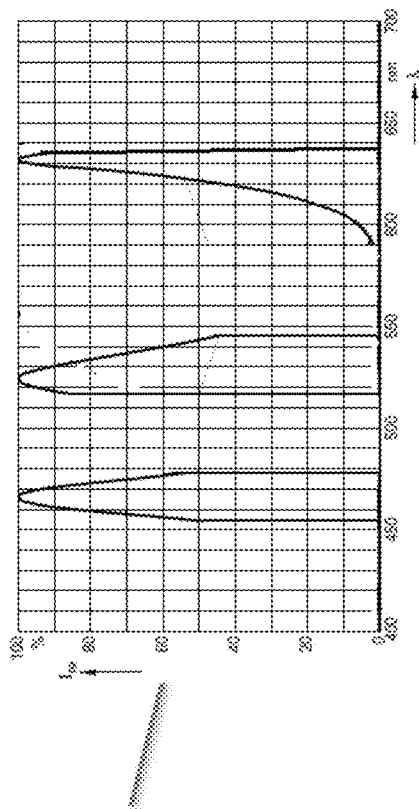

FIG. 11*a* illustrates a light source 1100 that may be used in association with the upper optics module 202. In embodiments, the light source 1100 may provide light to a backlighting optical system 1004 as described above in connection with FIG. 10. In embodiments, the light source 1100 includes a tristimulus notch filter 1102. The tristimulus notch filter 1102 has narrow band pass filters for three wavelengths, as indicated in FIG. 11*c* in a transmission graph 1108. The graph shown in FIG. 11*b*, as 1104 illustrates an output of three different colored LEDs. One can see that the bandwidths of emission are narrow, but they have long tails. The tristimulus notch filter 1102 can be used in connection with such LEDs to provide a light source 1100 that emits narrow filtered wavelengths of light as shown in FIG. 11*d* as the transmission graph 1110. Wherein the clipping effects of the tristimulus notch filter 1102 can be seen to have cut the tails from the LED emission graph 1104 to provide narrower wavelength bands of light to the upper optical module 202. The light source 1100 can be used in connection with a combiner 602 with a holographic mirror or tristimulus notch mirror to provide narrow bands of light that are reflected toward the wearer's eye with less waste light that does not get reflected by the combiner, thereby improving efficiency and reducing escaping light that can cause faceglow.

Figure 12A:
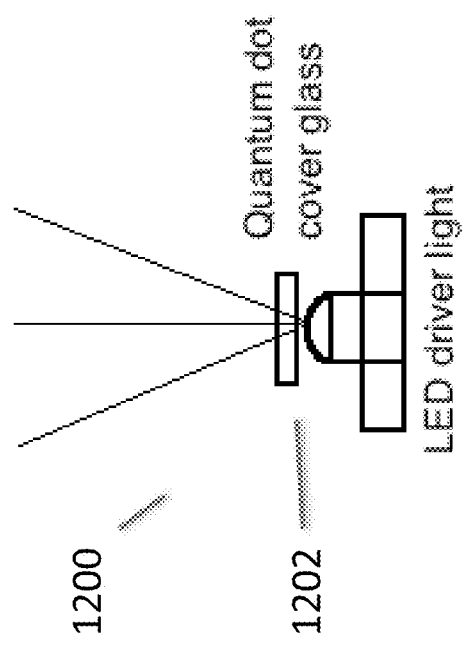
FIGS. 12a to 12c illustrate light source and quantum dot systems in accordance with the principles of the present invention.
Figure 12B:
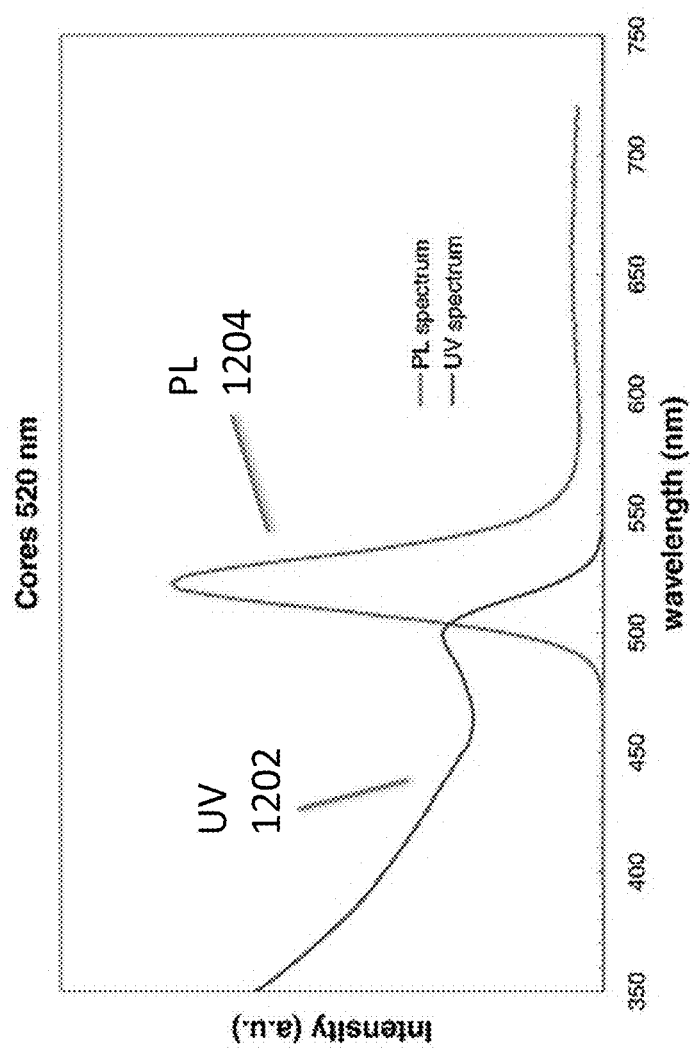
Figure 12C:
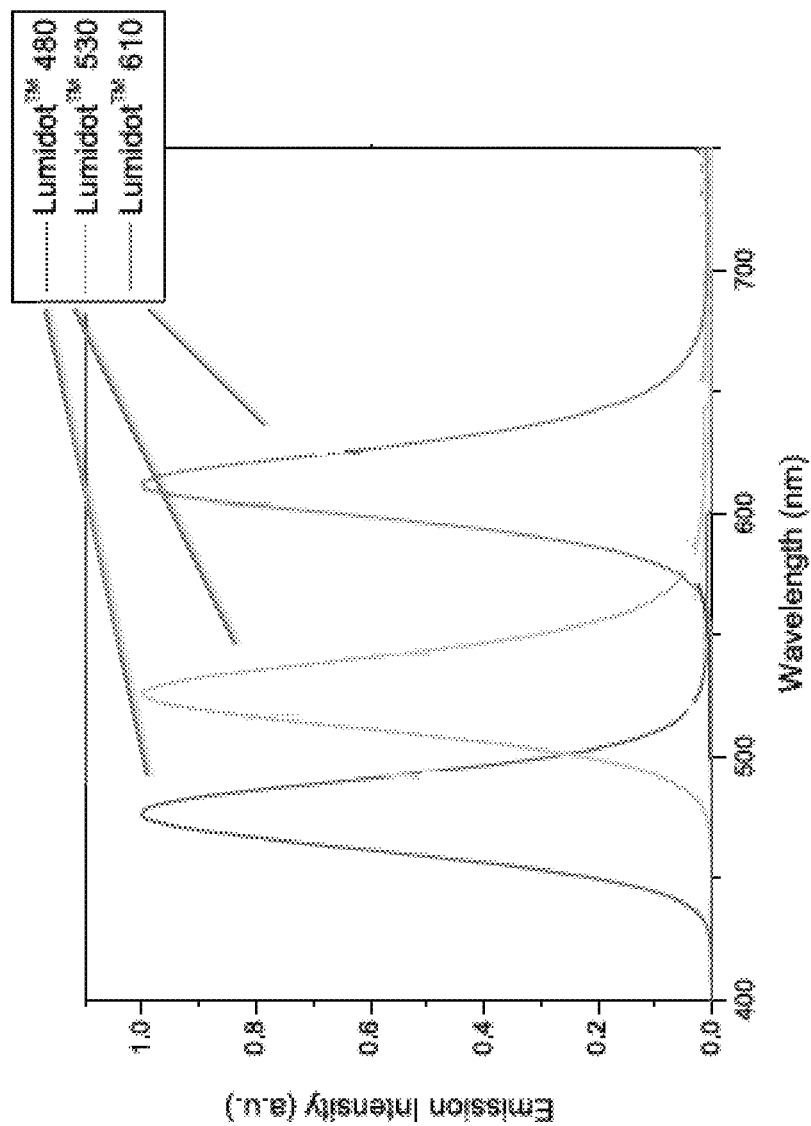

FIG. 12*a* illustrates another light source 1200 that may be used in association with the upper optics module 202. In embodiments, the light source 1200 may provide light to a backlighting optical system 1004 as described above in connection with FIG. 10. In embodiments, the light source 1200 includes a quantum dot cover glass 1202. Where the quantum dots absorb light of a shorter wavelength and emit light of a longer wavelength (FIG. 12b shows an example wherein a UV spectrum 1202 applied to a quantum dot results in the quantum dot emitting a narrow band shown as a PL spectrum 1204) that is dependent on the material makeup and size of the quantum dot. As a result, quantum dots in the quantum dot cover glass 1202 can be tailored to provide one or more bands of narrow bandwidth light (e.g. red, green and blue emissions dependent on the different quantum dots included as illustrated in the graph shown in FIG. 12c where three different quantum dots are used. In embodiments, the LED driver light emits UV light, deep blue or blue light. For sequential illumination of different colors, multiple light sources 1200 would be used where each light source 1200 would include a quantum dot cover glass 1202 with a quantum dot selected to emit at one of the desired colors. The light source 1100 can be used in connection with a combiner 602 with a holographic mirror or tristimulus notch mirror to provide narrow transmission bands of light that are reflected toward the wearer's eye with less waste light that does not get reflected.

Another aspect of the present invention relates to the generation of peripheral image lighting effects for a person wearing a HWC. In embodiments, a solid state lighting system (e.g. LED, OLED, etc), or other lighting system, may be included inside the optical elements of an lower optical module 204. The solid state lighting system may be arranged such that lighting effects outside of a field of view (FOV) of the presented digital content is presented to create an emersive effect for the person wearing the HWC. To this end, the lighting effects may be presented to any portion of the HWC that is visible to the wearer. The solid state lighting system may be digitally controlled by an integrated processor on the HWC. In embodiments, the integrated processor will control the lighting effects in coordination with digital content that is presented within the FOV of the HWC. For example, a movie, picture, game, or other content, may be displayed or playing within the FOV of the HWC. The content may show a bomb blast on the right side of the FOV and at the same moment, the solid state lighting system inside of the upper module optics may flash quickly in concert with the FOV image effect. The effect may not be fast, it may be more persistent to indicate, for example, a general glow or color on one side of the user. The solid state lighting system may be color controlled, with red, green and blue LEDs, for example, such that color control can be coordinated with the digitally presented content within the field of view.

Figure 13A:
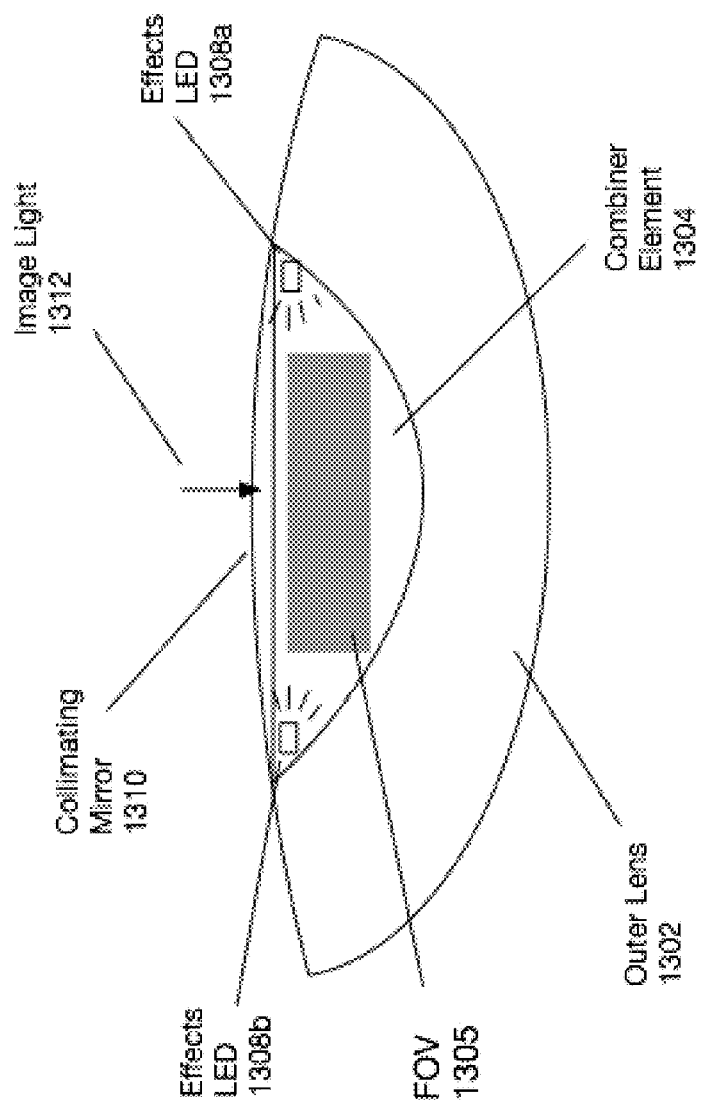

FIG. 13a illustrates optical components of a lower optical module 204 together with an outer lens 1302. FIG. 13a also shows an embodiment including effects LED's 1308a and 1308b. FIG. 13a illustrates image light 1312, as described herein elsewhere, directed into the upper optical module where it will reflect off of the combiner element 1304, as described herein elsewhere. The combiner element 1304 in this embodiment is angled towards the wearer's eye at the top of the module and away from the wearer's eye at the bottom of the module, as also illustrated and described in connection with FIG. 8 (e.g. at a 45 degree angle). The image light 1312 provided by an upper optical module 202 (not shown in FIG. 13a) reflects off of the combiner element 1304 towards the collimating mirror 1310, away from the wearer's eye, as described herein elsewhere. The image light 1312 then reflects and focuses off of the collimating mirror 1304, passes back through the combiner element 1304, and is directed into the wearer's eye. The wearer can also view the surrounding environment through the transparency of the combiner element 1304, collimating mirror 1310, and outer lens 1302 (if it is included). As described herein elsewhere, various surfaces are polarized to create the optical path for the image light and to provide transparency of the elements such that the wearer can view the surrounding environment. The wearer will generally perceive that the image light forms an image in the FOV 1305. In embodiments, the outer lens 1302 may be included. The outer lens 1302 is an outer lens that may or may not be corrective and it may be designed to conceal the lower optical module components in an effort to make the HWC appear to be in a form similar to standard glasses or sunglasses.

In the embodiment illustrated in FIG. 13a, the effects LEDs 1308a and 1308b are positioned at the sides of the combiner element 1304 and the outer lens 1302 and/or the collimating mirror 1310. In embodiments, the effects LEDs 1308a are positioned within the confines defined by the combiner element 1304 and the outer lens 1302 and/or the collimating mirror. The effects LEDs 1308a and 1308b are also positioned outside of the FOV 1305. In this arrangement, the effects LEDs 1308a and 1308b can provide lighting effects within the lower optical module outside of the FOV 1305. In embodiments the light emitted from the effects LEDs 1308a and 1308b may be polarized such that the light passes through the combiner element 1304 toward the wearer's eye and does not pass through the outer lens 1302 and/or the collimating mirror 1310. This arrangement provides peripheral lighting effects to the wearer in a more private setting by not transmitting the lighting effects through the front of the HWC into the surrounding environment. However, in other embodiments, the effects LEDs 1308a and 1308b may be unpolarized so the lighting effects provided are made to be purposefully viewable by others in the environment for entertainment such as giving the effect of the wearer's eye glowing in correspondence to the image content being viewed by the wearer.

Figure 13B:
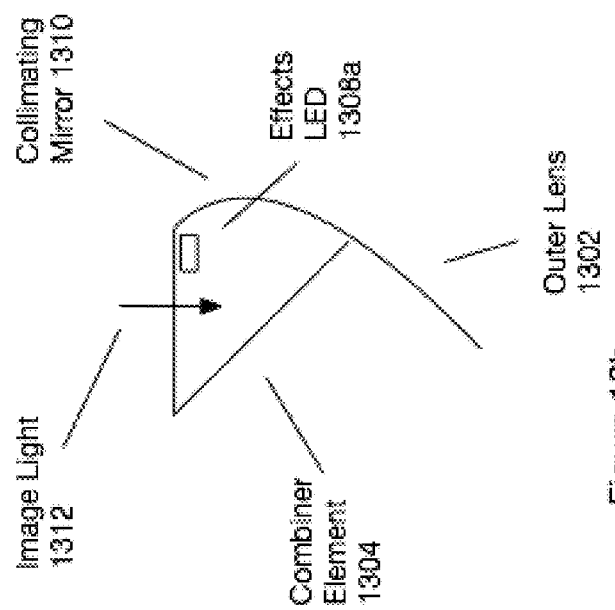

FIG. 13b illustrates a cross section of the embodiment described in connection with FIG. 13a. As illustrated, the effects LED 1308a is located in the upper-front area inside of the optical components of the lower optical module. It should be understood that the effects LED 1308a position in the described embodiments is only illustrative and alternate placements are encompassed by the present invention. Additionally, in embodiments, there may be one or more effects LEDs 1308a in each of the two sides of HWC to provide peripheral lighting effects near one or both eyes of the wearer.

FIG. 13c illustrates an embodiment where the combiner element 1304 is angled away from the eye at the top and towards the eye at the bottom (e.g. in accordance with the holographic or notch filter embodiments described herein). In this embodiment, the effects LED 1308a is located on the outer lens 1302 side of the combiner element 1304 to provide a concealed appearance of the lighting effects. As with other embodiments, the effects LED 1308a of FIG. 13c may include a polarizer such that the emitted light can pass through a polarized element associated with the combiner element 1304 and be blocked by a polarized element associated with the outer lens 1302.

Another aspect of the present invention relates to the mitigation of light escaping from the space between the wearer's face and the HWC itself. Another aspect of the present invention relates to maintaining a controlled lighting environment in proximity to the wearer's eyes. In embodiments, both the maintenance of the lighting environment and the mitigation of light escape are accomplished by including a removable and replaceable flexible shield for the HWC.

Wherein the removable and replaceable shield can be provided for one eye or both eyes in correspondence to the use of the displays for each eye. For example, in a night vision application, the display to only one eye could be used for night vision while the display to the other eye is turned off to provide good see-thru when moving between areas where visible light is available and dark areas where night vision enhancement is needed.

Figure 14A:
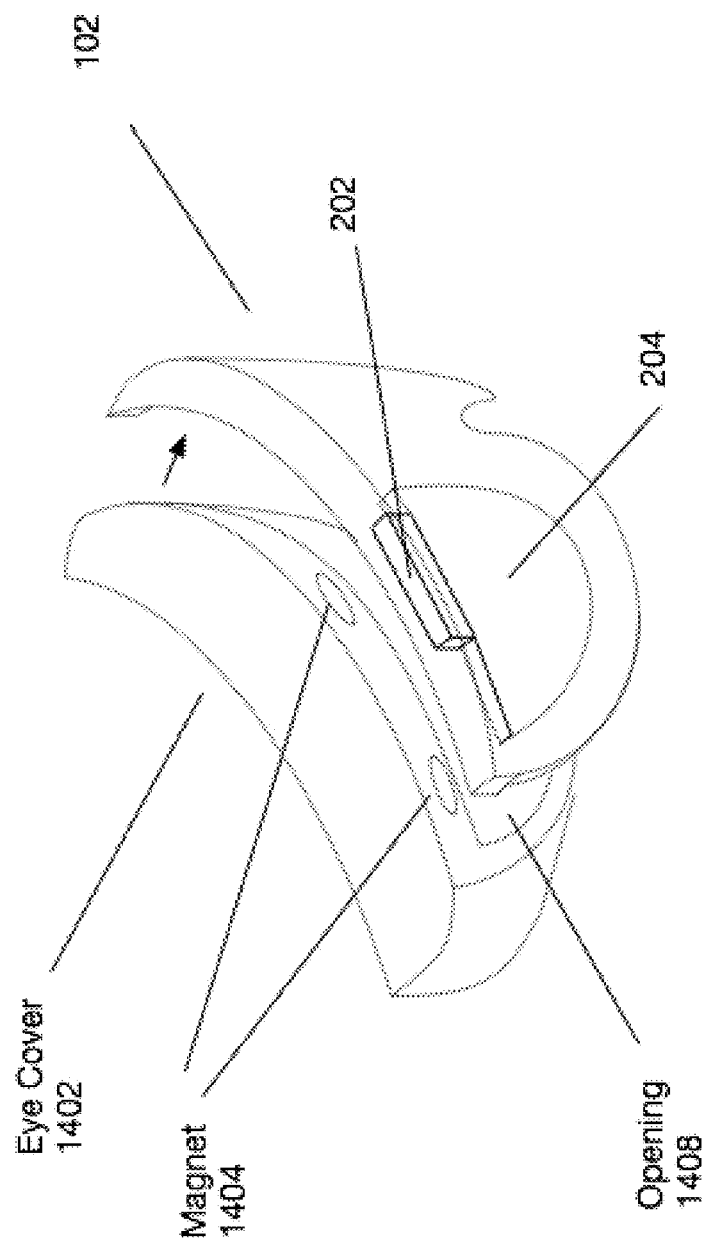
FIGS. 14a to 14c illustrate a light suppression systems in accordance with the principles of the present invention.
Figure 14B:
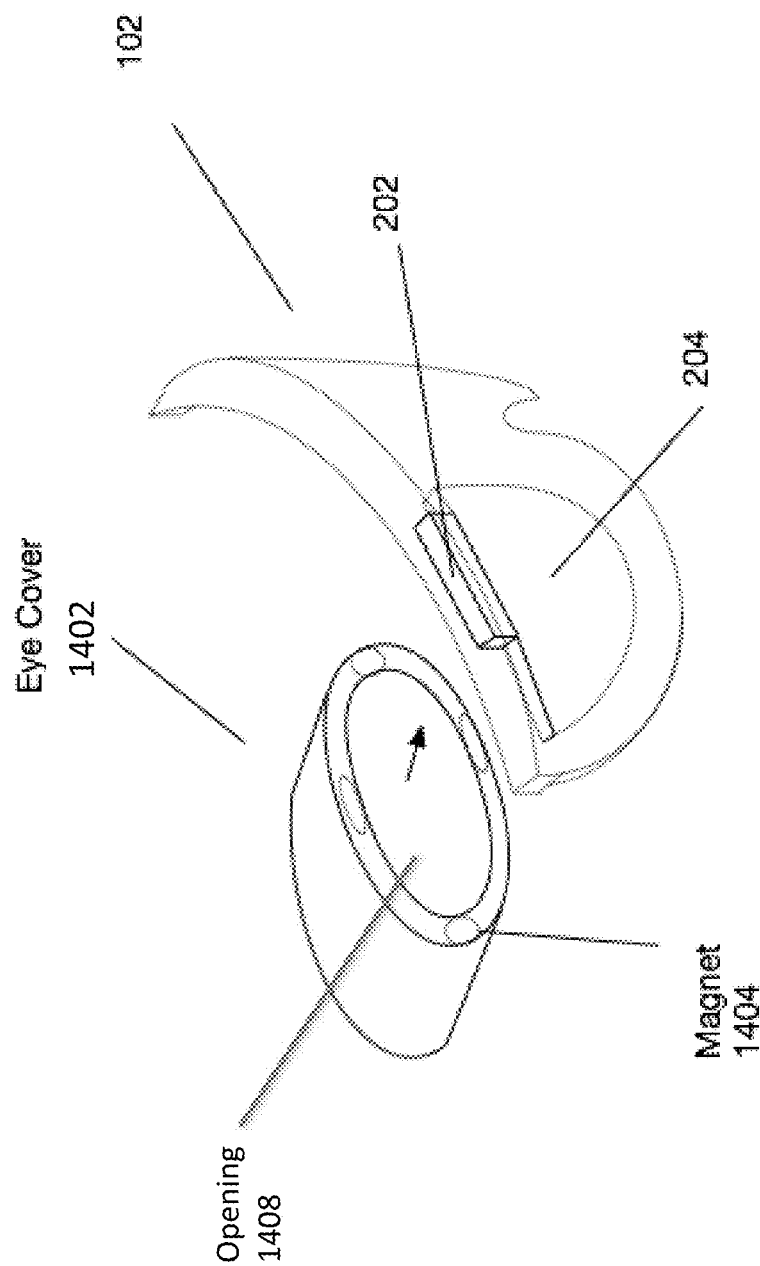

FIG. 14a illustrates a removable and replaceable flexible eye cover 1402 with an opening 1408 that can be attached and removed quickly from the HWC 102 through the use of magnets. Other attachment methods may be used, but for illustration of the present invention we will focus on a magnet implementation. In embodiments, magnets may be included in the eye cover 1402 and magnets of an opposite polarity may be included (e.g. embedded) in the frame of the HWC 102. The magnets of the two elements would attract quite strongly with the opposite polarity configuration. In another embodiment, one of the elements may have a magnet and the other side may have metal for the attraction. In embodiments, the eye cover 1402 is a flexible elastomeric shield. In embodiments, the eye cover 1402 may be an elastomeric bellows design to accommodate flexibility and more closely align with the wearer's face. FIG. 14b illustrates a removable and replaceable flexible eye cover 1404 that is adapted as a single eye cover. In embodiments, a single eye cover may be used for each side of the HWC to cover both eyes of the wearer. In embodiments, the single eye cover may be used in connection with a HWC that includes only one computer display for one eye. These configurations prevent light that is generated and directed generally towards the wearer's face by covering the space between the wearer's face and the HWC. The opening 1408 allows the wearer to look through the opening 1408 to view the displayed content and the surrounding environment through the front of the HWC. The image light in the lower optical module 204 can be prevented from emitting from the front of the HWC through internal optics polarization schemes, as described herein, for example.

Figure 14C:
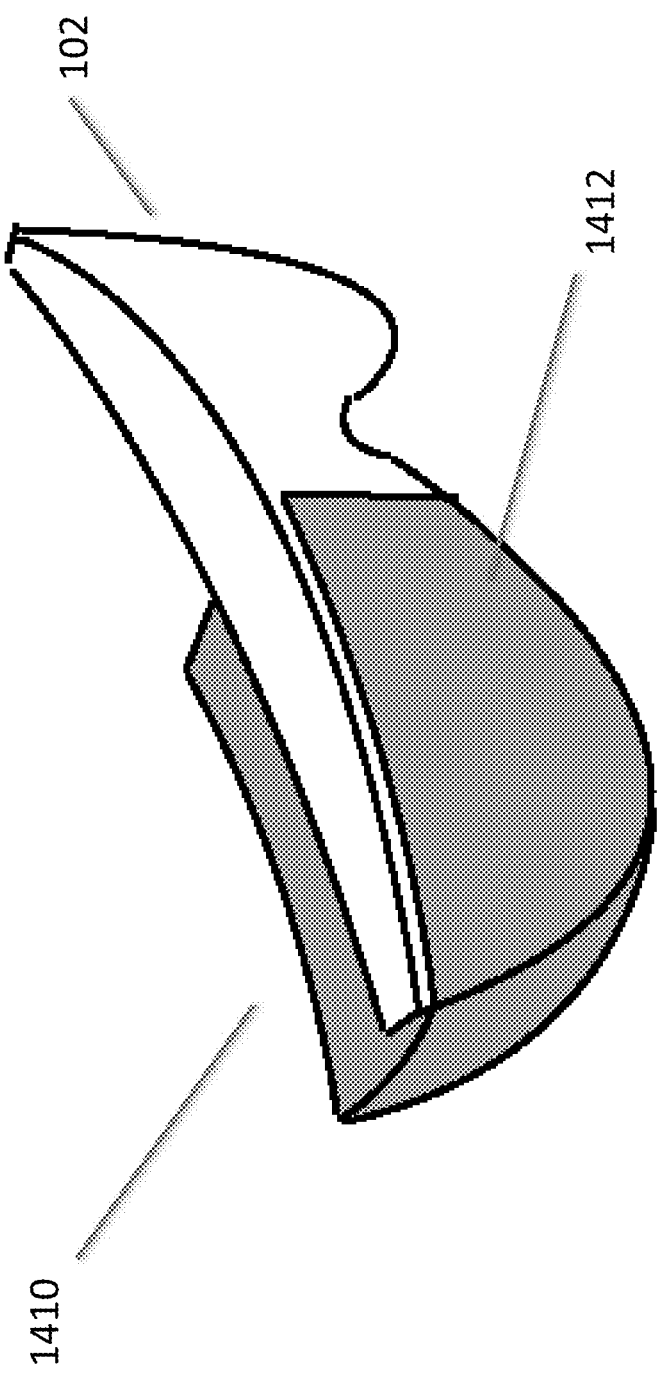

FIG. 14c illustrates another embodiment of a light suppression system. In this embodiment, the eye cover 1410 may be similar to the eye cover 1402, but eye cover 1410 includes a front light shield 1412. The front light shield 1412 may be opaque to prevent light from escaping the front lens of the HWC. In other embodiments, the front light shield 1412 is polarized to prevent light from escaping the front lens. In a polarized arrangement, in embodiments, the internal optical elements of the HWC (e.g. of the lower optical module 204) may polarize light transmitted towards the front of the HWC and the front light shield 1412 may be polarized to prevent the light from transmitting through the front light shield 1412.

In embodiments, an opaque front light shield 1412 may be included and the digital content may include images of the surrounding environment such that the wearer can visualize the surrounding environment. One eye may be presented with night vision environmental imagery and this eye's surrounding environment optical path may be covered using an opaque front light shield 1412. In other embodiments, this arrangement may be associated with both eyes.

Another aspect of the present invention relates to automatically configuring the lighting system(s) used in the HWC 102. In embodiments, the display lighting and/or effects lighting, as described herein, may be controlled in a manner suitable for when an eye cover 1408 is attached or removed from the HWC 102. For example, at night, when the light in the environment is low, the lighting system(s) in the HWC may go into a low light mode to further control any amounts of stray light escaping from the HWC and the areas around the HWC. Covert operations at night, while using night vision or standard vision, may require a solution which prevents as much escaping light as possible so a user may clip on the eye cover(s) 1408 and then the HWC may go into a low light mode. The low light mode may, in some embodiments, only go into a low light mode when the eye cover 1408 is attached if the HWC identifies that the environment is in low light conditions (e.g. through environment light level sensor detection). In embodiments, the low light level may be determined to be at an intermediate point between full and low light dependent on environmental conditions.

Another aspect of the present invention relates to automatically controlling the type of content displayed in the HWC when eye covers 1408 are attached or removed from the HWC. In embodiments, when the eye cover(s) 1408 is attached to the HWC, the displayed content may be restricted in amount or in color amounts. For example, the display(s) may go into a simple content delivery mode to restrict the amount of information displayed. This may be done to reduce the amount of light produced by the display(s). In an embodiment, the display(s) may change from color displays to monochrome displays to reduce the amount of light produced. In an embodiment, the monochrome lighting may be red to limit the impact on the wearer's eyes to maintain an ability to see better in the dark.

Figure 15:
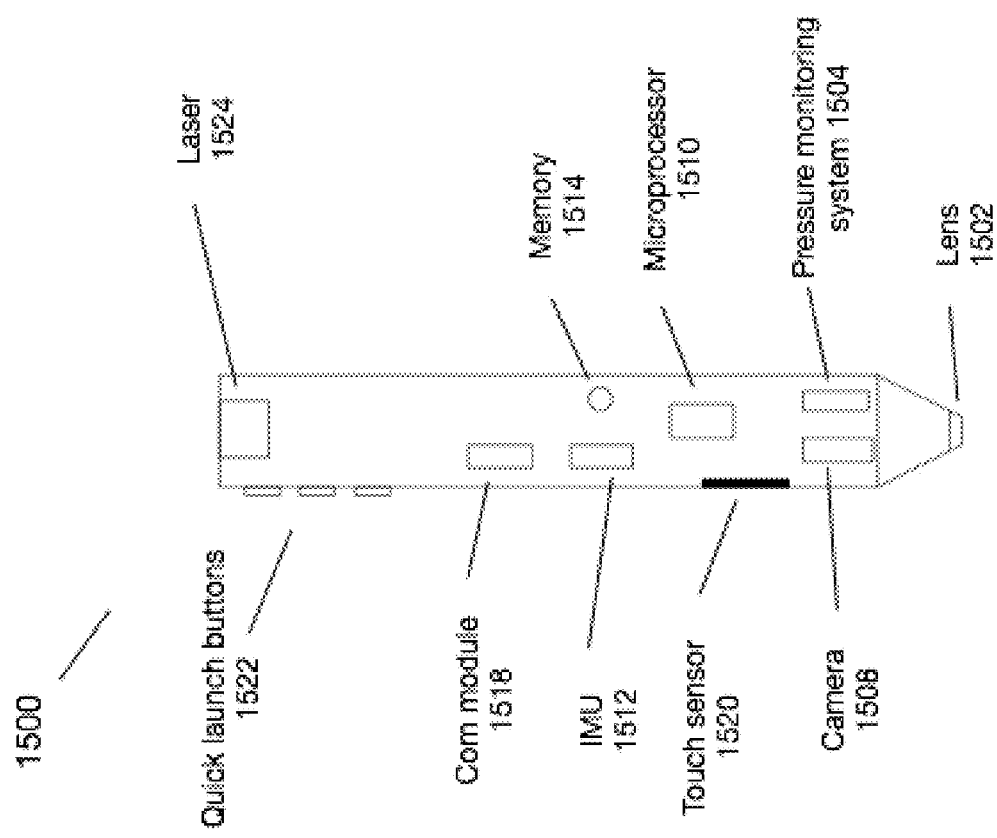
FIG. 15 illustrates an external user interface in accordance with the principles of the present invention.

Referring to FIG. 15, we now turn to describe a particular external user interface 104, referred to generally as a pen 1500. The pen 1500 is a specially designed external user interface 104 and can operate as a user interface, such as to many different styles of HWC 102. The pen 1500 generally follows the form of a conventional pen, which is a familiar user handled device and creates an intuitive physical interface for many of the operations to be carried out in the HWC system 100. The pen 1500 may be one of several user interfaces 104 used in connection with controlling operations within the HWC system 100. For example, the HWC 102 may watch for and interpret hand gestures 116 as control signals, where the pen 1500 may also be used as a user interface with the same HWC 102. Similarly, a remote keyboard may be used as an external user interface 104 in concert with the pen 1500. The combination of user interfaces or the use of just one control system generally depends on the operation(s) being executed in the HWC's system 100.

While the pen 1500 may follow the general form of a conventional pen, it contains numerous technologies that enable it to function as an external user interface 104. FIG. 15 illustrates technologies comprised in the pen 1500. As can be seen, the pen 1500 may include a camera 1508, which is arranged to view through lens 1502. The camera may then be focused, such as through lens 1502, to image a surface upon which a user is writing or making other movements to interact with the HWC 102. There are situations where the pen 1500 will also have an ink, graphite, or other system such that what is being written can be seen on the writing surface. There are other situations where the pen 1500 does not have such a physical writing system so there is no deposit on the writing surface, where the pen would only be communicating data or commands to the HWC 102. The lens configuration is described in greater detail herein. The function of the camera is to capture information from an unstructured writing surface such that pen strokes can be interpreted as intended by the user. To assist in the predication of the intended stroke path, the pen 1500 may include a sensor, such as an IMU 1512. Of course, the IMU could be included in the pen 1500 in its separate parts (e.g. gyro, accelerometer, etc.) or an IMU could be included as a single unit. In this instance, the IMU 1512 is used to measure and predict the motion of the pen 1500. In turn, the integrated microprocessor 1510 would take the IMU information and camera information as inputs and process the information to form a prediction of the pen tip movement.

The pen 1500 may also include a pressure monitoring system 1504, such as to measure the pressure exerted on the lens 1502. As will be described in greater detail herein, the pressure measurement can be used to predict the user's intention for changing the weight of a line, type of a line, type of brush, click, double click, and the like. In embodiments, the pressure sensor may be constructed using any force or pressure measurement sensor located behind the lens 1502, including for example, a resistive sensor, a current sensor, a capacitive sensor, a voltage sensor such as a piezoelectric sensor, and the like.

The pen 1500 may also include a communications module 1518, such as for bi-directional communication with the HWC 102. In embodiments, the communications module 1518 may be a short distance communication module (e.g. Bluetooth). The communications module 1518 may be security matched to the HWC 102. The communications module 1518 may be arranged to communicate data and commands to and from the microprocessor 1510 of the pen 1500. The microprocessor 1510 may be programmed to interpret data generated from the camera 1508, IMU 1512, and pressure sensor 1504, and the like, and then pass a command onto the HWC 102 through the communications module 1518, for example. In another embodiment, the data collected from any of the input sources (e.g. camera 1508, IMU 1512, pressure sensor 1504) by the microprocessor may be communicated by the communication module 1518 to the HWC 102, and the HWC 102 may perform data processing and prediction of the user's intention when using the pen 1500. In yet another embodiment, the data may be further passed on through a network 110 to a remote device 112, such as a server, for the data processing and prediction. The commands may then be communicated back to the HWC 102 for execution (e.g. display writing in the glasses display, make a selection within the UI of the glasses display, control a remote external device 112, control a local external device 108), and the like. The pen may also include memory 1514 for long or short term uses.

The pen 1500 may also include a number of physical user interfaces, such as quick launch buttons 1522, a touch sensor 1520, and the like. The quick launch buttons 1522 may be adapted to provide the user with a fast way of jumping to a software application in the HWC system 100. For example, the user may be a frequent user of communication software packages (e.g. email, text, Twitter, Instagram, Facebook, Google+, and the like), and the user may program a quick launch button 1522 to command the HWC 102 to launch an application. The pen 1500 may be provided with several quick launch buttons 1522, which may be user programmable or factory programmable. The quick launch button 1522 may be programmed to perform an operation. For example, one of the buttons may be programmed to clear the digital display of the HWC 102. This would create a fast way for the user to clear the screens on the HWC 102 for any reason, such as for example to better view the environment. The quick launch button functionality will be discussed in further detail below. The touch sensor 1520 may be used to take gesture style input from the user. For example, the user may be able to take a single finger and run it across the touch sensor 1520 to affect a page scroll.

The pen 1500 may also include a laser pointer 1524. The laser pointer 1524 may be coordinated with the IMU 1512 to coordinate gestures and laser pointing. For example, a user may use the laser 1524 in a presentation to help with guiding the audience with the interpretation of graphics and the IMU 1512 may, either simultaneously or when the laser 1524 is off, interpret the user's gestures as commands or data input.

FIGS. 16A-C illustrate several embodiments of lens and camera arrangements 1600 for the pen 1500. One aspect relates to maintaining a constant distance between the camera and the writing surface to enable the writing surface to be kept in focus for better tracking of movements of the pen 1500 over the writing surface. Another aspect relates to maintaining an angled surface following the circumference of the writing tip of the pen 1500 such that the pen 1500 can be rolled or partially rolled in the user's hand to create the feel and freedom of a conventional writing instrument.

FIG. 16A illustrates an embodiment of the writing lens end of the pen 1500. The configuration includes a ball lens 1604, a camera or image capture surface 1602, and a domed cover lens 1608. In this arrangement, the camera views the writing surface through the ball lens 1604 and dome cover lens 1608. The ball lens 1604 causes the camera to focus such that the camera views the writing surface when the pen 1500 is held in the hand in a natural writing position, such as with the pen 1500 in contact with a writing surface. In embodiments, the ball lens 1604 should be separated from the writing surface to obtain the highest resolution of the writing surface at the camera 1602. In embodiments, the ball lens 1604 is separated by approximately 1 to 3 mm. In this configuration, the domed cover lens 1608 provides a surface that can keep the ball lens 1604 separated from the writing surface at a constant distance, such as substantially independent of the angle used to write on the writing surface. For instance, in embodiments the field of view of the camera in this arrangement would be approximately 60 degrees.

The domed cover lens, or other lens 1608 used to physically interact with the writing surface, will be transparent or transmissive within the active bandwidth of the camera 1602. In embodiments, the domed cover lens 1608 may be spherical or other shape and comprised of glass, plastic, sapphire, diamond, and the like. In other embodiments where low resolution imaging of the surface is acceptable. The pen 1500 can omit the domed cover lens 1608 and the ball lens 1604 can be in direct contact with the surface.

FIG. 16B illustrates another structure where the construction is somewhat similar to that described in connection with FIG. 16A; however this embodiment does not use a dome cover lens 1608, but instead uses a spacer 1610 to maintain a predictable distance between the ball lens 1604 and the writing surface, wherein the spacer may be spherical, cylindrical, tubular or other shape that provides spacing while allowing for an image to be obtained by the camera 1602 through the lens 1604. In a preferred embodiment, the spacer 1610 is transparent. In addition, while the spacer 1610 is shown as spherical, other shapes such as an oval, doughnut shape, half sphere, cone, cylinder or other form may be used.

FIG. 16C illustrates yet another embodiment, where the structure includes a post 1614, such as running through the center of the lensed end of the pen 1500. The post 1614 may be an ink deposition system (e.g. ink cartridge), graphite deposition system (e.g. graphite holder), or a dummy post whose purpose is mainly only that of alignment. The selection of the post type is dependent on the pen's use. For instance, in the event the user wants to use the pen 1500 as a conventional ink depositing pen as well as a fully functional external user interface 104, the ink system post would be the best selection. If there is no need for the 'writing' to be visible on the writing surface, the selection would be the dummy post. The embodiment of FIG. 16C includes camera(s) 1602 and an associated lens 1612, where the camera 1602 and lens 1612 are positioned to capture the writing surface without substantial interference from the post 1614. In embodiments, the pen 1500 may include multiple cameras 1602 and lenses 1612 such that more or all of the circumference of the tip 1614 can be used as an input system. In an embodiment, the pen 1500 includes a contoured grip that keeps the pen aligned in the user's hand so that the camera 1602 and lens 1612 remains pointed at the surface.

Another aspect of the pen 1500 relates to sensing the force applied by the user to the writing surface with the pen 1500. The force measurement may be used in a number of ways. For example, the force measurement may be used as a discrete value, or discontinuous event tracking, and compared against a threshold in a process to determine a user's intent. The user may want the force interpreted as a 'click' in the selection of an object, for instance. The user may intend multiple force exertions interpreted as multiple clicks. There may be times when the user holds the pen 1500 in a certain position or holds a certain portion of the pen 1500 (e.g. a button or touch pad) while clicking to affect a certain operation (e.g. a 'right click'). In embodiments, the force measurement may be used to track force and force trends. The force trends may be tracked and compared to threshold limits, for example. There may be one such threshold limit, multiple limits, groups of related limits, and the like. For example, when the force measurement indicates a fairly constant force that generally falls within a range of related threshold values, the microprocessor 1510 may interpret the force trend as an indication that the user desires to maintain the current writing style, writing tip type, line weight, brush type, and the like. In the event that the force trend appears to have gone outside of a set of threshold values intentionally, the microprocessor may interpret the action as an indication that the user wants to change the current writing style, writing tip type, line weight, brush type, and the like. Once the microprocessor has made a determination of the user's intent, a change in the current writing style, writing tip type, line weight, brush type, and the like may be executed. In embodiments, the change may be noted to the user (e.g. in a display of the HWC 102), and the user may be presented with an opportunity to accept the change.

FIG. 17A illustrates an embodiment of a force sensing surface tip 1700 of a pen 1500. The force sensing surface tip 1700 comprises a surface connection tip 1702 (e.g. a lens as described herein elsewhere) in connection with a force or pressure monitoring system 1504. As a user uses the pen 1500 to write on a surface or simulate writing on a surface the force monitoring system 1504 measures the force or pressure the user applies to the writing surface and the force monitoring system communicates data to the microprocessor 1510 for processing. In this configuration, the microprocessor 1510 receives force data from the force monitoring system 1504 and processes the data to make predictions of the user's intent in applying the particular force that is currently being applied. In embodiments, the processing may be provided at a location other than on the pen (e.g. at a server in the HWC system 100, on the HWC 102). For clarity, when reference is made herein to processing information on the microprocessor 1510, the processing of information contemplates processing the information at a location other than on the pen. The microprocessor 1510 may be programmed with force threshold(s), force signature(s), force signature library and/or other characteristics intended to guide an inference program in determining the user's intentions based on the measured force or pressure. The microprocessor 1510 may be further programmed to make inferences from the force measurements as to whether the user has attempted to initiate a discrete action (e.g. a user interface selection 'click') or is performing a constant action (e.g. writing within a particular writing style). The inferencing process is important as it causes the pen 1500 to act as an intuitive external user interface 104.

FIG. 17B illustrates a force 1708 versus time 1710 trend chart with a single threshold 1718. The threshold 1718 may be set at a level that indicates a discrete force exertion indicative of a user's desire to cause an action (e.g. select an object in a GUI). Event 1712, for example, may be interpreted as a click or selection command because the force quickly increased from below the threshold 1718 to above the threshold 1718. The event 1714 may be interpreted as a double click because the force quickly increased above the threshold 1718, decreased below the threshold 1718 and then essentially repeated quickly. The user may also cause the force to go above the threshold 1718 and hold for a period indicating that the user is intending to select an object in the GUI (e.g. a GUI presented in the display of the HWC 102) and 'hold' for a further operation (e.g. moving the object).

While a threshold value may be used to assist in the interpretation of the user's intention, a signature force event trend may also be used. The threshold and signature may be used in combination or either method may be used alone. For example, a single-click signature may be represented by a certain force trend signature or set of signatures. The single-click signature(s) may require that the trend meet a criteria of a rise time between x any y values, a hold time of between a and b values and a fall time of between c and d values, for example. Signatures may be stored for a variety of functions such as click, double click, right click, hold, move, etc. The microprocessor 1510 may compare the real-time force or pressure tracking against the signatures from a signature library to make a decision and issue a command to the software application executing in the GUI.

FIG. 17C illustrates a force 1708 versus time 1710 trend chart with multiple thresholds 1718. By way of example, the force trend is plotted on the chart with several pen force or pressure events. As noted, there are both presumably intentional events 1720 and presumably non-intentional events 1722. The two thresholds 1718 of FIG. 4C create three zones of force: a lower, middle and higher range. The beginning of the trend indicates that the user is placing a lower zone amount of force. This may mean that the user is writing with a given line weight and does not intend to change the weight, the user is writing. Then the trend shows a significant increase 1720 in force into the middle force range. This force change appears, from the trend to have been sudden and thereafter it is sustained. The microprocessor 1510 may interpret this as an intentional change and as a result change the operation in accordance with preset rules (e.g. change line width, increase line weight, etc.). The trend then continues with a second apparently intentional event 1720 into the higher-force range. During the performance in the higher-force range, the force dips below the upper threshold 1718. This may indicate an unintentional force change and the microprocessor may detect the change in range however not affect a change in the operations being coordinated by the pen 1500. As indicated above, the trend analysis may be done with thresholds and/or signatures.

Generally, in the present disclosure, instrument stroke parameter changes may be referred to as a change in line type, line weight, tip type, brush type, brush width, brush pressure, color, and other forms of writing, coloring, painting, and the like.

Another aspect of the pen 1500 relates to selecting an operating mode for the pen 1500 dependent on contextual information and/or selection interface(s). The pen 1500 may have several operating modes. For instance, the pen 1500 may have a writing mode where the user interface(s) of the pen 1500 (e.g. the writing surface end, quick launch buttons 1522, touch sensor 1520, motion based gesture, and the like) is optimized or selected for tasks associated with writing. As another example, the pen 1500 may have a wand mode where the user interface(s) of the pen is optimized or selected for tasks associated with software or device control (e.g. the HWC 102, external local device, remote device 112, and the like). The pen 1500, by way of another example, may have a presentation mode where the user interface(s) is optimized or selected to assist a user with giving a presentation (e.g. pointing with the laser pointer 1524 while using the button(s) 1522 and/or gestures to control the presentation or applications relating to the presentation). The pen may, for example, have a mode that is optimized or selected for a particular device that a user is attempting to control. The pen 1500 may have a number of other modes and an aspect of the present invention relates to selecting such modes.

FIG. 18A illustrates an automatic user interface(s) mode selection based on contextual information. The microprocessor 1510 may be programmed with IMU thresholds 1814 and 1812. The thresholds 1814 and 1812 may be used as indications of upper and lower bounds of an angle 1804 and 1802 of the pen 1500 for certain expected positions during certain predicted modes. When the microprocessor 1510 determines that the pen 1500 is being held or otherwise positioned within angles 1802 corresponding to writing thresholds 1814, for example, the microprocessor 1510 may then institute a writing mode for the pen's user interfaces. Similarly, if the microprocessor 1510 determines (e.g. through the IMU 1512) that the pen is being held at an angle 1804 that falls between the predetermined wand thresholds 1812, the microprocessor may institute a wand mode for the pen's user interface. Both of these examples may be referred to as context based user interface mode selection as the mode selection is based on contextual information (e.g. position) collected automatically and then used through an automatic evaluation process to automatically select the pen's user interface(s) mode.

As with other examples presented herein, the microprocessor 1510 may monitor the contextual trend (e.g. the angle of the pen over time) in an effort to decide whether to stay in a mode or change modes. For example, through signatures, thresholds, trend analysis, and the like, the microprocessor may determine that a change is an unintentional change and therefore no user interface mode change is desired.

FIG. 18B illustrates an automatic user interface(s) mode selection based on contextual information. In this example, the pen 1500 is monitoring (e.g. through its microprocessor) whether or not the camera at the writing surface end 1508 is imaging a writing surface in close proximity to the writing surface end of the pen 1500. If the pen 1500 determines that a writing surface is within a predetermined relatively short distance, the pen 1500 may decide that a writing surface is present 1820 and the pen may go into a writing mode user interface(s) mode. In the event that the pen 1500 does not detect a relatively close writing surface 1822, the pen may predict that the pen is not currently being used to as a writing instrument and the pen may go into a non-writing user interface(s) mode.

FIG. 18C illustrates a manual user interface(s) mode selection. The user interface(s) mode may be selected based on a twist of a section 1824 of the pen 1500 housing, clicking an end button 1828, pressing a quick launch button 1522, interacting with touch sensor 1520, detecting a predetermined action at the pressure monitoring system (e.g. a click), detecting a gesture (e.g. detected by the IMU), etc. The manual mode selection may involve selecting an item in a GUI associated with the pen 1500 (e.g. an image presented in the display of HWC 102).

In embodiments, a confirmation selection may be presented to the user in the event a mode is going to change. The presentation may be physical (e.g. a vibration in the pen 1500), through a GUI, through a light indicator, etc.

FIG. 19 illustrates a couple pen use-scenarios 1900 and 1901. There are many use scenarios and we have presented a couple in connection with FIG. 19 as a way of illustrating use scenarios to further the understanding of the reader. As such, the use-scenarios should be considered illustrative and non-limiting.

Use scenario 1900 is a writing scenario where the pen 1500 is used as a writing instrument. In this example, quick launch button 122A is pressed to launch a note application 1910 in the GUI 1908 of the HWC 102 display 1904. Once the quick launch button 122A is pressed, the HWC 102 launches the note program 1910 and puts the pen into a writing mode. The user uses the pen 1500 to scribe symbols 1902 on a writing surface, the pen records the scribing and transmits the scribing to the HWC 102 where symbols representing the scribing are displayed 1912 within the note application 1910.

Use scenario 1901 is a gesture scenario where the pen 1500 is used as a gesture capture and command device. In this example, the quick launch button 122B is activated and the pen 1500 activates a wand mode such that an application launched on the HWC 102 can be controlled. Here, the user sees an application chooser 1918 in the display(s) of the HWC 102 where different software applications can be chosen by the user. The user gestures (e.g. swipes, spins, turns, etc.) with the pen to cause the application chooser 1918 to move from application to application. Once the correct application is identified (e.g. highlighted) in the chooser 1918, the user may gesture or click or otherwise interact with the pen 1500 such that the identified application is selected and launched. Once an application is launched, the wand mode may be used to scroll, rotate, change applications, select items, initiate processes, and the like, for example.

In an embodiment, the quick launch button 122A may be activated and the HWC 102 may launch an application chooser presenting to the user a set of applications. For example, the quick launch button may launch a chooser to show all communication programs (e.g. SMS, Twitter, Instagram, Facebook, email, etc.) available for selection such that the user can select the program the user wants and then go into a writing mode. By way of further example, the launcher may bring up selections for various other groups that are related or categorized as generally being selected at a given time (e.g. Microsoft Office products, communication products, productivity products, note products, organizational products, and the like)

Figure 20:
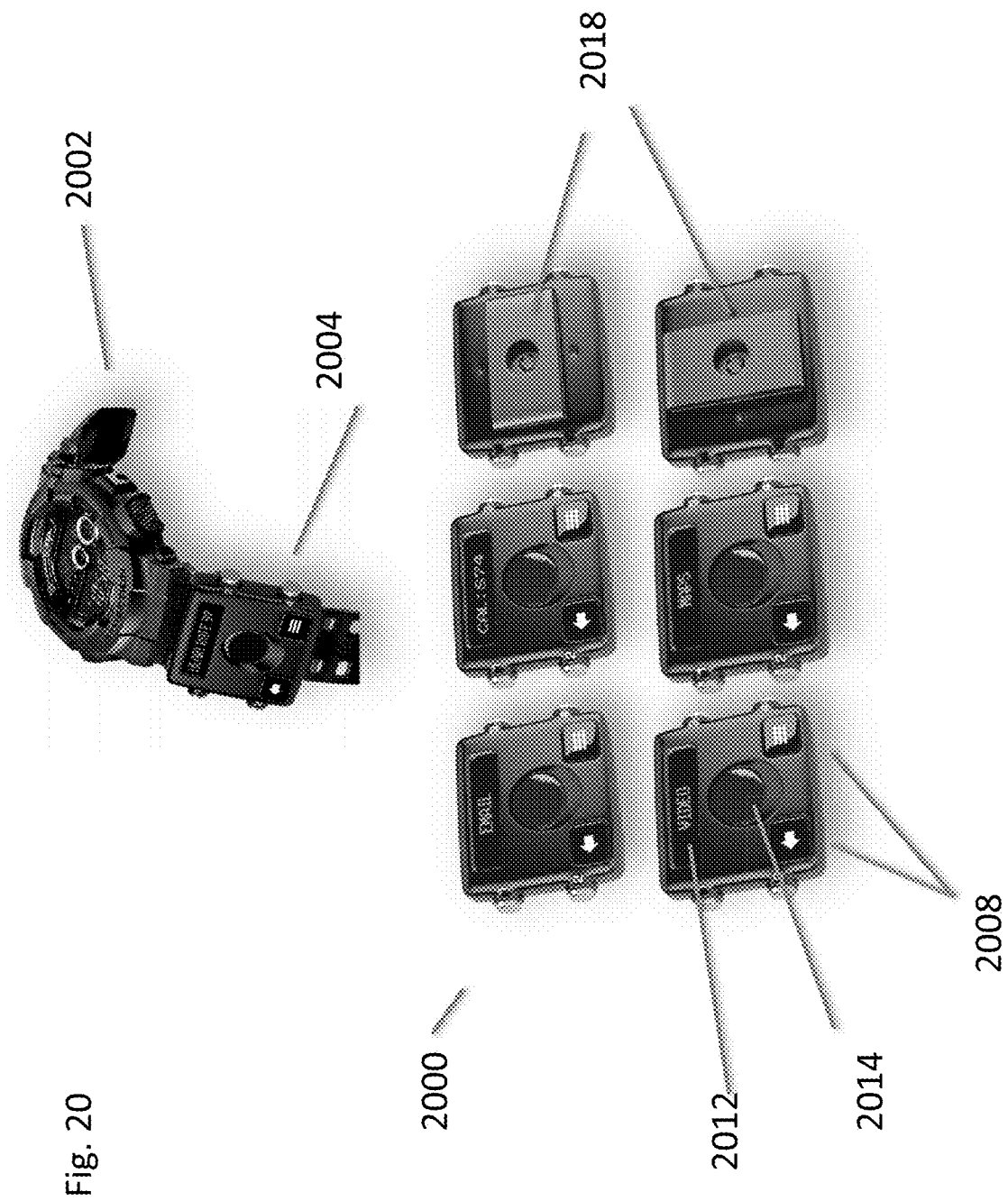
FIG. 20 illustrates external user interfaces in accordance with the principles of the present invention.

FIG. 20 illustrates yet another embodiment of the present invention. FIG. 2000 illustrates a watchband clip on controller 2000. The watchband clip on controller may be a controller used to control the HWC 102 or devices in the HWC system 100. The watchband clip on controller 2000 has a fastener 2018 (e.g. rotatable clip) that is mechanically adapted to attach to a watchband, as illustrated at 2004.

The watchband controller 2000 may have quick launch interfaces 2008 (e.g. to launch applications and choosers as described herein), a touch pad 2014 (e.g. to be used as a touch style mouse for GUI control in a HWC 102 display) and a display 2012. The clip 2018 may be adapted to fit a wide range of watchbands so it can be used in connection with a watch that is independently selected for its function. The clip, in embodiments, is rotatable such that a user can position it in a desirable manner. In embodiments the clip may be a flexible strap. In embodiments, the flexible strap may be adapted to be stretched to attach to a hand, wrist, finger, device, weapon, and the like.

In embodiments, the watchband controller may be configured as a removable and replaceable watchband. For example, the controller may be incorporated into a band with a certain width, segment spacing's, etc. such that the watchband, with its incorporated controller, can be attached to a watch body. The attachment, in embodiments, may be mechanically adapted to attach with a pin upon which the watchband rotates. In embodiments, the watchband controller may be electrically connected to the watch and/or watch body such that the watch, watch body and/or the watchband controller can communicate data between them.

The watchband controller may have 3-axis motion monitoring (e.g. through an IMU, accelerometers, magnetometers, gyroscopes, etc.) to capture user motion. The user motion may then be interpreted for gesture control.

In embodiments, the watchband controller may comprise fitness sensors and a fitness computer. The sensors may track heart rate, calories burned, strides, distance covered, and the like. The data may then be compared against performance goals and/or standards for user feedback.

Another aspect of the present invention relates to visual display techniques relating to micro Doppler ("mD") target tracking signatures ("mD signatures"). mD is a radar technique that uses a series of angle dependent electromagnetic pulses that are broadcast into an environment and return pulses are captured. Changes between the broadcast pulse and return pulse are indicative of changes in the shape, distance and angular location of objects or targets in the environment. These changes provide signals that can be used to track a target and identify the target through the mD signature. Each target or target type has a unique mD signature. Shifts in the radar pattern can be analyzed in the time domain and frequency domain based on mD techniques to derive information about the types of targets present (e.g. whether people are present), the motion of the targets and the relative angular location of the targets and the distance to the targets. By selecting a frequency used for the mD pulse relative to known objects in the environment, the pulse can penetrate the known objects to enable information about targets to be gathered even when the targets are visually blocked by the known objects. For example, pulse frequencies can be used that will penetrate concrete buildings to enable people to be identified inside the building. Multiple pulse frequencies can be used as well in the mD radar to enable different types of information to be gathered about the objects in the environment. In addition, the mD radar information can be combined with other information such as distance measurements or images captured of the environment that are analyzed jointly to provide improved object identification and improved target identification and tracking. In embodiments, the analysis can be performed on the HWC or the information can be transmitted to a remote network for analysis and results transmitted back to the HWC. Distance measurements can be provided by laser range finding, structured lighting, stereoscopic depth maps or sonar measurements. Images of the environment can be captured using one or more cameras capable of capturing images from visible, ultraviolet or infrared light. The mD radar can be attached to the HWC, located adjacently (e.g. in a vehicle) and associated wirelessly with the HWC or located remotely. Maps or other previously determined information about the environment can also be used in the analysis of the mD radar information. Embodiments of the present invention relate to visualizing the mD signatures in useful ways.

FIG. 21 illustrates a FOV 2102 of a HWC 102 from a wearer's perspective. The wearer, as described herein elsewhere, has a see-through FOV 2102 wherein the wearer views adjacent surroundings, such as the buildings illustrated in FIG. 21. The wearer, as described herein elsewhere, can also see displayed digital content presented within a portion of the FOV 2102. The embodiment illustrated in FIG. 21 is indicating that the wearer can see the buildings and other surrounding elements in the environment and digital content representing traces, or travel paths, of bullets being fired by different people in the area. The surroundings are viewed through the transparency of the FOV 2102. The traces are presented via the digital computer display, as described herein elsewhere. In embodiments, the trace presented is based on a mD signature that is collected and communicated to the HWC in real time. The mD radar itself may be on or near the wearer of the HWC 102 or it may be located remote from the wearer. In embodiments, the mD radar scans the area, tracks and identifies targets, such as bullets, and communicates traces, based on locations, to the HWC 102.

There are several traces 2108 and 2104 presented to the wearer in the embodiment illustrated in FIG. 21. The traces communicated from the mD radar may be associated with GPS locations and the GPS locations may be associated with objects in the environment, such as people, buildings, vehicles, etc, both in latitude and longitude perspective and an elevation perspective. The locations may be used as markers for the HWC such that the traces, as presented in the FOV, can be associated, or fixed in space relative to the markers. For example, if the friendly fire trace 2108 is determined, by the mD radar, to have originated from the upper right window of the building on the left, as illustrated in FIG. 21, then a virtual marker may be set on or near the window. When the HWC views, through it's camera or other sensor, for example, the building's window, the trace may then virtually anchor with the virtual marker on the window. Similarly, a marker may be set near the termination position or other flight position of the friendly fire trace 2108, such as the upper left window of the center building on the right, as illustrated in FIG. 21. This technique fixes in space the trace such that the trace appears fixed to the environmental positions independent of where the wearer is looking. So, for example, as the wearer's head turns, the trace appears fixed to the marked locations.

In embodiments, certain user positions may be known and thus identified in the FOV. For example, the shooter of the friendly fire trace 2108 may be from a known friendly combatant and as such his location may be known. The position may be known based on his GPS location based on a mobile communication system on him, such as another HWC 102. In other embodiments, the friendly combatant may be marked by another friendly. For example, if the friendly position in the environment is known through visual contact or communicated information, a wearer of the HWC 102 may use a gesture or external user interface 104 to mark the location. If a friendly combatant location is known the originating position of the friendly fire trace 2108 may be color coded or otherwise distinguished from unidentified traces on the displayed digital content. Similarly, enemy fire traces 2104 may be color coded or otherwise distinguished on the displayed digital content. In embodiments, there may be an additional distinguished appearance on the displayed digital content for unknown traces.

In addition to situationally associated trace appearance, the trace colors or appearance may be different from the originating position to the terminating position. This path appearance change may be based on the mD signature. The mD signature may indicate that the bullet, for example, is slowing as it propagates and this slowing pattern may be reflected in the FOV 2102 as a color or pattern change. This can create an intuitive understanding of wear the shooter is located. For example, the originating color may be red, indicative of high speed, and it may change over the course of the trace to yellow, indicative of a slowing trace. This pattern changing may also be different for a friendly, enemy and unknown combatant. The enemy may go blue to green for a friendly trace, for example.

FIG. 21 illustrates an embodiment where the user sees the environment through the FOV and may also see color coded traces, which are dependent on bullet speed and combatant type, where the traces are fixed in environmental positions independent on the wearer's perspective. Other information, such as distance, range, range rings, time of day, date, engagement type (e.g. hold, stop firing, back away, etc.) may also be displayed in the FOV.

Another aspect of the present invention relates to mD radar techniques that trace and identify targets through other objects, such as walls (referred to generally as through wall mD), and visualization techniques related therewith. FIG. 22 illustrates a through wall mD visualization technique according to the principles of the present invention. As described herein elsewhere, the mD radar scanning the environment may be local or remote from the wearer of a HWC 102. The mD radar may identify a target (e.g. a person) that is visible 2204 and then track the target as he goes behind a wall 2208. The tracking may then be presented to the wearer of a HWC 102 such that digital content reflective of the target and the target's movement, even behind the wall, is presented in the FOV 2202 of the HWC 102. In embodiments, the target, when out of visible sight, may be represented by an avatar in the FOV to provide the wearer with imagery representing the target.

mD target recognition methods can identify the identity of a target based on the vibrations and other small movements of the target. This can provide a personal signature for the target. In the case of humans, this may result in a personal identification of a target that has been previously characterized. The cardio, heart beat, lung expansion and other small movements within the body may be unique to a person and if those attributes are pre-identified they may be matched in real time to provide a personal identification of a person in the FOV 2202. The person's mD signatures may be determined based on the position of the person. For example, the database of personal mD signature attributes may include mD signatures for a person standing, sitting, laying down, running, walking, jumping, etc. This may improve the accuracy of the personal data match when a target is tracked through mD signature techniques in the field. In the event a person is personally identified, a specific indication of the person's identity may be presented in the FOV 2202. The indication may be a color, shape, shade, name, indication of the type of person (e.g. enemy, friendly, etc.), etc. to provide the wearer with intuitive real time information about the person being tracked. This may be very useful in a situation where there is more than one person in an area of the person being tracked. If just one person in the area is personally identified, that person or the avatar of that person can be presented differently than other people in the area.

FIG. 23 illustrates an mD scanned environment 2300. An mD radar may scan an environment in an attempt to identify objects in the environment. In this embodiment, the mD scanned environment reveals two vehicles 2302*a* and 2302*b*, an enemy combatant 2309, two friendly combatants 2308*a* and 2308*b* and a shot trace 2318. Each of these objects may be personally identified or type identified. For example, the vehicles 2302*a* and 2302*b* may be identified through the mD signatures as a tank and heavy truck. The enemy combatant 2309 may be identified as a type (e.g. enemy combatant) or more personally (e.g. by name). The friendly combatants may be identified as a type (e.g. friendly combatant) or more personally (e.g. by name). The shot trace 2318 may be characterized by type of projectile or weapon type for the projectile, for example.

Figure 23A:
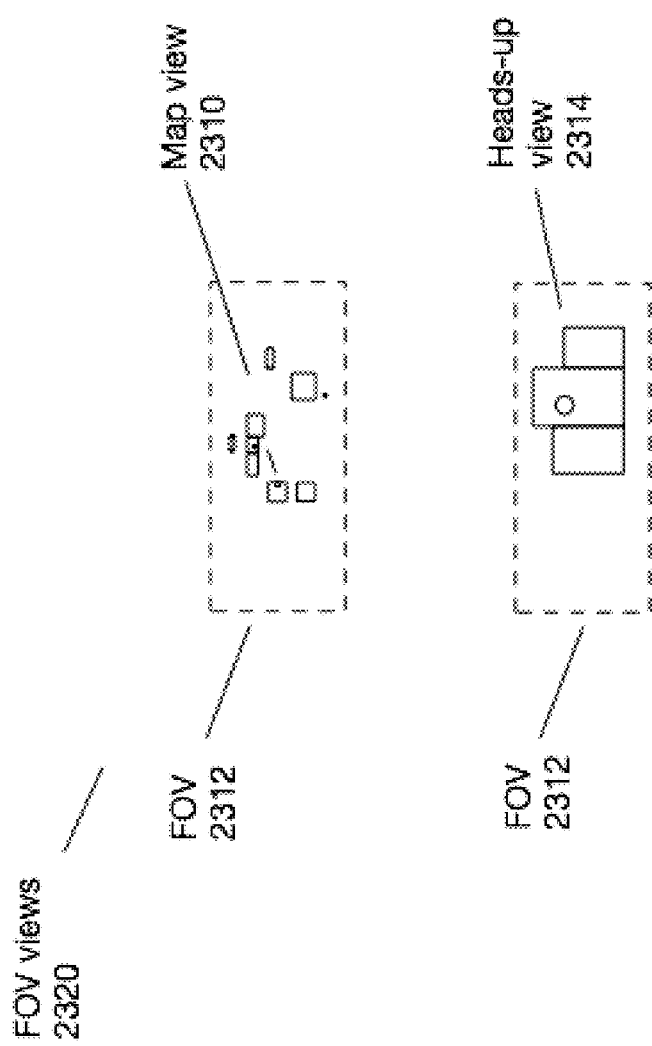
FIG. 23a illustrates mD trace representations presented in accordance with the principles of the present invention.

FIG. 23*a* illustrates two separate HWC 102 FOV display techniques according to the principles of the present invention. FOV 2312 illustrates a map view 2310 where the mD scanned environment is presented. Here, the wearer has a perspective on the mapped area so he can understand all tracked targets in the area. This allows the wearer to traverse the area with knowledge of the targets. FOV 2312 illustrates a heads-up view to provide the wearer with an augmented reality style view of the environment that is in proximity of the wearer.

An aspect of the present invention relates to suppression of extraneous or stray light. As discussed herein elsewhere, eyeglow and faceglow are two such artifacts that develop from such light. Eyeglow and faceglow can be caused by image light escaping from the optics module. The escaping light is then visible, particularly in dark environments when the user is viewing bright displayed images with the HWC. Light that escapes through the front of the HWC is visible as eyeglow as it that light that is visible in the region of the user's eyes. Eyeglow can appear in the form of a small version of the displayed image that the user is viewing. Light that escapes from the bottom of the HWC shines onto the user's face, cheek or chest so that these portions of the user appear to glow. Eyeglow and faceglow can both increase the visibility of the user and highlight the use of the HWC, which may be viewed negatively by the user. As such, reducing eyeglow and faceglow is advantageous. In combat situations (e.g. the mD trace presentation scenarios described herein) and certain gaming situations, the suppression of extraneous or stray light is very important.

The disclosure relating to FIG. 6 shows an example where a portion of the image light passes through the combiner 602 such that the light shines onto the user's face, thereby illuminating a portion of the user's face in what is generally referred to herein as faceglow. Faceglow be caused by any portion of light from the HWC that illuminates the user's face.

An example of the source for the faceglow light can come from wide cone angle light associated with the image light incident onto the combiner 602. Where the combiner can include a holographic mirror or a notch mirror in which the narrow bands of high reflectivity are matched to wavelengths of light by the light source. The wide cone angle associated with the image light corresponds with the field of view provided by the HWC. Typically the reflectivity of holographic mirrors and notch mirrors is reduced as the cone angle of the incident light is increased above 8 degrees. As a result, for a field of view of 30 degrees, substantial image light can pass through the combiner and cause faceglow.

Figure 24:
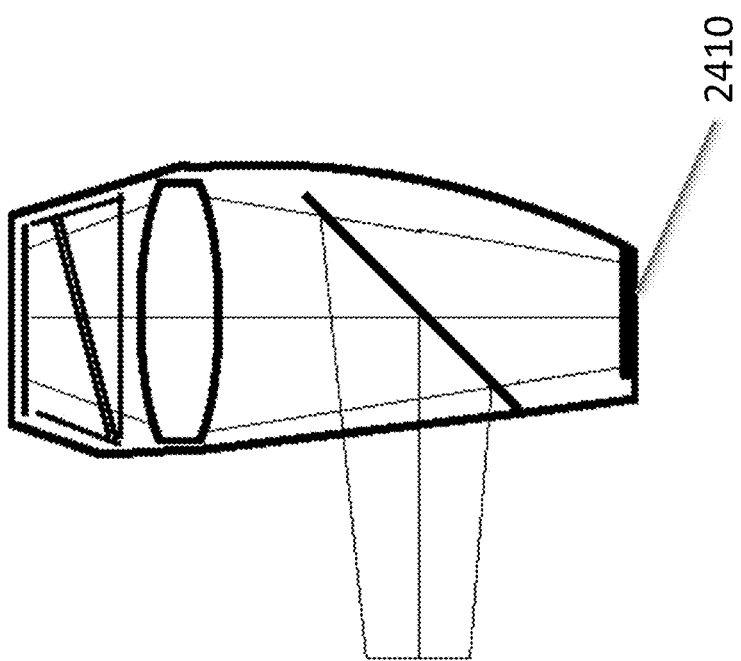
FIG. 24 illustrates a stray light suppression technology in accordance with the principles of the present invention.

FIG. 24 shows an illustration of a light trap 2410 for the faceglow light. In this embodiment, an extension of the outer shield lens of the HWC is coated with a light absorbing material in the region where the converging light responsible for faceglow is absorbed in a light trap 2410. The light absorbing material can be black or it can be a filter designed to absorb only the specific wavelengths of light provided by the light source(s) in the HWC. In addition, the surface of the light trap 2410 may be textured or fibrous to further improve the absorption.

Figure 25:
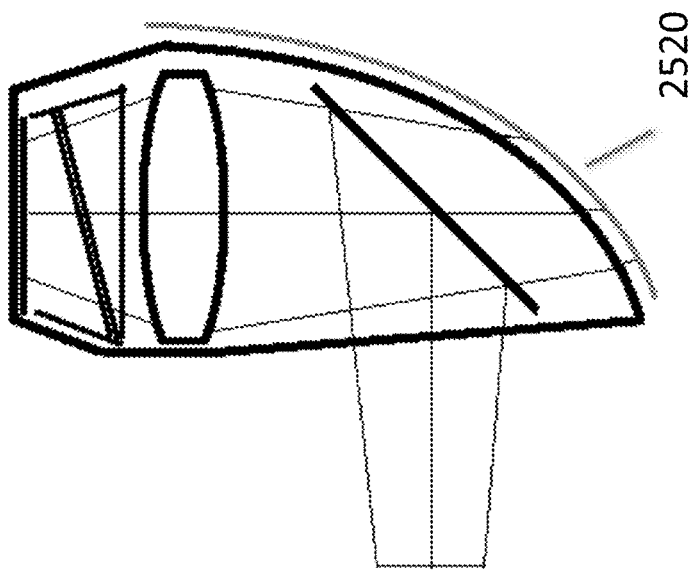
FIG. 25 illustrates a stray light suppression technology in accordance with the principles of the present invention.

FIG. 25 illustrates an optical system for a HWC that includes an outer absorptive polarizer 2520 to block the faceglow light. In this embodiment, the image light is polarized and as a result the light responsible for faceglow is similarly polarized. The absorptive polarizer is oriented with a transmission axis such that the faceglow light is absorbed and not transmitted. In this case, the rest of the imaging system in the HWC may not require polarized image light and the image light may be polarized at any point before the combiner. In embodiments, the transmission axis of the absorptive polarizer 2520 is oriented vertically so that external glare from water (S polarized light) is absorbed and correspondingly, the polarization of the image light is selected to be horizontal (S polarization). Consequently, image light that passes through the combiner 602 and is then incident onto the absorptive polarizer 2520, is absorbed. In FIG. 25 the absorptive polarizer 2520 is shown outside the shield lens, alternatively the absorptive polarizer 2520 can be located inside the shield lens.

Figure 26:
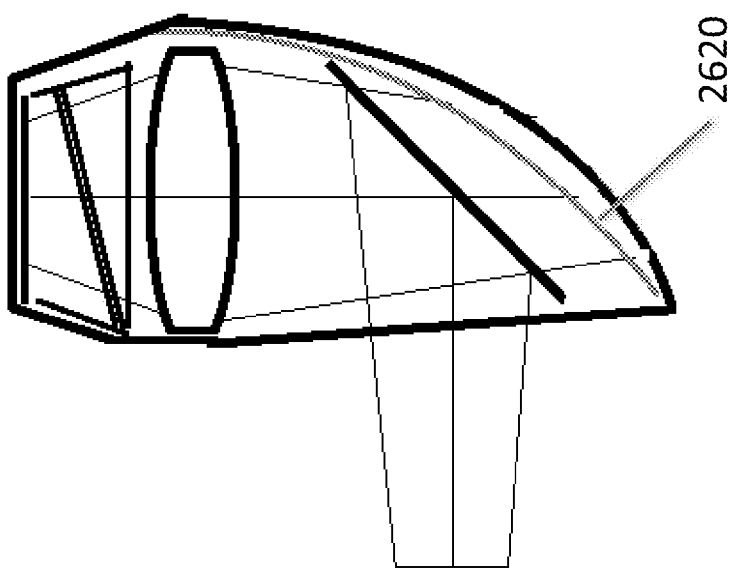
FIG. 26 illustrates a stray light suppression technology in accordance with the principles of the present invention.

FIG. 26 illustrates an optical system for a HWC that includes a film with an absorptive notch filter 2620. In this case, the absorptive notch filter absorbs narrow bands of light that are selected to match the light provided by the optical system's light source. As a result, the absorptive notch filter is opaque with respect to the faceglow light and is transparent to the remainder of the wavelengths included in the visible spectrum so that the user has a clear view of the surrounding environment. A triple notch filter suitable for this approach is available from Iridian Spectral Technologies, Ottawa, ON: http://www.ilphotonics.com/cdv2/Iridian-Interference %20Filters/New %20filters/Triple %20Notch %20Filter.pdf In embodiments, the combiner 602 may include a notch mirror coating to reflect the wavelengths of light in the image light and a notch filter 2620 can be selected in correspondence to the wavelengths of light provided by the light source and the narrow bands of high reflectivity provided by the notch mirror. In this way, image light that is not reflected by the notch mirror is absorbed by the notch filter 2620. In embodiments of the invention the light source can provide one narrow band of light for a monochrome imaging or three narrow bands of light for full color imaging. The notch mirror and associated notch filter would then each provide one narrow band or three narrow bands of high reflectivity and absorption respectively.

Figure 27:
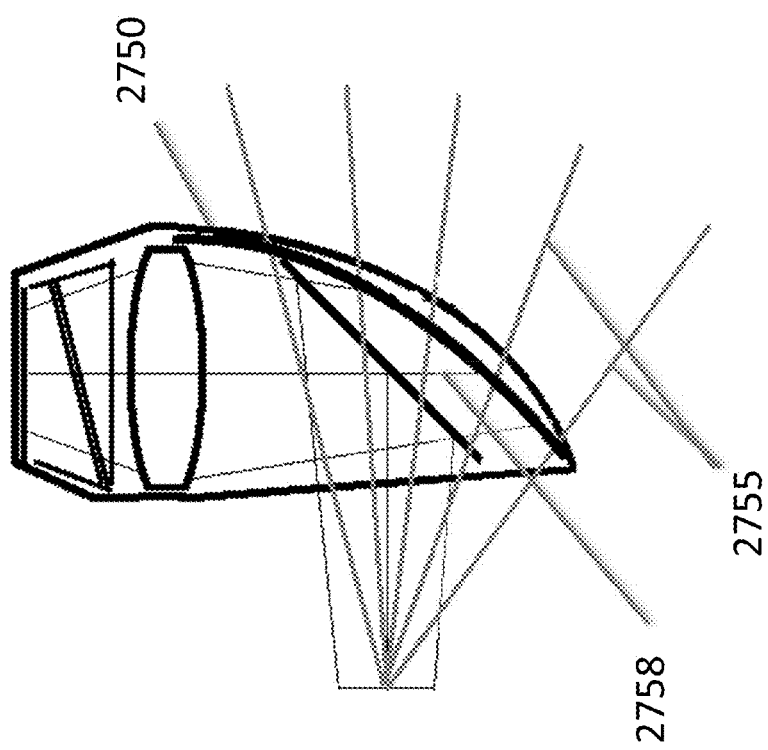
FIG. 27 illustrates a stray light suppression technology in accordance with the principles of the present invention.

FIG. 27 includes a microlouver film 2750 to block the faceglow light. Microlouver film is sold by 3M as ALCF-P, for example and is typically used as a privacy filter for computer. See http://multimedia.3 m.com/mws/mediawebserver?mwsId=SSSSSuH8gc7nZxtUoY_x lY_eevUqe17zHvTSevTSeSSSSSS--&fn=ALCF-P_ABR2_Control_Film_DS.pdf The microlouver film transmits light within a somewhat narrow angle (e.g. 30 degrees of normal and absorbs light beyond 30 degrees of normal). In FIG. 27, the microlouver film 2750 is positioned such that the faceglow light 2758 is incident beyond 30 degrees from normal while the see-through light 2755 is incident within 30 degrees of normal to the microlouver film 2750. As such, the faceglow light 2758 is absorbed by the microlouver film and the see-through light 2755 is transmitted so that the user has a bright see-thru view of the surrounding environment.

We now turn back to a description of eye imaging technologies. Aspects of the present invention relate to various methods of imaging the eye of a person wearing the HWC 102. In embodiments, technologies for imaging the eye using an optical path involving the "off" state and "no power" state, which is described in detail below, are described. In embodiments, technologies for imaging the eye with optical configurations that do not involve reflecting the eye image off of DLP mirrors is described. In embodiments, unstructured light, structured light, or controlled lighting conditions, are used to predict the eye's position based on the light reflected off of the front of the wearer's eye. In embodiments, a reflection of a presented digital content image is captured as it reflects off of the wearer's eye and the reflected image may be processed to determine the quality (e.g. sharpness) of the image presented. In embodiments, the image may then be adjusted (e.g. focused differently) to increase the quality of the image presented based on the image reflection.

Figure 28:
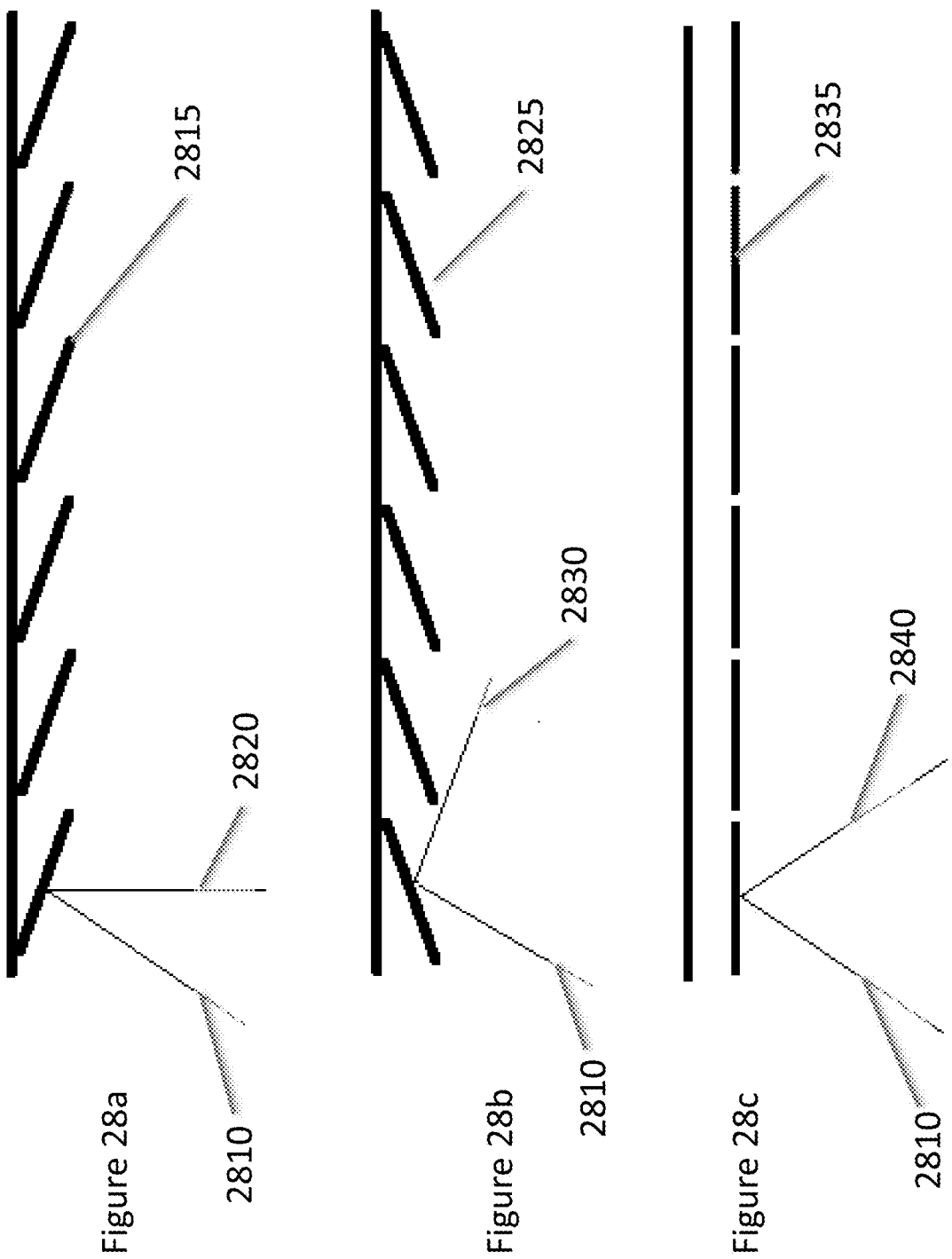
FIGS. 28a to 28c illustrate DLP mirror angles.

FIGS. 28a, 28b and 28c show illustrations of the various positions of the DLP mirrors. FIG. 28a shows the DLP mirrors in the "on" state 2815. With the mirror in the "on" state 2815, illumination light 2810 is reflected along an optical axis 2820 that extends into the lower optical module 204. FIG. 28b shows the DLP mirrors in the "off" state 2825. With the mirror in the "off" state 2825, illumination light 2810 is reflected along an optical axis 2830 that is substantially to the side of optical axis 2820 so that the "off" state light is directed toward a dark light trap as has been described herein elsewhere. FIG. 28c shows the DLP mirrors in a third position, which occurs when no power is applied to the DLP. This "no power" state differs from the "on" and "off" states in that the mirror edges are not in contact with the substrate and as such are less accurately positioned. FIG. 28c shows all of the DLP mirrors in the "no power" state 2835. The "no power" state is achieved by simultaneously setting the voltage to zero for the "on" contact and "off" contact for a DLP mirror, as a result, the mirror returns to a no stress position where the DLP mirror is in the plane of the DLP platform as shown in FIG. 28c. Although not normally done, it is also possible to apply the "no power" state to individual DLP mirrors. When the DLP mirrors are in the "no power" state they do not contribute image content. Instead, as shown in FIG. 28c, when the DLP mirrors are in the "no power" state, the illumination light 2810 is reflected along an optical axis 2840 that is between the optical axes 2820 and 2830 that are respectively associated with the "on" and "off" states and as such this light doesn't contribute to the displayed image as a bright or dark pixel. This light can however contribute scattered light into the lower optical module 204 and as a result the displayed image contrast can be reduced or artifacts can be created in the image that detract from the image content. Consequently, it is generally desirable, in embodiments, to limit the time associated with the "no power" state to times when images are not displayed or to reduce the time associated with having DLP mirrors in the "no power" state so that the affect of the scattered light is reduced.

Figure 29:
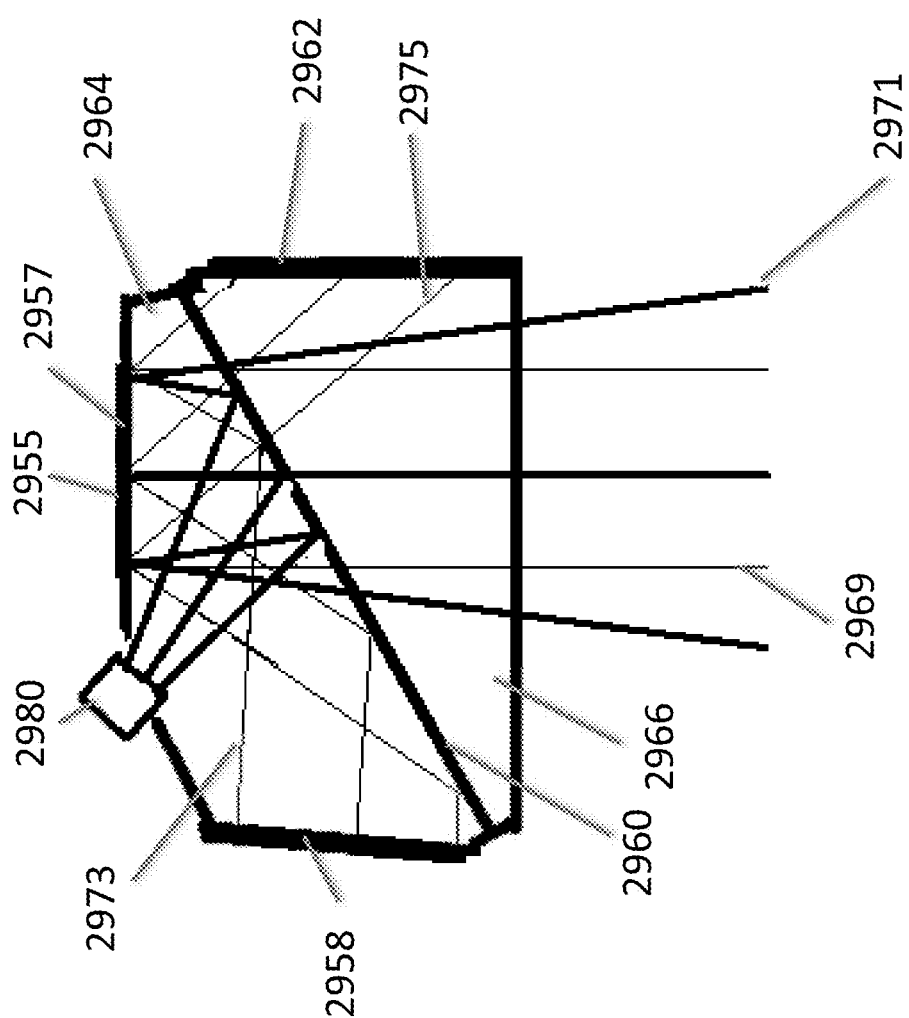
FIGS. 29 to 33 illustrate eye imaging systems according to the principles of the present invention.

FIG. 29 shows an embodiment of the invention that can be used for displaying digital content images to a wearer of the HWC 102 and capturing images of the wearer's eye. In this embodiment, light from the eye 2971 passes back through the optics in the lower module 204, the solid corrective wedge 2966, at least a portion of the light passes through the partially reflective layer 2960, the solid illumination wedge 2964 and is reflected by a plurality of DLP mirrors on the DLP 2955 that are in the "no power" state. The reflected light then passes back through the illumination wedge 2964 and at least a portion of the light is reflected by the partially reflective layer 2960 and the light is captured by the camera 2980.

For comparison, illuminating light rays 2973 from the light source 2958 are also shown being reflected by the partially reflective layer 2960. Where the angle of the illuminating light 2973 is such that the DLP mirrors, when in the "on" state, reflect the illuminating light 2973 to form image light 2969 that substantially shares the same optical axis as the light from the wearer's eye 2971. In this way, images of the wearer's eye are captured in a field of view that overlaps the field of view for the displayed image content. In contrast, light reflected by DLP mirrors in the "off" state form dark light 2975 which is directed substantially to the side of the image light 2969 and the light from eye 2971. Dark light 2975 is directed toward a light trap 2962 that absorbs the dark light to improve the contrast of the displayed image as has been described above in this specification.

In an embodiment, partially reflective layer 2960 is a reflective polarizer. The light that is reflected from the eye 2971 can then be polarized prior to entering the corrective wedge 2966 (e.g with an absorptive polarizer between the upper module 202 and the lower module 204), with a polarization orientation relative to the reflective polarizer that enables the light reflected from the eye 2971 to substantially be transmitted by the reflective polarizer. A quarter wave retarder layer 2957 is then included adjacent to the DLP 2955 (as previously disclosed in FIG. 3b) so that the light reflected from the eye 2971 passes through the quarter wave retarder layer 2957 once before being reflected by the plurality of DLP mirrors in the "no power" state and then passes through a second time after being reflected. By passing through the quarter wave retarder layer 2957 twice, the polarization state of the light from the eye 2971 is reversed, such that when it is incident upon the reflective polarizer, the light from the eye 2971 is then substantially reflected toward the camera 2980. By using a partially reflective layer 2960 that is a reflective polarizer and polarizing the light from the eye 2971 prior to entering the corrective wedge 2964, losses attributed to the partially reflective layer 2960 are reduced.

FIG. 28c shows the case wherein the DLP mirrors are simultaneously in the "no power" state, this mode of operation can be particularly useful when the HWC 102 is first put onto the head of the wearer. When the HWC 102 is first put onto the head of the wearer, it is not necessary to display an image yet. As a result, the DLP can be in a "no power" state for all the DLP mirrors and an image of the wearer's eyes can be captured. The captured image of the wearer's eye can then be compared to a database, using iris identification techniques, or other eye pattern identification techniques to determine, for example, the identity of the wearer.

In a further embodiment illustrated by FIG. 29 all of the DLP mirrors are put into the "no power" state for a portion of a frame time (e.g. 50% of a frame time for the displayed digital content image) and the capture of the eye image is synchronized to occur at the same time and for the same duration. By reducing the time that the DLP mirrors are in the "no power" state, the time where light is scattered by the DLP mirrors being in the "no power" state is reduced such that the wearer doesn't perceive a change in the displayed image quality. This is possible because the DLP mirrors have a response time on the order of microseconds while typical frame times for a displayed image are on the order of 0.016 seconds. This method of capturing images of the wearer's eye can be used periodically to capture repetitive images of the wearer's eye. For example, eye images could be captured for 50% of the frame time of every 10th frame displayed to the wearer. In another example, eye images could be captured for 10% of the frame time of every frame displayed to the wearer.

Alternately, the "no power" state can be applied to a subset of the DLP mirrors (e.g. 10% of the DLP mirrors) within while another subset is in busy generating image light for content to be displayed. This enables the capture of an eye image(s) during the display of digital content to the wearer. The DLP mirrors used for eye imaging can, for example, be distributed randomly across the area of the DLP to minimize the impact on the quality of the digital content being displayed to the wearer. To improve the displayed image perceived by the wearer, the individual DLP mirrors put into the "no power" state for capturing each eye image, can be varied over time such as in a random pattern, for example. In yet a further embodiment, the DLP mirrors put into the "no power" state for eye imaging may be coordinated with the digital content in such a way that the "no power" mirrors are taken from a portion of the image that requires less resolution.

In the embodiments of the invention as illustrated in FIGS. 9 and 29, in both cases the reflective surfaces provided by the DLP mirrors do not preserve the wavefront of the light from the wearer's eye so that the image quality of captured image of the eye is somewhat limited. It may still be useful in certain embodiments, but it is somewhat limited. This is due to the DLP mirrors not being constrained to be on the same plane. In the embodiment illustrated in FIG. 9, the DLP mirrors are tilted so that they form rows of DLP mirrors that share common planes. In the embodiment illustrated in FIG. 29, the individual DLP mirrors are not accurately positioned to be in the same plane since they are not in contact with the substrate. Examples of advantages of the embodiments associated with FIG. 29 are: first, the camera 2980 can be located between the DLP 2955 and the illumination light source 2958 to provide a more compact upper module 202. Second, the polarization state of the light reflected from the eye 2971 can be the same as that of the image light 2969 so that the optical path of the light reflected from the eye and the image light can be the same in the lower module 204.

Figure 30:
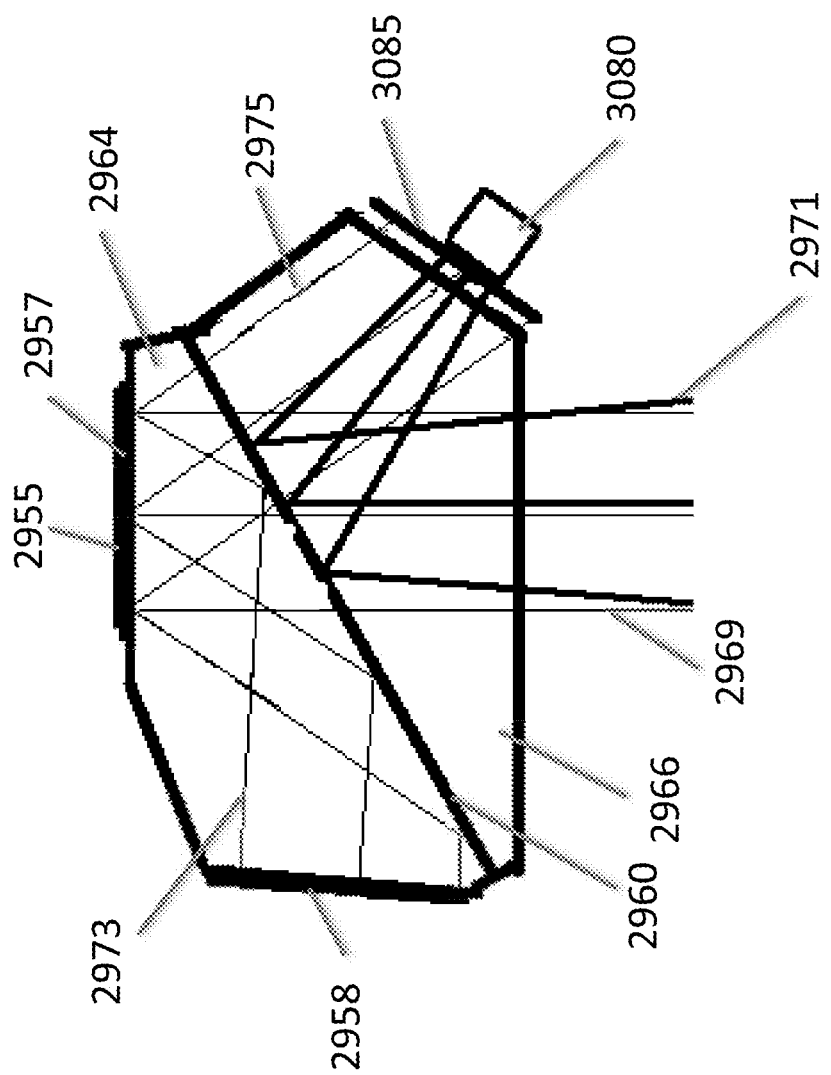

FIG. 30 shows an illustration of an embodiment for displaying images to the wearer and simultaneously capturing images of the wearer's eye, wherein light from the eye 2971 is reflected towards a camera 3080 by the partially reflective layer 2960. The partially reflective layer 2960 can be an optically flat layer such that the wavefront of the light from the eye 2971 is preserved and as a result, higher quality images of the wearer's eye can be captured. In addition, since the DLP 2955 is not included in the optical path for the light from the eye 2971, and the eye imaging process shown in FIG. 30 does not interfere with the displayed image, images of the wearer's eye can be captured independently (e.g. with independent of timing, impact on resolution, or pixel count used in the image light) from the displayed images.

In the embodiment illustrated in FIG. 30, the partially reflective layer 2960 is a reflective polarizer, the illuminating light 2973 is polarized, the light from the eye 2971 is polarized and the camera 3080 is located behind a polarizer 3085. The polarization axis of the illuminating light 2973 and the polarization axis of the light from the eye are oriented perpendicular to the transmission axis of the reflective polarizer so that they are both substantially reflected by the reflective polarizer. The illumination light 2973 passes through a quarter wave layer 2957 before being reflected by the DLP mirrors in the DLP 2955. The reflected light passes back through the quarter wave layer 2957 so that the polarization states of the image light 2969 and dark light 2975 are reversed in comparison to the illumination light 2973. As such, the image light 2969 and dark light 2975 are substantially transmitted by the reflective polarizer. Where the DLP mirrors in the "on" state provide the image light 2969 along an optical axis that extends into the lower optical module 204 to display an image to the wearer. At the same time, DLP mirrors in the "off" state provide the dark light 2975 along an optical axis that extends to the side of the upper optics module 202. In the region of the corrective wedge 2966 where the dark light 2975 is incident on the side of the upper optics module 202, an absorptive polarizer 3085 is positioned with it's transmission axis perpendicular to the polarization axis of the dark light and parallel to the polarization axis of the light from the eye so that the dark light 2975 is absorbed and the light from the eye 2971 is transmitted to the camera 3080.

Figure 31:
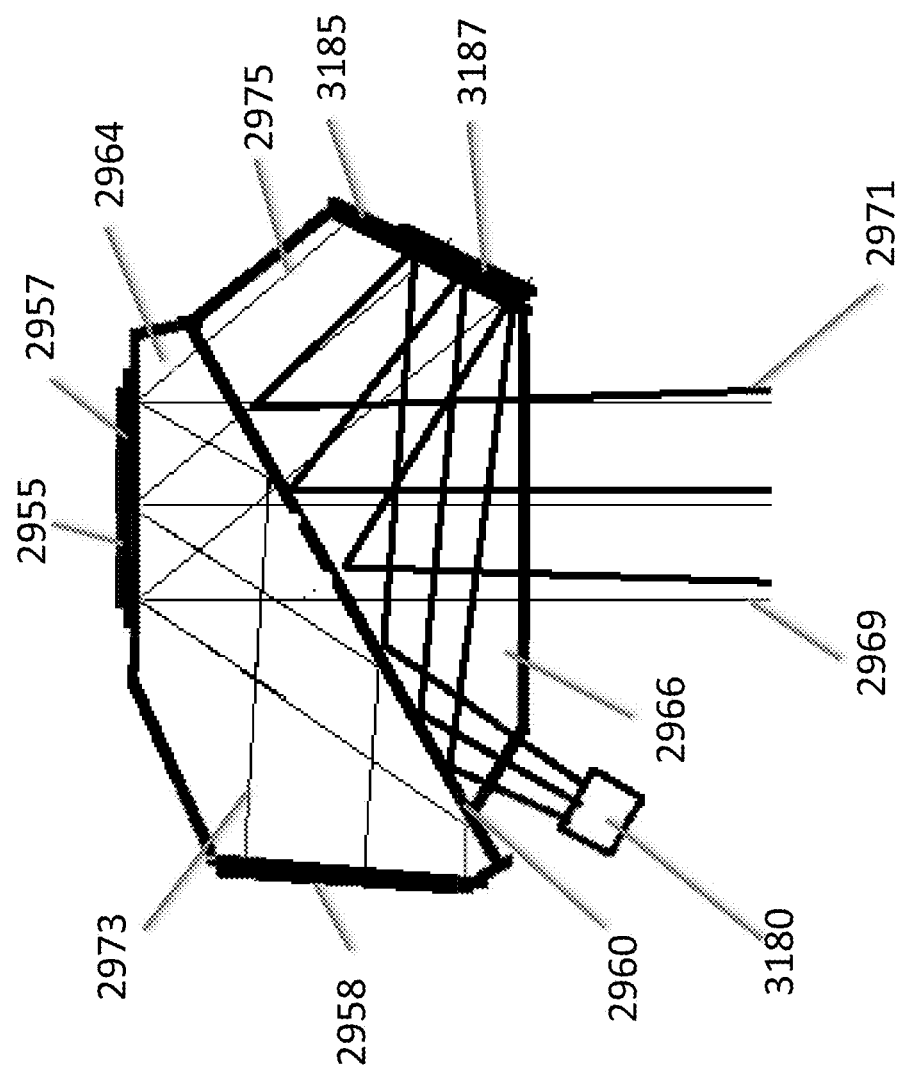

FIG. 31 shows an illustration of another embodiment of a system for displaying images and simultaneously capturing image of the wearer's eye that is similar to the one shown in FIG. 30. The difference in the system shown in FIG. 31 is that the light from the eye 2971 is subjected to multiple reflections before being captured by the camera 3180. To enable the multiple reflections, a mirror 3187 is provided behind the absorptive polarizer 3185. Therefore, the light from the eye 2971 is polarized prior to entering the corrective wedge 2966 with a polarization axis that is perpendicular to the transmission axis of the reflective polarizer that comprises the partially reflective layer 2960. In this way, the light from the eye 2971 is reflected first by the reflective polarizer, reflected second by the mirror 3187 and reflected third by the reflective polarizer before being captured by the camera 3180. While the light from the eye 2971 passes through the absorptive polarizer 3185 twice, since the polarization axis of the light from the eye 2971 is oriented parallel to the polarization axis of the light from the eye 2971, it is substantially transmitted by the absorptive polarizer 3185. As with the system described in connection with FIG. 30, the system shown in FIG. 31 includes an optically flat partially reflective layer 2960 that preserves the wavefront of the light from the eye 2971 so that higher quality images of the wearer's eye can be captured. Also, since the DLP 2955 is not included in the optical path for the light reflected from the eye 2971 and the eye imaging process shown in FIG. 31 does not interfere with the displayed image, images of the wearer's eye can be captured independently from the displayed images.

Figure 32:
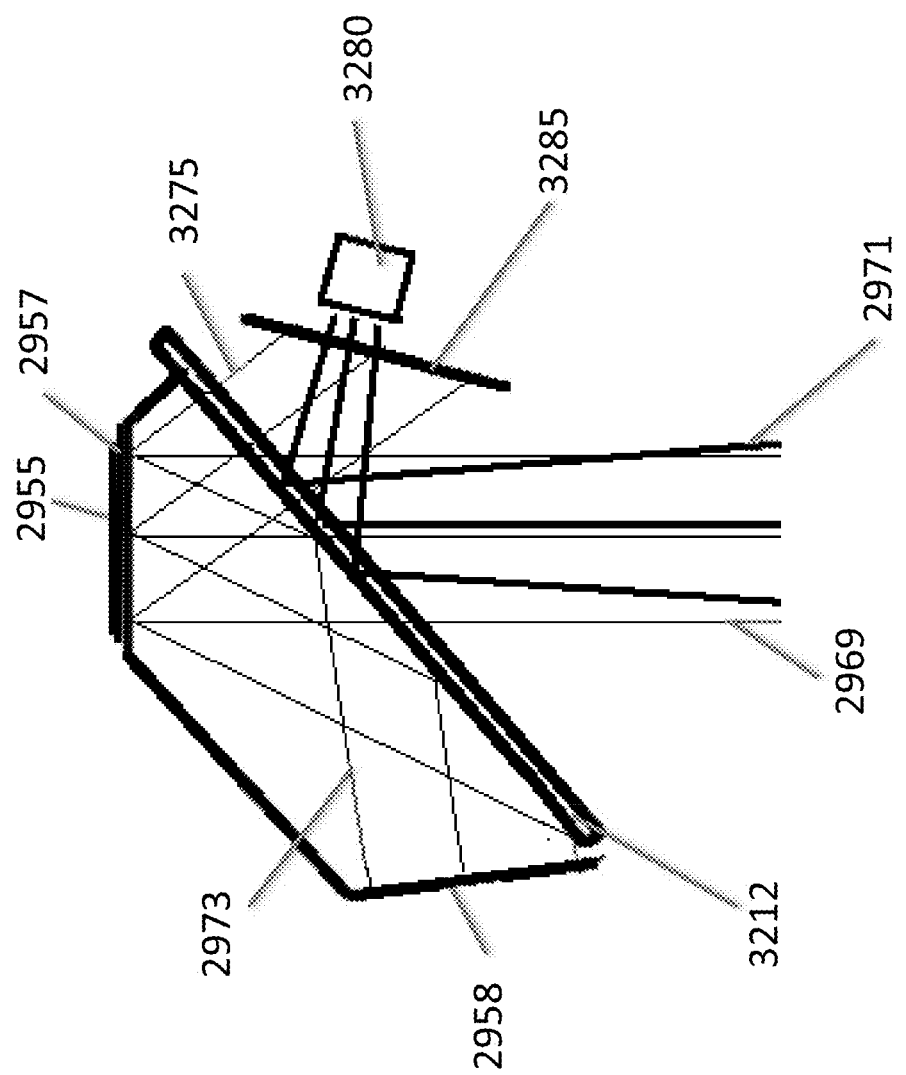

FIG. 32 shows an illustration of a system for displaying images and simultaneously capturing images of the wearer's eye that includes a beam splitter plate 3212 comprised of a reflective polarizer, which is held in air between the light source 2958, the DLP 2955 and the camera 3280. The illumination light 2973 and the light from the eye 2971 are both polarized with polarization axes that are perpendicular to the transmission axis of the reflective polarizer. As a result, both the illumination light 2973 and the light from the eye 2971 are substantially reflected by the reflective polarizer. The illumination light 2873 is reflected toward the DLP 2955 by the reflective polarizer and split into image light 2969 and dark light 3275 depending on whether the individual DLP mirrors are respectively in the "on" state or the "off" state. By passing through the quarter wave layer 2957 twice, the polarization state of the illumination light 2973 is reversed in comparison to the polarization state of the image light 2969 and the dark light 3275. As a result, the image light 2969 and the dark light 3275 are then substantially transmitted by the reflective polarizer. The absorptive polarizer 3285 at the side of the beam splitter plate 3212 has a transmission axis that is perpendicular to the polarization axis of the dark light 3275 and parallel to the polarization axis of the light from the eye 2971 so that the dark light 3275 is absorbed and the light from the eye 2971 is transmitted to the camera 3280. As in the system shown in FIG. 30, the system shown in FIG. 31 includes an optically flat beam splitter plate 3212 that preserves the wavefront of the light from the eye 2971 so that higher quality images of the wearer's eye can be captured. Also, since the DLP 2955 is not included in the optical path for the light from the eye 2971 and the eye imaging process shown in FIG. 31 does not interfere with the displayed image, images of the wearer's eye can be captured independently from the displayed images.

Eye imaging systems where the polarization state of the light from the eye 2971 needs to be opposite to that of the image light 2969 (as shown in FIGS. 30, 31 and 32), need to be used with lower modules 204 that include combiners that will reflect both polarization states. As such, these upper modules 202 are best suited for use with the lower modules 204 that include combiners that are reflective regardless of polarization state, examples of these lower modules are shown in FIGS. 6, 8a, 8b, 8c and 24-27.

Figure 33:
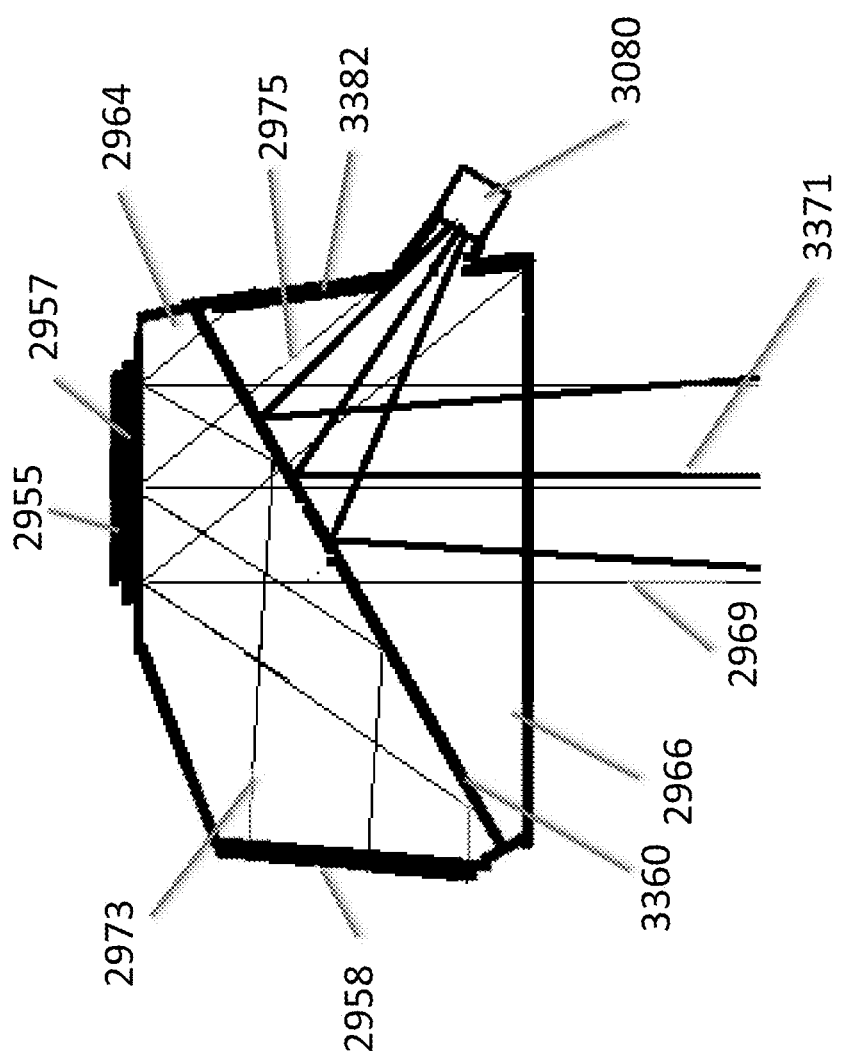

In a further embodiment shown in FIG. 33, the partially reflective layer 3360 is comprised of a reflective polarizer on the side facing the illumination light 2973 and a short pass dichroic mirror on the side facing the light from the eye 3371 and the camera 3080. Where the short pass dichroic mirror is a dielectric mirror coating that transmits visible light and reflects infrared light. The partially reflective layer 3360 can be comprised of a reflective polarizer bonded to the inner surface of the illumination wedge 2964 and a short pass dielectric mirror coating on the opposing inner surface of the corrective wedge 2966, wherein the illumination wedge 2964 and the corrective wedge 2966 are then optically bonded together. Alternatively, the partially reflective layer 3360 can be comprised of a thin substrate that has a reflective polarizer bonded to one side and a short pass dichroic mirror coating on the other side, where the partially reflective layer 3360 is then bonded between the illumination wedge 2964 and the corrective wedge 2966. In this embodiment, an infrared light is included to illuminate the eye so that the light from the eye and the images captured of the eye are substantially comprised of infrared light. The wavelength of the infrared light is then matched to the reflecting wavelength of the shortpass dichroic mirror and the wavelength that the camera can capture images, for example an 800 nm wavelength can be used. In this way, the short pass dichroic mirror transmits the image light and reflects the light from the eye. The camera 3080 is then positioned at the side of the corrective wedge 2966 in the area of the absorbing light trap 3382, which is provided to absorb the dark light 2975. By positioning the camera 3080 in a depression in the absorbing light trap 3382, scattering of the dark light 2975 by the camera 3080 can be reduced so that higher contrast images can be displayed to the wearer. An advantage of this embodiment is that the light from the eye need not be polarized, which can simplify the optical system and increase efficiency for the eye imaging system.

Figure 32A:
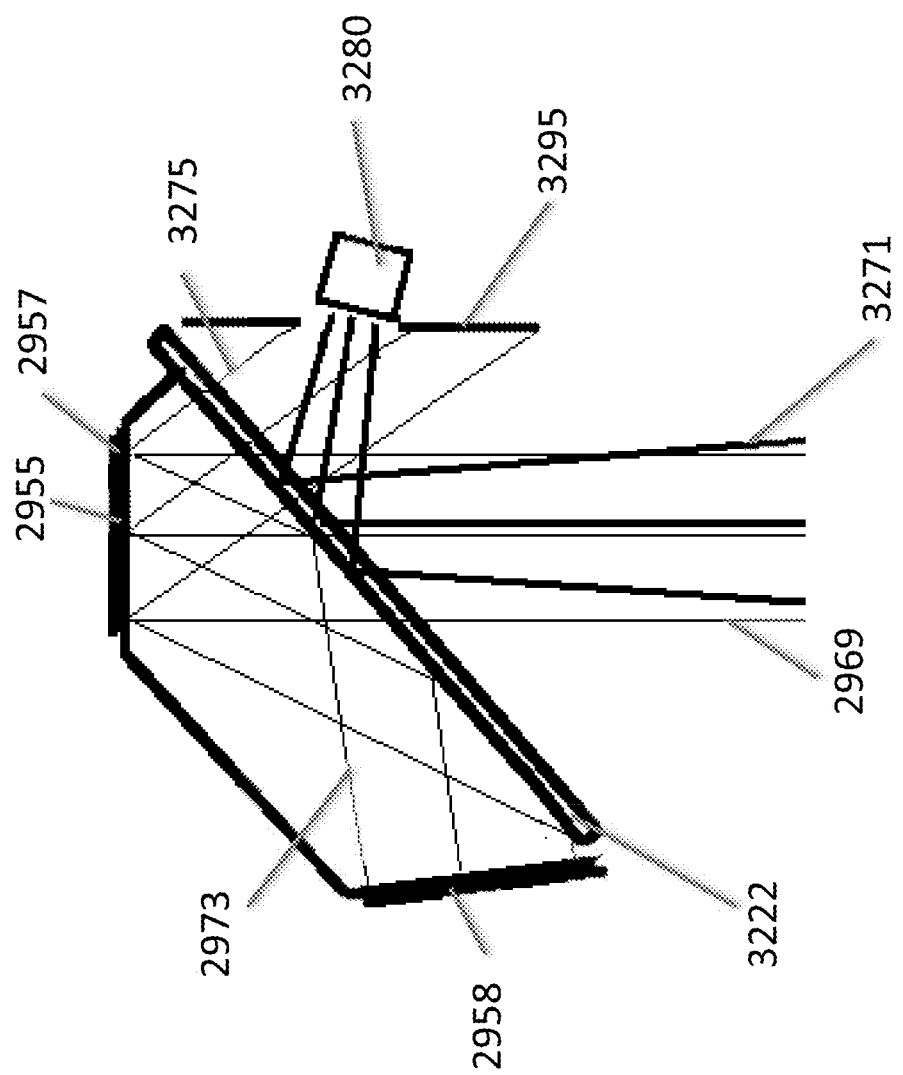

In yet another embodiment shown in FIG. 32*a* a beam splitter plate 3222 is comprised of a reflective polarizer on the side facing the illumination light 2973 and a short pass dichroic mirror on the side facing the light from the eye 3271 and the camera 3280. An absorbing surface 3295 is provided to trap the dark light 3275 and the camera 3280 is positioned in an opening in the absorbing surface 3295. In this way the system of FIG. 32 can be made to function with unpolarized light from the eye 3271.

Figure 34:
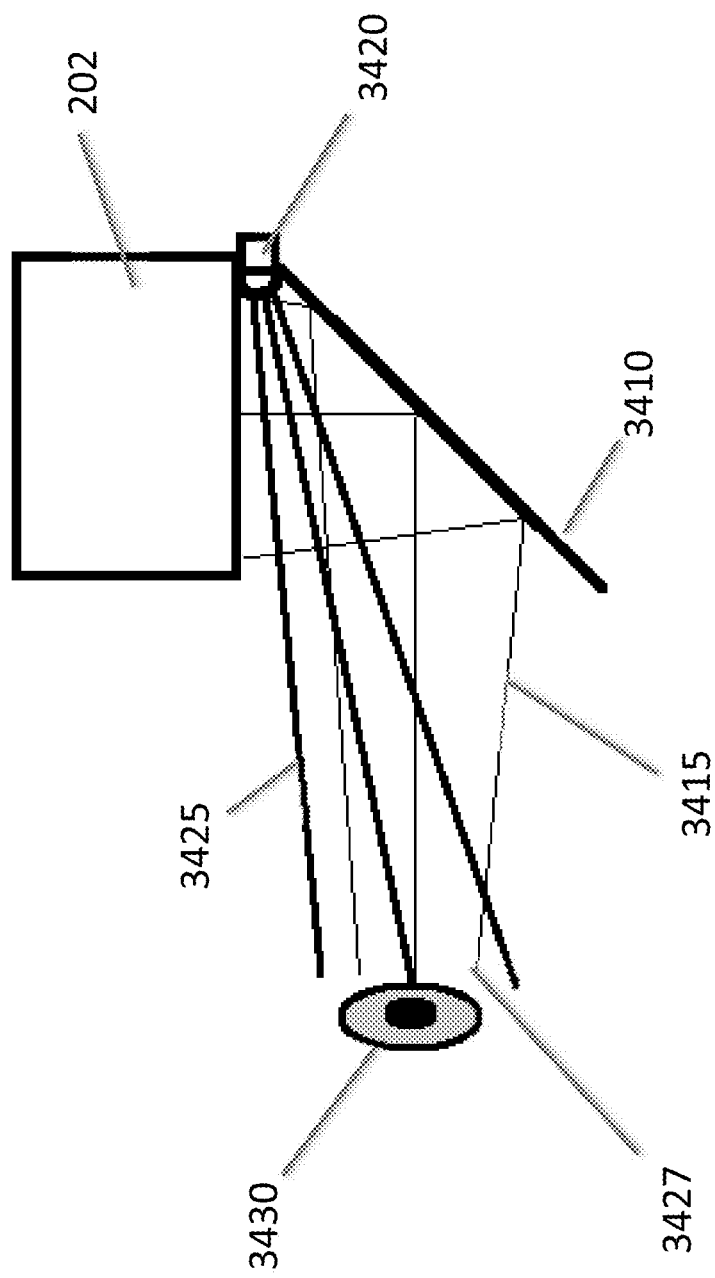
FIGS. 34 and 34a illustrate structured eye lighting systems according to the principles of the present invention.
Figure 34A:
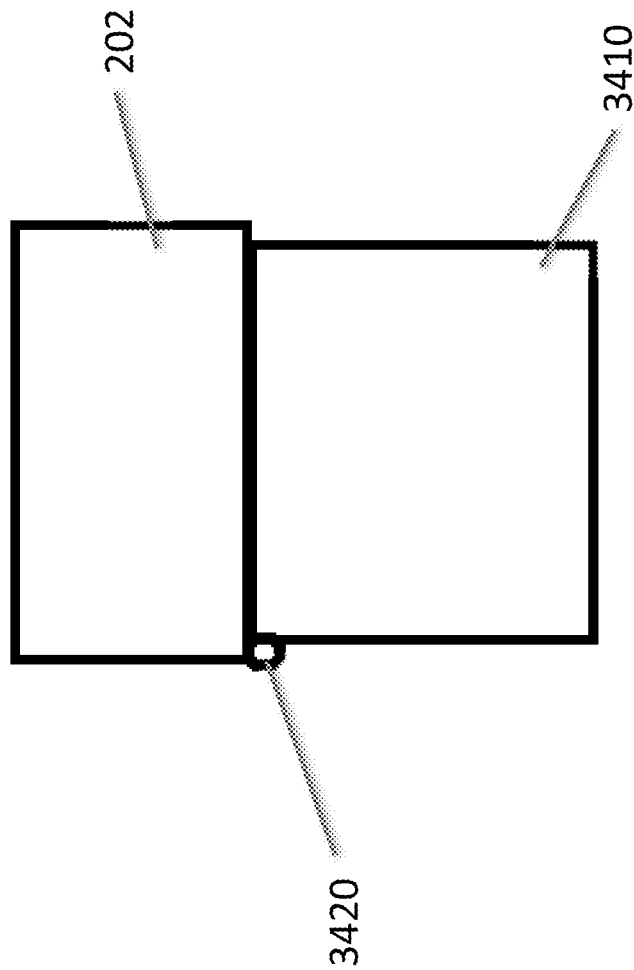

In embodiments directed to capturing images of the wearer's eye, light to illuminate the wearer's eye can be provided by several different sources including: light from the displayed image (i.e. image light); light from the environment that passes through the combiner or other optics; light provided by a dedicated eye light, etc. FIGS. 34 and 34*a* show illustrations of dedicated eye illumination lights 3420. FIG. 34 shows an illustration from a side view in which the dedicated illumination eye light 3420 is positioned at a corner of the combiner 3410 so that it doesn't interfere with the image light 3415. The dedicated eye illumination light 3420 is pointed so that the eye illumination light 3425 illuminates the eyebox 3427 where the eye 3430 is located when the wearer is viewing displayed images provided by the image light 3415. FIG. 34*a* shows an illustration from the perspective of the eye of the wearer to show how the dedicated eye illumination light 3420 is positioned at the corner of the combiner 3410. While the dedicated eye illumination light 3420 is shown at the upper left corner of the combiner 3410, other positions along one of the edges of the combiner 3410, or other optical or mechanical components, are possible as well. In other embodiments, more than one dedicated eye light 3420 with different positions can be used. In an embodiment, the dedicated eye light 3420 is an infrared light that is not visible by the wearer (e.g. 800 nm) so that the eye illumination light 3425 doesn't interfere with the displayed image perceived by the wearer.

Figure 35:
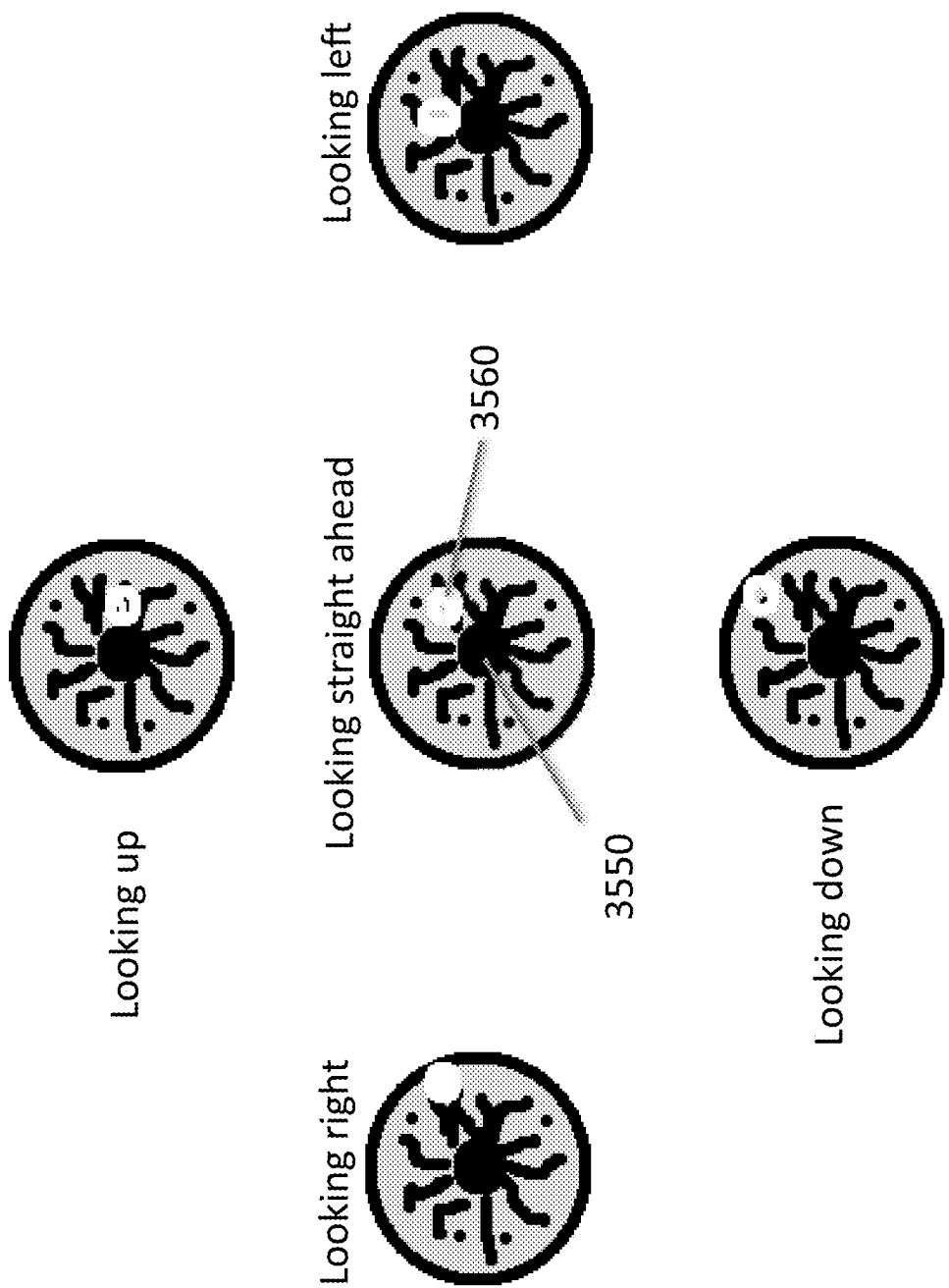
FIG. 35 illustrates eye glint in the prediction of eye direction analysis in accordance with the principles of the present invention.

FIG. 35 shows a series of illustrations of captured eye images that show the eye glint (i.e. light that reflects off the front of the eye) produced by a dedicated eye light. In this embodiment of the invention, captured images of the wearer's eye are analyzed to determine the relative positions of the iris 3550, pupil, or other portion of the eye, and the eye glint 3560. The eye glint is a reflected image of the dedicated eye light 3420 when the dedicated light is used. FIG. 35 illustrates the relative positions of the iris 3550 and the eye glint 3560 for a variety of eye positions. By providing a dedicated eye light 3420 in a fixed position, combined with the fact that the human eye is essentially spherical, or at least a reliably repeatable shape, the eye glint provides a fixed reference point against which the determined position of the iris can be compared to determine where the wearer is looking, either within the displayed image or within the see-through view of the surrounding environment. By positioning the dedicated eye light 3420 at a corner of the combiner 3410, the eye glint 3560 is formed away from the iris 3550 in the captured images. As a result, the positions of the iris and the eye glint can be determined more easily and more accurately during the analysis of the captured images, since they do not interfere with one another. In a further embodiment, the combiner includes an associated cut filter that prevents infrared light from the environment from entering the HWC and the camera is an infrared camera, so that the eye glint is only provided by light from the dedicated eye light. For example, the combiner can include a low pass filter that passes visible light while absorbing infrared light and the camera can include a high pass filter that absorbs visible light while passing infrared light.

In an embodiment of the eye imaging system, the lens for the camera is designed to take into account the optics associated with the upper module 202 and the lower module 204. This is accomplished by designing the camera to include the optics in the upper module 202 and optics in the lower module 204, so that a high MTF image is produced, at the image sensor in the camera, of the wearer's eye. In yet a further embodiment, the camera lens is provided with a large depth of field to eliminate the need for focusing the camera to enable sharp image of the eye to be captured. Where a large depth of field is typically provided by a high f/#lens (e.g. f/#>5). In this case, the reduced light gathering associated with high f/#lenses is compensated by the inclusion of a dedicated eye light to enable a bright image of the eye to be captured. Further, the brightness of the dedicated eye light can be modulated and synchronized with the capture of eye images so that the dedicated eye light has a reduced duty cycle and the brightness of infrared light on the wearer's eye is reduced.

Figures 36A, 36B:
FIG. 36a illustrates eye characteristics that may be used in personal identification through analysis of a system according to the principles of the present invention.
FIG. 36b illustrates a digital content presentation reflection off of the wearer's eye that may be analyzed in accordance with the principles of the present invention.

In a further embodiment, FIG. 36*a* shows an illustration of an eye image that is used to identify the wearer of the HWC. In this case, an image of the wearer's eye 3611 is captured and analyzed for patterns of identifiable features 3612. The patterns are then compared to a database of eye images to determine the identity of the wearer. After the identity of the wearer has been verified, the operating mode of the HWC and the types of images, applications, and information to be displayed can be adjusted and controlled in correspondence to the determined identity of the wearer. Examples of adjustments to the operating mode depending on who the wearer is determined to be or not be include: making different operating modes or feature sets available, shutting down or sending a message to an external network, allowing guest features and applications to run, etc.

is an illustration of another embodiment using eye imaging, in which the sharpness of the displayed image is determined based on the eye glint produced by the reflection of the displayed image from the wearer's eye surface. By capturing images of the wearer's eye 3611, an eye glint 3622, which is a small version of the displayed image can be captured and analyzed for sharpness. If the displayed image is determined to not be sharp, then an automated adjustment to the focus of the HWC optics can be performed to improve the sharpness. This ability to perform a measurement of the sharpness of a displayed image at the surface of the wearer's eye can provide a very accurate measurement of image quality. Having the ability to measure and automatically adjust the focus of displayed images can be very useful in augmented reality imaging where the focus distance of the displayed image can be varied in response to changes in the environment or changes in the method of use by the wearer.

An aspect of the present invention relates to controlling the HWC 102 through interpretations of eye imagery. In embodiments, eye-imaging technologies, such as those described herein, are used to capture an eye image or series of eye images for processing. The image(s) may be process to determine a user intended action, an HWC predetermined reaction, or other action. For example, the imagery may be interpreted as an affirmative user control action for an application on the HWC 102. Or, the imagery may cause, for example, the HWC 102 to react in a pre-determined way such that the HWC 102 is operating safely, intuitively, etc.

FIG. 37 illustrates a eye imagery process that involves imaging the HWC 102 wearer's eye(s) and processing the images (e.g. through eye imaging technologies described herein) to determine in what position 3702 the eye is relative to it's neutral or forward looking position and/or the FOV 3708. The process may involve a calibration step where the user is instructed, through guidance provided in the FOV of the HWC 102, to look in certain directions such that a more accurate prediction of the eye position relative to areas of the FOV can be made. In the event the wearer's eye is determined to be looking towards the right side of the FOV 3708 (as illustrated in FIG. 37, the eye is looking out of the page) a virtual target line may be established to project what in the environment the wearer may be looking towards or at. The virtual target line may be used in connection with an image captured by camera on the HWC 102 that images the surrounding environment in front of the wearer. In embodiments, the field of view of the camera capturing the surrounding environment matches, or can be matched (e.g. digitally), to the FOV 3708 such that making the comparison is made more clear. For example, with the camera capturing the image of the surroundings in an angle that matches the FOV 3708 the virtual line can be processed (e.g. in 2d or 3d, depending on the camera images capabilities and/or the processing of the images) by projecting what surrounding environment objects align with the virtual target line. In the event there are multiple objects along the virtual target line, focal planes may be established corresponding to each of the objects such that digital content may be placed in an area in the FOV 3708 that aligns with the virtual target line and falls at a focal plane of an intersecting object. The user then may see the digital content when he focuses on the object in the environment, which is at the same focal plane. In embodiments, objects in line with the virtual target line may be established by comparison to mapped information of the surroundings.

In embodiments, the digital content that is in line with the virtual target line may not be displayed in the FOV until the eye position is in the right position. This may be a predetermined process. For example, the system may be set up such that a particular piece of digital content (e.g. an advertisement, guidance information, object information, etc.) will appear in the event that the wearer looks at a certain object(s) in the environment. A virtual target line(s) may be developed that virtually connects the wearer's eye with an object(s) in the environment (e.g. a building, portion of a building, mark on a building, gps location, etc.) and the virtual target line may be continually updated depending on the position and viewing direction of the wearer (e.g. as determined through GPS, e-compass, IMU, etc.) and the position of the object. When the virtual target line suggests that the wearer's pupil is substantially aligned with the virtual target line or about to be aligned with the virtual target line, the digital content may be displayed in the FOV 3704.

In embodiments, the time spent looking along the virtual target line and/or a particular portion of the FOV 3708 may indicate that the wearer is interested in an object in the environment and/or digital content being displayed. In the event there is no digital content being displayed at the time a predetermined period of time is spent looking at a direction, digital content may be presented in the area of the FOV 3708. The time spent looking at an object may be interpreted as a command to display information about the object, for example. In other embodiments, the content may not relate to the object and may be presented because of the indication that the person is relatively inactive. In embodiments, the digital content may be positioned in proximity to the virtual target line, but not in-line with it such that the wearer's view of the surroundings are not obstructed but information can augment the wearer's view of the surroundings. In embodiments, the time spent looking along a target line in the direction of displayed digital content may be an indication of interest in the digital content. This may be used as a conversion event in advertising. For example, an advertiser may pay more for an add placement if the wearer of the HWC 102 looks at a displayed advertisement for a certain period of time. As such, in embodiments, the time spent looking at the advertisement, as assessed by comparing eye position with the content placement, target line or other appropriate position may be used to determine a rate of conversion or other compensation amount due for the presentation.

Figure 38:
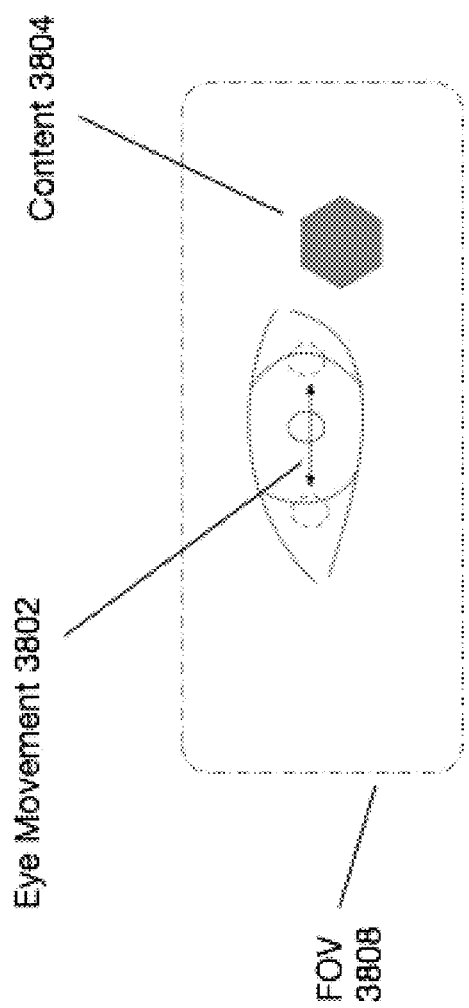
FIG. 38 illustrates content control with respect to eye movement based on eye imaging in accordance with the principles of the present invention.

An aspect of the invention relates to removing content from the FOV of the HWC 102 when the wearer of the HWC 102 apparently wants to view the surrounding environments clearly. FIG. 38 illustrates a situation where eye imagery suggests that the eye has or is moving quickly so the digital content 3804 in the FOV 3808 is removed from the FOV 3808. In this example, the wearer may be looking quickly to the side indicating that there is something on the side in the environment that has grabbed the wearer's attention. This eye movement 3802 may be captured through eye imaging techniques (e.g. as described herein) and if the movement matches a predetermined movement (e.g. speed, rate, pattern, etc.) the content may be removed from view. In embodiments, the eye movement is used as one input and HWC movements indicated by other sensors (e.g. IMU in the HWC) may be used as another indication. These various sensor movements may be used together to project an event that should cause a change in the content being displayed in the FOV.

Another aspect of the present invention relates to determining a focal plane based on the wearer's eye convergence. Eyes are generally converged slightly and converge more when the person focuses on something very close. This is generally referred to as convergence. In embodiments, convergence is calibrated for the wearer. That is, the wearer may be guided through certain focal plane exercises to determine how much the wearer's eyes converge at various focal planes and at various viewing angles. The convergence information may then be stored in a database for later reference. In embodiments, a general table may be used in the event there is no calibration step or the person skips the calibration step. The two eyes may then be imaged periodically to determine the convergence in an attempt to understand what focal plane the wearer is focused on. In embodiments, the eyes may be imaged to determine a virtual target line and then the eye's convergence may be determined to establish the wearer's focus, and the digital content may be displayed or altered based thereon.

Figure 39:
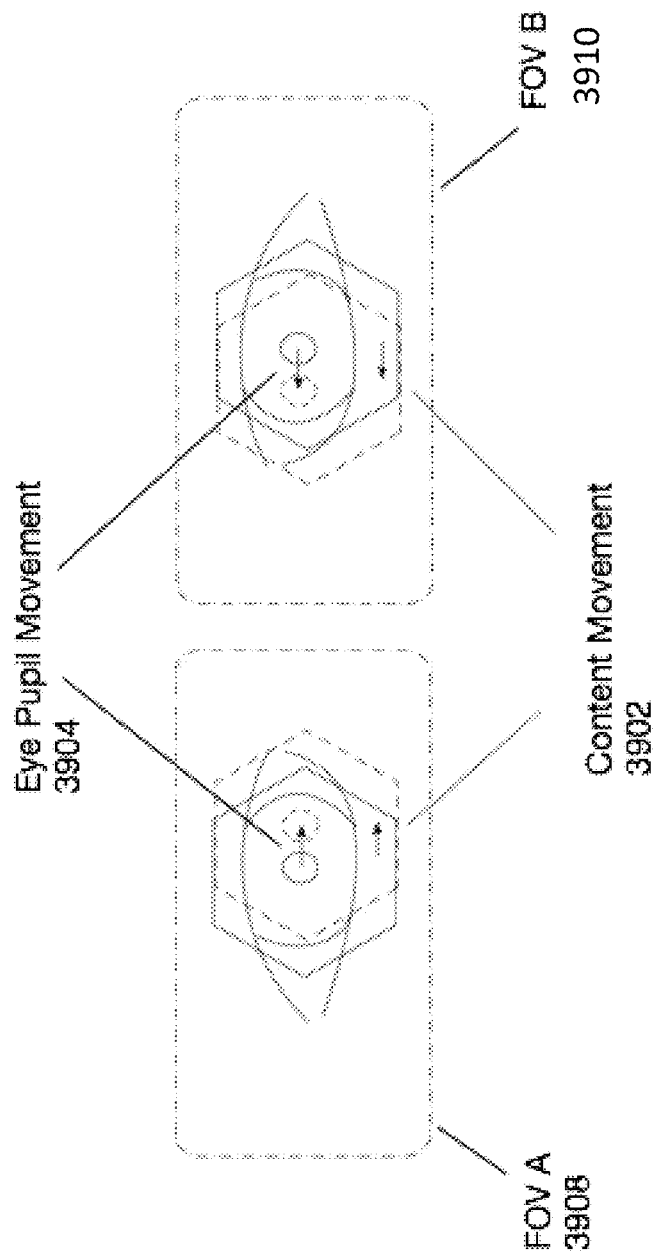
FIG. 39 illustrates eye imaging and eye convergence in accordance with the principles of the present invention.

FIG. 39 illustrates a situation where digital content is moved 3902 within one or both of the FOVs 3908 and 3910 to align with the convergence of the eyes as determined by the pupil movement 3904. By moving the digital content to maintain alignment, in embodiments, the overlapping nature of the content is maintained so the object appears properly to the wearer. This can be important in situations where 3D content is displayed.

An aspect of the present invention relates to controlling the HWC 102 based on events detected through eye imaging. A wearer winking, blinking, moving his eyes in a certain pattern, etc. may, for example, control an application of the HWC 102. Eye imaging (e.g. as described herein) may be used to monitor the eye(s) of the wearer and once a predetermined pattern is detected an application control command may be initiated.

An aspect of the invention relates to monitoring the health of a person wearing a HWC 102 by monitoring the wearer's eye(s). Calibrations may be made such that the normal performance, under various conditions (e.g. lighting conditions, image light conditions, etc.) of a wearer's eyes may be documented. The wearer's eyes may then be monitored through eye imaging (e.g. as described herein) for changes in their performance. Changes in performance may be indicative of a health concern (e.g. concussion, brain injury, stroke, loss of blood, etc.). If detected the data indicative of the change or event may be communicated from the HWC 102.

Aspects of the present invention relate to security and access of computer assets (e.g. the HWC itself and related computer systems) as determined through eye image verification. As discussed herein elsewhere, eye imagery may be compared to known person eye imagery to confirm a person's identity. Eye imagery may also be used to confirm the identity of people wearing the HWCs 102 before allowing them to link together or share files, streams, information, etc.

A variety of use cases for eye imaging are possible based on technologies described herein. An aspect of the present invention relates to the timing of eye image capture. The timing of the capture of the eye image and the frequency of the capture of multiple images of the eye can vary dependent on the use case for the information gathered from the eye image. For example, capturing an eye image to identify the user of the HWC may be required only when the HWC has been turned ON or when the HWC determines that the HWC has been put onto a wearer's head, to control the security of the HWC and the associated information that is displayed to the user. Wherein, the orientation, movement pattern, stress or position of the earhorns (or other portions of the HWC) of the HWC can be used to determine that a person has put the HWC onto their head with the intention to use the HWC. Those same parameters may be monitored in an effort to understand when the HWC is dismounted from the user's head. This may enable a situation where the capture of an eye image for identifying the wearer may be completed only when a change in the wearing status is identified. In a contrasting example, capturing eye images to monitor the health of the wearer may require images to be captured periodically (e.g. every few seconds, minutes, hours, days, etc.). For example, the eye images may be taken in minute intervals when the images are being used to monitor the health of the wearer when detected movements indicate that the wearer is exercising. In a further contrasting example, capturing eye images to monitor the health of the wearer for long-term effects may only require that eye images be captured monthly. Embodiments of the invention relate to selection of the timing and rate of capture of eye images to be in correspondence with the selected use scenario associated with the eye images. These selections may be done automatically, as with the exercise example above where movements indicate exercise, or these selections may be set manually. In a further embodiment, the selection of the timing and rate of eye image capture is adjusted automatically depending on the mode of operation of the HWC. The selection of the timing and rate of eye image capture can further be selected in correspondence with input characteristics associated with the wearer including age and health status, or sensed physical conditions of the wearer including heart rate, chemical makeup of the blood and eye blink rate.

Figure 40:
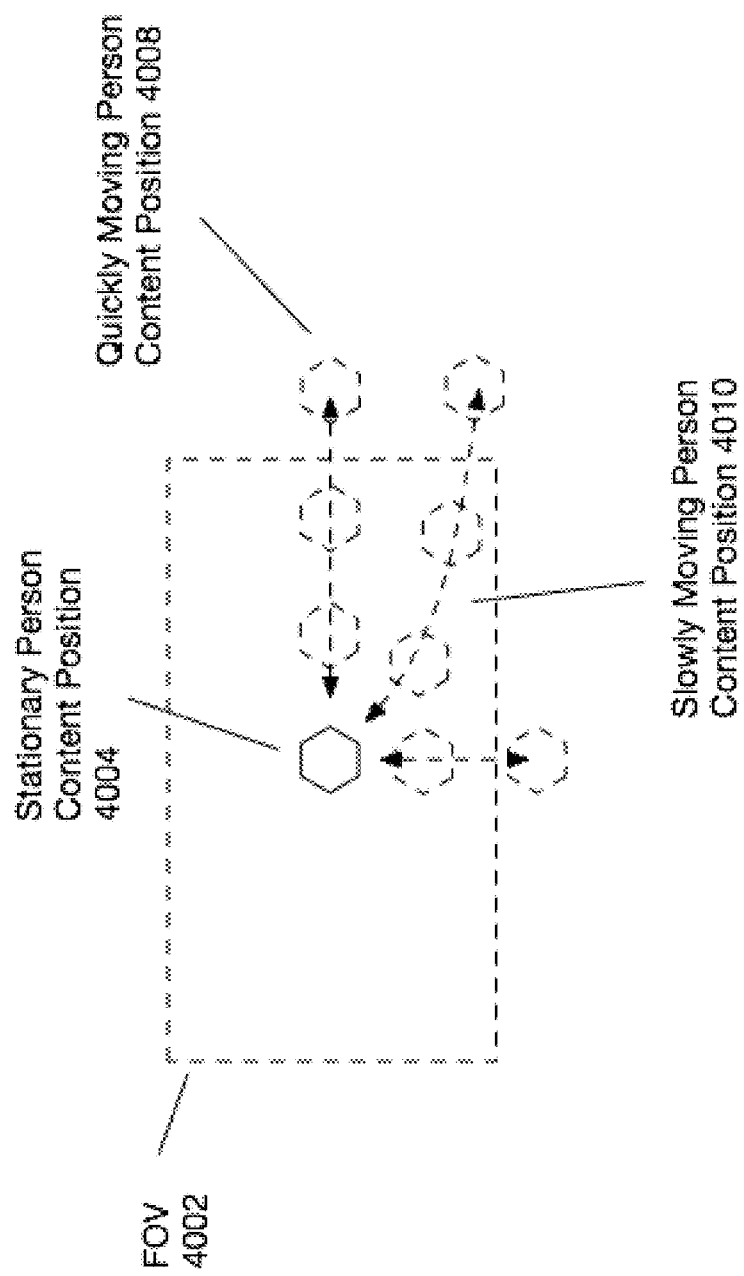
FIG. 40 illustrates content position dependent on sensor feedback in accordance with the principles of the present invention.

FIG. 40 illustrates an embodiment in which digital content presented in a see-through FOV is positioned based on the speed in which the wearer is moving. When the person is not moving, as measured by sensor(s) in the HWC 102 (e.g. IMU, GPS based tracking, etc.), digital content may be presented at the stationary person content position 4004. The content position 4004 is indicated as being in the middle of the see-through FOV 4002; however, this is meant to illustrate that the digital content is positioned within the see-through FOV at a place that is generally desirable knowing that the wearer is not moving and as such the wearer's surrounding see through view can be somewhat obstructed. So, the stationary person content position, or neutral position, may not be centered in the see-through FOV; it may be positioned somewhere in the see-through FOV deemed desirable and the sensor feedback may shift the digital content from the neutral position. The movement of the digital content for a quickly moving person is also shown in FIG. 40 wherein as the person turns their head to the side, the digital content moves out of the see-through FOV to content position 4008 and then moves back as the person turns their head back. For a slowly moving person, the head movement can be more complex and as such the movement of the digital content in an out of the see-through FOV can follow a path such as that shown by content position 4010.

In embodiments, the sensor that assesses the wearer's movements may be a GPS sensor, IMU, accelerometer, etc. The content position may be shifted from a neutral position to a position towards a side edge of the field of view as the forward motion increases. The content position may be shifted from a neutral position to a position towards a top or bottom edge of the field of view as the forward motion increases. The content position may shift based on a threshold speed of the assessed motion. The content position may shift linearly based on the speed of the forward motion. The content position may shift non-linearly based on the speed of the forward motion. The content position may shift outside of the field of view. In embodiments, the content is no longer displayed if the speed of movement exceeds a predetermined threshold and will be displayed again once the forward motion slows.

In embodiments, the content position may generally be referred to as shifting; it should be understood that the term shifting encompasses a process where the movement from one position to another within the see-through FOV or out of the FOV is visible to the wearer (e.g. the content appears to slowly or quickly move and the user perceives the movement itself) or the movement from one position to another may not be visible to the wearer (e.g. the content appears to jump in a discontinuous fashion or the content disappears and then reappears in the new position).

Another aspect of the present invention relates to removing the content from the field of view or shifting it to a position within the field of view that increases the wearer's view of the surrounding environment when a sensor causes an alert command to be issued. In embodiments, the alert may be due to a sensor or combination of sensors that sense a condition above a threshold value. For example, if an audio sensor detects a loud sound of a certain pitch, content in the field of view may be removed or shifted to provide a clear view of the surrounding environment for the wearer. In addition to the shifting of the content, in embodiments, an indication of why the content was shifted may be presented in the field of view or provided through audio feedback to the wearer. For instance, if a carbon monoxide sensor detects a high concentration in the area, content in the field of view may be shifted to the side of the field of view or removed from the field of view and an indication may be provided to the wearer that there is a high concentration of carbon monoxide in the area. This new information, when presented in the field of view, may similarly be shifted within or outside of the field of view depending on the movement speed of the wearer.

Figure 41:
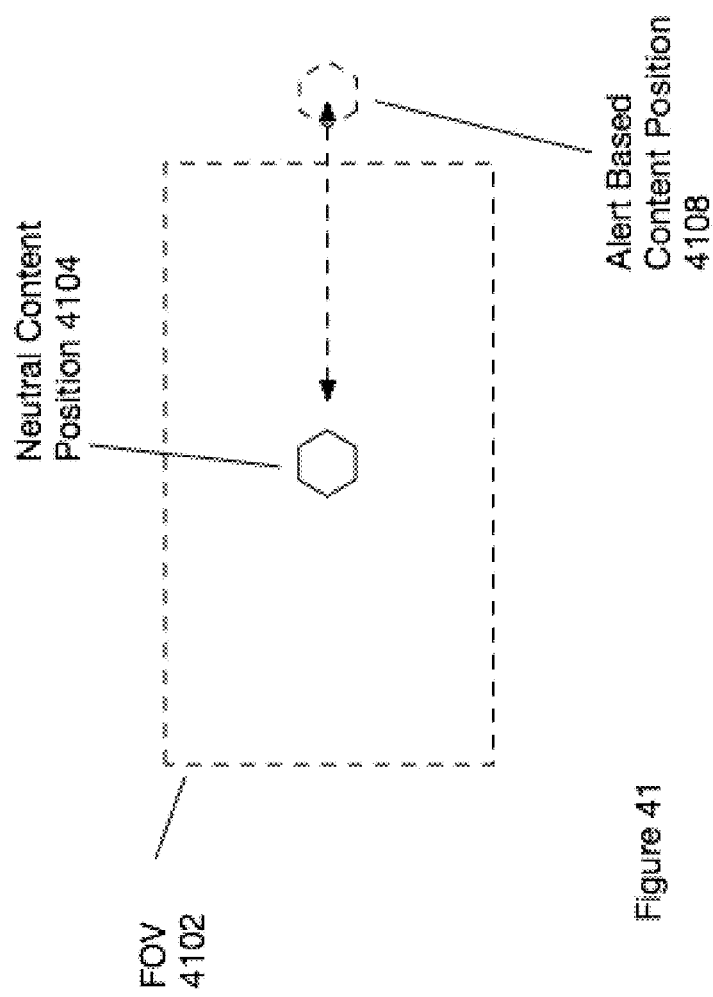
FIG. 41 illustrates content position dependent on sensor feedback in accordance with the principles of the present invention.

FIG. 41 illustrates how content may be shifted from a neutral position 4104 to an alert position 4108. In this embodiment, the content is shifted outside of the see-through FOV 4102. In other embodiments, the content may be shifted as described herein.

Another aspect of the present invention relates to identification of various vectors or headings related to the HWC 102, along with sensor inputs, to determine how to position content in the field of view. In embodiments, the speed of movement of the wearer is detected and used as an input for position of the content and, depending on the speed, the content may be positioned with respect to a movement vector or heading (i.e. the direction of the movement), or a sight vector or heading (i.e. the direction of the wearer's sight direction). For example, if the wearer is moving very fast the content may be positioned within the field of view with respect to the movement vector because the wearer is only going to be looking towards the sides of himself periodically and for short periods of time. As another example, if the wearer is moving slowly, the content may be positioned with respect to the sight heading because the user may more freely be shifting his view from side to side.

Figure 42:
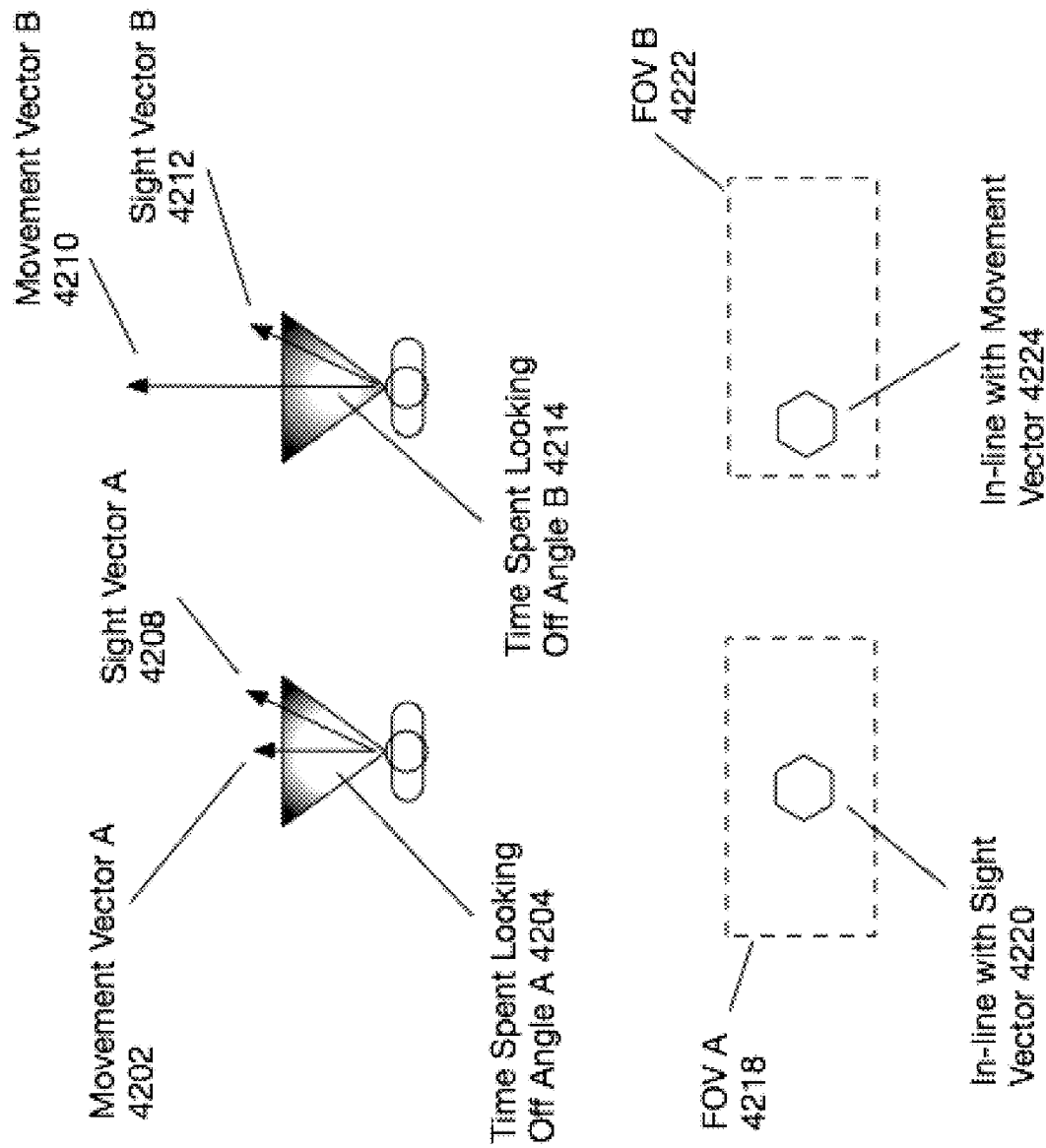
FIG. 42 illustrates content position dependent on sensor feedback in accordance with the principles of the present invention.

FIG. 42 illustrates two examples where the movement vector may effect content positioning. Movement vector A 4202 is shorter than movement vector B 4210 indicating that the forward speed and/or acceleration of movement of the person associated with movement vector A 4202 is lower than the person associated with movement vector B 4210. Each person is also indicated as having a sight vector or heading 4208 and 4212. The sight vectors A 4208 and B 4210 are the same from a relative perspective. The white area inside of the black triangle in front of each person is indicative of how much time each person likely spends looking at a direction that is not in line with the movement vector. The time spent looking off angle A 4204 is indicated as being more than that of the time spent looking off angle B 4214. This may be because the movement vector speed A is lower than movement vector speed B. The faster the person moves forward the more the person tends to look in the forward direction, typically. The FOVs A 4218 and B 4222 illustrate how content may be aligned depending on the movement vectors 4202 and 4210 and sight vectors 4208 and 4212. FOV A 4218 is illustrated as presenting content in-line with the sight vector 4220. This may be due to the lower speed of the movement vector A 4202. This may also be due to the prediction of a larger amount of time spent looking off angle A 4204. FOV B 4222 is illustrated as presenting content in line with the movement vector 4224. This may be due to the higher speed of movement vector B 4210. This may also be due to the prediction of a shorter amount of time spent looking off angle B 4214.

Figure 43:
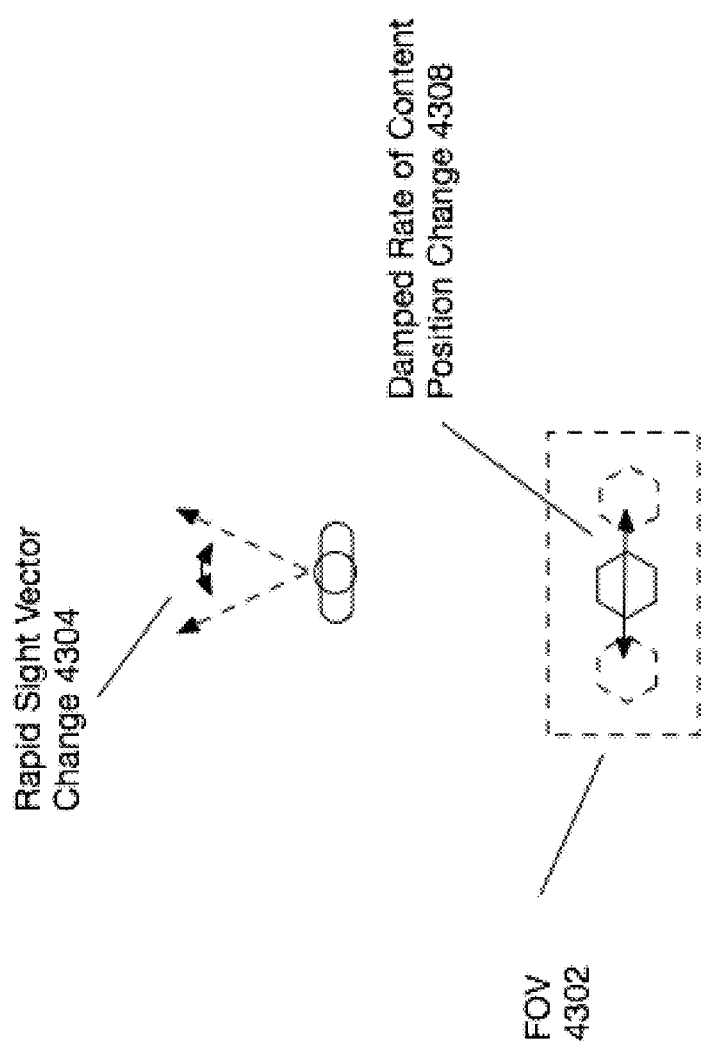
FIG. 43 illustrates content position dependent on sensor feedback in accordance with the principles of the present invention.

Another aspect of the present invention relates to damping a rate of content position change within the field of view. As illustrated in FIG. 43, the sight vector may undergo a rapid change 4304. This rapid change may be an isolated event or it may be made at or near a time when other sight vector changes are occurring. The wearer's head may be turning back and forth for some reason. In embodiments, the rapid successive changes in sight vector may cause a damped rate of content position change 4308 within the FOV 4302. For example, the content may be positioned with respect to the sight vector, as described herein, and the rapid change in sight vector may normally cause a rapid content position change; however, since the sight vector is successively changing, the rate of position change with respect to the sight vector may be damped, slowed, or stopped. The position rate change may be altered based on the rate of change of the sight vector, average of the sight vector changes, or otherwise altered.

Figure 44:
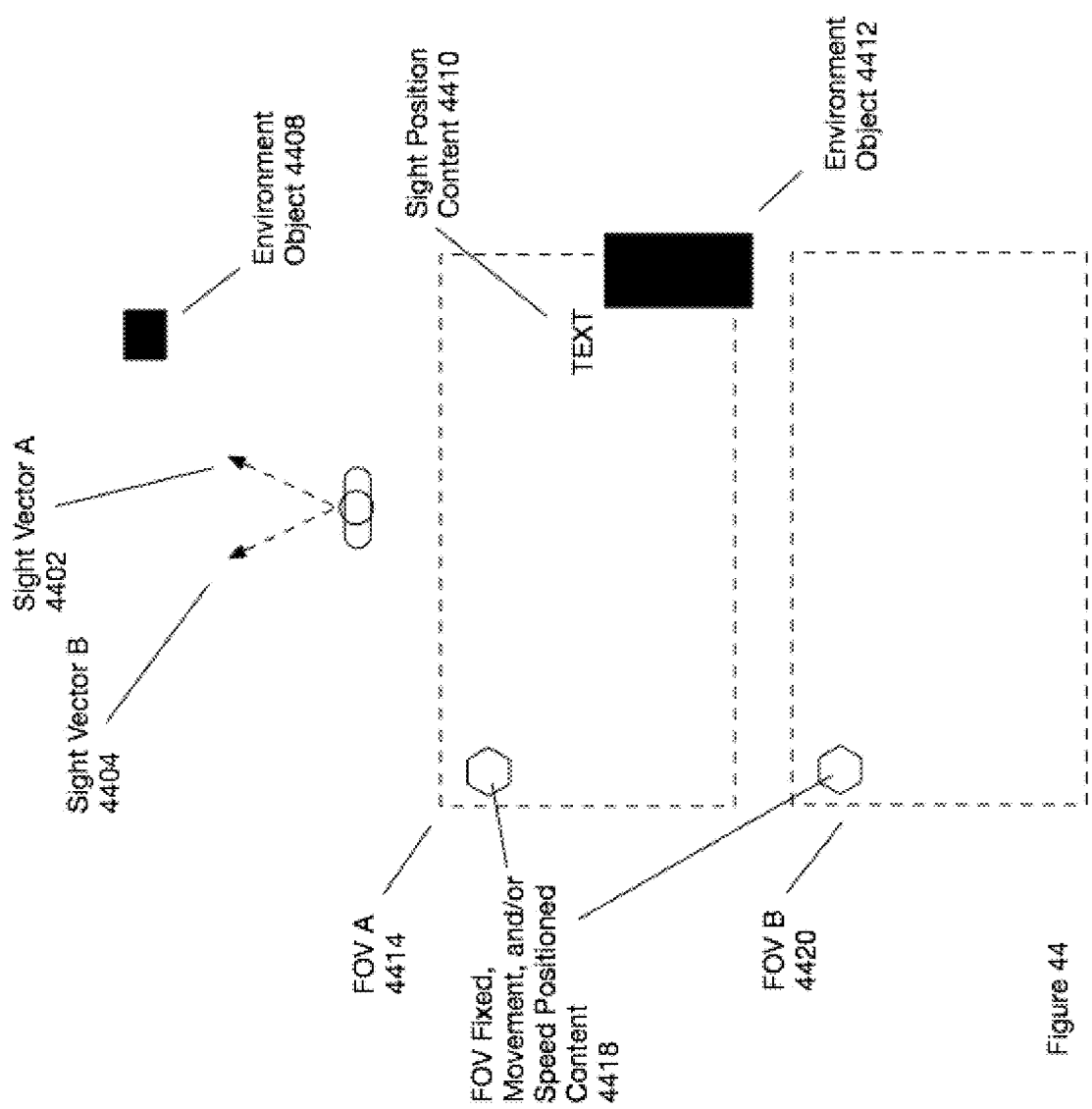
FIG. 44 illustrates content position dependent on sensor feedback in accordance with the principles of the present invention.
Figure 45:
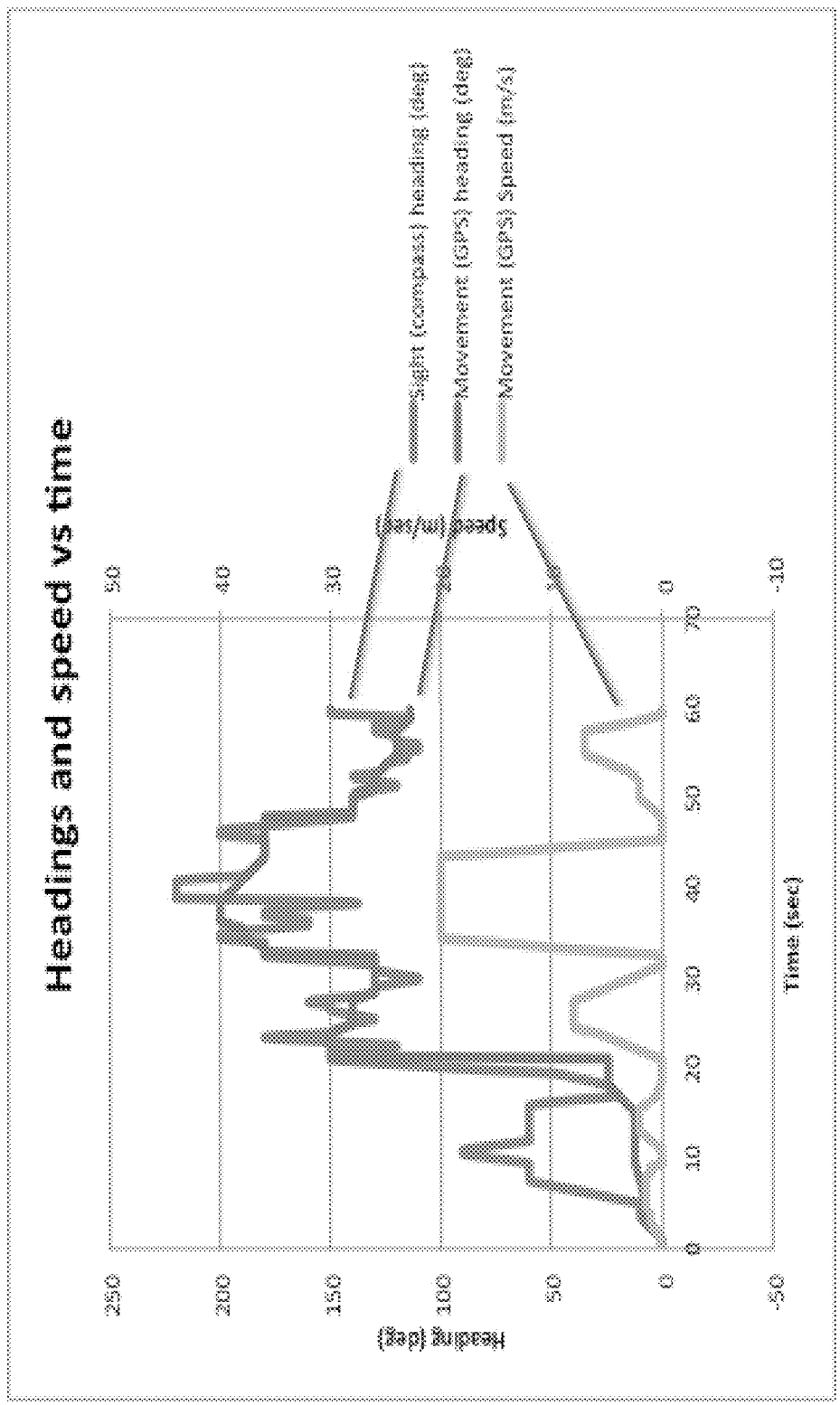
FIG. 45 illustrates various headings over time in an example.
Figure 46:
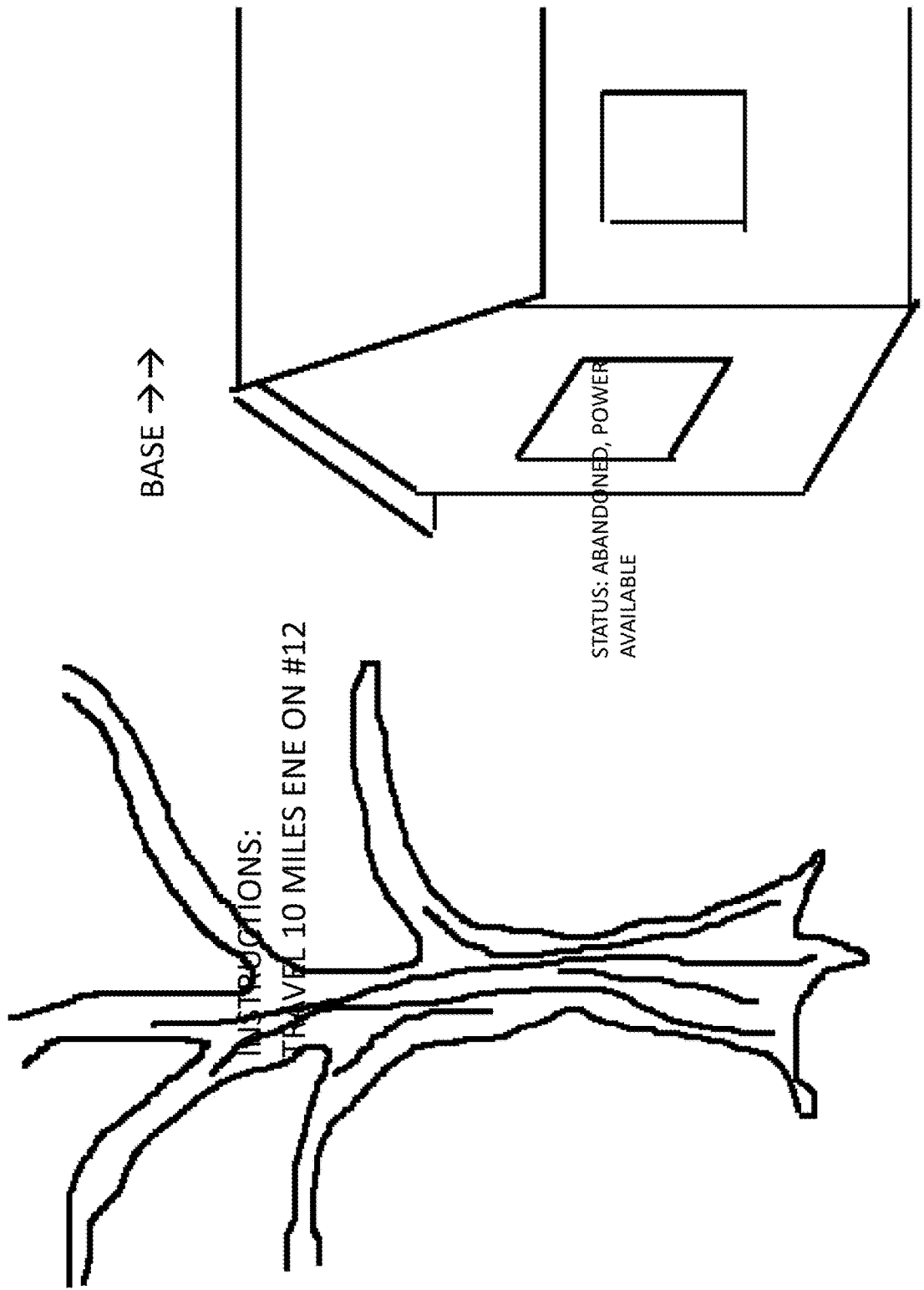
FIG. 46 illustrates content position dependent on sensor feedback in accordance with the principles of the present invention.
Figure 49:
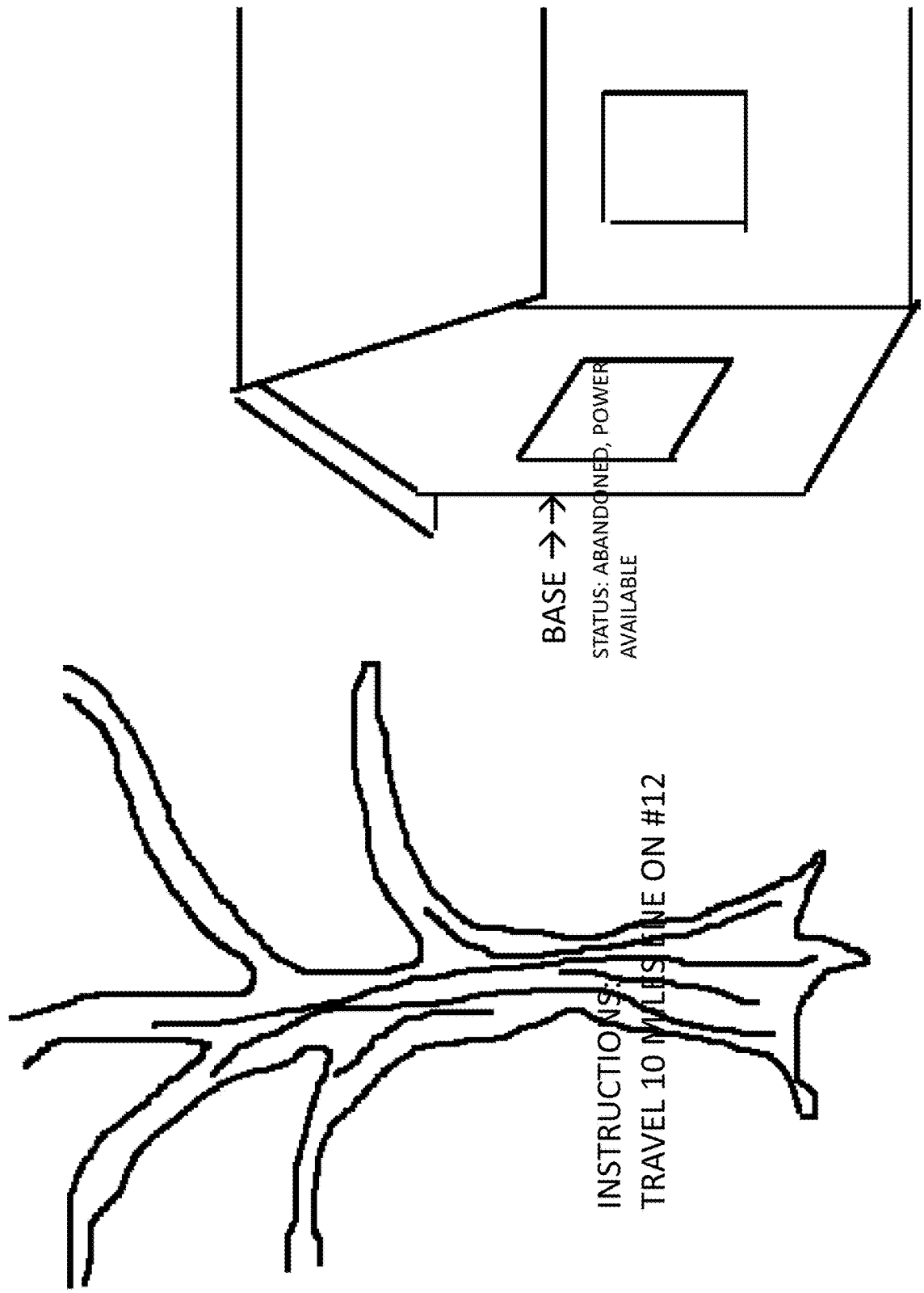
FIG. 49 illustrates content position dependent on sensor feedback in accordance with the principles of the present invention.

Another aspect of the present invention relates to simultaneously presenting more than one content in the field of view of a see-through optical system of a HWC 102 and positioning one content with the sight heading and one content with the movement heading. FIG. 44 illustrates two FOV's A 4414 and B 4420, which correspond respectively to the two identified sight vectors A 4402 and B 4404. FIG. 44 also illustrates an object in the environment 4408 at a position relative to the sight vectors A 4402 and B 4404. When the person is looking along sight vector A 4402, the environment object 4408 can be seen through the field of view A 4414 at position 4412. As illustrated, sight heading aligned content is presented as TEXT in proximity with the environment object 4412. At the same time, other content 4418 is presented in the field of view A 4414 at a position aligned in correspondence with the movement vector. As the movement speed increases, the content 4418 may shift as described herein. When the sight vector of the person is sight vector B 4404 the environmental object 4408 is not seen in the field of view B 4420. As a result, the sight aligned content 4410 is not presented in field of view B 4420; however, the movement aligned content 4418 is presented and is still dependent on the speed of the motion.

In a further embodiment, in an operating mode such as when the user is moving in an environment, digital content is presented at the side of the user's see-through FOV so that the user can only view the digital content by turning their head. In this case, when the user is looking straight ahead, such as when the movement heading matches the sight heading, the see-through view FOV does not include digital content. The user then accesses the digital content by turning their head to the side whereupon the digital content moves laterally into the user's see-through FOV. In another embodiment, the digital content is ready for presentation and will be presented if an indication for it's presentation is received. For example, the information may be ready for presentation and if the sight heading or predetermined position of the HWC 102 is achieved the content may then be presented. The wearer may look to the side and the content may be presented. In another embodiment, the user may cause the content to move into an area in the field of view by looking in a direction for a predetermined period of time, blinking, winking, or displaying some other pattern that can be captured through eye imaging technologies (e.g. as described herein elsewhere).

In yet another embodiment, an operating mode is provided wherein the user can define sight headings wherein the associated see-through FOV includes digital content or does not include digital content. In an example, this operating mode can be used in an office environment where when the user is looking at a wall digital content is provided within the FOV, whereas when the user is looking toward a hallway, the FOV is unencumbered by digital content. In another example, when the user is looking horizontally digital content is provided within the FOV, but when the user looks down (e.g. to look at a desktop or a cellphone) the digital content is removed from the FOV.

Another aspect of the present invention relates to collecting and using eye position and sight heading information. Head worn computing with motion heading, sight heading, and/or eye position prediction (sometimes referred to as "eye heading" herein) may be used to identify what a wearer of the HWC 102 is apparently interested in and the information may be captured and used. In embodiments, the information may be characterized as viewing information because the information apparently relates to what the wearer is looking at. The viewing information may be used to develop a personal profile for the wearer, which may indicate what the wearer tends to look at. The viewing information from several or many HWC's 102 may be captured such that group or crowd viewing trends may be established. For example, if the movement heading and sight heading are known, a prediction of what the wearer is looking at may be made and used to generate a personal profile or portion of a crowd profile. In another embodiment, if the eye heading and location, sight heading and/or movement heading are known, a prediction of what is being looked at may be predicted. The prediction may involve understanding what is in proximity of the wearer and this may be understood by establishing the position of the wearer (e.g. through GPS or other location technology) and establishing what mapped objects are known in the area. The prediction may involve interpreting images captured by the camera or other sensors associated with the HWC 102. For example, if the camera captures an image of a sign and the camera is in-line with the sight heading, the prediction may involve assessing the likelihood that the wearer is viewing the sign. The prediction may involve capturing an image or other sensory information and then performing object recognition analysis to determine what is being viewed. For example, the wearer may be walking down a street and the camera that is in the HWC 102 may capture an image and a processor, either on-board or remote from the HWC 102, may recognize a face, object, marker, image, etc. and it may be determined that the wearer may have been looking at it or towards it.

Figure 50:
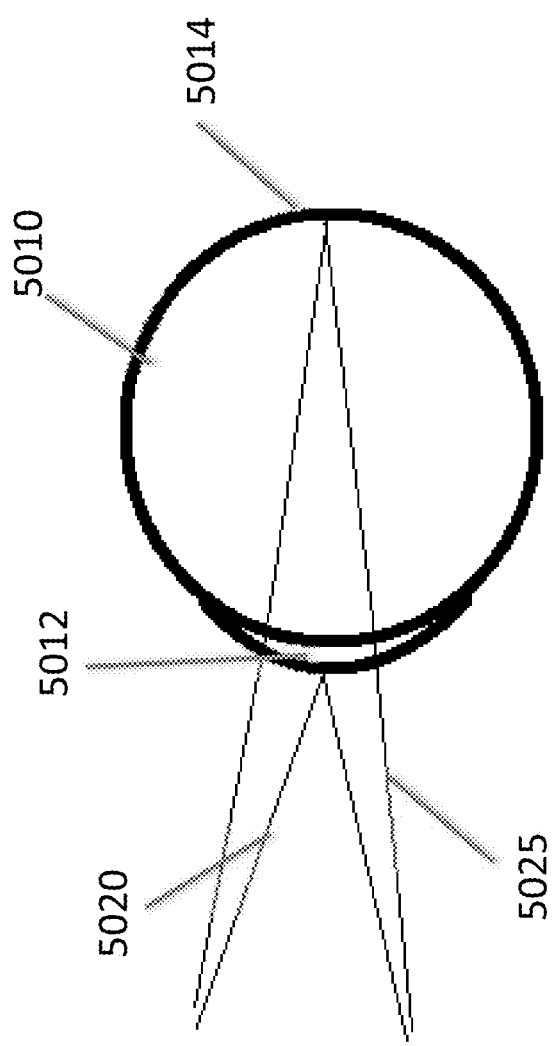
FIG. 50 illustrates light impinging an eye in accordance with the principles of the present invention.
Figure 51:
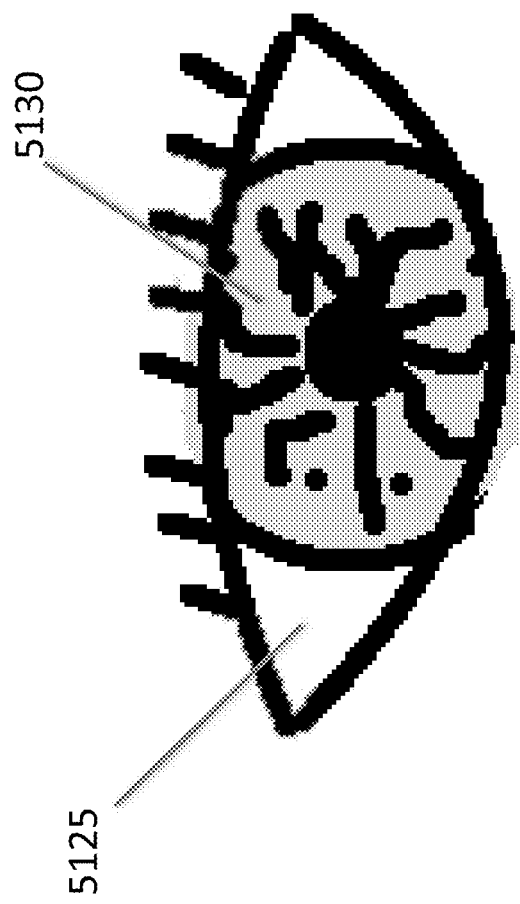
FIG. 51 illustrates a view of an eye in accordance with the principles of the present invention.

FIG. 50 illustrates a cross section of an eyeball of a wearer of an HWC with focus points that can be associated with the eye imaging system of the invention. The eyeball 5010 includes an iris 5012 and a retina 5014. Because the eye imaging system of the invention provides coaxial eye imaging with a display system, images of the eye can be captured from a perspective directly in front of the eye and inline with where the wearer is looking. In embodiments of the invention, the eye imaging system can be focused at the iris 5012 and/or the retina 5014 of the wearer, to capture images of the external surface of the iris 5012 or the internal portions of the eye, which includes the retina 5014. FIG. 50 shows light rays 5020 and 5025 that are respectively associated with capturing images of the iris 5012 or the retina 5014 wherein the optics associated with the eye imaging system are respectively focused at the iris 5012 or the retina 5014. Illuminating light can also be provided in the eye imaging system to illuminate the iris 5012 or the retina 5014. FIG. 51 shows an illustration of an eye including an iris 5130 and a sclera 5125. In embodiments, the eye imaging system can be used to capture images that include the iris 5130 and portions the sclera 5125. The images can then be analyzed to determine color, shapes and patterns that are associated with the user. In further embodiments, the focus of the eye imaging system is adjusted to enable images to be captured of the iris 5012 or the retina 5014. Illuminating light can also be adjusted to illuminate the iris 5012 or to pass through the pupil of the eye to illuminate the retina 5014. The illuminating light can be visible light to enable capture of colors of the iris 5012 or the retina 5014, or the illuminating light can be ultraviolet (e.g. 340 nm), near infrared (e.g. 850 nm) or mid-wave infrared (e.g. 5000 nm) light to enable capture of hyperspectral characteristics of the eye.

Figure 53:
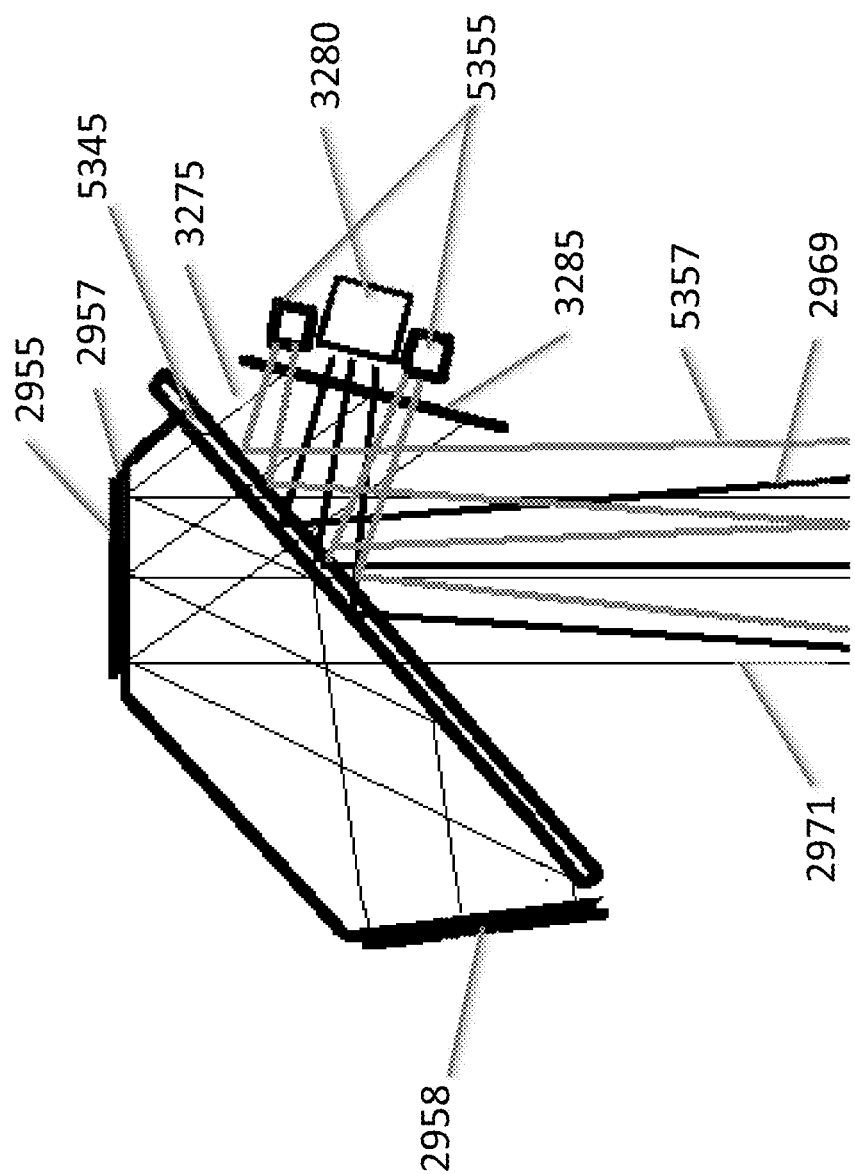
FIG. 53 illustrates an optics module in accordance with the principles of the present invention.

FIG. 53 illustrates a display system that includes an eye imaging system. The display system includes a polarized light source 2958, a DLP 2955, a quarter wave film 2957 and a beam splitter plate 5345. The eye imaging system includes a camera 3280, illuminating lights 5355 and beam splitter plate 5345. Where the beam splitter plate 5345 can be a reflective polarizer on the side facing the polarized light source 2958 and a hot mirror on the side facing the camera 3280. Wherein the hot mirror reflects infrared light (e.g. wavelengths 700 to 2000 nm) and transmits visible light (e.g. wavelengths 400 to 670 nm). The beam splitter plate 5345 can be comprised of multiple laminated films, a substrate film with coatings or a rigid transparent substrate with films on either side. By providing a reflective polarizer on the one side, the light from the polarized light source 2958 is reflected toward the DLP 2955 where it passes through the quarter wave film 2957 once, is reflected by the DLP mirrors in correspondence with the image content being displayed by the DLP 2955 and then passes back through the quarter wave film 2957. In so doing, the polarization state of the light from the polarized light source is changed, so that it is transmitted by the reflective polarizer on the beam splitter plate 5345 and the image light 2971 passes into the lower optics module 204 where the image is displayed to the user. At the same time, infrared light 5357 from the illuminating lights 5355 is reflected by the hot mirror so that it passes into the lower optics module 204 where it illuminates the user's eye. Portions of the infrared light 2969 are reflected by the user's eye and this light passes back through the lower optics module 204, is reflected by the hot mirror on the beam splitter plate 5345 and is captured by the camera 3280. In this embodiment, the image light 2971 is polarized while the infrared light 5357 and 2969 can be unpolarized. In an embodiment, the illuminating lights 5355 provide two different infrared wavelengths and eye images are captured in pairs, wherein the pairs of eye images are analyzed together to improve the accuracy of identification of the user based on iris analysis.

Figure 54:
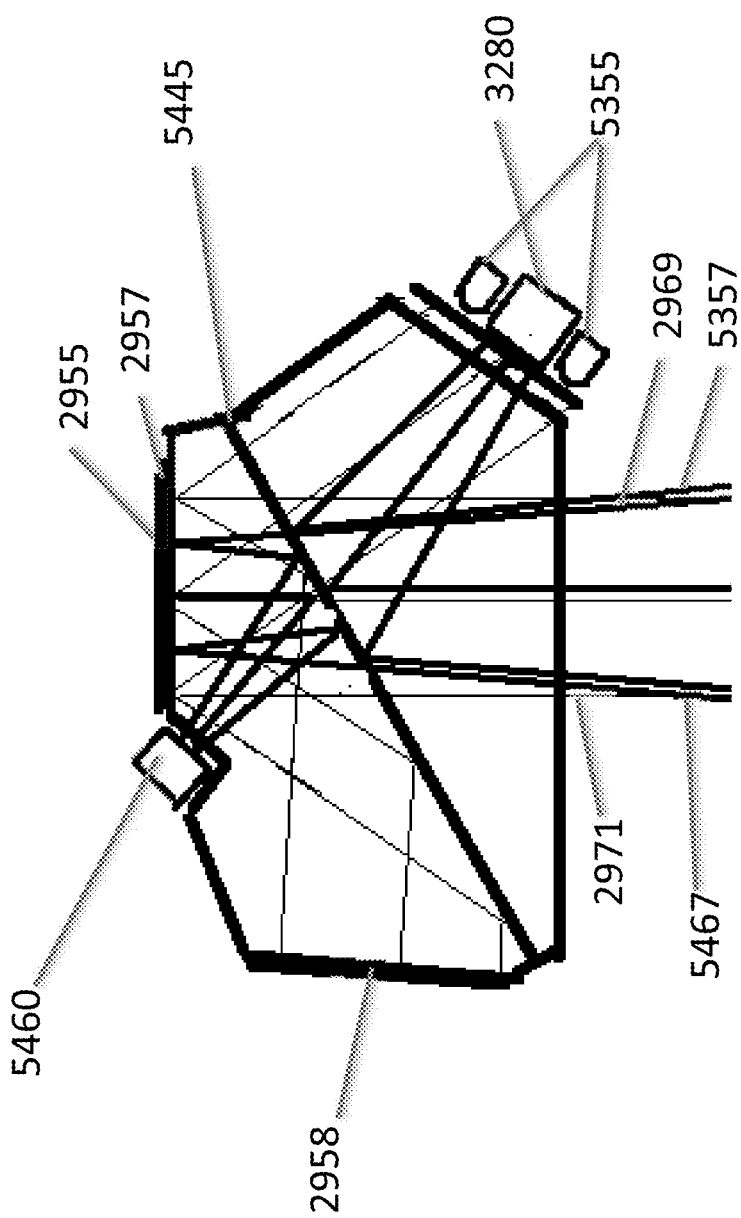
FIG. 54 illustrates an optics module in accordance with the principles of the present invention.

FIG. 54 shows an illustration of a further embodiment of a display system with an eye imaging system. In addition to the features of FIG. 53, this system includes a second camera 5460. Wherein the second camera 5460 is provided to capture eye images in the visible wavelengths. Illumination of the eye can be provided by the displayed image or by see-through light from the environment. Portions of the displayed image can be modified to provide improved illumination of the user's eye when images of the eye are to be captured such as by increasing the brightness of the displayed image or increasing the white areas within the displayed image. Further, modified displayed images can be presented briefly for the purpose of capturing eye images and the display of the modified images can be synchronized with the capture of the eye images. As shown in FIG. 54, visible light 5467 is polarized when it is captured by the second camera 5460 since it passes through the beam splitter 5445 and the beam splitter 5445 is a reflective polarizer on the side facing the second camera 5460. In this eye imaging system, visible eye images can be captured by the second camera 5460 at the same time that infrared eye images are captured by the camera 3280. Wherein, the characteristics of the camera 3280 and the second camera 5460 and the associated respective images captured can be different in terms of resolution and capture rate.

Figure 52B:
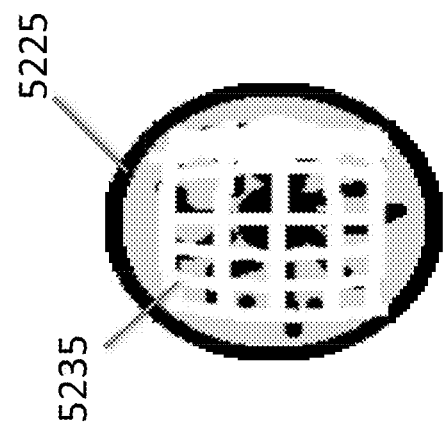
FIGS. 52a and 52b illustrate views of an eye with a structured light pattern in accordance with the principles of the present invention.
Figure 52A:
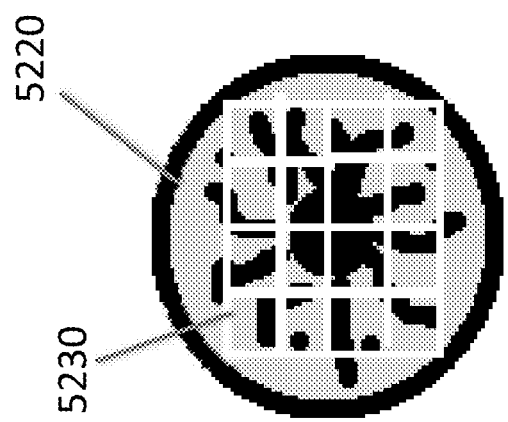

FIGS. 52a and 52b illustrate captured images of eyes where the eyes are illuminated with structured light patterns. In FIG. 52a, an eye 5220 is shown with a projected structured light pattern 5230, where the light pattern is a grid of lines. A light pattern of such as 5230 can be provided by the light source 5355 show in FIG. 53 by including a diffractive or a refractive device to modify the light 5357 as are known by those skilled in the art. A visible light source can also be included for the second camera 5460 shown in FIG. 54 which can include a diffractive or refractive to modify the light 5467 to provide a light pattern. FIG. 52b illustrates how the structured light pattern of 5230 becomes distorted to 5235 when the user's eye 5225 looks to the side. This distortion comes from the fact that the human eye is not spherical in shape, instead the iris sticks out slightly from the eyeball to form a bump in the area of the iris. As a result, the shape of the eye and the associated shape of the reflected structured light pattern is different depending on which direction the eye is pointed, when images of the eye are captured from a fixed position. Changes in the structured light pattern can subsequently be analyzed in captured eye images to determine the direction that the eye is looking.

Figure 55:
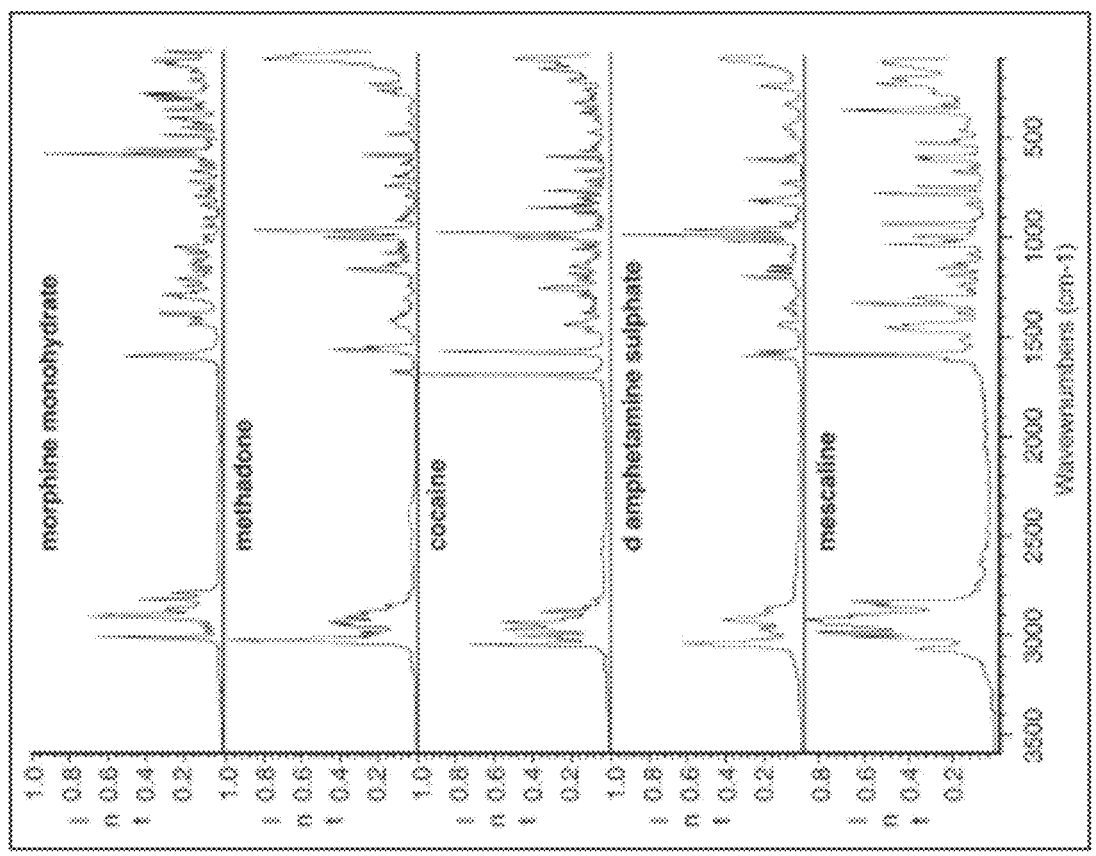
FIG. 55 shows a series of example spectrum for a variety of controlled substances as measured using a form of infrared spectroscopy.
Figure 56:
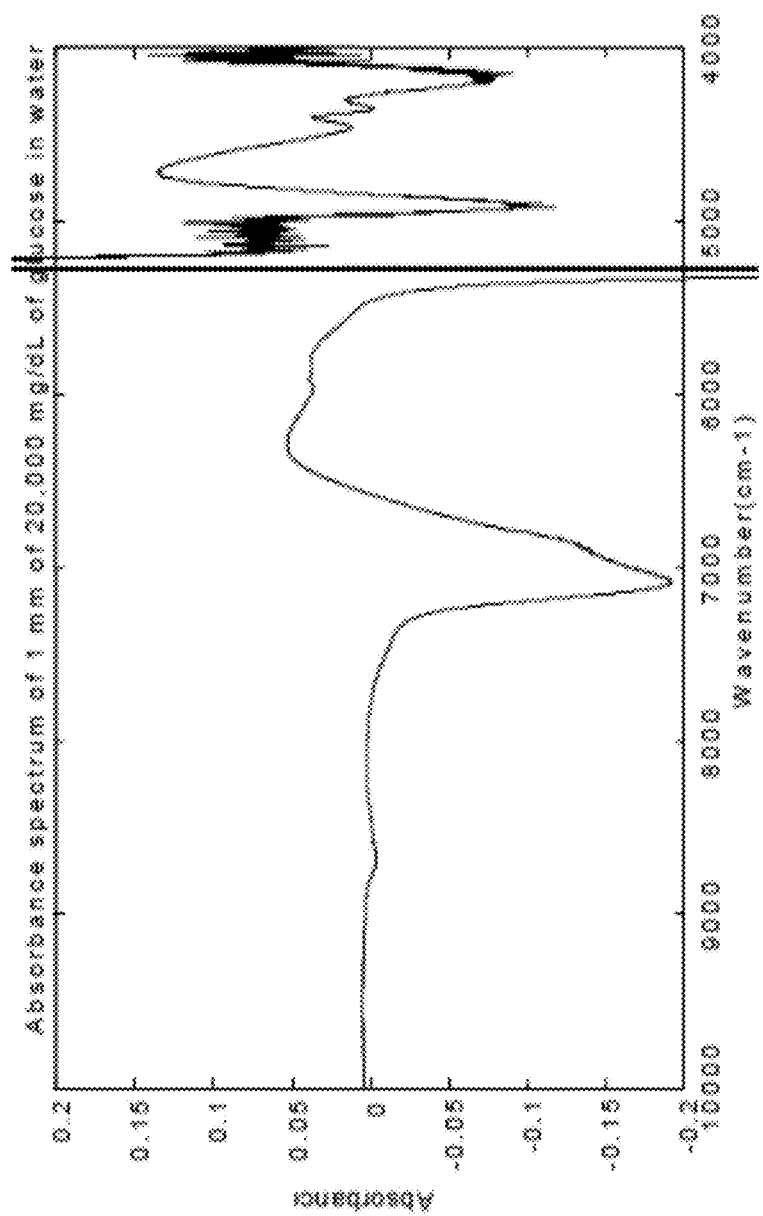
FIG. 56 shows an infrared absorbance spectrum for glucose.

The eye imaging system can also be used for the assessment of aspects of health of the user. In this case, information gained from analyzing captured images of the iris 5012 is different from information gained from analyzing captured images of the retina 5014. Where images of the retina 5014 are captured using light 5357 that illuminates the inner portions of the eye including the retina 5014. The light 5357 can be visible light, but in an embodiment, the light 5357 is infrared light (e.g. wavelength 1 to 5 microns) and the camera 3280 is an infrared light sensor (e.g. an InGaAs sensor) or a low resolution infrared image sensor that is used to determine the relative amount of light 5357 that is absorbed, reflected or scattered by the inner portions of the eye. Wherein the majority of the light that is absorbed, reflected or scattered can be attributed to materials in the inner portion of the eye including the retina where there are densely packed blood vessels with thin walls so that the absorption, reflection and scattering are caused by the material makeup of the blood. These measurements can be conducted automatically when the user is wearing the HWC, either at regular intervals, after identified events or when prompted by an external communication. In a preferred embodiment, the illuminating light is near infrared or mid infrared (e.g. 0.7 to 5 microns wavelength) to reduce the chance for thermal damage to the wearer's eye. In another embodiment, the polarizer 3285 is antireflection coated to reduce any reflections from this surface from the light 5357, the light 2969 or the light 3275 and thereby increase the sensitivity of the camera 3280. In a further embodiment, the light source 5355 and the camera 3280 together comprise a spectrometer wherein the relative intensity of the light reflected by the eye is analyzed over a series of narrow wavelengths within the range of wavelengths provided by the light source 5355 to determine a characteristic spectrum of the light that is absorbed, reflected or scattered by the eye. For example, the light source 5355 can provide a broad range of infrared light to illuminate the eye and the camera 3280 can include: a grating to laterally disperse the reflected light from the eye into a series of narrow wavelength bands that are captured by a linear photodetector so that the relative intensity by wavelength can be measured and a characteristic absorbance spectrum for the eye can be determined over the broad range of infrared. In a further example, the light source 5355 can provide a series of narrow wavelengths of light (ultraviolet, visible or infrared) to sequentially illuminate the eye and camera 3280 includes a photodetector that is selected to measure the relative intensity of the series of narrow wavelengths in a series of sequential measurements that together can be used to determine a characteristic spectrum of the eye. The determined characteristic spectrum is then compared to known characteristic spectra for different materials to determine the material makeup of the eye. In yet another embodiment, the illuminating light 5357 is focused on the retina 5014 and a characteristic spectrum of the retina 5014 is determined and the spectrum is compared to known spectra for materials that may be present in the user's blood. For example, in the visible wavelengths 540 nm is useful for detecting hemoglobin and 660 nm is useful for differentiating oxygenated hemoglobin. In a further example, in the infrared, a wide variety of materials can be identified as is known by those skilled in the art, including: glucose, urea, alcohol and controlled substances. FIG. 55 shows a series of example spectrum for a variety of controlled substances as measured using a form of infrared spectroscopy (ThermoScientific Application Note 51242, by C. Petty, B. Garland and the Mesa Police Department Forensic Laboratory, which is hereby incorporated by reference herein). FIG. 56 shows an infrared absorbance spectrum for glucose (Hewlett Packard Company 1999, G. Hopkins, G. Mauze; "In-vivo NIR Diffuse-reflectance Tissue Spectroscopy of Human Subjects," which is hereby incorporated by reference herein). U.S. Pat. No. 6,675,030, which is hereby incorporated by reference herein, provides a near infrared blood glucose monitoring system that includes infrared scans of a body part such as a foot. United States Patent publication 2006/0183986, which is hereby incorporated by reference herein, provides a blood glucose monitoring system including a light measurement of the retina. Embodiments of the present invention provide methods for automatic measurements of specific materials in the user's blood by illuminating at one or more narrow wavelengths into the iris of the wearer's eye and measuring the relative intensity of the light reflected by the eye to identify the relative absorbance spectrum and comparing the measured absorbance spectrum with known absorbance spectra for the specific material, such as illuminating at 540 and 660 nm to determine the level of hemoglobin present in the user's blood.

Another aspect of the present invention relates to collecting and using eye position and sight heading information. Head worn computing with motion heading, sight heading, and/or eye position prediction (sometimes referred to as "eye heading" herein) may be used to identify what a wearer of the HWC 102 is apparently interested in and the information may be captured and used. In embodiments, the information may be characterized as viewing information because the information apparently relates to what the wearer is looking at. The viewing information may be used to develop a personal profile for the wearer, which may indicate what the wearer tends to look at. The viewing information from several or many HWC's 102 may be captured such that group or crowd viewing trends may be established. For example, if the movement heading and sight heading are known, a prediction of what the wearer is looking at may be made and used to generate a personal profile or portion of a crowd profile. In another embodiment, if the eye heading and location, sight heading and/or movement heading are known, a prediction of what is being looked at may be predicted. The prediction may involve understanding what is in proximity of the wearer and this may be understood by establishing the position of the wearer (e.g. through GPS or other location technology) and establishing what mapped objects are known in the area. The prediction may involve interpreting images captured by the camera or other sensors associated with the HWC 102. For example, if the camera captures an image of a sign and the camera is in-line with the sight heading, the prediction may involve assessing the likelihood that the wearer is viewing the sign. The prediction may involve capturing an image or other sensory information and then performing object recognition analysis to determine what is being viewed. For example, the wearer may be walking down a street and the camera that is in the HWC 102 may capture an image and a processor, either on-board or remote from the HWC 102, may recognize a face, object, marker, image, etc. and it may be determined that the wearer may have been looking at it or towards it.

Figure 57:
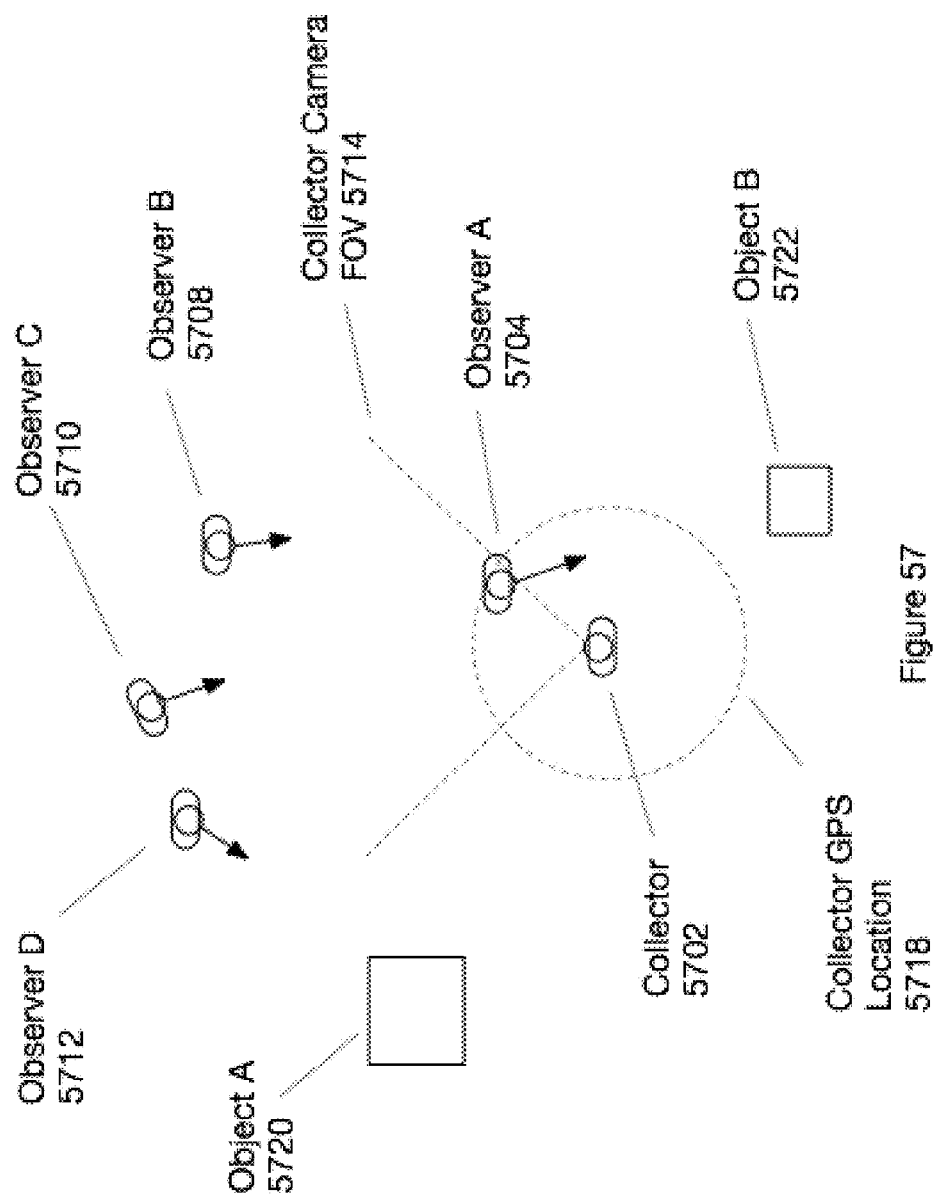
FIG. 57 illustrates a scene where a person is walking with a HWC mounted on his head.

FIG. 57 illustrates a scene where a person is walking with a HWC 102 mounted on his head. In this scene, the person's geo-spatial location 5704 is known through a GPS sensor, which could be another location system, and his movement heading, sight heading 5714 and eye heading 5702 are known and can be recorded (e.g. through systems described herein). There are objects and a person in the scene. Person 5712 may be recognized by the wearer's HWC 102 system, the person may be mapped (e.g. the person's GPS location may be known or recognized), or otherwise known. The person may be wearing a garment or device that is recognizable. For example, the garment may be of a certain style and the HWC may recognize the style and record it's viewing. The scene also includes a mapped object 5718 and a recognized object 5720. As the wearer moves through the scene, the sight and/or eye headings may be recorded and communicated from the HWC 102. In embodiments, the time that the sight and/or eye heading maintains a particular position may be recorded. For example, if a person appears to look at an object or person for a predetermined period of time (e.g. 2 seconds or longer), the information may be communicated as gaze persistence information as an indication that the person may have been interested in the object.

In embodiments, sight headings may be used in conjunction with eye headings or eye and/or sight headings may be used alone. Sight headings can do a good job of predicting what direction a wearer is looking because many times the eyes are looking forward, in the same general direction as the sight heading. In other situations, eye headings may be a more desirable metric because the eye and sight headings are not always aligned. In embodiments herein examples may be provided with the term "eye/sight" heading, which indicates that either or both eye heading and sight heading may be used in the example.

Figure 58:
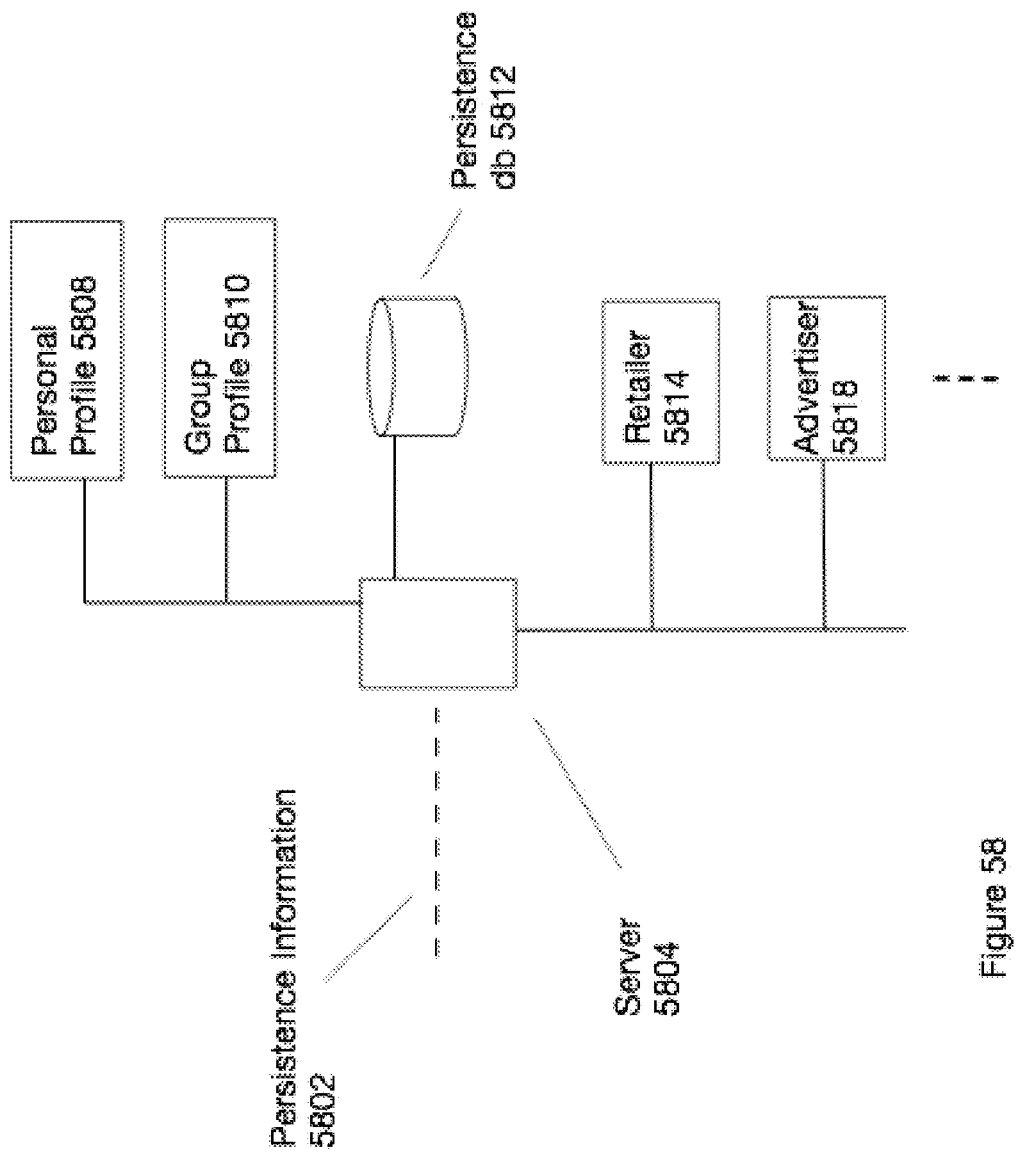
FIG. 58 illustrates a system for receiving, developing and using movement heading, sight heading, eye heading and/or persistence information from HWC(s).

FIG. 58 illustrates a system for receiving, developing and using movement heading, sight heading, eye heading and/or persistence information from HWC(s) 102. The server 5804 may receive heading or gaze persistence information, which is noted as persistence information 5802, for processing and/or use. The heading and/or gaze persistence information may be used to generate a personal profile 5808 and/or a group profile 5810. The personal profile 5718 may reflect the wearer's general viewing tendencies and interests. The group profile 5810 may be an assemblage of different wearer's heading and persistence information to create impressions of general group viewing tendencies and interests. The group profile 5810 may be broken into different groups based on other information such as gender, likes, dislikes, biographical information, etc. such that certain groups can be distinguished from other groups. This may be useful in advertising because an advertiser may be interested in what a male adult sports go'er is generally looking at as oppose to a younger female. The profiles 5808 and 5810 and raw heading and persistence information may be used by retailers 5814, advertisers 5818, trainers, etc. For example, an advertiser may have an advertisement posted in an environment and may be interested in knowing how many people look at the advertisement, how long they look at it and where they go after looking at it. This information may be used as conversion information to assess the value of the advertisement and thus the payment to be received for the advertisement.

In embodiments, the process involves collecting eye and/or sight heading information from a plurality of head-worn computers that come into proximity with an object in an environment. For example, a number of people may be walking through an area and each of the people may be wearing a head worn computer with the ability to track the position of the wearer's eye(s) as well as possibly the wearer's sight and movement headings. The various HWC wearing individuals may then walk, ride, or otherwise come into proximity with some object in the environment (e.g. a store, sign, person, vehicle, box, bag, etc.). When each person passes by or otherwise comes near the object, the eye imaging system may determine if the person is looking towards the object. All of the eye/sight heading information may be collected and used to form impressions of how the crowd reacted to the object. A store may be running a sale and so the store may put out a sign indicating such. The storeowners and managers may be very interested to know if anyone is looking at their sign. The sign may be set as the object of interest in the area and as people navigate near the sign, possibly determined by their GPS locations, the eye/sight heading determination system may record information relative to the environment and the sign. Once, or as, the eye/sight heading information is collected and associations between the eye headings and the sign are determined, feedback may be sent back to the storeowner, managers, advertiser, etc. as an indication of how well their sign is attracting people. In embodiments, the sign's effectiveness at attracting people's attention, as indicated through the eye/sight headings, may be considered a conversion metric and impact the economic value of the sign and/or the signs placement.

In embodiments, a map of the environment with the object may be generated by mapping the locations and movement paths of the people in the crowd as they navigate by the object (e.g. the sign). Layered on this map may be an indication of the various eye/sight headings. This may be useful in indicating wear people were in relation to the object when then viewed they object. The map may also have an indication of how long people looked at the object from the various positions in the environment and where they went after seeing the object.

In embodiments, the process involves collecting a plurality of eye/sight headings from a head-worn computer, wherein each of the plurality of eye/sight headings is associated with a different pre-determined object in an environment. This technology may be used to determine which of the different objects attracts more of the person's attention. For example, if there are three objects placed in an environment and a person enters the environment navigating his way through it, he may look at one or more of the objects and his eye/sight heading may persist on one or more objects longer than others. This may be used in making or refining the person's personal attention profile and/or it may be used in connection with other such people's data on the same or similar objects to determine an impression of how the population or crowd reacts to the objects. Testing advertisements in this way may provide good feedback of its effectiveness.

In embodiments, the process may involve capturing eye/sight headings once there is substantial alignment between the eye/sight heading and an object of interest. For example, the person with the HWC may be navigating through an environment and once the HWC detects substantial alignment or the projected occurrence of an upcoming substantial alignment between the eye/sight heading and the object of interest, the occurrence and/or persistence may be recorded for use.

In embodiments, the process may involve collecting eye/sight heading information from a head-worn computer and collecting a captured image from the head-worn computer that was taken at substantially the same time as the eye/sight heading information was captured. These two pieces of information may be used in conjunction to gain an understanding of what the wearer was looking at and possibly interested in. The process may further involve associating the eye/sight heading information with an object, person, or other thing found in the captured image. This may involve processing the captured image looking for objects or patterns. In embodiments, gaze time or persistence may be measured and used in conjunction with the image processing. The process may still involve object and/or pattern recognition, but it may also involve attempting to identify what the person gazed at for the period of time by more particularly identifying a portion of the image in conjunction with image processing.

In embodiments, the process may involve setting a pre-determined eye/sight heading from a pre-determined geo-spatial location and using them as triggers. In the event that a head worn computer enters the geospatial location and an eye/sight heading associated with the head worn computer aligns with the pre-determined eye/sight heading, the system may collect the fact that there was an apparent alignment and/or the system may record information identifying how long the eye/sight heading remains substantially aligned with the pre-determined eye/sight heading to form a persistence statistic. This may eliminate or reduce the need for image processing as the triggers can be used without having to image the area. In other embodiments, image capture and processing is performed in conjunction with the triggers. In embodiments, the triggers may be a series a geospatial locations with corresponding eye/sight headings such that many spots can be used as triggers that indicate when a person entered an area in proximity to an object of interest and/or when that person actually appeared to look at the object.

Figure 59:
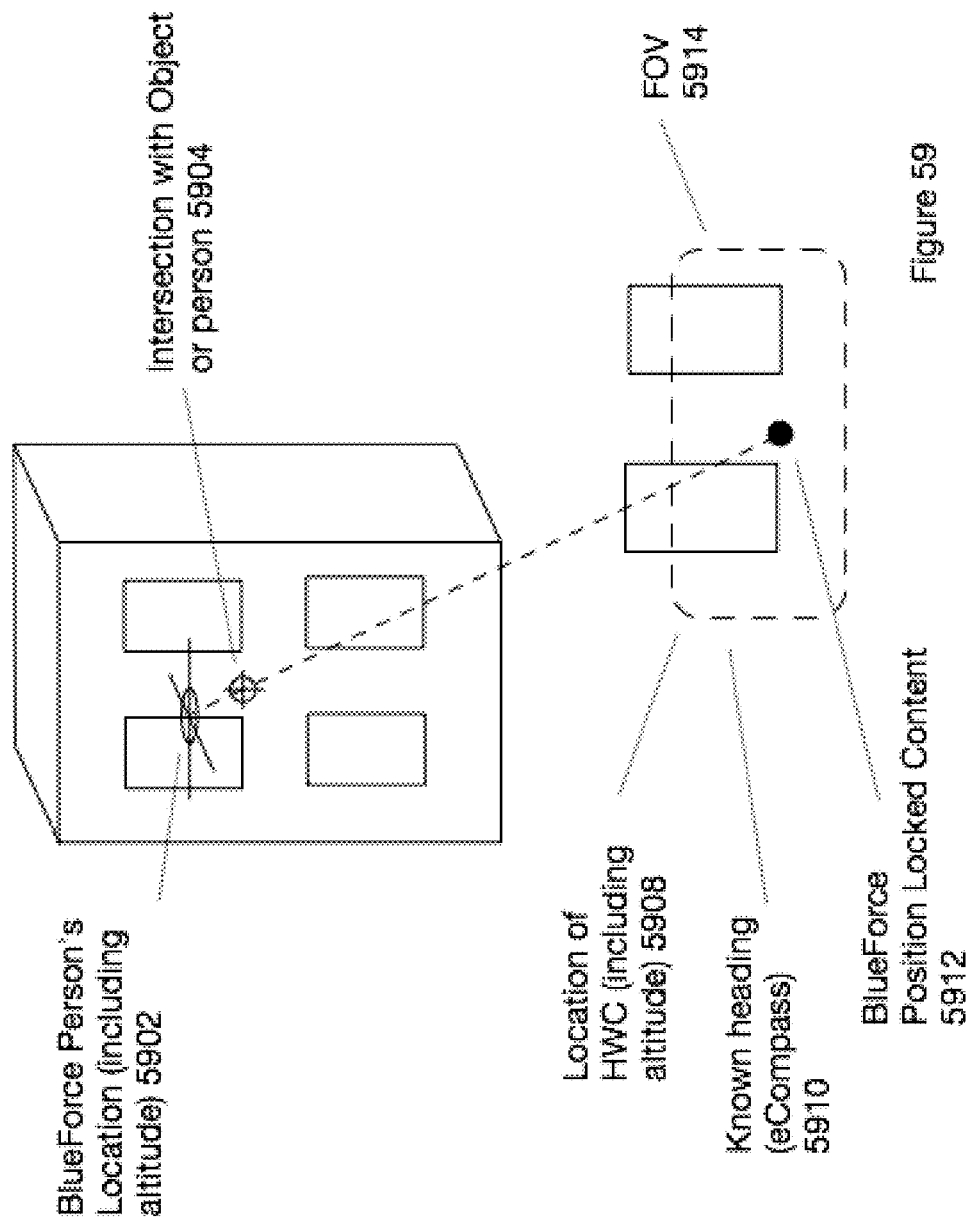
FIG. 59 illustrates a presentation technology in accordance with the principles of the present invention.

In embodiments, eye imaging may be used to capture images of both eyes of the wearer in order to determine the amount of convergence of the eyes (e.g. through technologies described herein elsewhere) to get an understanding of what focal plane is being concentrated on by the wearer. For example, if the convergence measurement suggests that the focal plane is within 15 feet of the wearer, than, even though the eye/sight headings may align with an object that is more than 15 feet away it may be determined that the wearer was not looking at the object. If the object were within the 15 foot suggested focal plane, the determination may be that the wearer was looking at the object. FIG. 59 illustrates an environmentally position locked digital content 5912 that is indicative of a person's location 5902. In this disclosure the term "BlueForce" is generally used to indicate team members or members for which geo-spatial locations are known and can be used. In embodiments, "BlueForce" is a term to indicate members of a tactical arms team (e.g. a police force, secret service force, security force, military force, national security force, intelligence force, etc.). In many embodiments herein one member may be referred to as the primary or first BlueForce member and it is this member, in many described embodiments, that is wearing the HWC. It should be understood that this terminology is to help the reader and make for clear presentations of the various situations and that other members of the Blueforce, or other people, may have HWC's 102 and have similar capabilities. In this embodiment, a first person is wearing a head-worn computer 102 that has a see through field of view ("FOV") 5914. The first person can see through the FOV to view the surrounding environment through the FOV and digital content can also be presented in the FOV such that the first person can view the actual surroundings, through the FOV, in a digitally augmented view. The other BlueForce person's location is known and is indicated at a position inside of a building at point 5902. This location is known in three dimensions, longitude, latitude and altitude, which may have been determined by GPS along with an altimeter associated with the other Blueforce person. Similarly, the location of the first person wearing the HWC 102 is also known, as indicated in FIG. 59 as point 5908. In this embodiment, the compass heading 5910 of the first person is also known. With the compass heading 5910 known, the angle in which the first person is viewing the surroundings can be estimated. A virtual target line between the location of the first person 5908 and the other person's location 5902 can be established in three dimensional space and emanating from the HWC 102 proximate the FOV 5914. The three dimensionally oriented virtual target line can then be used to present environmentally position locked digital content in the FOV 5914, which is indicative of the other person's location 5902. The environmentally position locked digital content 5902 can be positioned within the FOV 5914 such that the first person, who is wearing the HWC 102, perceives the content 5902 as locked in position within the environment and marking the location of the other person 5902.

The three dimensionally positioned virtual target line can be recalculated periodically (e.g. every millisecond, second, minute, etc.) to reposition the environmentally position locked content 5912 to remain in-line with the virtual target line. This can create the illusion that the content 5912 is staying positioned within the environment at a point that is associated with the other person's location 5902 independent of the location of the first person 5908 wearing the HWC 102 and independent of the compass heading of the HWC 102.

In embodiments, the environmentally locked digital content 5912 may be positioned with an object 5904 that is between the first person's location 5908 and the other person's location 5902. The virtual target line may intersect the object 5904 before intersecting with the other person's location 5902. In embodiments, the environmentally locked digital content 5912 may be associated with the object intersection point 5904. In embodiments, the intersecting object 5904 may be identified by comparing the two person's locations 5902 and 5908 with obstructions identified on a map. In embodiments the intersecting object 5904 may be identified by processing images captured from a camera, or other sensor, associated with the HWC 102. In embodiments, the digital content 5912 has an appearance that is indicative of being at the location of the other person 5902, at the location of the intersecting object 5904 to provide a more clear indication of the position of the other person's position 5902 in the FOV 5914.

Figure 60:
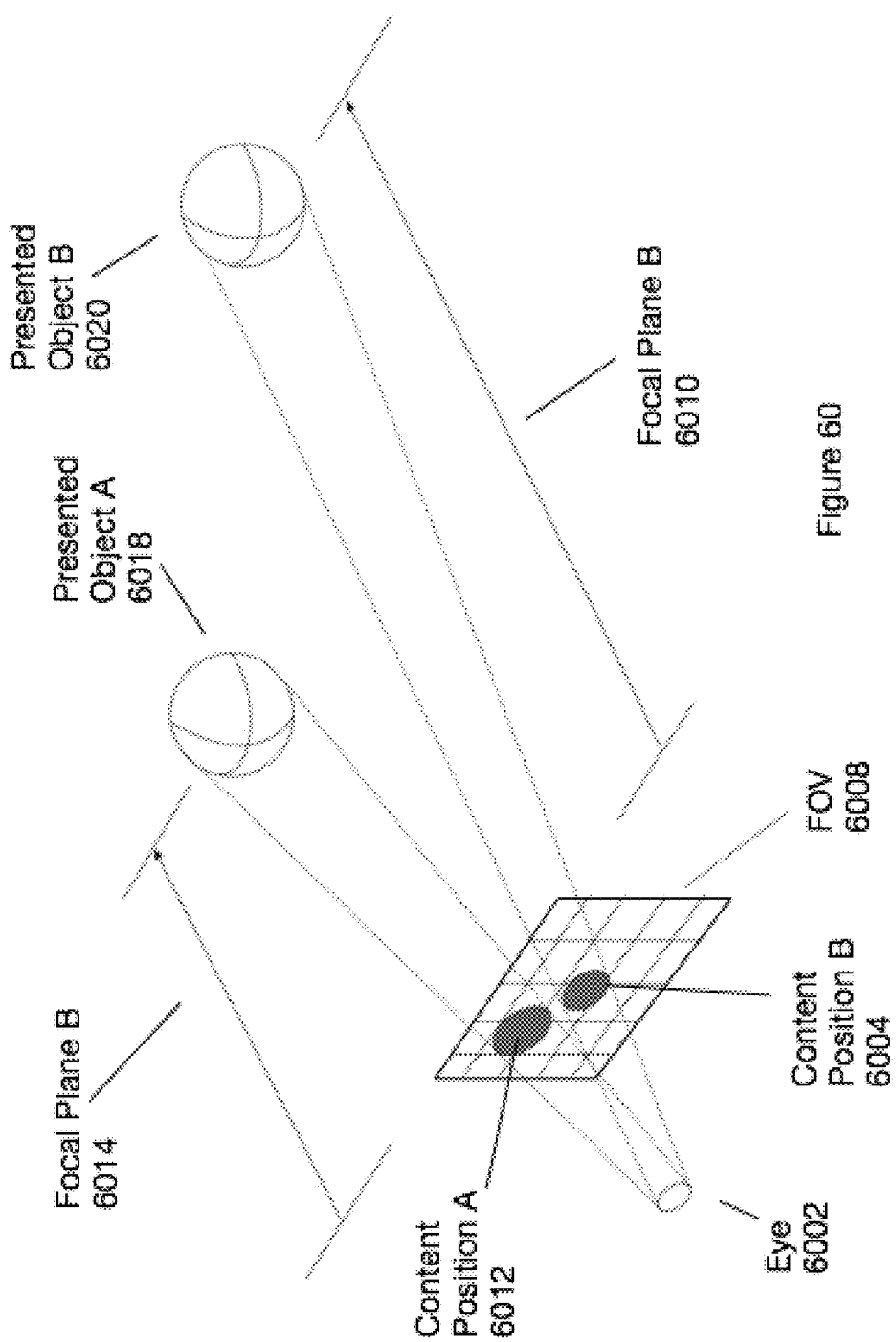
FIG. 60 illustrates a presentation technology in accordance with the principles of the present invention.

FIG. 60 illustrates how and where digital content may be positioned within the FOV 6008 based on a virtual target line between the location of the first person 5908, who's wearing the HWC 102, and the other person 5902. In addition to positioning the content in a position within the FOV 6008 that is in-line with the virtual target line, the digital content may be presented such that it comes into focus by the first person when the first person focuses at a certain plane or distance in the environment. Presented object A 6018 is digitally generated content that is presented as an image at content position A 6012. The position 6012 is based on the virtual target line. The presented object A 6018 is presented not only along the virtual target line but also at a focal plane B 6014 such that the content at position A 6012 in the FOV 6008 comes into focus by the first person when the first person's eye 6002 focuses at something in the surrounding environment at the focal plane B 6014 distance. Setting the focal plane of the presented content provides content that does not come into focus until the eye 6002 focuses at the set focal plane. In embodiments, this allows the content at position A to be presented without when the HWC's compass is indicative of the first person looking in the direction of the other person 5902 but it will only come into focus when the first person focuses on in the direction of the other person 5902 and at the focal plane of the other person 5902.

Presented object B 6020 is aligned with a different virtual target line then presented object A 6018. Presented object B 6020 is also presented at content position B 6004 at a different focal plane than the content position A 6012. Presented content B 6020 is presented at a further focal plane, which is indicative that the other person 5902 is physically located at a further distance. If the focal planes are sufficiently different, the content at position A will come into focus at a different time than the content at position B because the two focal planes require different focus from the eye 6002.

Figure 61:
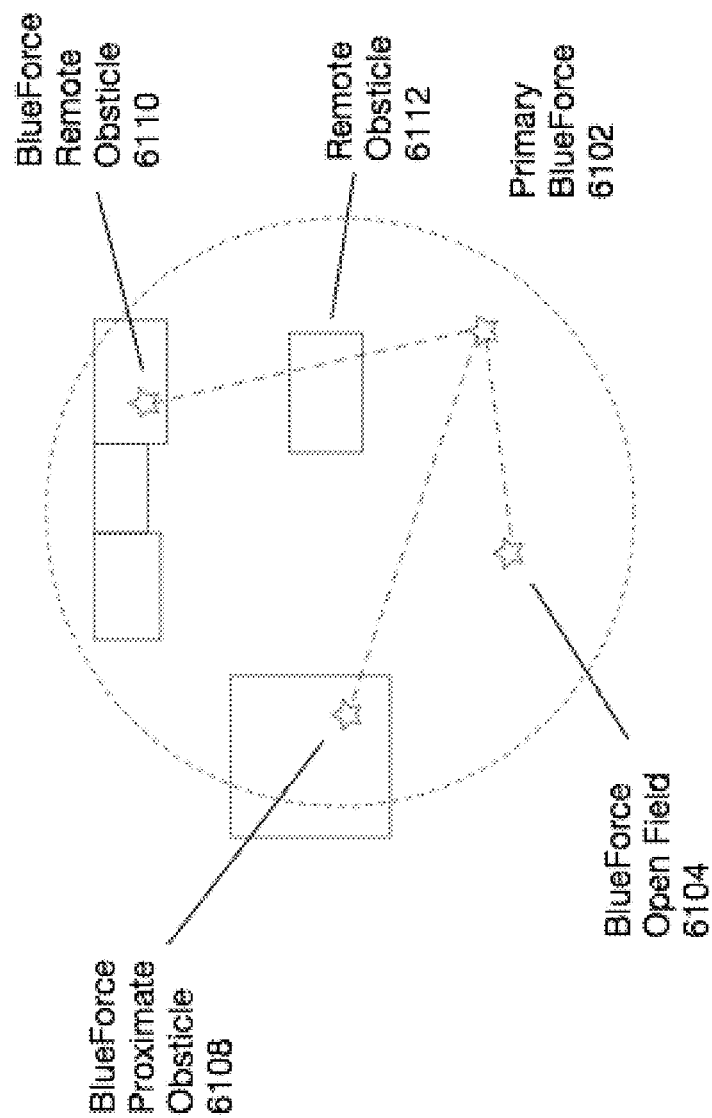
FIG. 61 illustrates a presentation technology in accordance with the principles of the present invention.

FIG. 61 illustrates several BlueForce members at locations with various points of view from the first person's perspective. In embodiments, the relative positions, distances and obstacles may cause the digital content indicative of the other person's location to be altered. For example, if the other person can be seen by the first person through the first person's FOV, the digital content may be locked at the location of the other person and the digital content may be of a type that indicates the other person's position is being actively marked and tracked. If the other person is in relatively close proximity, but cannot be seen by the first person, the digital content may be locked to an intersecting object or area and the digital content may indicate that the actual location of the other person cannot be seen but the mark is generally tracking the other persons general position. If the other person is not within a pre-determined proximity or is otherwise more significantly obscured from the first person's view, the digital content may generally indicate a direction or area where the other person is located and the digital content may indicate that the other person's location is not closely identified or tracked by the digital content, but that the other person is in the general area.

Continuing to refer to FIG. 61, several BlueForce members are presented at various positions within an area where the first person is located. The primary BlueForce member 6102 (also referred to generally as the first person, or the person wherein the HWC with the FOV for example purposes) can directly see the BlueForce member in the open field 6104. In embodiments, the digital content provided in the FOV of the primary BlueForce member may be based on a virtual target line and virtually locked in an environment position that is indicative of the open field position of the BlueForce member 6104. The digital content may also indicate that the location of the open field BlueForce member is marked and is being tracked. The digital content may change forms if the BlueForce member becomes obscured from the vision of the primary BlueForce member or otherwise becomes unavailable for direct viewing.

BlueForce member 6108 is obscured from the primary BlueForce member's 6102 view by an obstacle that is in close proximity to the obscured member 6108. As depicted, the obscured member 6108 is in a building but close to one of the front walls. In this situation, the digital content provided in the FOV of the primary member 6102 may be indicative of the general position of the obscured member 6108 and the digital content may indicate that, while the other person's location is fairly well marked, it is obscured so it is not as precise as if the person was in direct view. In addition, the digital content may be virtually positionally locked to some feature on the outside of the building that the obscured member is in. This may make the environmental locking more stable and also provide an indication that the location of the person is somewhat unknown.

BlueForce member 6110 is obscured by multiple obstacles. The member 6110 is in a building and there is another building 6112 in between the primary member 6102 and the obscured member 6110. In this situation, the digital content in the FOV of the primary member will be spatially quite short of the actual obscured member and as such the digital content may need to be presented in a way that indicates that the obscured member 6110 is in a general direction but that the digital marker is not a reliable source of information for the particular location of obscured member 6110.

Figure 62:
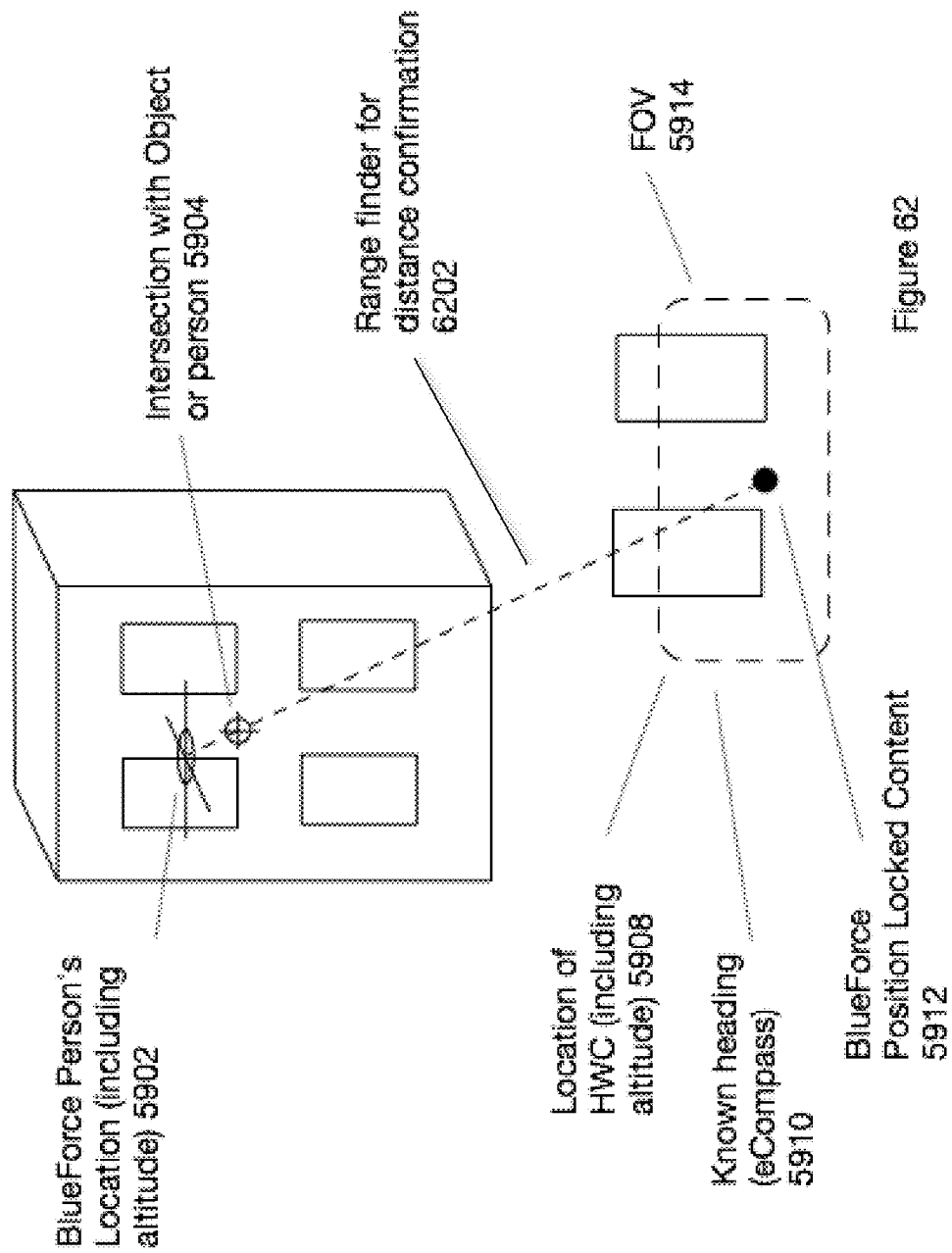
FIG. 62 illustrates a presentation technology in accordance with the principles of the present invention.

FIG. 62 illustrates yet another method for positioning digital content within the FOV of a HWC where the digital content is intended to indicate a position of another person. This embodiment is similar to the embodiment described in connection with FIG. 62 herein. The main additional element in this embodiment is the additional step of verifying the distance between the first person 5908, the one wearing the HWC with the FOV digital content presentation of location, and the other person at location 5902. Here, the range finder may be included in the HWC and measure a distance at an angle that is represented by the virtual target line. In the event that the range finder finds an object obstructing the path of the virtual target line, the digital content presentation in the FOV may indicate such (e.g. as described herein elsewhere). In the event that the range finder confirms that there is a person or object at the end of the presecribed distance and angle defined by the virtual target line, the digital content may represent that the proper location has been marked, as described herein elsewhere.

Figure 63:
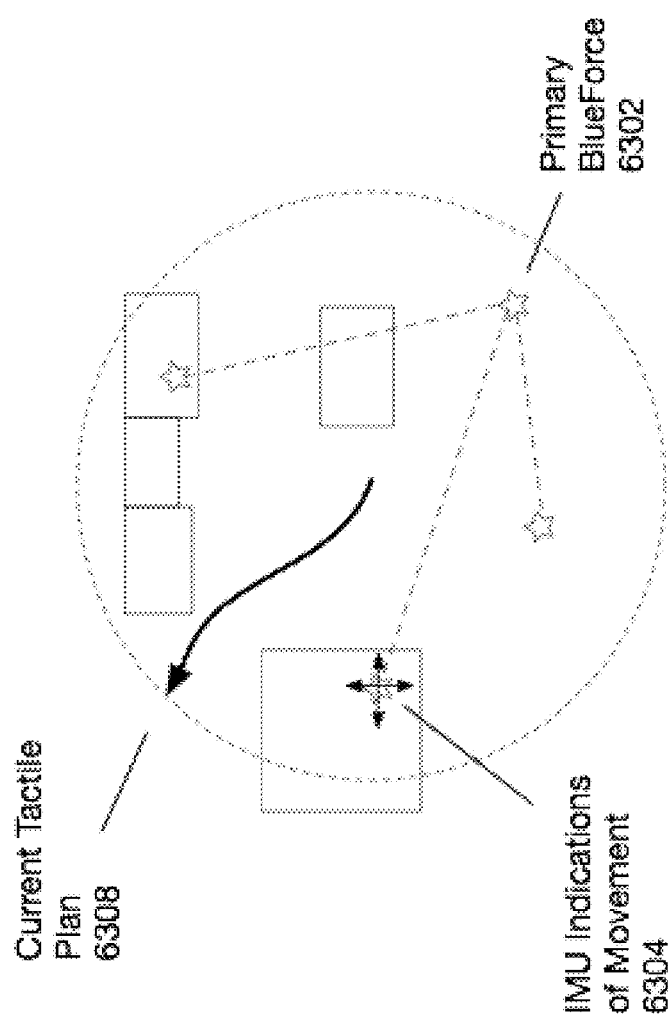
FIG. 63 illustrates a presentation technology in accordance with the principles of the present invention.

Another aspect of the present invention relates to predicting the movement of BlueForce members to maintain proper virtual marking of the BlueForce member locations. FIG. 63 illustrates a situation where the primary BlueForce member 6302 is tracking the locations of the other BlueForce members through an augmented environment using a HWC 102, as described herein elsewhere (e.g. as described in connection with the above figures). The primary BlueForce member 6302 may have knowledge of the tactical movement plan 6308. The tactical movement plan maybe maintained locally (e.g. on the HWCs 102 with sharing of the plan between the BlueForce members) or remotely (e.g. on a server and communicated to the HWC's 102, or communicated to a subset of HWC's 102 for HWC 102 sharing). In this case, the tactical plan involves the BlueForce group generally moving in the direction of the arrow 6308. The tactical plan may influence the presentations of digital content in the FOV of the HWC 102 of the primary BlueForce member. For example, the tactical plan may assist in the prediction of the location of the other BlueForce member and the virtual target line may be adjusted accordingly. In embodiments, the area in the tactical movement plan may be shaded or colored or otherwise marked with digital content in the FOV such that the primary BlueForce member can manage his activities with respect to the tactical plan. For example, he may be made aware that one or more BlueForce members are moving towards the tactical path 6308. He may also be made aware of movements in the tactical path that do not appear associated with BlueForce members.

FIG. 63 also illustrates that internal IMU sensors in the HWCs worn by the BlueForce members may provide guidance on the movement of the members 6304. This may be helpful in identifying when a GPS location should be updated and hence updating the position of the virtual marker in the FOV. This may also be helpful in assessing the validity of the GPS location. For example, if the GPS location has not updated but there is significant IMU sensor activity, the system may call into question the accuracy of the identified location. The IMU information may also be useful to help track the position of a member in the event the GPS information is unavailable. For example, dead reckoning may be used if the GPS signal is lost and the virtual marker in the FOV may indicate both indicated movements of the team member and indicate that the location identification is not ideal. The current tactical plan 6308 may be updated periodically and the updated plans may further refine what is presented in the FOV of the HWC 102.

Figure 64:
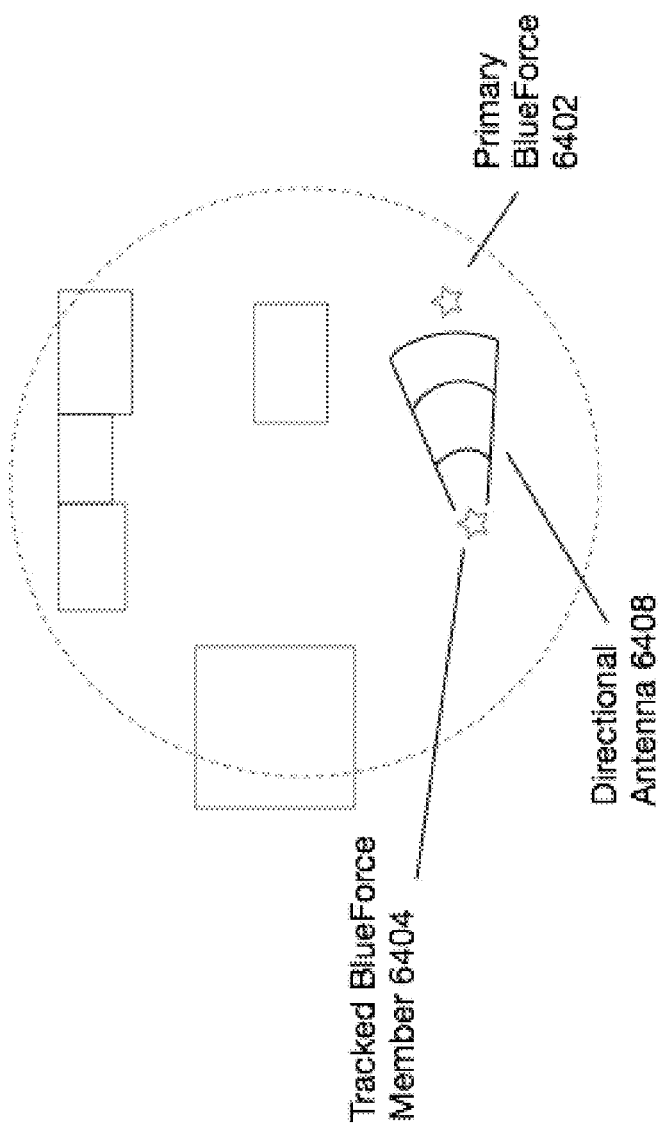
FIG. 64 illustrates a presentation technology in accordance with the principles of the present invention.

FIG. 64 illustrates a BlueForce tracking system in accordance with the principles of the present invention. In embodiments, the BlueForce HWC's 102 may have directional antenna's that emit relatively low power directional RF signals such that other BlueForce members within the range of the relatively low power signal can receive and assess it's direction and/or distance based on the strength and varying strength of the signals. In embodiments, the tracking of such RF signals can be used to alter the presentation of the virtual markers of persons locations within the FOV of HWC 102.

Another aspect of the present invention relates to monitoring the health of BlueForce members. Each BlueForce member may be automatically monitored for health and stress events. For example, the members may have a watchband as described herein elsewhere or other wearable biometric monitoring device and the device may continually monitor the biometric information and predict health concerns or stress events. As another example, the eye imaging systems described herein elsewhere may be used to monitor pupil dilatations as compared to normal conditions to predict head trauma. Each eye may be imaged to check for differences in pupil dilation for indications of head trauma. As another example, an IMU in the HWC 102 may monitor a person's walking gate looking for changes in pattern, which may be an indication of head or other trauma. Biometric feedback from a member indicative of a health or stress concern may be uploaded to a server for sharing with other members or the information may be shared with local members, for example. Once shared, the digital content in the FOF that indicates the location of the person having the health or stress event may include an indication of the health event.

Figure 65:
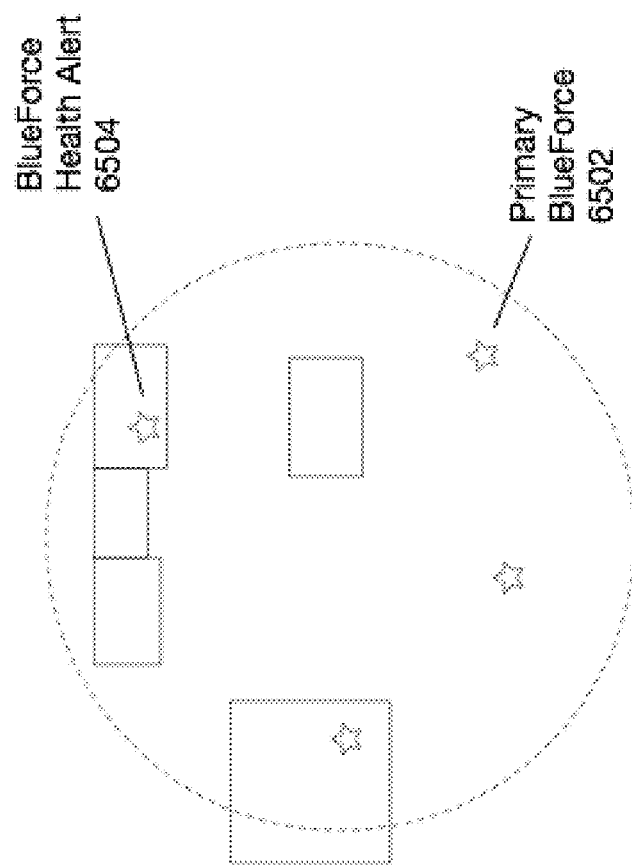
FIG. 65 illustrates a presentation technology in accordance with the principles of the present invention.

FIG. 65 illustrates a situation where the primary BlueForce member 6502 is monitoring the location of the BlueForce member 6504 that has had a heath event and caused a health alert to be transmitted from the HWC 102. As described herein elsewhere, the FOV of the HWC 102 of the primary BlueForce member may include an indication of the location of the BlueForce member with the health concern 6504. The digital content in the FOV may also include an indication of the health condition in association with the location indication. In embodiments, non-biometric sensors (e.g. IMU, camera, ranger finder, accelerometer, altimeter, etc.) may be used to provide health and/or situational conditions to the BlueForce team or other local or remote persons interested in the information. For example, if one of the BlueForce members is detected as quickly hitting the ground from a standing position an alter may be sent as an indication of a fall, the person is in trouble and had to drop down, was shot, etc.

Figure 66:
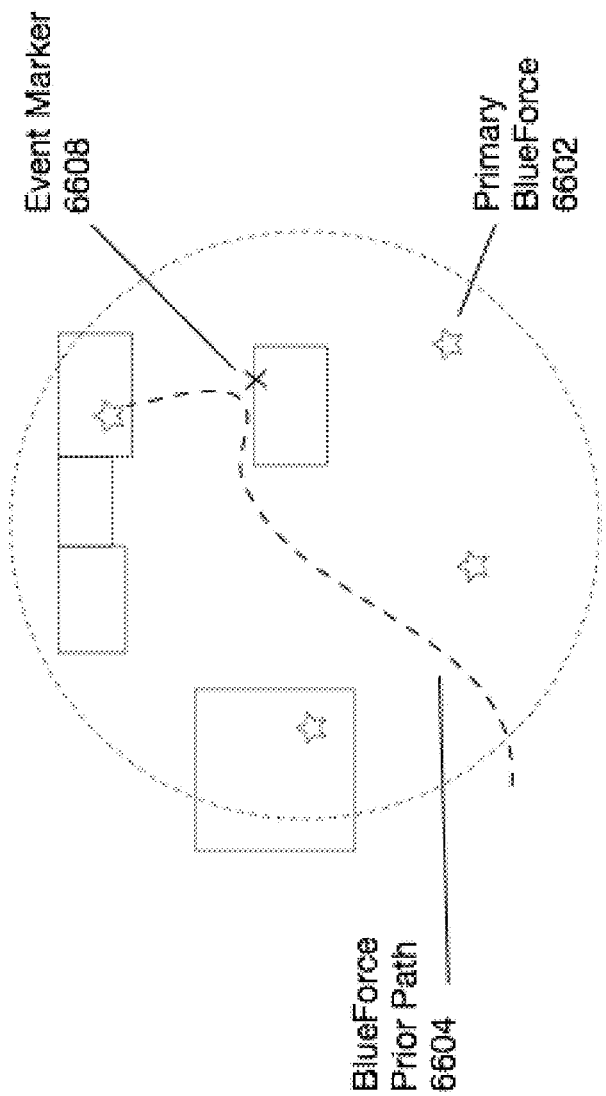
FIG. 66 illustrates a presentation technology in accordance with the principles of the present invention.

Another aspect of the present invention relates to virtually marking various prior acts and events. For example, as depicted in FIG. 66, the techniques described herein elsewhere may be used to construct a virtual prior movement path 6604 of a BlueForce member. The virtual path may be displayed as digital content in the FOV of the primary BlueForce member 6602 using methods described herein elsewhere. As the BlueForce member moved along the path 6604 he may have virtually placed an event marker 6608 such that when another member views the location the mark can be displayed as digital content. For example, the BlueForce member may inspect and clear an area and then use an external user interface or gesture to indicate that the area has been cleared and then the location would be virtually marked and shared with BlueForce members. Then, when someone wants to understand if the location was inspected he can view the location's information. As indicated herein elsewhere, if the location is visible to the member, the digital content may be displayed in a way that indicates the specific location and if the location is not visible from the person's perspective, the digital content may be somewhat different in that it may not specifically mark the location.

Turning back to optical configurations, another aspect of the present invention relates to an optical configuration that provides digitally displayed content to an eye of a person wearing a head-worn display (e.g. as used in a HWC 102) and allows the person to see through the display such that the digital content is perceived by the person as augmenting the see through view of the surrounding environment. The optical configuration may have a variable transmission optical element that is in-line with the person's see-through view such that the transmission of the see-through view can be increased and decreased. This may be helpful in situations where a person wants or would be better served with a high transmission see-through view and when, in the same HWC 102, the person wants or would be better served with less see-through transmission. The lower see-through transmission may be used in bright conditions and/or in conditions where higher contrast for the digitally presented content is desirable. The optical system may also have a camera that images the surrounding environment by receiving reflected light from the surrounding environment off of an optical element that is in-line with the person's see-through view of the surrounding. In embodiments, the camera may further be aligned in a dark light trap such that light reflected and/or transmitted in the direction of the camera that is not captured by the camera is trapped to reduce stray light.

Figure 67:
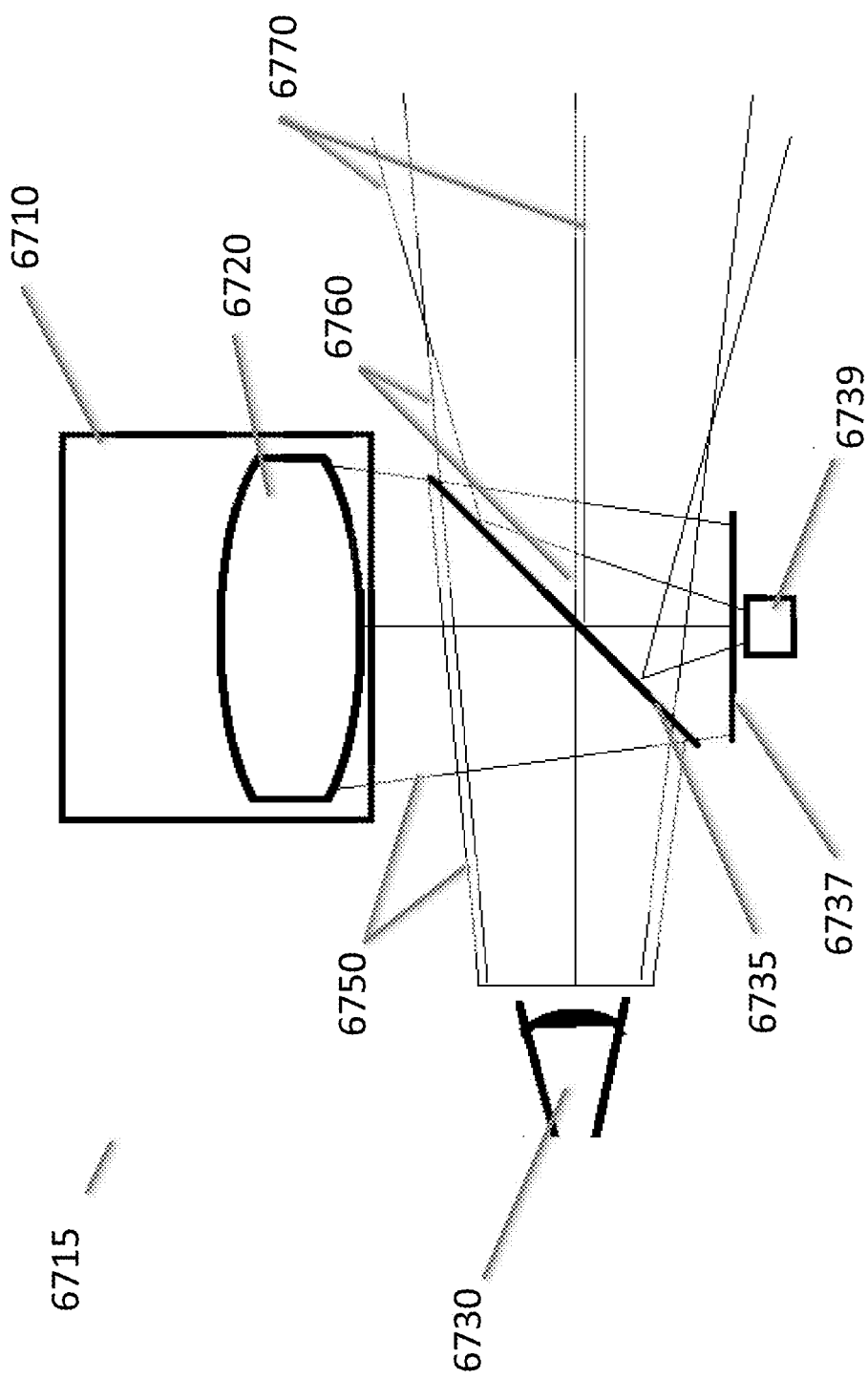
FIG. 67 illustrates an optical configuration in accordance with the principles of the present invention.

In embodiments, a HWC 102 is provided that includes a camera that is coaxially aligned with the direction that the user is looking. FIG. 67 shows an illustration of an optical system 6715 that includes an absorptive polarizer 6737 and a camera 6739. The image source 6710 can include light sources, displays and reflective surfaces as well as one or more lenses 6720. Image light 6750 is provided by the image source 6710 wherein, a portion of the image light 6750 is reflected toward the user's eye 6730 by a partially reflective combiner 6735. At the same time, a portion of the image light 6750 may be transmitted by the combiner 6735 such that it is incident onto the absorptive polarizer 6737. In this embodiment, the image light 6750 is polarized light with the polarization state of the image light 6750 oriented relative to the transmission axis of the absorptive polarizer 6737 such that the incident image light 6750 is absorbed by the absorptive polarizer 6737. In this way, faceglow produced by escaping image light 6750 is reduced. In embodiments, the absorptive polarizer 6737 includes an antireflection coating to reduce reflections from the surface of the absorptive polarizer 6737.

FIG. 67 further shows a camera 6739 for capturing images of the environment in the direction that the user is looking. The camera 6739 is positioned behind the absorptive polarizer 6737 and below the combiner 6735 so that a portion of light from the environment 6770 is reflected by the combiner 6735 toward the camera 6739. Light from the environment 6770 can be unpolarized so that a portion of the light from the environment 6770 that is reflected by the combiner 6735 passes through the absorptive polarizer 6737 and it is this light that is captured by the camera 6739. As a result, the light captured by the camera will have a polarization state that is opposite that of the image light 6750. In addition, the camera 6739 is aligned relative to the combiner 6735 such that the field of view associated with the camera 6739 is coaxial to the display field of view provided by image light 6750. At the same time, a portion of scene light 6760 from the environment is transmitted by the combiner 6735 to provide a see-through view of the environment to the user's eye 6730. Where the display field of view associated with the image light 6750 is typically coincident to the see-through field of view associated with the scene light 6760 and thereby the see through field of view and the field of view of the camera 6739 are at least partially coaxial. By attaching the camera 6739 to the lower portion of the optical system 6715, the field of view of the camera 6739 as shown by the light from the environment 6770 moves as the user moves their head so that images captured by the camera 6739 correspond to the area of the environment that the user is looking at. By coaxially aligning the camera field of view with the displayed image and the user's view of the scene, augmented reality images with improved alignment to objects in the scene can be provided. This is because the captured images from the camera 6739 provide an accurate representation of the user's perspective view of the scene. As an example, when the user sees an object in the scene as being located in the middle of the see-through view of the HWC, the object will be located in the middle of the image captured by the camera and any augmented reality imagery that is to be associated with the object can be located in the middle of the displayed image. As the user moves their head, the relative position of the object as seen in the see-through view of the scene will change and the position of the augmented reality imagery can be changed within the displayed image in a corresponding manner. When a camera 6739 is provided for each of the user's eyes, an accurate representation of the 3D view of the scene can be provided as well. This is an important advantage provided by the invention because images captured by a camera located in the frame of the HWC (e.g. between the eyes or at the corners) capture images that are laterally offset from the user's perspective of the scene and as a result it is difficult to align augmented reality images with objects in the scene as seen from the user's perspective.

In the optical system 6715 shown in FIG. 67, the absorptive polarizer 6737 simultaneously functions as a light trap for escaping image light 6750, a light blocker of the image light 6750 for the camera 6739 and a window for light from the environment 6770 to the camera 6739. This is possible because the polarization state of the image light 6750 is perpendicular to the transmission axis of the absorptive polarizer 6737 while the light from the environment 6770 is unpolarized so that a portion of the light from the environment 6770 that is the opposite polarization state to the image light is transmitted by the absorptive polarizer 6737. The combiner 6735 can be any partially reflective surface including a simple partial mirror, a notch mirror and a holographic mirror. The reflectivity of the combiner 6735 can be selected to be greater than 50% (e.g. 55% reflectivity and 45% transmission over the visible wavelength spectral band) whereby a majority of the image light 6750 will be reflected toward the user's eye 6730 and a majority of light from the environment 6770 will be reflected toward the camera 6739, this system will provide a brighter displayed image, a brighter captured image with a dimmer see-through view of the environment. Alternatively, the reflectivity of the combiner 6735 can be selected to be less than 50% (e.g. 20% reflectivity and 80% transmission over the visible wavelength spectral band) whereby the majority of the image light 6750 will be transmitted by the combiner 6735 and a majority of light from the environment 6770 will be transmitted to the user's eye 6730, this system will provide a brighter see-through view of the environment, while providing a dimmer displayed image and a dimmer captured image. As such, the system can be designed to favor the anticipated use by the user.

In embodiments, the combiner 6735 is planar with an optical flatness that is sufficient to enable a sharp displayed image and a sharp captured image, such as a flatness of less than 20 waves of light within the visible wavelengths. However, in embodiments, the combiner 6735 may be curved in which case the displayed image and the captured image will both be distorted and this distortion will have to be digitally corrected by the associated image processing system. In the case of the displayed image, the image is digitally distorted by the image processing system in a direction that is opposite to the distortion that is caused by the curved combiner so the two distortions cancel one another and as a result the user sees an undistorted displayed image. In the case of the captured image, the captured image is digitally distorted after capture to cancel out the distortion caused by the curved combiner so that the image appears to be undistorted after image processing.

In embodiments, the combiner 6735 is an adjustable partial mirror in which the reflectivity can be changed by the user or automatically to better function within different environmental conditions or different use cases. The adjustable partial mirror can be an electrically controllable mirror such as for example, the e-Transflector that can be obtained from Kent Optronics (http://www.kentoptronics.com/mirror.html) where the reflectivity can be adjusted based on an applied voltage. The adjustable partial mirror can also be a fast switchable mirror (e.g. a switching time of less than 0.03 seconds) wherein the perceived transparency is derived from the duty cycle of the mirror rapidly switching between a reflecting state and a transmitting state. In embodiments, the images captured by the camera 6739 can be synchronized to occur when the fast switchable mirror is in the reflecting state to provide an increased amount of light to the camera 6739 during image capture. As such, an adjustable partial mirror allows for the transmissivity of the partial mirror to be changed corresponding to the environmental conditions, e.g. the transmissivity can be low when the environment is bright and the transmissivity can be high when the environment is dim.

In a further embodiment, the combiner 6735 includes a hot mirror coating on the side facing the camera 6739 wherein visible wavelength light is substantially transmitted while a spectral wavelength band of infrared light is substantially reflected and the camera 6739 captures images that include at least a portion of the infrared wavelength light. In these embodiments, the image light 6750 includes visible wavelength light and a portion of the visible wavelength light is transmitted by the combiner 6735, where it is then absorbed by the absorptive polarizer 6737. A portion of the scene light 6760 is comprised of visible wavelength light and this is also transmitted by the combiner 6735, to provide the user with a see-through view of the environment. The light from the environment 6770 is comprised of visible wavelength light and infrared wavelength light. A portion of the visible wavelength light along with substantially all of the infrared wavelength light within the spectral wavelength band associated with the hot mirror, is reflected by the combiner 6735 toward the camera 6739 thereby passing through the absorptive polarizer 6737. In embodiments, the camera 6739 is selected to include an image sensor that is sensitive to infrared wavelengths of light and the absorptive polarizer 6737 is selected to substantially transmit infrared wavelengths of light of both polarization states (e.g. ITOS XP44 polarizer which transmits both polarization states of light with wavelengths above 750 nm: see http://www.itos.de/english/polarisatoren/linear/linear.php) so that an increased % of infrared light is captured by the camera 6739. In these embodiments, the absorptive polarizer 6737 functions as a light trap for the escaping image light 6750 and thereby blocking the image light 6750 that is in the visible wavelengths from the camera 6739 while simultaneously acting as a window for infrared wavelength light from the environment 6770 for the camera 6739.

By coaxially aligning the camera field of view with the displayed image and the user's view of the scene, augmented reality images with improved alignment to objects in the scene can be provided. This is because the captured images from the camera provide an accurate representation of the user's perspective view of the scene. In embodiments, the camera that is coaxially aligned with the user's view captures an image of the scene, the processor then identifies an object in the captured image and identifies a field of view position for the object, which can be compared to the displayed field of view correlated position so digital content is then displayed relative to the position of the object.

Another aspect of the present invention relates to an optical assembly that uses a reflective display where the reflective display is illuminated with a front light arranged to direct the illumination at angles around 90 degrees from the active reflective surface of the reflective display. In embodiments, the optical configuration is light weight, small and produces a high quality image in a head-worn see-through display.

Figure 68:
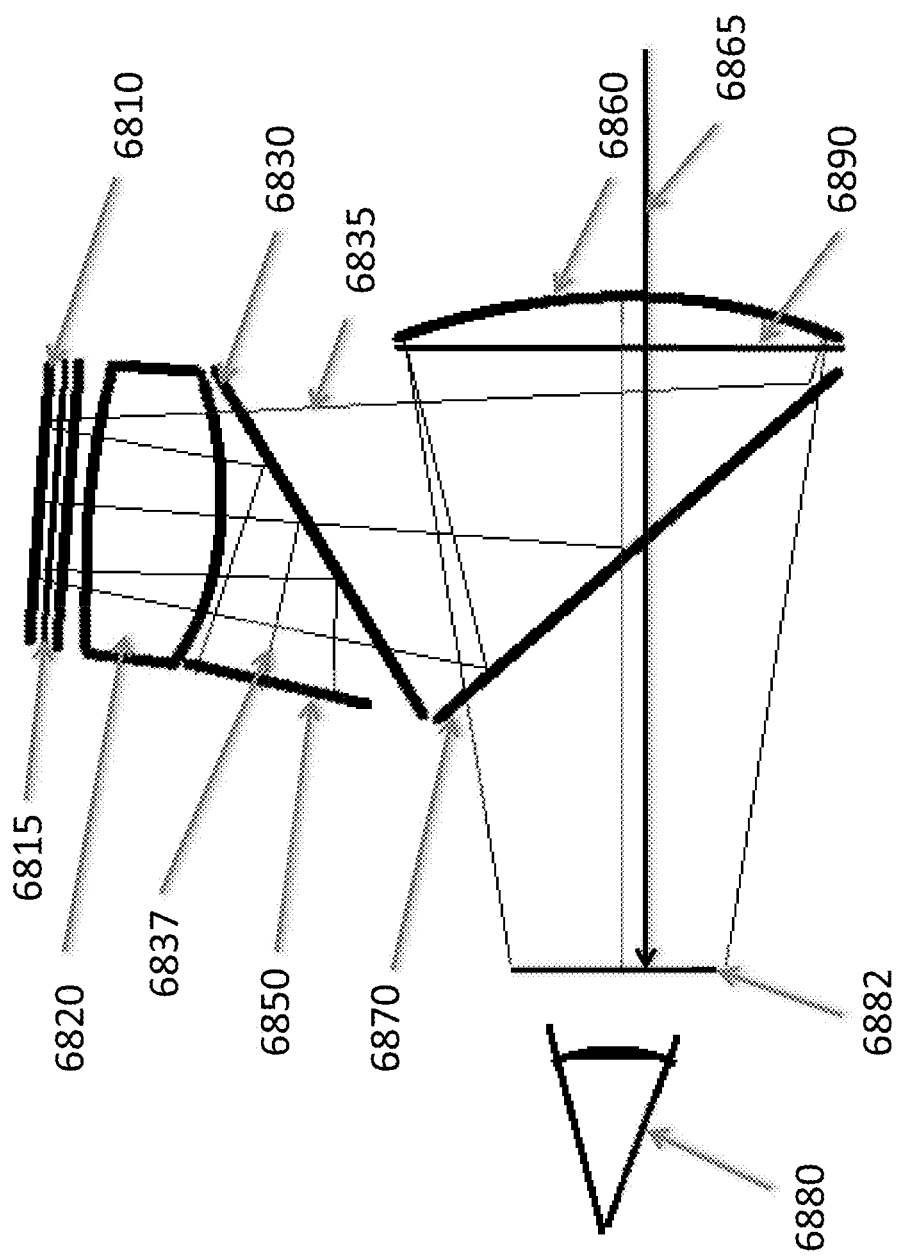
FIG. 68 illustrates an optical configuration in accordance with the principles of the present invention.

FIG. 68 provides a cross sectional illustration of the compact optical display assembly for a HWC 102 according to principles of the present invention along with illustrative light rays to show how the light passes through the assembly. The display assembly is comprised of upper optics and lower optics. The upper optics include a reflective image source 6810, a quarter wave film 6815, a field lens 6820, a reflective polarizer 6830 and a polarized light source 6850. The upper optics convert illumination light 6837 into image light 6835. The lower optics comprise a beam splitter plate 6870 and a rotationally curved partial mirror 6860. The lower optics deliver the image light to a user who is wearing the HWC 102. The compact optical display assembly provides the user with image light 6835 that conveys a displayed image along with scene light 6865 that provides a see-through view of the environment so that user sees the displayed image overlaid onto the view of the environment.

In the upper optics, linearly polarized light is provided by the polarized light source 6850. Where the polarized light source 6850 can include one or more lights such as LEDs, QLEDs, laser diodes, fluorescent lights, etc. The polarized light source 6850 can also include a backlight assembly with light scattering surfaces or diffusers to spread the light uniformly across the output area of the polarized light source. Light control films or light control structures can be included as well to control the distribution of the light (also known as the cone angle) that is provided by the polarized light source 6850. The light control films can include, for example, diffusers, elliptical diffusers, prism films and lenticular lens arrays. The light control structures can include prism arrays, lenticular lenses, cylindrical lenses, Fresnel lenses, refractive lenses, diffractive lenses or other structures that control the angular distribution of the illumination light 6837. The output surface of the polarized light source 6850 is a polarizer film to ensure that the illumination light 6837 provided to the upper optics is linearly polarized.

The illumination light 6837 provided by the polarized light source 6850 is reflected by a reflective polarizer 6830. Where the polarizer on the output surface of the polarized light source 6850 and the reflective polarizer 6830 are oriented so that their respective transmission axes are perpendicular to one another. As a result, the majority of the illumination light 6837 provided by the polarized light source 6850 is reflected by the reflective polarizer 6830. In addition, the reflective polarizer 6830 is angled so that the illumination light 6837 is reflected toward the reflective image source 6810 thereby illuminating the reflective image source 6810 as shown in FIG. 68.

The illumination light 6837 passes through a field lens 6820 and is then incident onto the reflective image source 6810. The illumination light 6837 is then reflected by the reflective image source (otherwise referred to as a reflective display herein elsewhere) 6810. Wherein the reflective image source 6810 can comprise a liquid crystal on silicon (LCOS) display, a ferroelectric liquid crystal on silicon (FLCSO) display, a reflective liquid crystal display, a cholesteric liquid crystal display, a bistable nematic liquid crystal display, or other such reflective display. The display can be a monochrome reflective display that is used with sequential red/green/blue illumination light 6837 or a full color display that is used with white illumination light 6837. The reflective image source 6810 locally changes the polarization state of the illumination light 6837 in correspondence to the pixel by pixel image content that is displayed by the reflective image source 6810 thereby forming image light 6835. Wherein if the reflective image source 6810 is a normally white display, the areas of the image light 6835 that correspond to bright areas of the image content end up with a polarization state that is opposite to the polarization state of the illumination light and dark areas of the image light 6835 end up with a polarization state that is the same as the illumination light 6837 (it should be noted that the invention can be used with normally black displays which provide an opposite effect on polarization in the image light). As such, the image light 6835 as initially reflected by the reflective image source 6810 has a mixed polarization state pixel by pixel. The image light 6835 then passes through the field lens 6820 which modifies the distribution of the image light 6835 while preserving the wavefront to match the requirements (such as for example, magnification and focus) of the lower optics. As the image light 6835 passes through the reflective polarizer 6830, the bright areas of the image light 6835 that have a polarization state that is opposite to the illumination light 6837 are transmitted through the reflective polarizer 6830 and the dark areas of the image light 6835 that have the same polarization state as the illumination light 6837 are reflected back toward the polarized light source 6850, as a result, the image light 6835 after passing through the reflective polarizer 6830 is linearly polarized with a single polarization state in all the pixels of the image but now with different intensities pixel by pixel. Thus the reflective polarizer 6830 acts first as a reflector for the illumination light 6837 and then second as an analyzer polarizer for the image light 6835.

As such, the optical axis of the illumination light 6837 is coincident with the optical axis of the image light 6835 between the reflective polarizer 6830 and the reflective image source 6810. The illumination light 6837 and the image light 6835 both pass through the field lens 6820, but in opposite directions. Wherein the field lens acts to expand the illumination light 6837 so it illuminates the entire active area of the reflective image source 6810 and also to expand the image light 6835 so it fills the eyebox 6882 after passing through the rest of the compact optical display system. By overlapping the portion of the compact optical display assembly associated with the illumination light 6837 with the portion of the compact optical display assembly associated with the image light 6835, the overall size of the compact optical display assembly is reduced. Given that the focal length associated with the field lens 6820 requires some space in the compact optical display assembly, the reflective polarizer 6830 and the polarized light source 6850 are located in space that would otherwise be unused so the overall size of the display assembly is more compact.

The reflective polarizer 6830 can be a relatively thin film (e.g. 80 microns) or thin plate (e.g. 0.2 mm) as shown in FIG. 68. The reflective polarizer 6830 can be a wiregrid polarizer such as is available from Asahi Kasei under the name WGF, or a multilayer dielectric film polarizer such as is available from 3M under the name DBEF. As previously described, the reflective polarizer 6830 has two functions. First, the reflective polarizer 6830 reflects the illumination light 6837 provided by the polarized light source 6850 and redirects the illumination light 6837 toward the reflective image source 6810. Second, the reflective polarizer 6830 acts as an analyzer polarizer to the image light 6835 thereby converting the mixed polarization state of the image light 6835 above the reflective polarizer 6830 to linearly polarized light with a single polarization state below the reflective polarizer 6830. While the illumination light 6837 incident on the reflective polarizer 6830 is incident on a relatively small portion of the reflective polarizer 6830, the image light 6835 is incident on the majority of the area of the reflective polarizer 6830. Consequently, the reflective polarizer 6830 extends at least across the entire area of the field lens 6820 and may extend across the entire area between the field lens 6820 and the beam splitter 6870 as shown in FIG. 68. In addition, the reflective polarizer 6830 is angled at least in the portion where the illumination light 6837 is incident to redirect the illumination light 6837 toward the reflective image source 6810. However, since reflective polarizers (such as a wiregrid polarizer) can be relatively insensitive to the incident angle, in a preferred embodiment, the reflective polarizer 6830 is a flat surface angled to redirect the illumination light 6837 toward the reflective image source 6810 wherein the flat surface extends substantially across the entire area between the field lens 6820 and the beam splitter 6870 in one continuously flat surface to make manufacturing easier. The thin film or thin plate of the reflective polarizer 6870 can be retained at the edges to position it at the desired angle and to make the surface flat.

The systems and methods described herein with respect to FIGS. 68 through 71 have a number of advantages. By avoiding grazing angles of the illumination light 6837 and the image light 6835 at all the surfaces in the compact optical display assembly, scattering of light in the assembly is reduced and as a result the contrast of the image presented to the user's eye 6880 is higher with blacker blacks. In addition, the reflective image source 6810 can include a compensating retarder film 6815 as is known to those skilled in the art, to enable the reflective image source 6810 to provide a higher contrast image with more uniform contrast over the area of the displayed image. Further, by providing an optical display assembly that is largely comprised of air, the weight of the compact optical display assembly is substantially reduced. By using coincident optical axes for the illumination light 6837 and the image light 6835 and overlapping the illumination light 6837 and image light 6835 for a substantial portion of the optical display assembly, the overall size of the compact optical display assembly is reduced. Where the coincident optical axes are provided by passing the illumination light 6837 and the image light 6835 in opposite directions through the field lens 6820. To maintain a uniform polarization state for the illumination light 6837, the field lens 6820 is made from a low birefringence material such as glass or a plastic such as OKP4 as available from Osaka Gas Chemicals. By positioning the polarized light source 6850 and the associated illumination light 6837 below the field lens 6820, and by folding the optical path of both the illumination light 6837 at the reflective polarizer 6830 and the image light 6835 at the beam splitter 6870, the overall height of the compact optical display assembly is greatly reduced. For example the overall height of the compact optical display assembly can be less than 24 mm as measured from the reflective image source 6810 to the bottom edge of the rotationally curved partial mirror 6860 for a display that provides a 30 degree diagonal field of view with a 6×10 mm eyebox.

In a preferred case, the light control structure in the polarized light source 6850 includes a positive lens, such as for example a positive Fresnel lens, a positive diffractive lens or a positive refractive lens. Wherein a positive Fresnel lens or a positive diffractive lens is preferred because they can be very thin. The illumination light 6837 is thereby focused to form a smaller area or pupil at the reflective polarizer 6830 that has a direct relationship to the area of an eyebox 6882 at the other end of the optics wherein image light 6835 is provided to the user's eye 6880 as shown in FIG. 68. Where the positive lens concentrates the illumination light 6837 from the polarized light source 6850 both in terms of intensity and angular distribution to match the etendue of the optical system and thereby fills the eyebox with image light 6835. By using the positive lens to converge the light from the polarized light source 6850 as provided to the reflective polarizer 6830 and then using the field lens 6820 to expand the illumination light 6837 to illuminate the active area of the reflective image source 6810, efficiency is improved since illumination light 6837 is substantially delivered only where needed to form image light 6835. Further, illumination light 6837 outside the pupil can be controlled by the positive lens and clipped by masked edges of the positive lens. By focusing the illumination light 6837 and clipping light outside the pupil, illumination light 6837 is prevented from impinging adjacent surfaces at grazing angles in the compact optical display assembly to reduce scattering of light and thereby increase contrast in the image provided to the user's eye 6880 by providing blacker blacks.

Figure 69:
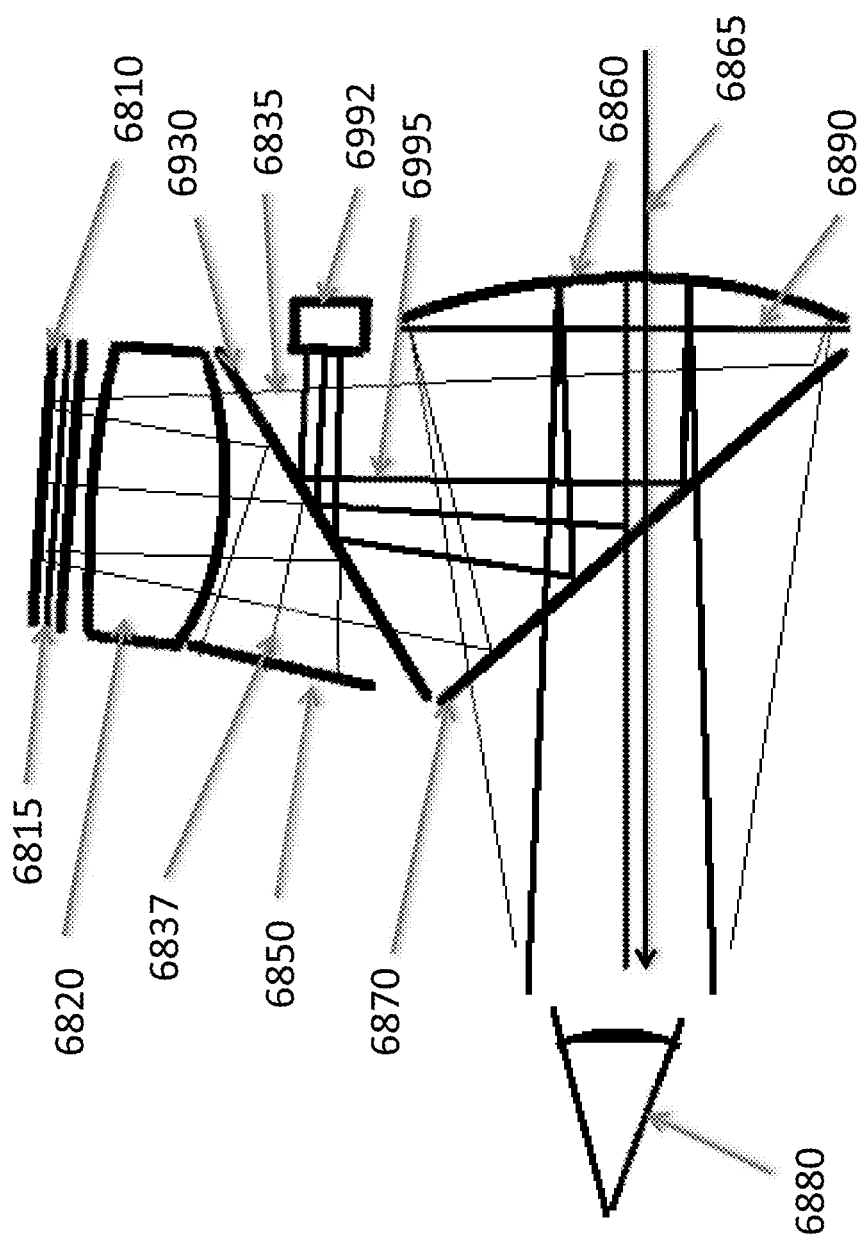
FIG. 69 illustrates an optical configuration in accordance with the principles of the present invention.
Figure 70:
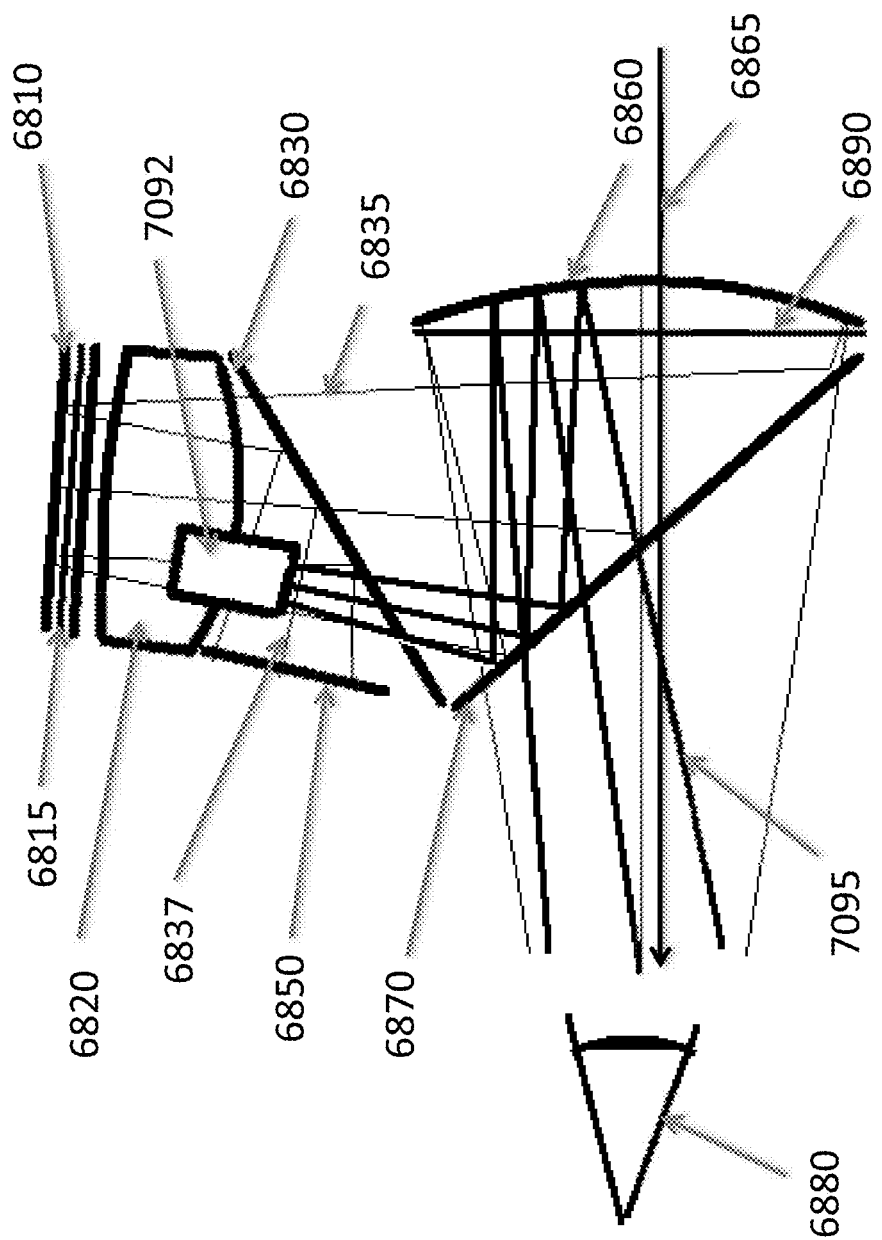
FIG. 70 illustrates an optical configuration in accordance with the principles of the present invention.

It should be noted that while FIGS. 68, 69 and 70 show optical layouts wherein the illumination light 6837 is provided from behind the rotationally curved partial mirror 6860, other optical layouts are possible within the invention. The location of the polarized light source 6850 can be changed for example to be at the side of the rotationally curved partial mirror 6860 wherein the reflective polarizer 6830 is oriented to receive the illumination light 6837 from the side. And reflect it toward the reflective image source 6810 (not shown).

In a further embodiment, the portion of the image light 6835 that is reflected back toward the polarized light source 6850 is recycled in the polarized light source 6850 to increase the efficiency of the polarized light source 6850. In this case, a diffuser and a reflective surface is provided behind the polarized light source 6850 so the polarization of the light is scrambled and reflected back toward the reflective polarizer 6830.

In yet another embodiment, another reflective polarizer is provided in the polarized light source 6850 and behind the linear polarizer previously disclosed. Wherein the respective transmission axes of the reflective polarizer and the linear polarizer are parallel to one another. The other reflective polarizer then reflects the light back into the backlight that has the polarization state that would not be transmitted by the linear polarizer. The light that is reflected back into the backlight passes through diffusers associated with the polarized light source 6850 where the polarization state is scrambled and reemitted thereby recycling the light and increasing efficiency.

In another embodiment, the system according to the principles of the present invention includes an eye imaging system. FIG. 69 is an illustration of a compact optical display assembly, which includes an eye imaging camera 6992 that captures an image of the user's eye 6880 that is coaxial with the displayed image provided to the user so that a full image of the user's iris can be reliably captured. The eye imaging camera 6992 is reflected into the lower optics by a reflective polarizer 6930 that includes a notch mirror coating, facing the eye imaging camera 6992, that reflects the wavelengths of light that are captured by the eye imaging camera 6992 (e.g. near infrared wavelengths) while transmitting wavelengths associated with the image light 6835 (e.g. visible wavelengths). Eye light rays 6995 shown in FIG. 69 illustrate how the field of view associated with the eye imaging camera 6992 is a relatively narrow field of view because it is multiply reflected through the lower optics to capture an image of the user's eye 6880. However, to enable the eye imaging camera 6992 to focus onto the user's eye 6880, the eye imaging camera 6992 needs to have a very near focus distance (e.g. 35 mm). In addition, the field of view and focus distance of the eye imaging camera must take into account the reducing effect of the optical power provided by the rotationally curved partial mirror 6860. To increase the efficiency of capturing the light reflected from the user's eye 6880 and thereby enable a brighter image of the eye, the rotationally curved partial mirror 6860 can be coated with a partial mirror coating that acts as a full mirror in the wavelengths being captured by the eye imaging camera 6992, for example the coating can reflect 50% of visible light associated with the image light and 90% of near infrared light associated with the eye light 6995. Where the reflections and associated changes in polarization state are similar to those associated with the image light 6835 but in the opposite order since the eye light rays 6995 are coming from the user's eye 6880. LEDs or other miniature lights are provided adjacent to the user's eye 6880 to illuminate the user's eye 6880 wherein the wavelengths associated with the LED's or other miniature lights are different than the wavelengths associated with the image light 6835 such as for example near infrared wavelengths (e.g. 850 nm, 940 nm or 1050 nm). Alternatively, the image light 6835 is used to illuminate the user's eye 6880 and a reflective polarizer 6930 with a low extinction ratio in reflection (e.g. reflective extinction ratio <15) is used so that some of the eye light rays are reflected toward the eye imaging camera 6992.

In an alternative embodiment, the reflective and partially reflective surfaces can extend laterally to the sides of the areas used for displaying an image to the user. In this case, the eye imaging camera can be located adjacent to the field lens and pointed in a direction to image the user's eye after reflecting from the beam splitter and the rotationally curved partial mirror as shown in FIG. 70. Where FIG. 70 is an illustration that shows an eye imaging camera 7092 positioned to the side of the field lens 6820 and reflective polarizer 6830. The eye imaging camera 7092 is pointed such that the field of view captured by the eye imaging camera 7092 includes the user's eye 6880 as illustrated by the eye light rays 7095. The quarter wave film 6890 is also extended laterally to change the polarization state of the eye light 7095 in the same way that the polarization state of the image light is changed so that the eye light passes through the beam splitter 6870 and quarter wave 6890, is partially reflected by the rotationally curved partial mirror 6860 and is then reflected by the beam splitter 6870 and is then captured by the eye imaging camera 7092. By positioning the eye imaging camera 7092 to the side of the field lens 6820 and reflective polarizer 6830, the complexity of the optics associated with displaying an image to the user is reduced. In addition, the space available for the eye imaging camera 7092 is increased since interferences with the display optics are reduced. By positioning the eye imaging camera 7092 adjacent to the display optics, the eye image is captured nearly coaxially with the displayed image.

Figure 71:
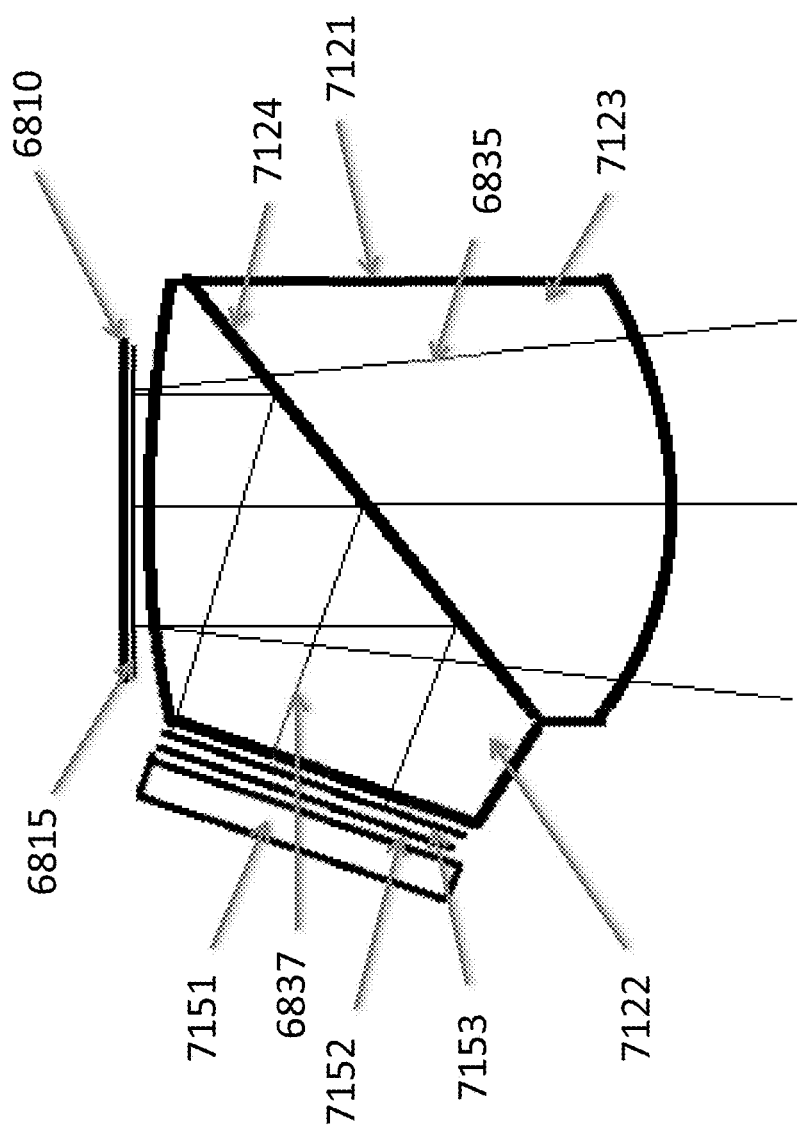
FIG. 71 illustrates an optical configuration in accordance with the principles of the present invention.

In a yet another embodiment, the systems according to the principles of the present invention include a field lens with an internal reflective polarizer and one or more surfaces with optical power. FIG. 71 is an illustration of the upper optics including a field lens 7121 comprised of upper prism 7122 and lower prism 7123. The upper prism 7122 and the lower prism 7123 can be molded to shape or grind and polished. A reflective polarizer 7124 is interposed on the flat surface between the upper prism 7122 and the lower prism 7123.

The reflective polarizer 7124 can be a wiregrid polarizer film or a multilayer dielectric polarizer as previously mentioned. The reflective polarizer 7124 can be bonded into place with a transparent UV curable adhesive that has the same refractive index as the upper prism 7122 or the lower prism 7123. Typically the upper prism 7122 and the lower prism 7123 would have the same refractive index. Wherein upper prism 7122 includes an angled surface for illumination light 6837 to be provided to illuminate the reflective image source 6810. The illumination light is provided by a light source that includes lights such as LEDs, a backlight 7151, a diffuser 7152 and a polarizer 7153 as has been previously described. The lower prism 7123 includes a curved surface on the exit surface for controlling the wavefront of the image light 6835 as supplied to the lower optics. The upper prism may also include a curved surface on the upper surface next to the reflective image source 6810 as shown in FIG. 71 for manipulating the chief ray angles of the light at the surface of the reflective image source 6810. Illumination light 6837 is polarized by the polarizer 7153 prior to entering the upper prism 7122. The transmission axes of the polarizer 7153 and the reflective polarizer 7124 are perpendicular to one another so that the illumination light 6837 is reflected by the reflective polarizer 7124 so that the illumination light is redirected toward the reflective image source 6810. The polarization state of the illumination light 6837 is then changed by the reflective image source 6810 in correspondence with the image content to be displayed as previously described and the resulting image light 6835 then passes through the reflective polarizer 7124 to form the bright and dark areas associated with the image that is displayed to the user's eye 6880.

In another embodiment, the field lens 7121 of FIG. 71 comprises a polarizing beam splitter cube including two prisms, upper prism 7122 and lower prism 7123. In this case, the reflective polarizer 7124 is replaced by a coating that is polarization sensitive so that light of one polarization state (typically S polarized light for example) is reflected and light of the other polarization state is transmitted. The illumination light 6837 is then provided with the polarization state that is reflected by the coating and the image light is provided with the polarization state that is transmitted by the coating. As shown in FIG. 71, the beam splitter cube includes one or more curved surfaces in the upper prism 7122 or the lower prism 7123. The beam splitter cube can also include one or more angled surfaces where the illumination light is supplied. The angled surface can include light control structures such as a microlens array to improve the uniformity of the illumination light 6837, or a lenticular array to collimate the illumination light 6837.

In yet another embodiment, the curved surface(s) or the angled surface(s) illustrated in FIG. 71 can be molded onto a rectangularly shaped beam splitter cube by casting a UV curable material (e.g. UV curable acrylic) onto a flat surface of a beam splitter cube, placing a transparent mold with a cavity that has the desired curve onto the flat surface to force the UV curable material into the desired curve and applying UV light to cure the UV curable material. The beam splitter cube can be made of a material that has the same or different refractive index than the UV curable material.

In a further embodiment, polarization sensitive reflective coatings such as dielectric partial mirror coatings, can be used in place of reflective polarizers or beam splitters as shown in FIG. 68. In this case, the reflective films and plates that comprise the reflective polarizers 6830 and beam splitters 6870 include polarization sensitive coatings that substantially reflect light with one polarization state (e.g. S polarization) while substantially transmitting light with the other polarization state (e.g. P polarization). Since the illumination light source includes a polarizer 7153, the illumination light 6837 is one polarization state and it is not important that the reflective polarizer 7124 be sensitive to the polarization state in reflection, the polarization state just needs to be maintained and presented uniformly over the surface of the reflective image source 6810. However, it is important that the reflective polarizer 7124 be highly sensitive to polarization state in transmission (e.g. extinction ratio >200) to be an effective polarizer analyzer and to provide a high contrast image (e.g. contrast ratio >200) to the user's eye 6880.

In a further embodiment, the field lens 7121 shown in FIG. 71 can comprise a reflective polarizer 7124 with a curved surface (not shown) instead of a flat surface and wherein the reflective polarizer 7124 is not a film and instead is a polarization sensitive coating, a printed wiregrid polarizer or a molded wiregrid pattern that is then metallized. In this case, the upper prism 7122 and the lower prism 7123 are made as a matched pair with mating curved surfaces that together form the surface of the reflective polarizer. Wherein the polarization sensitive coating, the printed wiregrid or the molded wiregrid pattern are applied to the mating curved surface associated either the upper prism 7122 or the lower prism 7123 and a transparent adhesive is applied to the other mating surface to bond the upper prism 7122 and lower prism 7123 together to form the field lens 7121 with an internal curved reflective polarizer 7121.

Another aspect of the present invention relates to the use of non-visible light in connection with medical procedures where the non-visible light is used in the presentation of an AR layer presented in a see-through display of a head-worn computer during the medical procedures. The non-visible light can be used to show what the patient looks like in the non-visible light by imaging the reflection of the non-visible light, converting the image to visible light content and presenting the content over a see-through view of the patient. The see-through view of the patient may be seen under conventional visible lighting conditions such that the medical professional can see the body under the visible light with the visible light reality view augmented with the non-visible light view. These technologies can be used to help identify certain areas of the body, guide a procedure to or around certain areas of the body, diagnose disease or other known conditions, etc. while the medical professional is with the patient.

Figure 72:
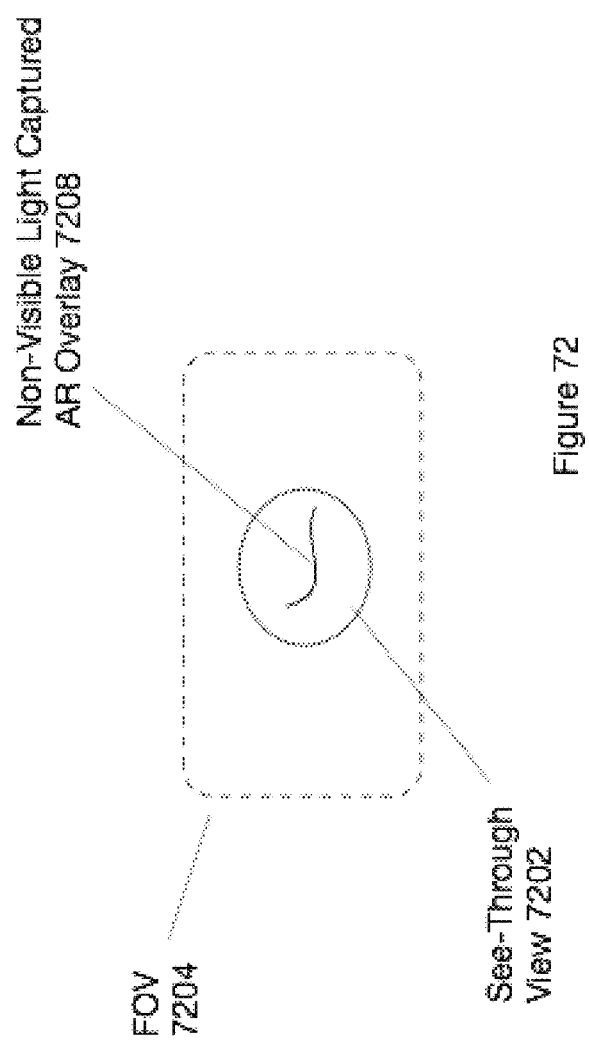
FIG. 72 illustrates an AR content presentation during a medical procedure in accordance with the principles of the present invention.
Figure 73:
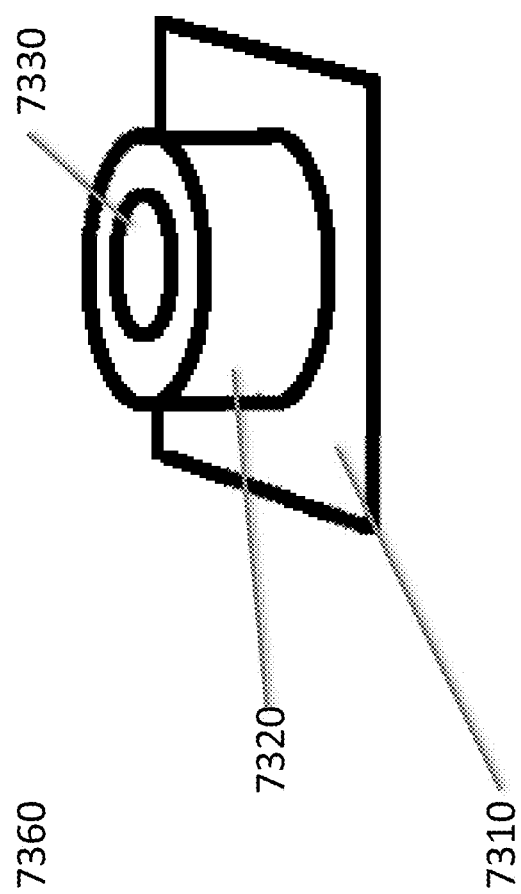
FIG. 73 illustrates a marker in accordance with the principles of the present invention.

FIG. 72 illustrates an AR see-through view of a combined visible and non-visible lighted view of material in accordance with the principles of the present invention. The FOV 7204 is a field-of-view of a see through display of a HWC 102. A medical professional wearing the HWC 102 can see through the display to obtain the see through view of the material 7202. The see-through view is based on visible light in the surroundings. The medical professional can also see a feature of the material that is not otherwise noticeable if only viewed under visible lighting conditions. The feature appears when it is lit with non-visible spectrum light, but can only be captured with a non-visible spectrum image capture system of the same non-visible spectrum (e.g. an NIR camera if NIR light is used to irradiate the material). The captured non-visible image is then converted into a visible light based image through image processing (e.g. on board the HWC 102 or remote from the HWC 102) in real time and then the visible light based image is presented in the FOV 7204 at a position such that it is perceived as an overlay on the subject material. Alignment of the AR layer may be important for certain medical procedures and technologies described below and herein elsewhere may be used to improve the placement accuracy.

A method used in connection with a HWC 102 may involve irradiating a portion of a human body with non-visible light and visible light; causing a medical professional to view the portion of the human body as illuminated by the visible light through a computer display positioned on the head of the medical professional; capturing reflections of the non-visible light from the portion of the human body with a non-visible image capture device; and converting the captured reflections into visible light based content and presenting the visible light based content as an augmented reality overlay in the computer display such that the medical professional perceives the visible light based content as overlaying the portion of the human body.

During a medical procedure, the non-visible lighting may be provided in a number of different ways. It may be presented by separately mounted lights in the area of the patient. In embodiments, the non-visible light may be emitted from a solid-state light source mounted on the HWC 102. An advantage to having the light source on the HWC 102 is that the light can be directed to the area where the medical professional is looking and the radiation can be directed onto the same side of the body as the medical professional. The non-visible light may be NIR, IR, Near-UV, UV, etc.

In embodiments, the non-visible light capture system may be adapted to capture thermal radiation from portions of the body in a similar way as was as described herein relating to supplemental non-visible light capture. For example, a head-worn computer equipped with a thermal imaging camera may be used during a medical procedure to produce a thermal content AR overlay. Another useful example is when the thermal camera equipped head-worn computer is used to image faces or other body parts, even in a low resolution mode, to assess the apparent body temperature of people in an attempt to diagnose high body temperatures. The head-worn computer could be worn in a crowd of people or at a checkpoint to identify people that might be running a temperature and therefore might be ill. In embodiments, the thermal monitor may be used in conjunction with facial recognition to more accurately identify people that may be ill. In embodiments, the recognition process may only be used to recognize that it is a face, and not to verify the identity of the person from facial features, such that it is known that the temperature being recorded is that of a face. Once it is known that it is a face, or other body part, reference to normal and non-normal facial temperatures can be made. AR overlay content may then be presented in the head-worn computer see-through display such that persons identified as having high facial temperatures can be identified.

In embodiments, multiple different wavelengths or wavelength bands of non-visible light are used to irradiate the subject body portion and the head-worn computer has capture systems adapted to capture the multiple different wavelengths for image processing and presentation in the see-through display. For example, the head-worn computer may have a NIR and UV emitters and it may further be adapted to capture the NIR and UV reflections from the subject body portion. Each wavelength band may be captured and image processed to generate visible light content such that each non-visible wavelength band can be presented as visible light content in the see-through display as an augmented reality layer. The multiple different wavelengths or bands may be within a category of non-visible light (e.g. two or more bands within the NIR spectrum), within separate categories of non-visible light (e.g. one or more bands from the UV and one or more bands from the NIR), etc. The multiple different wavelengths may be from the NIR, IR, UV, near UV, etc.

In embodiments, supplemental visible light at a particular wavelength or band may be provided to irradiate the subject body part. For example, it may be desirable to enhance the cells, tissues, or other body portions that highly reflect a particular color, like blue, or red, and that particular color may be emitted from the head-worn computer to increase the particular color irradiation of the body part. In embodiments, a supplemental band of visible light may be emitted from the head-worn computer in addition to one or more bands of non-visible light emitted from the head-worn computer for supplemental visible light enhancement along with non-visible light AR overlay(s) in the see-through display.

In embodiments, the visible and non-visible technologies described herein may be used for procedure guidance, medical diagnosis, discovery of materials of interest, such as indicators of pathogens in blood or serum, tissue condition discovery, etc.

In embodiments, a high-speed camera may be mounted on the head-worn computer to capture and analyze a body portion's small motions or fast color changes during a medical procedure. The high-speed camera may be a visible light camera or a non-visible light camera. For example, the camera may be capable of 330 fps at 672×380, 180 fps at 720 p, 120 fps at 1080 p to capture blood flow color shift in body portions. See http://people.csail.mit.edu/mrub/papers/vidmag.pdf and http://newsoffice.mit.edu/2013/seeing-the-human-pulse-0620 for reference on a type of high-speed camera that may be used in such a manner.

In embodiments, the portion of the human body may be an external portion. For example, a medical practitioner may be preparing to draw blood from a patient and the non-visible light AR overlay may provide indications of where it is most appropriate to draw from. Blood vessels may, for example, be highlighted in the overlay so the medical practitioner can target a larger or otherwise more appropriate blood vessel for the procedure. The non-visible AR overlay of the external body portion may also highlight skin conditions. For example, some skin portions may appear to look differently when lit under deep blue, near UV, UV, NIR or IR and the overlay may provide a helpful guide to diagnosing skin disorders or other disorders that can be diagnosed through skin inspections.

In embodiments, the portion of the human body may be an internal portion. For example, in an emergency situation, where the person has an injury, the non-visible light AR overlay may provide insight regarding the injury, which may include a cut in the body.

In embodiments, the portion of the human body may be an open cavity viewed during a surgical procedure.

In embodiments, the reflections of the non-visible light may be analyzed for a known condition. The known condition may be a blood condition, vascular condition, organ condition, cell condition, cancer condition or other medical condition. For example, the blood vessels of the person may be analyzed (as described herein elsewhere) for a known presence of a drug, alcohol, etc. The blood vessels may be highlighted for more pronounced visibility during a medical procedure. Cells or tissue may be analyzed through an evaluation of the reflected non-visible light.

In embodiments, the reflections of the non-visible light are presented for medical procedure guidance. The guidance may be general procedure guidance, internal procedure guidance, external procedure guidance, etc.

In embodiments, an in-line eye-imaging camera for capturing an image of an eye of the medical professional to identify the direction the medical professional is looking (as described herein elsewhere) may be included in the HWC 102 optical system. The in-line eye imaging may be used to enhance image quality or alignment of the AR layer in the direction in which the medical professional is looking.

In embodiments, a surrounding environment imaging system that is arranged to capture the surrounding environment in-line with the optical axis of the medical professional's surrounding environment view (as described herein elsewhere) may be included in the HWC 102. The in-line environment capture system may be used to better align the AR overlay with the body portion from an in-line perspective of the medical professional.

In embodiment positional instruments may be included in the head-worn computer to accurately assess its position during a medical procedure. For example, the head-worn computer may have positional cameras to assess the position of the head-worn computer with respect to known elements in the surroundings. A camera may, for example, be pointed upward and a pre-set pattern may be provided above the medical professional to provide a reliable reference from which to assess position and movements. An on-board IMU may also assist in position determination by assessing relative movements. An on-board e-compass may also assist in position determination by assessing the compass heading of the head-worn computer. Cameras may also be used to capture other elements in the surrounding environment, including the body or body portion to assist in the position determination. In embodiments, the positional assessment is used when determining where in the field of view of the see-through display to position the AR overlay such that it creates the proper perspective for the medical professional wearing the head-worn computer.

The non-visible light AR overlay may have attributes that are controllable and there may be several layers included in the overlay where each one or portion thereof may be selected and controllable. The control may be provided through an eye imaging control system, IMU motion determined control system, gesture control system, voice control system (e.g. as those control systems are described herein elsewhere), etc. The control systems may be serviced by an aid of a primary medical professional (e.g. a nurse). In embodiments, a command may be set to clear all content from the see-through display to quickly provide the medical professional with a clear view of the surrounding environment without having to look through or around digital content in the display that would otherwise be present.

Another aspect of the present invention relates to using a head-worn computer with a see-through display in a medical setting to automatically recognize a patient for confirmation of the patient's identity, medical needs, medical history, present procedure, present medicines required, medicine itself that is intended to be delivered to the patient, etc. Mistakes in the delivery of medical care based on a misunderstanding of identity or need can be devastating and the system and methods of identification confirmation according to the principles of the present invention can greatly reduce such mistakes.

In embodiments, a head-worn computer with a see-through display may be worn by a medical professional and used to confirm the identity of a patient throughout the medical services to be delivered to the patient. The head-worn computer may have a camera that captures the face or other identifying indicia of the patient. The captured image(s) may then be processed (e.g. either on-board the head-worn computer or remote from the head-worn computer) to match attributes to a known person's identity. This computer-matched identity can then be used to confirm the name, birth date, gender, ethnicity, etc. of the patient and provide digital content in the see-through display that confirms to the medical professional the identity and/or confirmation. This process may be repeated whenever the medical professional leaves and re-appears with the patient to avoid problems with proper identification.

In embodiments, the patient may wear an indication of identity (e.g. a wrist band) and the indication may be read by the head-worn computer (e.g. through image capture, bar code recognition, etc.) such that the worn indication can be matched with the facial recognition.

In embodiments, the automatic patient identification may be performed prior to providing the patient with any medicine or performing any procedure on the patient. For example, before medicine or procedure is administered or otherwise provided to the patient, the head-worn computer may facilitate a confirmation of the patient's identity, confirm that the medicine that is about to be provided is in fact the one that was ordered (e.g. through bar code or other auto-recognition of a label on the medicine). Once confirmed, the head-worn computer may record or otherwise monitor or warn the medical provider during the administration of the medicine or procedure. In a surgical or medical procedure situation, the head-worn computer may be used to monitor the procedure, compare the steps being taken to a prescription, standard or other instructions, and then record, advise, warn or otherwise provide feedback to the medical professional.

Facial recognition may also be used to confirm a patient's identity such that the patient's information can then be securely retrieved and presented in the see-through display. The information may include current biometric information (e.g. blood pressure, pulse, blood oxygen level, ekg information, respiration information, etc.), personal history information (e.g. known allergies, prior procedures, known disorders and conditions, etc.), current drug information indicating what drugs the patient is currently taking, drug interaction warnings, etc.

In embodiments, the head-worn computer may assist a medical practitioner in the mixing, dispensing and labeling of medications. For example, a pharmacist may wear a head-worn computer with a see-through display and the head-worn computer may further have sensors and image capture and processing systems such that the head-worn computer can read a prescription and monitor, record and assist the pharmacist in the preparation of the medicine and labeling the medication.

Another aspect of the present invention relates to the secure access to patient information through the use of a head-worn computer. In addition to the use of facial recognition for patient verification, the head-worn computer may verify that the medical professional wearing it is eligible to review the information. In embodiments, eye imaging verification, as described herein elsewhere, may be used to verify the identity of the medical professional wearing the head-worn computer and the verified identity may then be matched with a listed medical professional or organization that is permitted to see the information. The step of personal identity verification may be done periodically or when there is any indication that the head-worn computer has been removed from the medical professionals head (e.g. IMU movements consistent with the removal).

Another aspect of the present invention relates to organ or body part recognition through the use of head-worn computing for the confirmation, recordation, guidance, etc. of medical procedures. For example, it has become standard practice to physically mark a patient's body to confirm the body part that requires the planned procedure (e.g. marking the right leg with a pen). With the head-worn computing systems illustrated herein, the head-worn computer can be worn by a medical professional and constantly monitor a procedure, from pre-op to operation to post-op. For example, if the prescribed procedure relates to the right-side kidney of a patient, the prescription can be loaded into the system and the head-worn computer sensors (e.g. camera) can be used to recognize what the medical professionals are doing and ensure that they are targeting the correct kidney and the correct procedure by providing visual cues in the see-through display, audio cues, tactile cues, etc.

Another aspect of the present invention relates to the use of head-worn computing for the secure visualization of diagnosed conditions. As discussed herein, a head-worn computer may be worn by a medical professional during a medical procedure to securely view imagery of the patient's body, external or internal, may be lighting, either visible or non-visible, may be captured to assist with the procedure or diagnose a condition. In embodiments, the images may be processed internally on the head-worn computer or they may be communicated to another computing platform for processing. The image processing may involve comparing portions of the images with known images to further the guidance or diagnosis process. For example, at a stage in an operation procedure, cells, tissue, organ or other portion of the patient's body may be imaged and the image may be processed for the presence of certain known or unknown portions. The results, and/or information relating to the results, of the image processing may then be presented in the see-through display of the head-worn computer. This real time feedback on the procedure and/or diagnosis can help the medical practitioner during the procedure, helping with early and directed assistance.

Another aspect of the present invention relates to providing a medical professional with secure assistance by securely providing imagery captured by the sensors (e.g. camera images captured after eye image medical professional identity verification and/or patient facial recognized verification) on the head-worn computer during a medical procedure. For example, imagery may be sent to a remote expert and the expert may then be able to provide feedback to the medical professional in real time during the procedure. The expert may be presented visually in the see-through display of the medical professional to make the interaction more impactful. The expert may also provide other visuals to be presented to the medical professional in the see-through display. For example, the expert may send exemplary information to show the medical professional what a medical device or body portion is suppose to look like during or following the procedure.

Another aspect of the present invention relates to the diagnosis of medical conditions based on eye imagery taken on a patient through the use of head-worn computing and eye-imaging technologies such as those disclosed herein elsewhere. In embodiments, patient motion, as determined through motion sensors on the head-worn computer may also be used in determining medical conditions of the patient. In embodiments, the patient eye imagery and/or motion measurements and patterns may be communicated to a medical professional for diagnosis. In embodiments, the eye imagery is taken with a high-speed camera such that small motion and color changes in the eye can be monitored for the diagnosis. In embodiments, supplemental visible light and/or non-visible light may be directed towards the eye such that reactions can be noted. As described herein elsewhere, the visible and non-visible light reflections from the eye may also be processed for absorption, reflection, etc. in the diagnosis.

In embodiments, an image may be presented in the see-through display to cause the wearer to focus on the image while a diagnosis test it run.

In embodiments, a person wearing the head-worn computer may be inspected remotely through eye-imaging and motion detection. For example, a soldier may be wearing the head-worn computer and ask for medical assistance from a remote medical professional or other person. The head-worn computer may then go into a diagnosis mode and perform medical condition diagnosis. Similarly, a remote person may request a medical examination of someone in the field and the glasses may then go into the diagnosis mode and return results. In situations, the diagnosis mode may be periodic or it may be triggered by sensed events, such a loud noise, signature motion indicative of an abrupt move, bright flash, etc.

Another aspect of the present invention relates to aligning displayed content within the see-through head-worn display such that it properly aligns with a human body portion during a medical procedure. When using a head-mounted display that provides a displayed image overlaid onto a see-through view of a body part of a patient, it is important to be able to align the displayed image accurately within the see-through view. To this end, the systems in accordance with the principles of the present invention provide a device that is attached to a body part of the patient that can be detected by the head mounted display and used as a reference point to align the displayed images to. The invention provides one or more small light(s) that can be attached to a body part of the patient wherein the light provides a wavelength that can be detected by one or more camera(s) that are included in the head mounted display.

Figure 74:
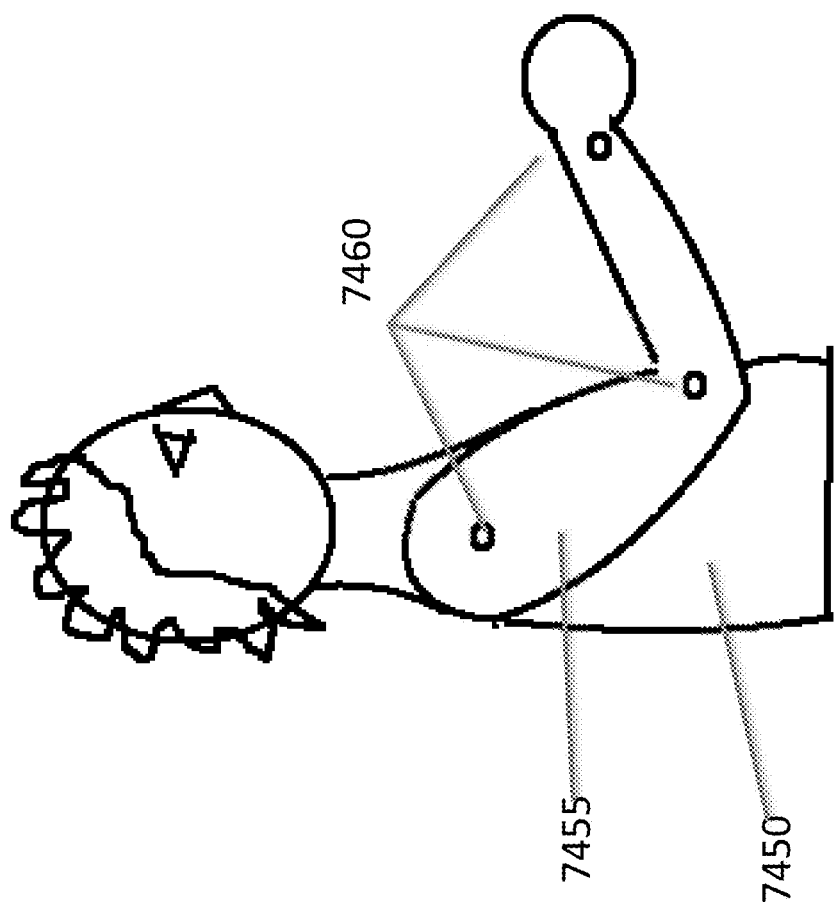
FIG. 74 illustrates a medical procedure in accordance with the principles of the present invention.

FIG. 74 shows a schematic illustration of a small light 7460 suitable for use in the present invention. The attaching of the small light 7460 to a body part can be done with adhesive tape 7310, other adhesive that is compatible with human skin, strap or other mounting device. A small battery 7320 can be included with the small light 7460 or a remote power source connected by wires can be used to power the small light. An LED 7330 or other small light source is included on the side opposite the adhesive tape 7310. The displayed image can then be aligned relative to the small light 7460 and the head-mounted display can automatically adjust the position of the displayed image presented to the user so that the alignment of the displayed image is maintained constant relative to the body part of the patient. Where the displayed image can include an Xray image, MRI image, a thermographic image, a chemical distribution image, a blood flow image, a blood pressure image, a diagram of physical structures, a diagram associated with a procedure, a hyper-spectral image, a dual spectral image, etc.

The small light 7460 can emit at any wavelength that can be captured by the camera in the head-mounted display. In a preferred embodiment, the small light 7460 emits infrared light that can be detected by the camera but cannot be seen by the user in the see-through view (e.g. 850 nm), so the user is not distracted by light from the small light 7460 as seen in the see-through view of the body part. Alternatively, the small light 7460 can provide a relatively narrow visible wavelength (e.g. 440-470 nm) and the optics associated with the see-through view in the head mounted display can include a notch filter coating that blocks the narrow wavelength associated with the small light 7460. In this way, the user is blocked from seeing the light, so the user is not distracted by the light associated with the small light 7460. In this case the camera can be a visible wavelength camera and the user will see a see-through view of the body part 7455 in the visible wavelengths minus the narrow wavelengths associated with the small light 7460 and overlaid by the displayed image.

FIG. 74 shows an illustration of a patient 7450 with several small lights 260 attached to a body part 7455 (three small lights are shown because the body part includes two independently moveable sections, but two small lights would be sufficient if the body part had only one moveable section). Small lights 260 can be attached to the body part of the patient prior to taking medical images (e.g. Xray images or MRI images) of the body part 7455 and left attached to the body part 7455 for subsequent viewing with the head mounted display. Since the small light 7460 will include metal portions, spots 7560 associated the small lights will be easily visible in Xray or MRI images. The user can then view the body part 7455 with the head mounted display and align spots 7560 in the displayed medical image 7620 with spots 7662 associated with the small lights 260 as seen in the see-through view. By attaching the small lights 260 to the body part 7455 prior to capture of a medical image 7570 and then leaving the small lights 260 attached during viewing with the head mounted display, a high degree of accuracy can be obtained between the displayed medical image 7620 and the body part 7455.

Figure 75:
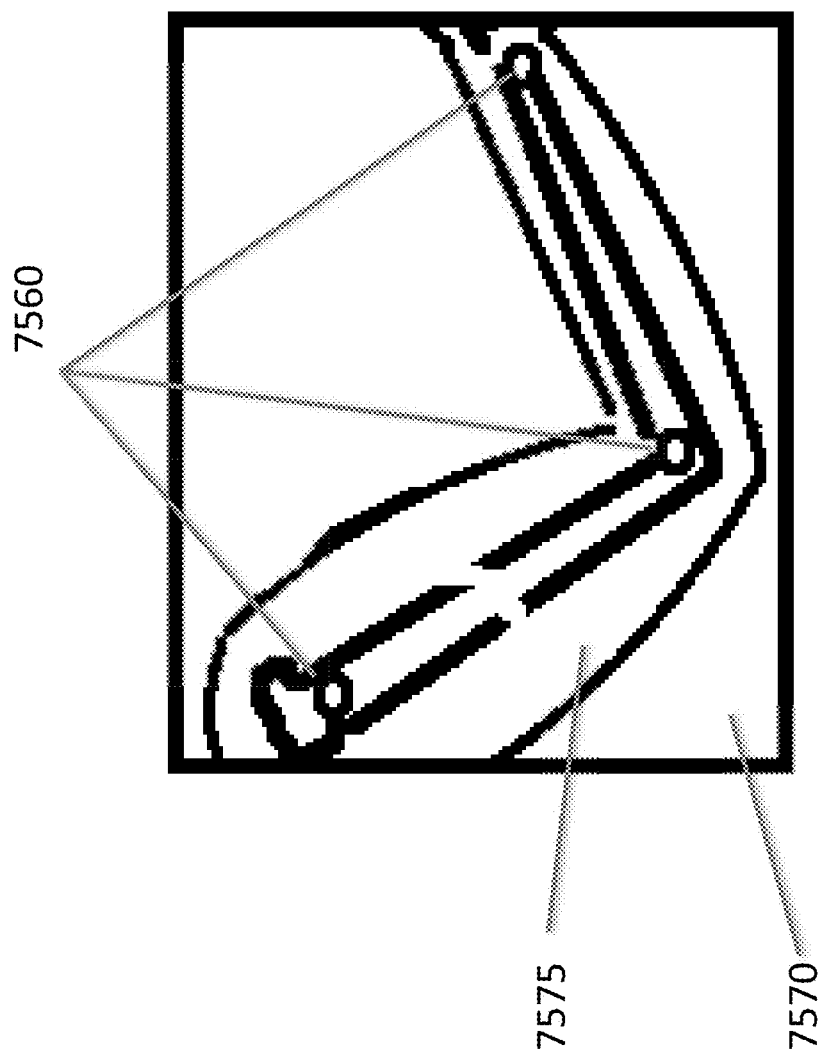
FIG. 75 illustrates a medical procedure in accordance with the principles of the present invention.
Figure 76B:
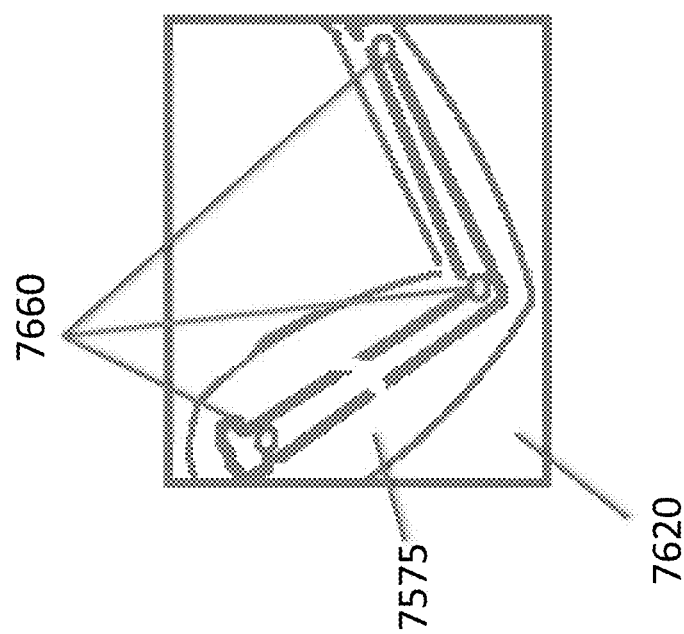
FIGS. 76a and 76b illustrate a medical procedure in accordance with the principles of the present invention.
Figure 76A:
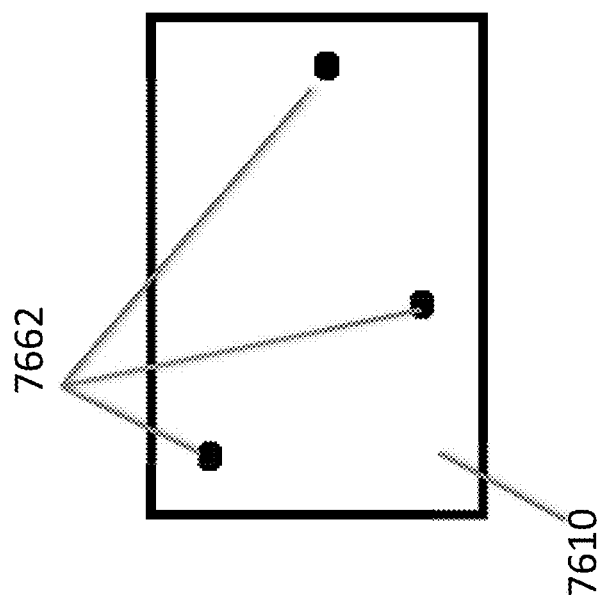

FIG. 75 shows an illustration of an Xray image 7570 wherein an outline of the body part 7575 is visible along with spots 7560 associated with the small lights 260. FIG. 76A shows an illustration of an infrared image 7610 captured by an infrared camera in the head mounted display wherein infrared light from the small lights 260 produces easily distinguishable spots 7662. These spots 7662 are used to identify the positions of the small lights 260 on the body part 7455. When the spots 7560 in the medical image 7570 are aligned to the spots 7662 in the captured image 7610 of the body part 7455, an accurate alignment of the medical image 7570 to the body part 7455 is provided so the user can view the medical image overlaid on the see-through view of the patient 7450.

Figure 77:
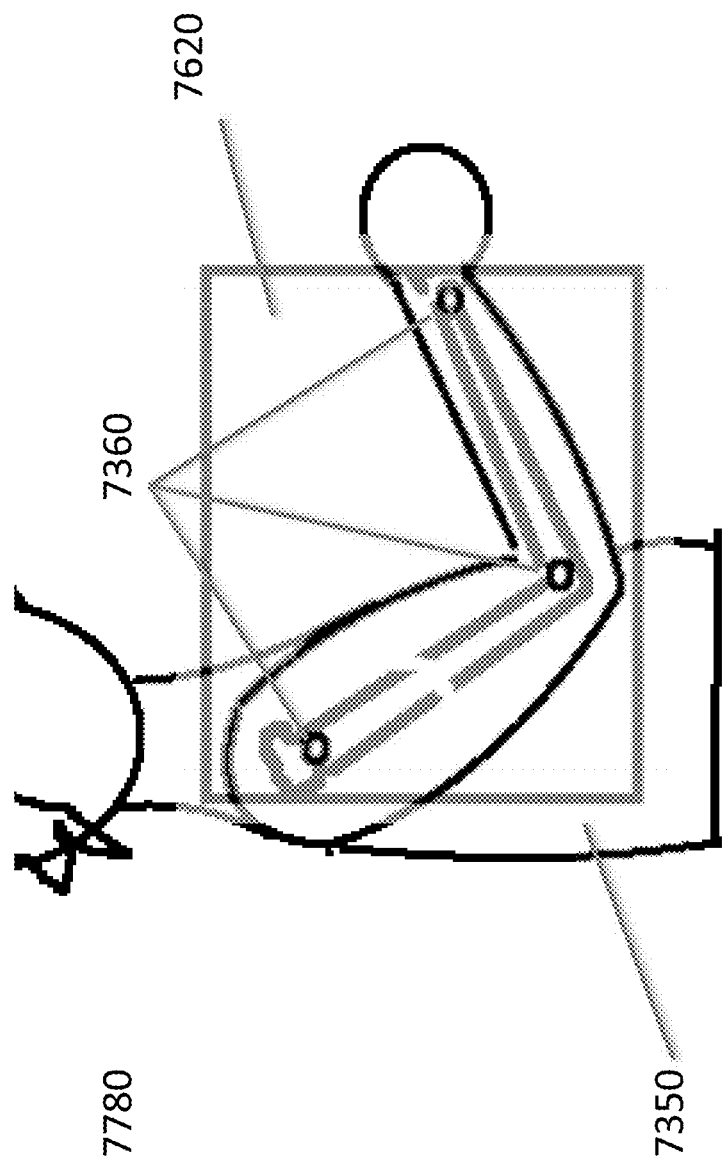
FIG. 77 illustrates a medical procedure in accordance with the principles of the present invention.

The captured image 7610 can be displayed in the head mounted display along with an overlaid version of the medical image 7570 so the user can move to manually align the spots 7560 in the medical image to the spots 7662 in the captured image 7610. Alternatively, the head mounted display can automatically identify the spots 7560 in the medical image 7570 and the spots 7662 in the captured image 7610 and then reposition and resize the displayed medical image 7620 to align the displayed medical image 7620 to the body part 7455 as seen by the user in the see-through view. FIG. 76B shows the displayed medical image 7620 wherein an outline of the body part 7575 can be seen along with spots 7660 from the small lights 260. FIG. 77 shows an illustration of a see-through view 7780 as seen by the user that includes a see-through view of the patient 7450 with an overlaid displayed medical image 7620 that has been aligned to the body part 7455 based on the detected locations of the small lights 7460. In this case, the camera needs to be capable of detecting infrared light in the wavelengths emitted by the small lights 7460 and the user sees a see-through view of the body part 7455 in the visible wavelengths overlaid by the displayed medical image 7620.

Alignment of the displayed medical image 7620 to the see-through view of the patient 7780 can be done manually by the user moving their head to position the displayed medical image 7620 over the body part 7455 and spots associated with the small lights 7460. For example, the user can move their head to align the spots 7660 in the displayed medical image 7620 to the corresponding spots 7662 in the captured image 7610 that is displayed the see-through view. In this case, the displayed medical image 7620 is displayed in a fixed position relative to the field of view of the head mounted display and the captured image 7610 is displayed as a live video image that changes with movements of the user's head and associated changes in the camera's field of view relative to the patient 7450. The user can then indicate to the head mounted display that the displayed medical image is aligned by for example pushing a button or issuing an audible command. Subsequent movements by the user can then be tracked relative to the locations of the small light as determined within subsequent captured images and the position of the displayed medical image 7620 within the display field of view in the head mounted display can be automatically changed in correspondence to the movements to maintain alignment of the displayed medical image 7620 to the body part 7455.

In addition, the head mounted display can automatically align the displayed medical image 7620 to the body part 7455 if two or more small lights 260 are attached to the body part 7455. In this case the camera can capture one or more images 7610 of the body part 7455 with the two or more small lights 260 to determine the locations of the small lights 260 in the user's see-through view. Image processing can then be used to identify the locations of the small lights 260 in the medical image 7570 and in the one or more captured images 7610 of the body part 7455. The displayed medical image 7620 can then be moved within the displayed field of view and resized as needed to align the spots 7660 associated with the small lights 260 in the medical image 7570 to the locations of the small lights within the user's see-through field of view as determined from the identified spots 7662 in the captured images 7610. This alignment process can be done continuously as the camera captures video and the locations of the small lights are determined for each frame in the video to maintain alignment of the displayed image to the body part as the user moves around the patient.

In a further embodiment, two or more small lights are attached to a patient adjacent to an entrance point for an endoscope or other medical device that is used internal to the patient's body to mark the entry point and the end of the endoscope includes an inertial tracking device. Augmented reality images are then presented to the user in a head mounted display that include a visual indication of the path taken by the medical device inside the patient's body. The advantage of the invention is that the user is provided with an accurate visual indication of the location of the end of the medical device and the path followed by the end of the medical device as it moves inside the patient's body.

Figure 78:
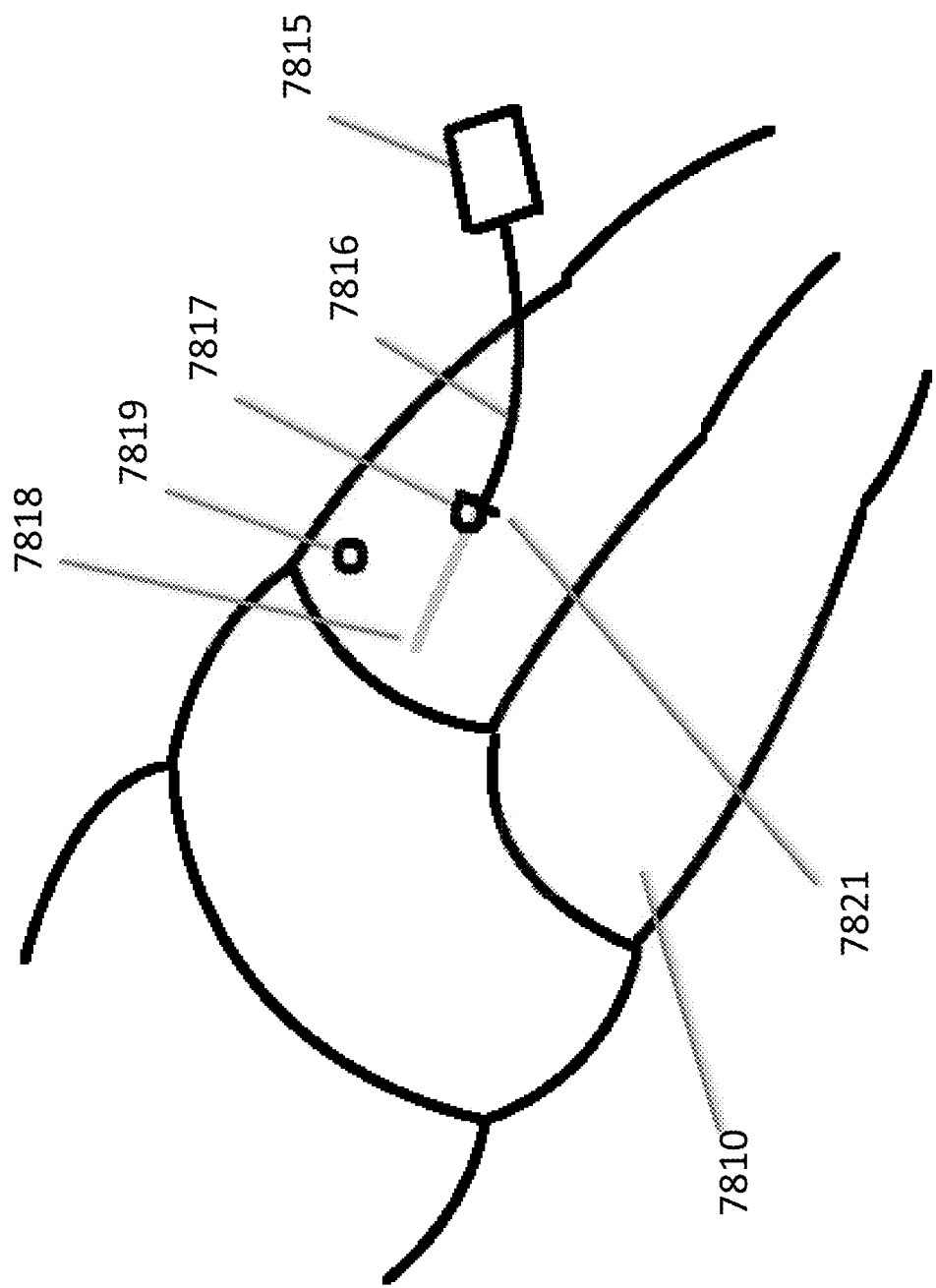
FIG. 78 illustrates a medical procedure in accordance with the principles of the present invention.
Figure 79:
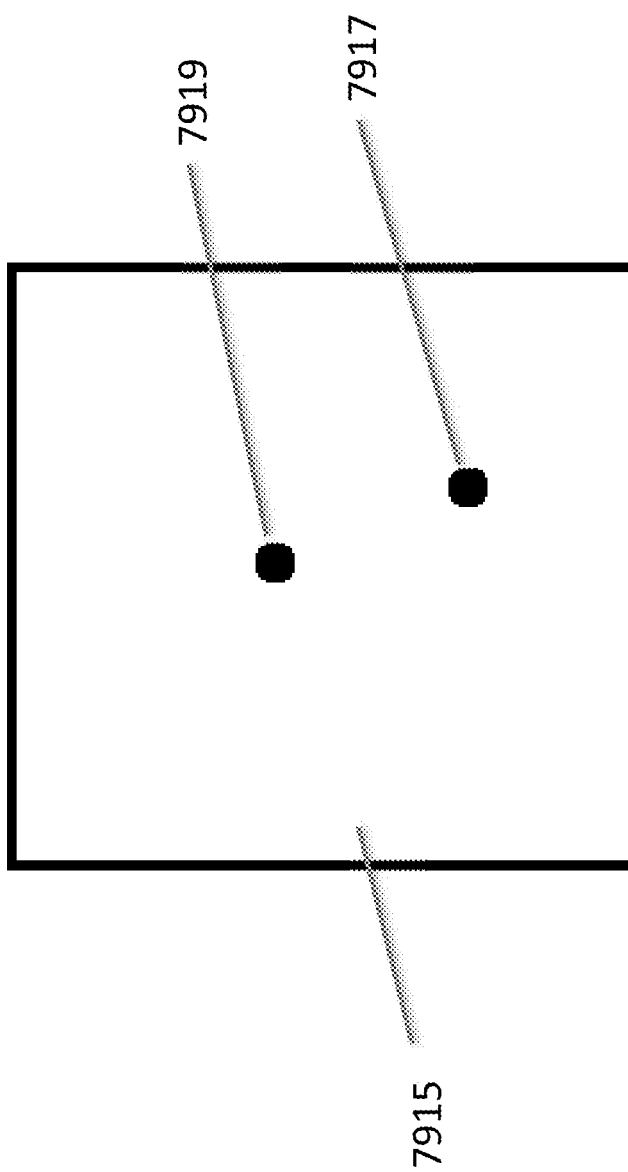
FIG. 79 illustrates a medical procedure in accordance with the principles of the present invention.

FIG. 78 shows an illustration of this embodiment. To insert a medical device such as an endoscope into a patient's body 7810, a small incision 7821 is made through which the medical device 7816 is inserted. Small lights 7817 and 7819 are attached to the patient's body 7810 adjacent to the small incision 7821. Where the small lights 7817 and 7819 include adhesive 7310, a battery 7320 and a light 7330 as shown in FIG. 74. The small lights 7817 and 7819 emit light at wavelengths that can be detected by a camera in the head mounted display. The camera then captures images 7915 of the patient's body 7810 wherein spots 7917 and 719 associated with locations of the small lights 7817 and 7819 are determined as shown in FIG. 79 and used to consistently orient an augmented reality image as displayed to the user relative to the patient's body as the user moves around the patient's body 7810. By using the camera in a video mode, images 7915 including spots 7917 and 719 are captured continuously. By measuring the relative location of the spots 7917 and 719 within the camera's field of view, the movement of the user relative to the patient's body 7810 can be determined.

The medical device 7816 includes electronics 7815 and an end 7818 that moves inside the patient's body 7810 where, the end 7818 includes an inertial measurement unit (IMU) to measure the movement of the end 7818 inside the patient's body 7810. The IMU can include multiple accelerometers, gyroscopes and magnetometers. A suitably compact IMU is the MPU-9250 which is 3×3×1 mm in size and can be obtained from Invensense located in San Jose, Calif. The IMU can be powered by a small battery or by wires connected to the electronics 7815. The measured movement of the end 7818 as determined by the IMU can be communicated wirelessly or through wires connected to the electronics 7815. The measured movement can be expressed in terms of X, Y and Z or distance and direction, this information is used to track the movement of the end 7818 as it passes through the patient's body 7810 and identify a path followed by the end 7818. Data related to the measured movement of the end 7818 is then used to generate an augmented reality image that includes a graphic of the path followed by the end 7818. The augmented reality image is communicated to the head mounted display where it is aligned in correspondence to the relative locations of small lights 7817 and 7819.

Figure 80:
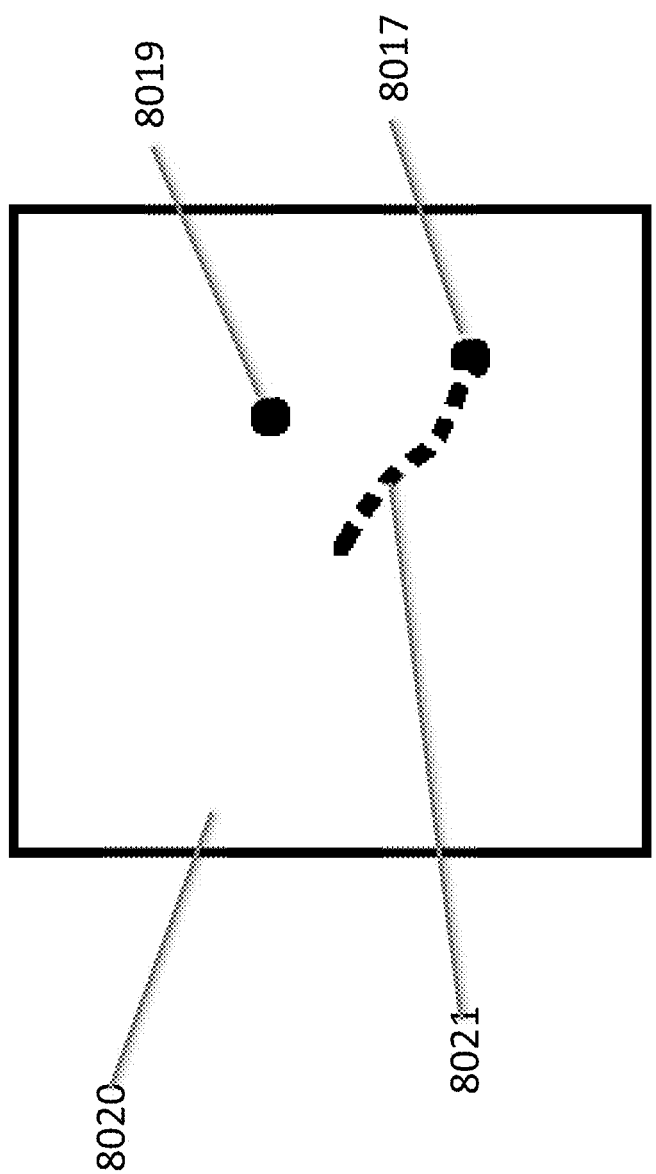
FIG. 80 illustrates a medical procedure in accordance with the principles of the present invention.

FIG. 80 shows an illustration of an augmented reality image 8020 that includes spots 8017 and 8019 associated respectively with small lights 7817 and 7819. Spots 8017 and 8019 are aligned to the patient's body 7810 by aligning respectively to the relative locations of spots 7917 and 719 within the images 7915 captured by the camera. Thereby the graphic 8021 of the path followed by the end 7818 is accurately aligned to the patient's body 7810. The graphic of the path followed by the end 7818 is updated continuously from measured movements of the end 7818 and determined relative locations of the small light 7817 and 7819 as determined from the captured images 7915 and the associated spots 7917 and 719.

Figure 81:
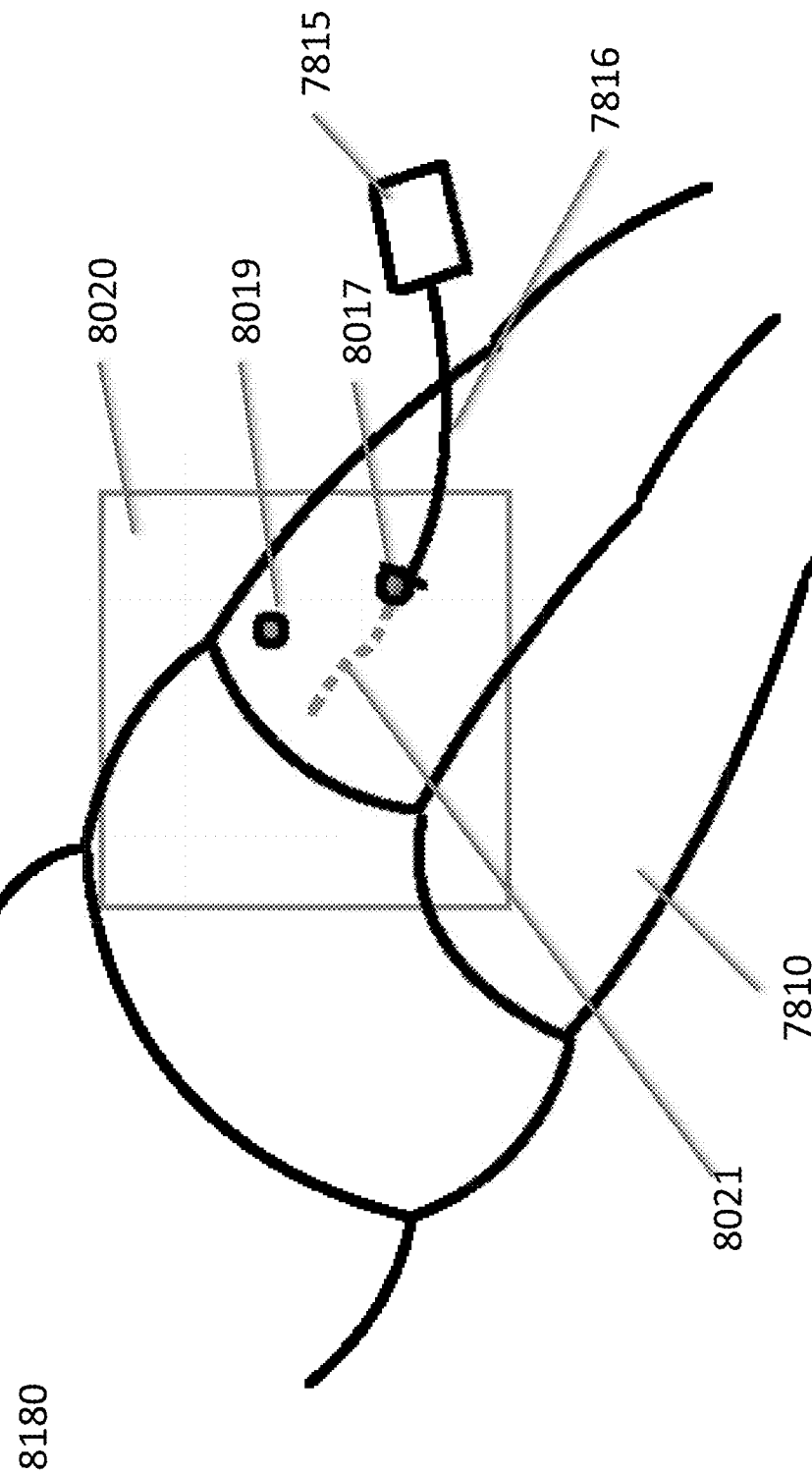
FIG. 81 illustrates a medical procedure in accordance with the principles of the present invention.

FIG. 81 shows an illustration of the view 8180 seen by the user through the head mounted display. The patient's body 7810 can be seen in the see-through view and the displayed augmented reality image 8020 shows the graphic 8021 of the path followed by the end 7818. Wherein, the graphic 8021 of the path followed by the end 7818 is aligned to the patient's body by aligning spots 8017 and 8019 to the small lights 7817 and 7819 as determined from images 7915 that are continuously captured by the camera in the head mounted display. Thereby, as the user moves around the patient's body 7810, the augmented reality image 8020 is reoriented to maintain a constant alignment of the graphic 8021 of the path followed by the end 7818 that is inside the patient's body 7810.

Although embodiments of HWC have been described in language specific to features, systems, computer processes and/or methods, the appended claims are not necessarily limited to the specific features, systems, computer processes and/or methods described. Rather, the specific features, systems, computer processes and/or and methods are disclosed as non-limited example implementations of HWC. All documents referenced herein are hereby incorporated by reference.

I claim:

1. A method of aligning augmented reality (AR) content with first and second body portions, the AR content presented on a display of a wearable head device, the method comprising:
    attaching a first light emitting marker to the first body portion and a second light emitting marker to the second body portion;
    at a first time, capturing a first image of the first and second body portions, the first image including the first emitter marker and the second light emitting markers, anatomical information associated with the first and second body portions, and identification information associated with the first and second body portions;
    at a second time after the first time, generating incoming lights using a third light emitting marker attached to the first body portion and a fourth light emitting marker attached to the second body portion;
    detecting the incoming lights from the third and fourth light emitting markers;
    receiving, from a sensor of the wearable head device, an eye image of an eye of a user of the wearable head device;
    based on the eye image, determining a position of the eye relative to a field of view of the display;
    based on the position of the eye, determining a line of sight;
    based on the line of sight, determining a content position in the field of view of the display, wherein the line of sight intersects the content position;
    displaying, on the display:
        the first image at the content position in a field of view of the display, and
        a second image including the incoming lights and information indicating positions of the third and fourth light emitting markers, wherein the first image is resized to match sizes of the first and second body portions in the first image to sizes of the first and second body portions in the second image;
    reducing, with an input to a user interface of the wearable head device, a first distance between the first and third light emitters on the display and a second distance between the second and third light emitters on the display;
    receiving the input to the user interface; and
    in response to receiving the input to the user interface, aligning, based on the reduced first and second distances, the first image with the second image, wherein each light emitting marker comprises a battery and a light emitting element.

2. The method of claim 1, wherein the first image comprises a pre-procedure diagnostic image comprising at least one of an X-Ray image and a CAT Scan image.

3. The method of claim 1, wherein detecting the incoming lights comprises capturing, with a camera, an image of the body portion, and the camera is oriented in a direction normal to the display.

4. The method of claim 1, wherein the incoming lights comprise infrared light.

5. The method of claim 1, wherein the incoming lights comprise visible light.

6. The method of claim 5, wherein the display comprises a notch filter adapted to attenuate the visible incoming light reaching the user.

7. The method of claim 1, wherein the input to the user interface includes a voice input.

8. The method of claim 1, wherein the input to the user interface includes a head movement.

9. The method of claim 1, further comprising, after aligning the first image with the second image, fixing a location of the first image on the display.

10. The method of claim 1, further comprising:
receiving a second input; and
in response to receiving the second input, displaying the first image without interruptions.

11. The method of claim 10, wherein the second input comprises the eye image.

12. The method of claim 10, wherein the second input comprises an inertial input.

13. The method of claim 10, wherein the second input comprises a gesture input.

14. The method of claim 10, wherein the second input comprises a voice input.

15. A system comprising:
a wearable head device comprising a display and a sensor;
one or more processors configured to execute a method comprising:
receiving a first image, captured at a first time, of a first body portion and a second body portion, the first image including a first emitter marker attached to the first body portion and a second light emitting markers attached to the second body portion, anatomical information associated with the first and second body portions, and identification information associated with the first and second body portions;
at a second time after the first time, detecting the incoming lights from third and fourth light emitting markers, wherein the incoming lights are generated using the third light emitting marker attached to the first body portion and the fourth light emitting marker attached to the second body portion;
receiving, from the sensor, an eye image of an eye of a user of the wearable head device;
based on the eye image, determining a position of the eye relative to a field of view of the display;
based on the position of the eye, determining a line of sight;
based on the line of sight, determining a content position in the field of view of the display, wherein the line of sight intersects the content position;
displaying, on the display:
the first image at the content position in a field of view of the display, and
a second image including the incoming lights and information indicating positions of the third and fourth light emitting markers, wherein the first image is resized to match sizes of the first and second body portions in the first image to sizes of the first and second body portions in the second image;
reducing, with an input to a user interface of the wearable head device, a first distance between the first and third light emitters on the display and a second distance between the second and third light emitters on the display;
receiving the input to the user interface; and
in response to receiving the input to the user interface, aligning, based on the reduced first and second distances, the first image with the second image, wherein each light emitting marker comprises a battery and a light emitting element.

16. The system of claim 15, wherein the first image comprises a pre-procedure diagnostic image comprising at least one of an X-Ray image and a CAT Scan image.

17. The system of claim 15, wherein the input to the user interface includes a voice input.

18. A non-transitory computer-readable medium storing instructions, which, when executed by one or more processors, cause the one or more processors to perform a method comprising:
receiving a first image, captured at a first time, of a first body portion and a second body portion, the first image including a first emitter marker attached to the first body portion and a second light emitting markers attached to the second body portion, anatomical information associated with the first and second body portions, and identification information associated with the first and second body portions;
at a second time after the first time, detecting the incoming lights from third and fourth light emitting markers, wherein the incoming lights are generated using the third light emitting marker attached to the first body portion and the fourth light emitting marker attached to the second body portion;
receiving, from a sensor of a wearable head device, an eye image of an eye of a user of the wearable head device;
based on the eye image, determining a position of the eye relative to a field of view of the display;
based on the position of the eye, determining a line of sight;
based on the line of sight, determining a content position in the field of view of the display, wherein the line of sight intersects the content position;
displaying, on a display of the wearable head device:
the first image at the content position in a field of view of the display, and
a second image including the incoming lights and information indicating positions of the third and fourth light emitting markers, wherein the first image is resized to match sizes of the first and second body portions in the first image to sizes of the first and second body portions in the second image;
reducing, with an input to a user interface of the wearable head device, a first distance between the first and third light emitters on the display and a second distance between the second and third light emitters on the display;
receiving the input to the user interface; and
in response to receiving the input to the user interface, aligning, based on the reduced first and second distances, the first image with the second image, wherein each light emitting marker comprises a battery and a light emitting element.

19. The non-transitory computer-readable medium of claim 18, wherein the first image comprises a pre-procedure diagnostic image comprising at least one of an X-Ray image and a CAT Scan image.

20. The non-transitory computer-readable medium of claim 18, wherein the input to the user interface includes a voice input.

* * * * *